(12) United States Patent
Bui et al.

(10) Patent No.: US 11,046,699 B2
(45) Date of Patent: Jun. 29, 2021

(54) PYRAZOLO-PYRIMIDIN-AMINO-CYCLOALKYL COMPOUNDS AND THEIR THERAPEUTIC USES

(71) Applicant: RAPT THERAPEUTICS, INC., South San Francisco, CA (US)

(72) Inventors: Minna H. T. Bui, Oakland, CA (US); Adrian O. Dukes, Morgan Hill, CA (US); Xinping Han, Berkeley, CA (US); Dennis X. Hu, San Bruno, CA (US); Jeffrey J. Jackson, San Bruno, CA (US); Yoo Min Ko, South San Francisco, CA (US); Paul R. Leger, Oakland, CA (US); Anqi Ma, Foster City, CA (US); Jack Maung, Daly City, CA (US); Andrew A. Ng, San Mateo, CA (US); Akinori Okano, San Mateo, CA (US); Omar Robles, San Mateo, CA (US); Grant Shibuya, South San Francisco, CA (US); Hunter P. Shunatona, Oakland, CA (US); Jacob B. Schwarz, San Ramon, CA (US); Anton A. Shakhmin, Santa Clara, CA (US); David J. Wustrow, Los Gatos, CA (US); Mikhail Zibinsky, Redwood City, CA (US)

(73) Assignee: RAPT THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 16/431,504

(22) Filed: Jun. 4, 2019

(65) Prior Publication Data
US 2019/0375753 A1  Dec. 12, 2019

Related U.S. Application Data

(60) Provisional application No. 62/680,891, filed on Jun. 5, 2018, provisional application No. 62/831,006, filed on Apr. 8, 2019.

(51) Int. Cl.
C07D 487/04 (2006.01)
C07D 519/00 (2006.01)

(52) U.S. Cl.
CPC ......... *C07D 487/04* (2013.01); *C07D 519/00* (2013.01)

(58) Field of Classification Search
CPC .................................................. C07D 487/04
USPC ........................................................ 514/210.2
See application file for complete search history.

(56) References Cited

U.S. PATENT DOCUMENTS

| | | | | |
|---|---|---|---|---|
| 7,217,710 B2* | 5/2007 | Adams | ...................... | A61P 9/00 514/234.2 |
| 2010/0249067 A1* | 9/2010 | Kasibhatla | ........... | C07D 487/04 514/81 |
| 2013/0345268 A1 | 12/2013 | Ratner et al. | | |

FOREIGN PATENT DOCUMENTS

| | | | |
|---|---|---|---|
| WO | WO-03/029209 A2 | 4/2003 | |
| WO | WO-03/029209 A3 | 4/2003 | |
| WO | WO-03029209 A2 * | 4/2003 | .............. A61P 35/04 |
| WO | WO-2008/094575 A2 | 8/2008 | |
| WO | WO-2008/094575 A3 | 8/2008 | |
| WO | WO-2008/094602 A2 | 8/2008 | |
| WO | WO-2008/094602 A3 | 8/2008 | |
| WO | WO-2008094602 A2 * | 8/2008 | .............. A61P 35/00 |
| WO | WO-2012/098068 A1 | 7/2012 | |
| WO | WO-2014/135244 A1 | 9/2014 | |
| WO | WO-2014/135245 A1 | 9/2014 | |

OTHER PUBLICATIONS

Dunn, G.P. et al. (Aug. 2004). "The immunobiology of cancer immunosurveillance and immunoediting," *Immunity* 21(2):137-148.
Muller, A.J. et al. (Feb. 2007). "Indoleamine 2,3-dioxygenase in immune suppression and cancer," *Curr Cancer Drug Targets* 7(1):31-40.
Shankaran, V. et al. (Apr. 26, 2001). "IFNgamma and lymphocytes prevent primary tumour development and shape tumour immunogenicity," Nature 410(6832):1107-1111.
International Search Report dated Aug. 14, 2019, for PCT Application No. PCT/US2019/035462, filed Jun. 4, 2019, 8 pages.
Written Opinion dated Aug. 14, 2019, for PCT Application No. PCT/US2019/035462, filed Jun. 4, 2019, 8 pages.

* cited by examiner

*Primary Examiner* — Kahsay Habte
(74) *Attorney, Agent, or Firm* — Mintz, Levin, Cohn, Ferris, Glovsky and Popeo, P.C.

(57) ABSTRACT

Disclosed herein are pyrozolo-pyrimidin-amino-cycloalkyl compounds, analogs thereof, pharmaceutical compositions comprising thereof and therapeutic uses therefor.

46 Claims, No Drawings

PYRAZOLO-PYRIMIDIN-AMINO-CYCLOALKYL COMPOUNDS AND THEIR THERAPEUTIC USES

CROSS-REFERENCES TO RELATED APPLICATIONS

This application claims priority to U.S. Provisional Application No. 62/680,891 filed Jun. 5, 2018 and to U.S. Provisional Application No. 62,831,006 filed Apr. 8, 2019, the contents of which are hereby incorporated by reference in their intireties.

TECHNICAL FIELD

The present disclosure relates to compounds, and to the use of such compounds, in which the inhibition, regulation and/or modulation of signal transduction by GCN2 plays a role.

BACKGROUND

Many strategies of cancer treatment of solid tumors focus on the surgically removal of the tumor mass as far as possible and the subsequent eradication of any residual tumor cells by radiotherapy and chemotherapy with cytotoxic agents or inhibitors that target cancer cell pathways more specifically. However, the success of such approach is limited and often does not persist. This is mainly due to the narrow therapeutic window for such cytotoxic agents (specificity and side effects) and to the capability of cancer cells to adapt to the selective pressure applied by cytotoxic or other inhibitory agents. The survival of a small number of tumor (e.g., stem) cells that acquire resistance to the initial treatment can be sufficient to seed the regrowth of a tumor. These relapses are in most cases more difficult to treat compared to that of the initial tumors. As a consequence, the more successful targeting of tumor cells may require targeting multiple survival and escape mechanism of tumor cells in parallel (Muller A J, Prendergast G C. (2007). Indoleamine 2,3-dioxygenase in immune suppression and cancer. Curr Cancer Drug Targets 7: 31-40).

Development of malignancies is accompanied by a major roll up of the cellular physiology. During this process several qualities are acquired by the cancer cells that are basis for immortalization or insensitivity to growth inhibitory signals. In addition, the tumor cells also modify the interaction with the microenvironment and beyond. The latter area includes the strategies of tumor cells to escape from the immunological surveillance (Muller & Prendergast 2007). The immune surveillance limits malignant growth but also provides a selective pressure triggering the evolution of mechanisms for evading the immune response as reviewed by (Dunn, G. P.; Old, L. J.; Schreiber, R. D. The immunobiology of cancer immunosurveillance and immunoediting. Immunity 2004, 21, 137-148). Essentially it has been frequently observed that ablation of T cell immunity is sufficient to increase tumor incidence (Shankaran, V.; Ikeda, H.; Bruce, A. T.; White, J. M.; Swanson, P. E.; Old, L. J.; Schreiber, R. D. IFNgamma and lymphocytes prevent primary tumour development and shape tumour immunogenicity. Nature 2001, 410, 1107-1111). and it is believed that immune escape is affecting tumor dormancy versus progression, promoting invasion and metastasis and negatively impacting therapeutic response.

A key mechanism that is implicated in reduction of immune activity in the tumor microenvironment is reduction of amino acid concentrations, including tryptophan and arginine. Certain macrophages and dendritic cells in the tumor microenvironment express indolamine 2,3-dioxegynase (IDO) an enzyme that has been shown to reduce tryptophan levels in tumors by converting it kynurenine. This reduction in tryptophan levels is associated with reduced effector T cell proliferation. It has been shown that GCN2 expression is required for IDO-mediated inhibition of the activity of T cells. In tumor bearing mice and in cancer patients, metabolism of arginine by the enzyme arginase-1 (Arg-1) has also been shown to inhibit T cell immune responses in the tumor. Similar to the case of IDO, it has been shown that GCN2 is required for this reduction in arginine to inhibit proliferation of T cells. In both situations phosphorylation of EIF2α by GCN2 is the key signaling step in the translation of reduced amino acid levels into suppression of immune cells in the tumor microenvironment.

The GCN2 pathway is not only important for tumoral immune escape but also plays an active role in modulating tumor survival directly. ATF4, which is produced when EIF2α is phosphorylated, is over-expressed in human solid tumors suggesting an important function in tumor progression. GCN2 knockdown has been demonstrated to prevent AAD induced expression of Vascular Endothelial Growth Factor (VEGF) which tumors use to enhance nutrient supply via increased vascularization. Thus, activation of the GCN2/ATF4 pathway promotes tumor growth and angiogenesis through AAD-mediated VEGF expression.

Taken together these studies demonstrate that activation of GCN2 by AAD is both a merging point of the IDO and Arg-1 pathways which contribute to immune system suppression via Tcell inhibition in the tumor microenvironment as well as directly stimulating tumor growth through enhanced vascularization. Therefore, selective inhibition of GCN2 can both increase the activity of the immune system in the tumor microenvironment while at the same time directly preventing tumor growth.

Disclosed herein, inter alia, are solutions to these and other problems in the art.

SUMMARY

Provided herein, inter alia, are small molecule modulators of signal transduction by general control nonderepressible 2 (GCN2), pharmaceutical compositions comprising these compounds, and the use of these compounds for the treatment of conditions in which modulation of signal transduction by GCN2 plays a role.

In an aspect are provided compounds of formula (I):

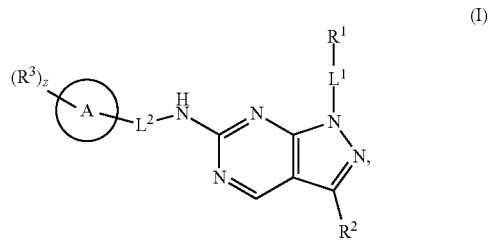

and pharmaceutically acceptable salts thereof; wherein: z is an integer from 0 to 6; ring A is substituted or unsubstituted cycloalkyl, or substituted or unsubstituted heterocycloalkyl; L and L² are independently a bond, substituted or unsubstituted alkylene, or substituted or unsubstituted heteroalkylene; $R^1$ is substituted or unsubstituted aryl or substituted or unsubstituted heteroaryl; $R^2$ is independently hydrogen, halogen, $-CX^2_3$, $-CHX^2_2$, $-CH_2X^2$, $-OCX^2_3$, $-OCHX^2_2$, $-OCH_2X^2$, $-CN$, $-S(O)_2R^{2A}$, $-SR^{2A}$, $-S(O)R^{2A}$, $-SO_2NR^{2A}R^{2B}$, $-NHC(O)NR^{2A}R^{2B}$, $-N(O)_2$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently halogen, $-CX^3_3$, $-CHX^3_2$, $-CH_2X_3$, $-OCX^3_3$, $-OCHX^3_2$, $-OCH_2X_3$, $-CN$, $-S(O)_2R^{3A}$, $-SR^{3A}$, $-S(O)R^{3A}$, $-SO_2NR^{3A}R^{3B}$, $-NHC(O)NR^{3A}R^{3B}$, $-N(O)_2$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-C(O)NHNR^{3A}R^{3B}$, $-P(O)R^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ may optionally be joined to form a substituted or unsubstituted heterocycloalkyl or substituted or unsubstituted heteroaryl; $R^{2A}$, $R^{2B}$, $R^{3A}$, and $R^{3B}$ are independently hydrogen, $-F$, $-Cl$, $Br$, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, $-NCH_3OCH_3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^{2A}$ and $R^{2B}$ may optionally be joined to form a substituted or unsubstituted heterocycloalkyl or substituted or unsubstituted heteroaryl; $R^{3A}$ and $R^{3B}$ may optionally be joined to form a substituted or unsubstituted heterocycloalkyl or substituted or unsubstituted heteroaryl; and $X^2$ and $X^3$ are independently halogen; with the proviso that when ring A is cyclohexyl, then $R^3$ is not an ortho-substituted $-NH_2$ or $-HNC=(O)t$-BuO, or para-substituted $-NHSO_2CH_2CH_2CF_3$, $-NHSO_2CH_3$, or $-OH$.

In certain embodiments of the Formula (I) compounds, $R^3$ is not a substituted or unsubstituted amine attached to ring A at the ortho position. In other embodiments of the Formula (I) compounds, $R^3$ is not attached to ring A at the ortho position.

In embodiments of the Formula (I) compounds, $L^1$ and $L^2$ are each a bond. In other embodiments of the Formula (I) compounds, $L^1$ and $L^2$ are independently substituted or unsubstituted $C_1$-$C_{10}$ alkylene or substituted or unsubstituted 2 to 10 membered heteroalkylene.

In still other embodiments of the Formula (I) compounds, $L^1$ and $L^2$ are independently unsubstituted $C_1$-$C_{10}$ alkylene or unsubstituted 2 to 10 membered heteroalkylene.

In an aspect is provided pharmaceutical compositions including a compound of Formula (I) and a pharmaceutically acceptable excipient. In embodiments, the pharmaceutical compositions are for use in treating a disorder modulated by general control nonderepressable 2 (GCN2) kinase inhibitors. In embodiments, the disorder is cancer.

In an aspect is provided methods of treating or preventing a disease or disorder mediated by GCN2, including administering to a subject in need thereof a therapeutically effective amount of a compound of Formula (I), or a pharmaceutical composition including a compound of Formula (I). In embodiments of such treatment methods, the disease or disorder is cancer. In other embodiments, the cancer is melanoma, non-small cell lung cancer, bladder cancer, pancreatic cancer, head and neck cancer or a brain tumor.

DETAILED DESCRIPTION

Provided herein are, for example, compounds and compositions for inhibition of general control nonderepressable 2 (GCN2), and pharmaceutical compositions including the same. Also provided herein are, for example, methods of treating or preventing a disease, disorder or condition, or a symptom thereof, mediated by modulation (e.g., inhibition) of GCN2.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($-O-$). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-S-CH_2$, $-S(O)-CH_3$, $-CH_2-CH_2-S(O)_2-CH_3$, $-CH=CHO-CH_3$, $-Si(CH_3)_3$, $-CH_2-CH=N-OCH_3$, $-CH=CH-N(CH_3)-CH_3$, $-CH_3$, $-CH_2-CH_3$, and $-CN$. Up to two or three heteroatoms may be consecutive, such as, for example, $-CH_2-NH-OCH_3$ and $-CH_2-O-Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $-CH_2-CH_2-S-CH_2-CH_2-$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$. As described above, heteroalkyl groups, as used herein, include those groups that are attached to the remainder of the molecule through a heteroatom, such as $-C(O)R'$, $-C(O)NR'$, $-NR'R''$, $-OR'$, $-SR'$, and/or $-SO_2R'$. Where "heteroalkyl" is recited, followed by recitations of specific heteroalkyl groups, such as $-NR'R''$ or the like, it will be understood that the terms heteroalkyl and $-NR'R''$ are not redundant or mutually exclusive. Rather, the specific heteroalkyl groups are recited to add clarity. Thus, the term "heteroalkyl" should not be interpreted herein as excluding specific heteroalkyl groups, such as $-NR'R''$ or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5- yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⸺" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In embodiments, the alkylarylene group has the formula:

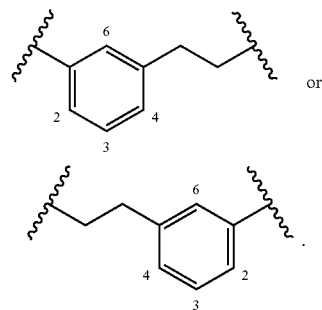

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, ☐$NHNH_2$, ☐$ONH_2$, ☐NHC(O)NHNH$_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', □NR'NR"R"', □ONR'R", □NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —C$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

(b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl/and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}O$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate" refers to the resulting association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulthydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^1$ substituents are present, each $R^1$ substituent may be distinguished as $R^{1A}$, $R^{1B}$, $R^{1C}$, $R^{3D}$, etc., wherein each of $R^{1A}$, $R^{1B}$, $R^{1C}$, $R^{1D}$, etc. is defined within the scope of the definition of $R^1$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the terms "GCN2 inhibitor", "GCN2 antagonist" and all other related art-accepted terms, many of which are set forth below, refer to a compound capable of modulating (e.g., reducing), either directly or indirectly, the GCN2 receptor in an in vitro assay, an in vivo model, and/or other means indicative of therapeutic efficacy. The terms also refer to a compound that exhibits at least some therapeutic benefit in a human subject.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues; immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme.

In some embodiments contacting includes allowing a compound described herein to interact with a protein or enzyme that is involved in a signaling pathway (e.g., MAP kinase pathway).

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition," "inhibit,", "inhibiting," and the like, in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The term "GCN2", which is an acronym for general control nonderepressible 2, refers to the serine/threonine-protein kinase that senses amino acid deficiency through binding to uncharged transfer RNA (tRNA). GCN2 plays a key role in modulating amino acid metabolism as a response to amino acid depletion (AAD). It inactivates eukaryotic translation initiation factor 2 (eIF2α) by phosphorylation at Serine 51 under conditions of AAD. GCN2 is one of four eIF2α kinases found in mammals. The others (HRI, PKR and PERK) each respond to different signals of cellular distress by phosphorylating the same Serine 51 in eIF2α. As eIF2α is the common downstream target that integrates signaling from all eIF2α kinases, in mammals this pathway was termed the Integrated Stress Response (ISR). Selectively blocking GCN2, as opposed to other eIF2a kinases, will preferentially inhibit cellular stress signals due to AAD.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "cancer" refers to all types of cancer, neoplasm or malignant tumors found in mammals (e.g. humans), including leukemia, carcinomas and sarcomas.

Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a GCN2 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyes, J. Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present invention can also be delivered as nanoparticles.

By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

Dosages may be varied depending upon the requirements of the patient and the compound being employed. The dose administered to a patient, in the context of the present invention should be sufficient to affect a beneficial therapeutic response in the patient over time.

The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g., melanoma, non-small cell lung cancer, bladder cancer, pancreatic cancer, head and neck cancer or brain tumor).

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g., melanoma, non-small cell lung cancer, bladder cancer, pancreatic cancer, head and neck cancer or brain tumor).

The compounds described herein can be administered to treat numerous types of cancer, in particular melanoma, non-small cell lung cancer, bladder cancer, pancreatic cancer, head and neck cancer or brain tumor. In this regard, the compounds disclosed herein may be administered either alone to treat such diseases or disorders or may be co-administered with another therapeutic agent to treat such diseases or disorders.

The compounds disclosed herein may be co-administered with a cytokine or agonist or antagonist of cytokine function, (including agents which act on cytokine signaling pathways such as modulators of the SOCS system) including alpha-, beta-, and gamma-interferons; insulin-like growth factor type I (IGF-1); interleukins (IL) including IL1 to 17, and interleukin antagonists or inhibitors such as analcinra; tumour necrosis factor alpha (TNF-.alpha.) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, P412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives;

balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole;

etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Iso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*Pseudomonas* exotoxin conjugate, etc.), and radioimmunotherapy (e.g., anti-CD20 monoclonal antibody conjugated to $^{111}$In, $^{90}$Y, or $^{131}$I, etc.).

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5.alpha.-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin .alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In embodiments, the compounds disclosed herein can be co-administered with an antibody, such as a monoclonal antibody targeting B-Lymphocytes (such as CD20 (rituximab), MRA-aIL16R and T-Lymphocytes, CTLA4-Ig, HuMax I1-15) or antibody modulating Ig function such as anti-IgE (for example omalizumab).

In embodiments, treatment of cancer includes administration of an effective amount of at least two of the following: a GCN2 inhibitor, an inhibitor of the PD-L1/PD-1 pathway, an inhibitor of CTLA-4, an agonistic antibody of CD137 (4-1BB). In some embodiments, the method may include the use of two or more combinations.

In embodiments, treatment of cancer includes an effective amount of at least two or more of the following: a GCN2 inhibitor and any combination of agent that may be an immune modulator such as, but not limited to, those listed in Table 1. These immune modulators can be depleting antibodies, neutralizing antibodies, blocking antibodies, agonistic antibodies, small molecule modulators (inhibitors or stimulators) or small molecule analogs.

TABLE 1

| Target or Therapy | Examples of Agents | Regulatory Mechanism |
|---|---|---|
| TIM-3 | TSR-022, MGB453 | Checkpoint-receptor |
| LAG-3 | BMS-986016, IMP321 | Checkpoint-receptor |
| B7-H3 | MGA271, MGD-009 | Checkpoint-receptor |
| TIGIT | RG-6058 | Checkpoint-receptor |
| BTLA | | Checkpoint-receptor |
| CD28 | AMG 557, | Checkpoint-receptor |
| CD40 | SEA-CD40, dacetuzumab, CP-870,893, Chi Lob 7/4, lucatumumab | Checkpoint-receptor |
| CD80 | galiximab | Checkpoint-receptor |
| GITR | INCAGN1876, TRX518, | Checkpoint-receptor |
| ICOS | MEDI-570 | Checkpoint-receptor |
| OX40 (CD134) | MEDI-6469, INCAGN1949, huMab OX40L, | Checkpoint-receptor |
| NKG2A | monalizumab | Checkpoint-receptor |
| TGF-beta | Galunisertib, luspatercept, YH-14618, dalantercept, BG-00011, trabedersen, isth-0036,, ace-083, | Cytokines |
| IL2 | NKTR-214, recombinant IL2, aldesleukin | Cytokines |
| IL12 | EGEN-001, NHS-IL12 | Cytokines |
| IL7 | Recombinant IL-7, | Cytokines |
| IL15 | NIZ-985, ALT-803, | Cytokines |
| IL21 | Recombinant IL-21, anti-CD20.1L21, | Cytokines |

TABLE 1-continued

| Target or Therapy | Examples of Agents | Regulatory Mechanism |
|---|---|---|
| IL13 | Tralokinumab, dupilumab | |
| CSF1R | cabiralizumab | Cytokine |
| PI3K delta | INCB50465, idealisib, TGR-1202, AMG319, | Kinase |
| PI3K gamma | IPI-549 | Kinase |
| DNMT (DNA methyl transferase inhibitor) | Azacytidine, decitabine, guadecitabine, | Epigenetic Regulator |
| HDAC (histone deacetylase) | Vorinostat, Panobinostat, belinostat, entinostat, mocetinostat, givinostat, chidamide, quisinostat, abexinostat, chr-3996, ar-42, | Epigenetic Regulator |
| Brd4 | INCN54329, INCB57643, birabresib, apabetalone, alvocidib, PLX-51107, FT-1101, RG-6146, AZD-8186, CPI-0610, JQ1 | Transcription regulator |
| HMT (histone methyl transferases) | | Epigenetic Regulator |
| LSD1 | INCB59872, IMG-7289, RG-6016, CC-90011, GSK-2879552, ORY-2001, 4SC-202, ORY-3001, | Epigenetic Regulator |
| TNFa | Recombinant TNFa, MEDI-1873, FPA-154, LKZ-145 | Cytokine |
| IL1 | Recombinant IL1 | Cytokine |
| IFNa | Recombinant interferon alpha-n1, Recombinant interferon alpha-2b, Recombinant interferon alpha-n3 | Cytokine |
| IFNb | Recombinant IFN beta-1a, | Cytokine |
| IFNg | actimmune | Cytokine |
| STING | Cyclic di-nucleotides | Signaling Molecule |
| TLR | Poly I:C, IMO-2055, TMX-101, imiquimod, CpG, MGN1703, glucopyranosyl lipid A, CBLB502, BCG, HILTONOL, AMPLIGEN, MOTOLIMOD, DUK-CPG-001, AS15 | Pathogen Recognition Receptor |
| IL10 | Recombinant IL-10 | Cytokine |
| CCR2 | CCX140, CCX872, BMS-813160, CENICRIVIROC, CNTX-6970. PF-4136309, plozalizumab, INCB-9471, PF-04634817 | Chemokine |
| CCR5 | Maraviroc, PRO-140, BMS-813160, NIFEVIROC, OHR-118 | Chemokine |
| CXCR4 | Ulocuplumab, plerixafor, x4p-001, usl-311, ly-2510924, APH-0812, BL-8040, BURIXAFOR, BALIXAFORTIDE, PTX-9908, GMT-1359, F-50067 | Chemokine |
| LFA1 | | Adhesion Molecule |
| MICA/B | IPH-4301 | Immune Receptor Ligand |
| VISTA | CA-170 | Checkpoint-Ligand |
| Adenosine | ISTRADEFYLLINE, TOZADENANT, PBF-509, PBF-999, CPI-444 | Nucleoside |
| CD39 | OREG-103. Anti-CD39 antibodies, | Ecto-enzyme |
| CD73 | Oleclumab, PBF-1662, anti-CD73 antibodies | Ecto-Enzyme |
| PD1 | Pembrolizumab, nivolumab, INCSHR1210, CT-011, AMP224 | Checkpoint-receptor |
| PD-L1 | Atezolizumab, avelumab | Checkpoint-Ligand |
| PD-L2 | | Checkpoint-Ligand |
| CTLA4 | Tremelimumab | Checkpoint-receptor |
| CD137 | Urelumab, utomilumab, BMS-663513, PF-05082566 | |
| AXL | BGB-324, BPI-9016M, S-49076 | Kinase |
| MERTK | BGB-324, BPI-9016M, S-49076 | Kinase |
| TYRO | BGB-324, BPI-9016M, S-49076 | |
| BTK | ibrutinib | Kinase |
| ITK | ibrutinib | Kinase |
| LCK | | Kinase |
| TET2 | | Enzyme |
| Arginase | Cb-1158 | Endo/ecto enzyme |
| GCN2 | | Kinase |
| B7-H4 | MDX-1140, AMP-110 | Checkpoint-receptor |
| HIF1alpha | PT2385 | Transcription Factor |
| LIGHT (TNFSF14) | | TNF Superfamily |
| FLT3 | CDX-301, FLX925, quizartinib, gilteritinib, PKC412, midostaurin, crenolanib | Kinase |
| CD158 | Lirlumab, IPH-2101 | |
| CD47 | Anti-CD47, TTI-621, NI-1701, SRF-231, Effi-DEM, RCT-1938 | |
| IDO | Epacadostat, F287, BM5983205, GDC-0919, indoximod, | |
| RORgamma | | |

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{513}$Sm, $^{166}$Ho, $^{177}$Lu, $^{186}$Re, $^{188}$Re, $^{211}$At, and $^{212}$Bi, optionally conjugated to antibodies directed against tumor antigens.

In addition, a GCN2 inhibitor may be combined with the therapeutic administration of immune cells, sometimes referred to as adoptive cell transfer. These cells may be cells from the patient, a genetically related or unrelated donor, they may be genetically modified (e.g. CAR-T cells, NK cells, etc), cell lines, genetically modified cell lines and live or dead versions of the above. GCN2 inhibitors may also be combined with vaccines of any kind (e.g. protein/peptide, viral, bacterial, cellular) to stimulate immune responses to cancer.

In embodiments, treatment is administration of an effective amount of a GCN2 inhibitor in combination with an inhibitor of the PD-L1/PD-1 pathway, an inhibitor of CTLA-4, an agonistic antibody of CD137 (4-1BB) or in combination with another immune modulator as listed in Table 1.

In embodiments, treatment is therapeutic administration of an effective amount of a GCN2 inhibitor in combination with an inhibitor of the PD-L1/PD-1 pathway, an inhibitor of CTLA-4, an agonistic antibody of CD137 (4-1BB) or in combination with another immune modulator as listed in Table 1. Here, treatment starts when tumors reach a size of 40-70 mm$^3$.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a GCN2 associated disease modulator is a compound that reduces the severity of one or more symptoms of a disease associated with GCN2 (e.g. cancer). A GCN2 modulator is a compound that increases or decreases the activity or function or level of activity or level of function of GCN2. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate", "modulation" and the like refer to the ability of a molecule (e.g., an activator or an inhibitor) to increase or decrease the function or activity of GCN2, either directly or indirectly, relative to the absence of the molecule.

The term "associated" or "associated with" in the context of a substance or substance activity or function associated with a disease (e.g. a protein associated disease, a cancer associated with GCN2 activity, GCN2 associated cancer, GCN2 associated disease (e.g., cancer, inflammatory disease, autoimmune disease, or infectious disease)) means that the disease (e.g. cancer, inflammatory disease, muscular and/or sensory neuropathic diseases such as Charcot-Marie-Tooth disease, autoimmune disease, or infectious disease) is caused by (in whole or in part), or a symptom of the disease is caused by (in whole or in part) the substance or substance activity or function. For example, a cancer associated with GCN2 activity or function may be a cancer that results (entirely or partially) from aberrant GCN2 function (e.g. enzyme activity, protein-protein interaction, signaling pathway) or a cancer wherein a particular symptom of the disease is caused (entirely or partially) by aberrant GCN2 activity or function. As used herein, what is described as being associated with a disease, if a causative agent, could be a target for treatment of the disease. For example, a cancer associated with GCN2 activity or function or a GCN2 associated disease (e.g., cancer), may be treated with a compound described herein (e.g., GCN2 modulator or GCN2 inhibitor), in the instance where increased GCN2 activity or function (e.g. signaling pathway activity) causes the disease (e.g., cancer).

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of GCN2 with a compound as described herein may reduce the level of a product of the GCN2 catalyzed reaction or the level of a downstream derivative of the product or binding may reduce the interactions between the GCN2 or a reaction product and downstream effectors or signaling pathway components (e.g., MAP kinase pathway), resulting in changes in cell growth, proliferation, or survival.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicate a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant thereof, with an affinity that is at least two-fold greater, at least 10-times greater, at least 20-times greater, or at least 100-times greater than the affinity with any other antibody, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The terms "DNA," "nucleic acid," "nucleic acid molecule," "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced; for example, the change is generated in the laboratory by human intervention ("hand of man"). Therefore, non-naturally occurring variants and homologs may also refer to those that differ from the naturally occurring sequences by one or more conservative substitutions and/or tags and/or conjugates.

The term "HATU" refers to (1-[Bis(dimethylamino)methylene]-1H-1,2,3-triazolo[4,5-b]pyridinium 3-oxid hexafluorophosphate, which is a reagent used in peptide coupling chemistry to generate an active ester from a carboxylic acid.

The term "T3P" refers to n-propane phosphonic acid anhydride, a reagent used for amide bond formation.

The term TMSCHN2 refers to trimethylsilyldiazomethane, a reagent used as a methylating agent.

II. Compounds

In an aspect are provided compounds of formula (I):

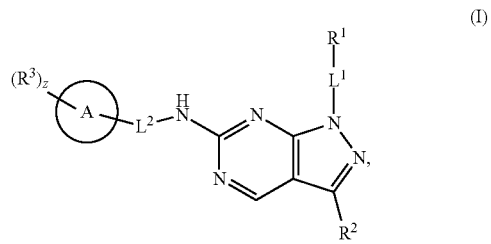

and pharmaceutically acceptable salts thereof.

z is an integer from 0 to 6; ring A is substituted or unsubstituted cycloalkyl, or substituted or unsubstituted heterocycloalkyl; $L^1$ and $L^2$ are independently a bond, substituted or unsubstituted alkylene, or substituted or unsubstituted heteroalkylene; $R^1$ is substituted or unsubstituted aryl or substituted or unsubstituted heteroaryl; $R^2$ is hydrogen, halogen, —$CX^2_3$, —$CHX^2_2$, —$CH_2X^2$, —$OCX^2_3$, —$OCHX^2_2$, —$OCH_2X^2$, —CN, —$S(O)_2R^{2A}$, —$SO_2NR^{2A}R^{2B}$, —$NHC(O)NR^{2A}R^{2B}$, —$N(O)_2$, —$NR^{2A}R^{2B}$, $NHNR^{2A}R^{2B}$, —$C(O)R^{2A}$, —$C(O)$—$OR^{2A}$, —$C(O)NR^{2A}R^{2B}$, —$C(O)NHNR^{2A}R^{2B}$, —$OR^{2A}$; —$NR^{2A}SO_2R^{2B}$, —$NR^{2A}C(O)R^{2B}$, —$NR^{2A}C(O)OR^{2B}$, —$NR^{2A}OR^{2B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is halogen, —$CX^3_3$, —$CHX^3_2$, —$CH_2X_3$, —$OCX^3_3$, —$OCHX^3_2$, —$OCH_2X_3$, —$OCH_2R^{3A}$, —CN, —$S(O)_2R^{3A}$, —$SO_2NR^{3A}R^{3B}$, —$NHC(O)NR^{3A}R^{3B}$, —$N(O)_2$, —$NR^{3A}R^{3B}$, $NHNR^{3A}R^{3B}$, —$C(O)R^{3A}$, —$C(O)$—$OR^{3A}$, —$C(O)NR^{3A}R^{3B}$, —$P(O)R^{3A}R^{3B}$, —$C(O)NHNR^{3A}R^{3B}$, —$OR^{3A}$, —$NR^{3A}SO_2R^{3B}$, —$NR^{3A}C(O)R^{3B}$, —$NR^{3A}C(O)OR^{3B}$, —$NR^{3A}OR^{3B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ may optionally be joined to form a substituted or unsubstituted heterocycloalkyl or substituted or unsubstituted heteroaryl; $R^{2A}$, $R^{2B}$, $R^{3A}$, and $R^{3B}$ are independently hydrogen, —$CX_3$, —$CHX_2$, —$CH_2X$, —C(O)OH, —C(O)NH_2, —CN, —OH, —NH_2, —COOH, —CONH_2, —NO_2, —SH, —SO_3H, —SO_4H, —SO_2NH_2, —NHNH_2, —ONH_2, —NHC=(O)NHNH_2, —NHC=(O)NH_2, —NHSO_2H, —NHC=(O)H, —NHC(O)OH, —NHOH, —OCX_3, —OCHX_2, —OCH_2X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ may optionally be joined to form a substituted or unsubstituted heterocycloalkyl or substituted or unsubstituted heteroaryl, $R^{3A}$ and $R^{3B}$ may optionally be joined to form a substituted or unsubstituted heterocycloalkyl or substituted or unsubstituted heteroaryl; and $X^2$ and $X^3$ are independently halogen; with the proviso that when ring A is cyclohexyl, then $R^3$ is not an ortho-substituted —$NH_2$ or —HNC=(O)t-BuO, or para-substituted —$NHSO_2CH_2CH_2CF_3$, —$NHSO_2CH_3$, or —OH.

Alternatively, and equivalently, rather than Z being an integer from 0 to 6, Z may be an integer from 1 to 6, in which case R³ may additionally be hydrogen. Thus, alternatively, Z is an integer from 1 to 6 and R³ is hydrogen, halogen, —CX³₃, —CHX³₂, —CH₂X₃, —OCX³₃, —OCHX³₂, —OCH₂X₃, —OCH₂R³ᴬ, —CN, —S(O)₂R³ᴬ, —SO₂NR³ᴬR³ᴮ, —NHC(O)NR³ᴬR³ᴮ, —N(O)₂, —NR³ᴬR³ᴮ, NHNR³ᴬR³ᴮ, —C(O)R³ᴬ, —C(O)—OR³ᴬ, —C(O)NR³ᴬR³ᴮ, —P(O)R³ᴬR³ᴮ, —C(O)NHNR³ᴬR³ᴮ, —OR³ᴬ, —NR³ᴬSO₂R³ᴮ, —NR³ᴬC(O)R³ᴮ, —NR³ᴬC(O)OR³ᴮ, —NR³ᴬOR³ᴮ, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two R³ may optionally be joined to form a substituted or unsubstituted heterocycloalkyl or substituted or unsubstituted heteroaryl.

In embodiments, provided are compounds of formula (I):

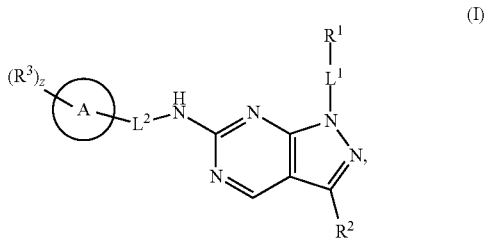

and pharmaceutically acceptable salts thereof.

z is an integer from 0 to 6; ring A is substituted or unsubstituted cycloalkyl, or substituted or unsubstituted heterocycloalkyl; L¹ and L² are independently a bond, substituted or unsubstituted alkylene, or substituted or unsubstituted heteroalkylene; R¹ is substituted or unsubstituted aryl or substituted or unsubstituted heteroaryl; R² is hydrogen, halogen, —CX²₃, —CHX²₂, —CH₂X², —OCX²₃, —OCHX²₂, —OCH₂X², —CN, —S(O)₂R²ᴬ, —SO₂NR²ᴬR²ᴮ, —NHC(O)NR²ᴬR²ᴮ, —N(O)₂, —NR²ᴬR²ᴮ, NHNR²ᴬR²ᴮ, —C(O)R²ᴬ, —C(O)—OR²ᴬ, —C(O)NR²ᴬR²ᴮ, —C(O)NHNR²ᴬR²ᴮ, —OR²ᴬ, —NR²ᴬSO₂R²ᴮ, —NR²ᴬC(O)R²ᴮ, —NR²ᴬC(O)OR²ᴮ, —NR²ᴬOR²ᴮ, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R³ is halogen, —CX³₃, —CHX³₂, —CH₂X₃, —OCX³₃, —OCHX³₂, —OCH₂X₃, —OCH₂R³ᴬ, —CN, —S(O)₂R³ᴬ, —SO₂NR³ᴬR³ᴮ, —NHC(O)NR³ᴬR³ᴮ, —N(O)₂, —NR³ᴬR³ᴮ, NHNR³ᴬR³ᴮ, —C(O)R³ᴬ, —C(O)—OR³ᴬ, —C(O)NR³ᴬR³ᴮ, —C(O)NHNR³ᴬR³ᴮ, —OR³ᴬ, —NR³ᴬSO₂R³ᴮ, —NR³ᴬC(O)R³ᴮ, —NR³ᴬC(O)OR³ᴮ, —NR³ᴬOR³ᴮ, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R²ᴬ, R²ᴮ, R³ᴬ, and R³ᴮ are independently hydrogen, —CX₃, —CHX₂, —CH₂X, —C(O)OH, —C(O)NH₂, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCX₃, —OCHX₂, —OCH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R²ᴬ and R²ᴮ may optionally be joined to form a substituted or unsubstituted heterocycloalkyl or substituted or unsubstituted heteroaryl, R³ᴬ and R³ᴮ may optionally be joined to form a substituted or unsubstituted heterocycloalkyl or substituted or unsubstituted heteroaryl; and X² and X³ are independently halogen; with the proviso that when ring A is cyclohexyl, then R³ is not an ortho-substituted —NH₂ or —HNC═(O)t-BuO, or para-substituted —NHSO₂CH₂CH₂CF₃, —NHSO₂CH₃, or —OH.

In embodiments, L¹ and L² is independently a bond, substituted or unsubstituted alkylene, or substituted or unsubstituted heteroalkylene.

In embodiments, L¹ is substituted (e.g., substituted with a substituent group, a size-limited substituent group, or lower substituent group) or unsubstituted alkylene (e.g., C₂-C₈, C₂-C₆, or C₂-C₄), or substituted (e.g., substituted with a substituent group, a size-limited substituent group, or lower substituent group) or unsubstituted heteroalkylene (e.g., 2 to 8 membered, 2 to 6 membered, or 2 to 4 membered).

In embodiments, L¹ is R²¹-substituted or unsubstituted alkylene (e.g., C₂-C₈, C₂-C₆, or C₂-C₄), or R²¹-substituted or unsubstituted heteroalkylene (e.g., 2 to 8 membered, 2 to 6 membered, or 2 to 4 membered).

R²¹ is hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, substituted (e.g., substituted with a substituent group, a size-limited substituent group, or lower substituent group) or unsubstituted alkyl (e.g., C₁-C₈, C₁-C₆, or C₁-C₄), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C₃-C₈, C₃-C₆, or C₅-C₆), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C₆-C₁₀, C₆, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R²¹ is hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, L$^1$ is a bond. In embodiments, L$^1$ is a substituted or unsubstituted alkylene. In embodiments, L$^1$ is a substituted or unsubstituted heteroalkylene. In embodiments, L$^1$ is (CH$_2$)$_n$, and n is an integer from 0 to 4. In embodiments, L$^1$ is methylene or ethylene.

In embodiments, L$^2$ is substituted (e.g., substituted with a substituent group, a size-limited substituent group, or lower substituent group) or unsubstituted alkylene (e.g., C$_2$-C$_8$, C$_2$-C$_6$, or C$_2$-C$_4$), or substituted (e.g., substituted with a substituent group, a size-limited substituent group, or lower substituent group) or unsubstituted heteroalkylene (e.g., 2 to 8 membered, 2 to 6 membered, or 2 to 4 membered).

In embodiments, L$^2$ is R$^{22}$-substituted or unsubstituted alkylene (e.g., C$_2$-C$_8$, C$_2$-C$_6$, or C$_2$-C$_4$), or R$^{22}$-substituted or unsubstituted heteroalkylene (e.g., 2 to 8 membered, 2 to 6 membered, or 2 to 4 membered).

R$^{22}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R$^{22}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, L$^2$ is a bond. In embodiments, L$^2$ is a substituted or unsubstituted alkylene. In embodiments, L$^2$ is a substituted or unsubstituted heteroalkylene. In embodiments, L$^2$ is (CH$_2$)$_n$, and n is an integer from 0 to 4. In embodiments, L$^2$ is methylene or ethylene.

In embodiments, ring A is substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), or substituted (e.g., substituted with a substituent group, a size-limited substituent group, or lower substituent group) or unsubstituted heterocycloalkyl (e.g., 3 to 8 membered, 3 to 6 membered, or 5 to 6 membered).

In embodiment, ring A is substituted (e.g., substituted with a substituent group, a size-limited substituent group, or lower substituent group) or unsubstituted C$_4$-C$_7$ cycloalkyl, or substituted (e.g., substituted with a substituent group, a size-limited substituent group, or lower substituent group) or unsubstituted 4- to 7-membered heterocycloalkyl.

In embodiments, ring A is R$^6$-substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), or substituted (e.g., substituted with a substituent group, a size-limited substituent group, or lower substituent group) or unsubstituted heterocycloalkyl (e.g., 3 to 8 membered, 3 to 6 membered, or 5 to 6 membered).

In embodiment, ring A is R$^6$-substituted (e.g., substituted with a substituent group, a size-limited substituent group, or lower substituent group) or unsubstituted C$_4$-C$_7$ cycloalkyl, or R$^6$-substituted (e.g., substituted with a substituent group, a size-limited substituent group, or lower substituent group) or unsubstituted 4- to 7-membered heterocycloalkyl.

In embodiments, when ring A is cyclohexyl, then R$^3$ is not an ortho —NH$_2$, ortho —HNC=(O)O(t-Bu), para —NHSO$_2$CH$_2$CH$_2$CF$_3$, para —NHSO$_2$CH$_3$, or para —OH.

R$^6$ is independently hydrogen, halogen, —CX$^6{}_3$, —CHX$^6{}_2$, —CH$_2$X$^6$, —OCX$^6{}_3$, —OCHX$^6{}_2$, —OCH$_2$X$^6$, —CN, —S(O)$_2$R$^{6A}$, —SR$^{6A}$, —S(O)R$^{6A}$, —SO$_2$NR$^{6A}$R$^{6B}$, —NHC(O)NR$^{6A}$R$^{6B}$, —N(O)$_2$, —NR$^{6A}$R$^B$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^6$ is hydrogen, halogen (e.g., —F, —Cl, Br, —I), —CX$^6{}_3$, —CHX$^6{}_2$, —CH$_2$X$^6$, —OCX$^6{}_3$, —OCHX$^6{}_2$, —OCH$_2$X$^6$, —CN, —S(O)$_2$R$^{6A}$, —SR$^{6A}$, —S(O)R$^{6A}$, —SO$_2$NR$^{6A}$R$^{6B}$, —NHC(O)NR$^{6A}$R$^{6B}$, —N(O)$_2$, —NR$^{6A}$R$^B$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^6$ is independently —F, —Cl, —Br, or —I.

In embodiments, R$^6$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R$^6$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, R$^6$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^8$-substituted or unsubstituted alkyl (e.g., C$_1$-C$_8$ alkyl, C$_1$-C$_6$ alkyl, or C$_1$-C$_4$ alkyl), R$^8$-substituted or unsubstituted heteroalkyl (e.g., 2 to 8 membered heteroalkyl, 2 to 6 membered heteroalkyl, or 2 to 4 membered heteroalkyl), Ra-substituted or unsubstituted cycloalkyl (e.g., C$_3$-C$_8$ cycloalkyl, C$_3$-C$_6$ cycloalkyl, or C$_5$-C$_6$ cycloalkyl), R$^8$-substituted or unsubstituted heterocycloalkyl (e.g., 3 to 8 membered heterocycloalkyl, 3 to 6 membered heterocycloalkyl, or 5 to 6 membered heterocycloalkyl), R$^8$-substituted or unsubstituted aryl (e.g., C$_6$-C$_{10}$ aryl, C$_{10}$ aryl, or phenyl), or R$^8$-substituted or unsubstituted heteroaryl (e.g., 5 to 10 membered heteroaryl, 5 to 9 membered heteroaryl, or 5 to 6 membered heteroaryl).

In embodiments, R$^6$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^6$ is R$^8$-substituted or unsubstituted alkyl (e.g., C$_1$-C$_8$ alkyl, C$_1$-C$_6$ alkyl, or C$_1$-C$_4$ alkyl). In embodiments, R$^6$ is R$^8$-substituted or unsubstituted heteroalkyl (e.g., 2 to 8 membered heteroalkyl, 2 to 6 membered heteroalkyl, or 2 to 4 membered heteroalkyl). In embodiments, R$^6$ is R$^8$-substituted or unsubstituted cycloalkyl (e.g., C$_3$-C$_8$ cycloalkyl, C$_3$-C$_6$ cycloalkyl, or C$_5$-C$_6$ cycloalkyl l). In embodiments, R$^6$ is R$^8$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^6$ is R$^8$-substituted or unsubstituted aryl (e.g., C$_6$-C$_{10}$ aryl, C$_{10}$ aryl, or phenyl). In embodiments, R$^6$ is R$^8$-substituted or unsubstituted heteroaryl (e.g., 5 to 10 membered heteroaryl, 5 to 9 membered heteroaryl, or 5 to 6 membered heteroaryl).

R$^8$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^9$-substituted or unsubstituted alkyl (e.g., C$_1$-C$_8$ alkyl, C$_1$-C$_6$ alkyl, or C$_1$-C$_4$ alkyl), R$^9$-substituted or unsubstituted heteroalkyl (e.g., 2 to 8 membered heteroalkyl, 2 to 6 membered heteroalkyl, or 2 to 4 membered heteroalkyl), R$^9$-substituted or unsubstituted cycloalkyl (e.g., C$_3$-C$_8$ cycloalkyl, C$_3$-C$_6$ cycloalkyl, or C$_5$-C$_6$ cycloalkyl), R$^9$-substituted or unsubstituted heterocycloalkyl (e.g., 3 to 8 membered heterocycloalkyl, 3 to 6 membered heterocycloalkyl, or 5 to 6 membered heterocycloalkyl), R$^9$-substituted or unsubstituted aryl (e.g., C$_6$-C$_{10}$ aryl, C$_{10}$ aryl, or phenyl), or R$^9$-substituted or unsubstituted heteroaryl (e.g., 5 to 10 membered heteroaryl, 5 to 9 membered heteroaryl, or 5 to 6 membered heteroaryl).

In embodiments, R$^8$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^8$ is R$^9$-substituted or unsubstituted alkyl (e.g., C$_1$-C$_8$ alkyl, C$_1$-C$_6$ alkyl, or C$_1$-C$_4$ alkyl). In embodiments, R$^8$ is R$^9$-substituted or unsubstituted heteroalkyl (e.g., 2 to 8 membered heteroalkyl, 2 to 6 membered heteroalkyl, or 2 to 4 membered heteroalkyl). In embodiments, R$^8$ is R$^9$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^8$ is R$^9$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^8$ is R$^9$-substituted or unsubstituted aryl (e.g., C$_6$-C$_{10}$ aryl, C$_{10}$ aryl, or phenyl). In embodiments, R$^8$ is R$^9$-substituted or unsubstituted heteroaryl (e.g., 5 to 10 membered heteroaryl, 5 to 9 membered heteroaryl, or 5 to 6 membered heteroaryl).

R$^9$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^9$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^9$ is independently unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{6A}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R$^{6A}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, R$^{6A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{8A}$-substituted or unsubstituted alkyl (e.g., C$_1$-C$_8$ alkyl, C$_1$-C$_6$ alkyl, or C$_1$-C$_4$ alkyl), R$^{8A}$-substituted or unsubstituted heteroalkyl (e.g., 2 to 8 membered heteroalkyl, 2 to 6 membered heteroalkyl, or 2 to 4 membered heteroalkyl), R$^{8A}$ substituted or unsubstituted cycloalkyl (e.g., C$_3$-C$_8$ cycloalkyl, C$_3$-C$_6$ cycloalkyl, or C$_5$-C$_6$ cycloalkyl), R$^{8A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{8A}$-substituted or unsubstituted aryl (e.g., C$_6$-C$_{10}$ aryl, C$_{10}$ aryl, or phenyl), or R$^{8A}$-substituted or unsubstituted heteroaryl (e.g., 5 to 10 membered heteroaryl, 5 to 9 membered heteroaryl, or 5 to 6 membered heteroaryl).

In embodiments, R$^{6A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{6A}$ is R$^{8A}$-substituted or unsubstituted alkyl (e.g., C$_1$-C$_8$ alkyl, C$_1$-C$_6$ alkyl, or C$_1$-C$_4$ alkyl). In embodiments, R$^{6A}$ is R$^{8A}$-substituted or unsubstituted heteroalkyl (e.g., 2 to 8 membered heteroalkyl, 2 to 6 membered heteroalkyl, or 2 to 4 membered heteroalkyl). In embodiments, R$^{6A}$ is R$^{8A}$-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, R$^{6A}$ is R$^{8A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6A}$ is R$^{8A}$-substituted or unsubstituted aryl (e.g., C$_6$-C$_{10}$ aryl, C$_{10}$ aryl, or phenyl). In embodiments, R$^{6A}$ is R$^{8A}$-substituted or unsubstituted heteroaryl (e.g., 5 to 10 membered heteroaryl, 5 to 9 membered heteroaryl, or 5 to 6 membered heteroaryl).

R$^{8A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{9A}$-substituted or unsubstituted alkyl (e.g., C$_1$-C$_8$ alkyl, C$_1$-C$_6$ alkyl, or C$_1$-C$_4$ alkyl), R$^{9A}$-substituted or unsubstituted heteroalkyl (e.g., 2 to 8 membered heteroalkyl, 2 to 6 membered heteroalkyl, or 2 to 4 membered heteroalkyl), R$^{9A}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{9A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{9A}$-substituted or unsubstituted aryl (e.g., C$_6$-C$_{10}$ aryl, C$_{10}$ aryl, or phenyl), or R$^{9A}$-substituted or unsubstituted heteroaryl (e.g., 5 to 10 membered heteroaryl, 5 to 9 membered heteroaryl, or 5 to 6 membered heteroaryl).

In embodiments, R$^{8A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{8A}$ is R$^{9A}$-substituted or unsubstituted alkyl (e.g., C$_1$-C$_8$ alkyl, C$_1$-C$_6$ alkyl, or C$_1$-C$_4$ alkyl). In embodiments, R$^{8A}$ is R$^{9A}$-substituted or unsubstituted heteroalkyl (e.g., 2 to 8 membered heteroalkyl, 2 to 6 membered heteroalkyl, or 2 to 4 membered heteroalkyl). In embodiments, R$^{8A}$ is R$^{9A}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{8A}$ is R$^{9A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{8A}$ is R$^{9A}$-substituted or unsubstituted aryl (e.g., C$_6$-C$_{10}$ aryl, C$_{10}$ aryl, or phenyl). In embodiments, R$^{8A}$ is R$^{9A}$-substituted or unsubstituted heteroaryl (e.g., 5 to 10 membered heteroaryl, 5 to 9 membered heteroaryl, or 5 to 6 membered heteroaryl).

R$^{9A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 17embered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), R unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{9A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{9A}$ is unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 17embered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), R unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{6B}$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)

$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^B$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{6B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{8B}$-substituted or unsubstituted alkyl (e.g., $C_1$-$C_8$ alkyl, $C_1$-$C_6$ alkyl, or $C_1$-$C_4$ alkyl), $R^{8B}$-substituted or unsubstituted heteroalkyl (e.g., 2 to 8 membered heteroalkyl, 2 to 6 membered heteroalkyl, or 2 to 4 membered heteroalkyl), $R^B$-substituted or unsubstituted cycloalkyl (e.g., $C_3$-$C_8$ cycloalkyl, $C_3$-$C_6$ cycloalkyl, or $C_5$-$C_6$ cycloalkyl), $R^{8B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{8B}$-substituted or unsubstituted aryl (e.g., $C_6$-$C_{10}$ aryl, $C_{10}$ aryl, or phenyl), or $R^{8B}$-substituted or unsubstituted heteroaryl (e.g., 5 to 10 membered heteroaryl, 5 to 9 membered heteroaryl, or 5 to 6 membered heteroaryl).

In embodiments, $R^{6B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{6B}$ is $R^8$-substituted or unsubstituted alkyl (e.g., $C_1$-$C_8$ alkyl, $C_1$-$C_6$ alkyl, or $C_1$-$C_4$ alkyl). In embodiments, $R^{6B}$ is $R^{8B}$-substituted or unsubstituted heteroalkyl (e.g., 2 to 8 membered heteroalkyl, 2 to 6 membered heteroalkyl, or 2 to 4 membered heteroalkyl). In embodiments, $R^{6B}$ is $R^{8B}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{6B}$ is $R^{6B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6B}$ is $R^{8B}$-substituted or unsubstituted aryl (e.g., $C_6$-$C_{10}$ aryl, $C_{10}$ aryl, or phenyl). In embodiments, $R^{6B}$ is $R^{8B}$-substituted or unsubstituted heteroaryl (e.g., 5 to 10 membered heteroaryl, 5 to 9 membered heteroaryl, or 5 to 6 membered heteroaryl).

$R^{8B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{9B}$-substituted or unsubstituted alkyl (e.g., $C_1$-$C_8$ alkyl, $C_1$-$C_6$ alkyl, or $C_1$-$C_4$ alkyl), $R^{9B}$-substituted or unsubstituted heteroalkyl (e.g., 2 to 8 membered heteroalkyl, 2 to 6 membered heteroalkyl, or 2 to 4 membered heteroalkyl), $R^{9B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{9B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{9B}$-substituted or unsubstituted aryl (e.g., $C_6$-$C_{10}$ aryl, $C_{10}$ aryl, or phenyl), or $R^{9B}$-substituted or unsubstituted heteroaryl (e.g., 5 to 10 membered heteroaryl, 5 to 9 membered heteroaryl, or 5 to 6 membered heteroaryl).

In embodiments, $R^{8B}$ is independently halogen, —$CF_3$, —$CCl_3$, —$CBr_3$, —$C_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{8B}$ is $R^{9B}$-substituted or unsubstituted alkyl (e.g., $C_1$-$C_8$ alkyl, $C_1$-$C_6$ alkyl, or $C_1$-$C_4$ alkyl). In embodiments, $R^{8B}$ is $R^{9B}$-substituted or unsubstituted heteroalkyl (e.g., 2 to 8 membered heteroalkyl, 2 to 6 membered heteroalkyl, or 2 to 4 membered heteroalkyl). In embodiments, $R^{8B}$ is $R^{9B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{8B}$ is $R^{9B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{8B}$ is $R^{9B}$-substituted or unsubstituted aryl (e.g., $C_6$-$C_{10}$ aryl, $C_{10}$ aryl, or phenyl). In embodiments, $R^{8B}$ is $R^9$-substituted or unsubstituted heteroaryl (e.g., 5 to 10 membered heteroaryl, 5 to 9 membered heteroaryl, or 5 to 6 membered heteroaryl).

$R^{9B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 7embered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), R unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{9B}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{9B}$ is unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 17embered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), R unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^1$ is substituted (e.g., substituted with a substituent group, a size-limited substituent group, or lower substituent group) or unsubstituted aryl (e.g., C$_6$-C$_{10}$ aryl, C$_{10}$ aryl, or phenyl), or substituted (e.g., substituted with a substituent group, a size-limited substituent group, or lower substituent group) or unsubstituted heteroaryl (e.g., 5 to 10 membered heteroaryl, 5 to 9 membered heteroaryl, or 5 to 6 membered heteroaryl).

In embodiments, R$^1$ is substituted or unsubstituted phenyl or substituted or unsubstituted quinolone.

In embodiments, R$^1$ is unsubstituted aryl (e.g., C$_6$-C$_{10}$ aryl, C$_{10}$ aryl, or phenyl) or unsubstituted heteroaryl (e.g., 5 to 10 membered heteroaryl, 5 to 9 membered heteroaryl, or 5 to 6 membered heteroaryl). In embodiments, R$^1$ is unsubstituted phenyl or unsubstituted quinolone.

In embodiment, R$^1$ is R$^7$-substituted (e.g., substituted with a substituent group, a size-limited substituent group, or lower substituent group) aryl (e.g., C6-C$_{10}$ aryl, C$_{10}$ aryl, or phenyl), or substituted (e.g., substituted with a substituent group, a size-limited substituent group, or lower substituent group) heteroaryl (e.g., 5 to 10 membered heteroaryl, 5 to 9 membered heteroaryl, or 5 to 6 membered heteroaryl).

R$^7$ is independently hydrogen, halogen, —CX$^7_3$, —CHX$^7_2$, —CH$_2$X$^7$, —OCX$^7_3$, —OCHX$^7_2$, —OCH$_2$X$^7$, —CN, —S(O)$_2$R, —SR$^{7A}$, —S(O)R$^{7A}$, —SO$_2$NR$^{7A}$R$^{7B}$, —NHC(O)NR$^{7A}$R$^{7B}$, —N(O)$_2$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^7$ is hydrogen, halogen (e.g., —F, —Cl, Br, —I), —CX$^7_3$, —CHX$^7_2$, —CH$_2$X$^7$, —OCX$^7_3$, —OCHX$^7_2$, —OCH$_2$X7, —CN, —S(O)$_2$R$^{7A}$, —SR$^{7A}$, —S(O)R$^{7A}$, —SO$_2$NR$^{7A}$R$^{7B}$, —NHC(O)NR$^{7A}$R$^{7B}$, —N(O)$_2$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$—N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^6$ is independently —F, —Cl, —Br, or —I.

In embodiments, R$^7$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^7$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^7$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{10}$-substituted or unsubstituted alkyl (e.g., $C_1$-$C_8$ alkyl, $C_1$-$C_6$ alkyl, or $C_1$-$C_4$ alkyl), $R^{10}$-substituted or unsubstituted heteroalkyl (e.g., 2 to 8 membered heteroalkyl, 2 to 6 membered heteroalkyl, or 2 to 4 membered heteroalkyl), $R^{10}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{10}$-substituted or unsubstituted heterocycloalkyl (e.g., 3 to 8 membered heterocycloalkyl, 3 to 6 membered heterocycloalkyl, or 5 to 6 membered heterocycloalkyl), $R^{10}$-substituted or unsubstituted aryl (e.g., $C_6$-$C_{10}$ aryl, $C_{10}$ aryl, or phenyl), or $R^{10}$-substituted or unsubstituted heteroaryl (e.g., 5 to 10 membered heteroaryl, 5 to 9 membered heteroaryl, or 5 to 6 membered heteroaryl).

In embodiments, $R^7$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^7$ is $R^{10}$-substituted or unsubstituted alkyl (e.g., $C_1$-$C_8$ alkyl, $C_1$-$C_6$ alkyl, or $C_1$-$C_4$ alkyl). In embodiments, $R^7$ is $R^{10}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{10}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^7$ is R-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{10}$-substituted or unsubstituted aryl (e.g., $C_6$-$C_{10}$ aryl, $C_{10}$ aryl, or phenyl). In embodiments, $R^7$ is $R^{10}$-substituted or unsubstituted heteroaryl (e.g., 5 to 10 membered heteroaryl, 5 to 9 membered heteroaryl, or 5 to 6 membered heteroaryl).

$R^{10}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{11}$-substituted or unsubstituted alkyl (e.g., $C_1$-$C_8$ alkyl, $C_1$-$C_6$ alkyl, or $C_1$-$C_4$ alkyl), $R^{11}$-substituted or unsubstituted heteroalkyl (e.g., 2 to 8 membered heteroalkyl, 2 to 6 membered heteroalkyl, or 2 to 4 membered heteroalkyl), $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11}$-substituted or unsubstituted aryl (e.g., $C_6$-$C_{10}$ aryl, $C_{10}$ aryl, or phenyl), or $R^{11}$-substituted or unsubstituted heteroaryl (e.g., 5 to 10 membered heteroaryl, 5 to 9 membered heteroaryl, or 5 to 6 membered heteroaryl).

In embodiments, $R^{10}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{10}$ is $R^{11}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R^{11}$-substituted or unsubstituted heteroalkyl (e.g., 2 to 8 membered heteroalkyl, 2 to 6 membered heteroalkyl, or 2 to 4 membered heteroalkyl). In embodiments, $R^{10}$ is $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{11}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{11}$-substituted or unsubstituted aryl (e.g., $C_6$-$C_{10}$ aryl, $C_{10}$ aryl, or phenyl). In embodiments, $R^{10}$ is $R^{11}$-substituted or unsubstituted heteroaryl (e.g., 5 to 10 membered heteroaryl, 5 to 9 membered heteroaryl, or 5 to 6 membered heteroaryl).

$R^{11}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{11}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{11}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^7$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{7A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{7A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{10A}$-substituted or unsubstituted alkyl (e.g., $C_1$-$C_8$ alkyl, $C_1$-$C_6$ alkyl, or $C_1$-$C_4$ alkyl), $R^{10}$-substituted or unsubstituted heteroalkyl (e.g., 2 to 8 membered heteroalkyl, 2 to 6 membered heteroalkyl, or 2 to 4 membered heteroalkyl), $R^{10A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{10A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{10A}$-substituted or unsubstituted aryl (e.g., $C_6$-$C_{10}$ aryl, $C_{10}$ aryl, or phenyl), or $R^{10A}$-substituted or unsubstituted heteroaryl (e.g., 5 to 10 membered heteroaryl, 5 to 9 membered heteroaryl, or 5 to 6 membered heteroaryl).

In embodiments, $R^{7A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{7A}$ is $R^{10A}$-substituted or unsubstituted alkyl (e.g., $C_1$-$C_8$ alkyl, $C_1$-$C_6$ alkyl, or $C_1$-$C_4$ alkyl). In embodiments, $R^{7A}$ is $R^{10A}$-substituted or unsubstituted heteroalkyl (e.g., 2 to 8 membered heteroalkyl, 2 to 6 membered heteroalkyl, or 2 to 4 membered heteroalkyl). In embodiments, $R^{7A}$ is $R^{10A}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{7A}$ is $R^{10A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{7A}$ is $R^{10A}$-substituted or unsubstituted aryl (e.g., $C_6$-$C_{10}$ aryl, $C_{10}$ aryl, or phenyl). In embodiments, $R^{7A}$ is $R^{7A}$-substituted or unsubstituted heteroaryl (e.g., 5 to 10 membered heteroaryl, 5 to 9 membered heteroaryl, or 5 to 6 membered heteroaryl).

$R^{10A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{11A}$-substituted or unsubstituted alkyl (e.g., $C_1$-$C_8$ alkyl, $C_1$-$C_6$ alkyl, or $C_1$-$C_4$ alkyl), $R^{11A}$-substituted or unsubstituted heteroalkyl (e.g., 2 to 8 membered heteroalkyl, 2 to 6 membered heteroalkyl, or 2 to 4 membered heteroalkyl), $R^{11A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{1A}$-substituted or unsubstituted aryl (e.g., $C_6$-$C_{10}$ aryl, $C_{10}$ aryl, or phenyl), or $R^{11A}$-substituted or unsubstituted heteroaryl (e.g., 5 to 10 membered heteroaryl, 5 to 9 membered heteroaryl, or 5 to 6 membered heteroaryl).

In embodiments, $R^{10A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{10A}$ is $R^{1A}$-substituted or unsubstituted alkyl (e.g., $C_1$-$C_8$ alkyl, $C_1$-$C_6$ alkyl, or $C_1$-$C_4$ alkyl). In embodiments, $R^{10A}$ is $R^{11A}$-substituted or unsubstituted heteroalkyl (e.g., 2 to 8 membered heteroalkyl, 2 to 6 membered heteroalkyl, or 2 to 4 membered heteroalkyl). In embodiments, $R^{10A}$ is $R^{11A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10A}$ is $R^{11A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10A}$ is $R^{11A}$-substituted or unsubstituted aryl (e.g., $C_6$-$C_{10}$ aryl, $C_{10}$ aryl, or phenyl). In embodiments, $R^{10A}$ is $R^{11A}$-substituted or unsubstituted heteroaryl (e.g., 5 to 10 membered heteroaryl, 5 to 9 membered heteroaryl, or 5 to 6 membered heteroaryl).

$R^{11A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 7embered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), R unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{11A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{11A}$ is unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 17embered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), R unsubstituted heterocycloalkyl (e.g., 3 to 8 membered heterocycloalkyl, 3 to 6 membered hetero-cycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{7B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{7B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{7B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{10B}$-substituted or unsubstituted alkyl (e.g., $C_1$-$C_8$ alkyl, $C_1$-$C_6$ alkyl, or $C_1$-$C_4$ alkyl), $R^{10B}$-substituted or unsubstituted heteroalkyl (e.g., 2 to 8 membered heteroalkyl, 2 to 6 membered heteroalkyl, or 2 to 4 membered heteroalkyl), $R^{10B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{10B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{10B}$-substituted or unsubstituted aryl (e.g., $C_6$-$C_{10}$ aryl, $C_{10}$ aryl, or phenyl), or $R^{10B}$-substituted or unsubstituted heteroaryl (e.g., 5 to 10 membered heteroaryl, 5 to 9 membered heteroaryl, or 5 to 6 membered heteroaryl).

In embodiments, $R^{7B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{7B}$ is $R^{10B}$-substituted or unsubstituted alkyl (e.g., $C_1$-$C_8$ alkyl, $C_1$-$C_6$ alkyl, or $C_1$-$C_4$ alkyl). In embodiments, $R^{7B}$ is $R^{10B}$-substituted or unsubstituted heteroalkyl (e.g., 2 to 8 membered heteroalkyl, 2 to 6 membered heteroalkyl, or 2 to 4 membered heteroalkyl). In embodiments, $R^{7B}$ is $R^{10B}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{7B}$ is $R^{10B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{7B}$ is $R^{10B}$-substituted or unsubstituted aryl (e.g., $C_6$-$C_{10}$ aryl, $C_{10}$ aryl, or phenyl). In embodiments, $R^{7B}$ is $R^{10B}$-substituted or unsubstituted heteroaryl (e.g., 5 to 10 membered heteroaryl, 5 to 9 membered heteroaryl, or 5 to 6 membered heteroaryl).

$R^{10B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{11B}$-substituted or unsubstituted alkyl (e.g., $C_1$-$C_8$ alkyl, $C_1$-$C_6$ alkyl, or $C_1$-$C_4$ alkyl), $R^B$-substituted or unsubstituted heteroalkyl (e.g., 2 to 8 membered heteroalkyl, 2 to 6 membered heteroalkyl, or 2 to 4 membered heteroalkyl), RIB-substituted or unsubstituted cycloalkyl (e.g., $C_3$-$C_8$ cycloalkyl, $C_3$-$C_6$ cycloalkyl, or $C_5$-$C_6$ cycloalkyl), $R^{11B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11B}$-substituted or unsubstituted aryl (e.g., $C_6$-$C_{10}$ aryl, $C_{10}$ aryl, or phenyl), or $R^{11B}$-substituted or unsubstituted heteroaryl (e.g., 5 to 10 membered heteroaryl, 5 to 9 membered heteroaryl, or 5 to 6 membered heteroaryl).

In embodiments, $R^{10B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{10B}$ is $R^{11B}$-substituted or unsubstituted alkyl (e.g., $C_1$-$C_8$ alkyl, $C_1$-$C_6$ alkyl, or $C_1$-$C_4$ alkyl). In embodiments, $R^{10B}$ is $R^{11B}$-substituted or unsubstituted heteroalkyl (e.g., 2 to 8 membered heteroalkyl, 2 to 6 membered heteroalkyl, or 2 to 4 membered heteroalkyl). In embodiments, $R^{10B}$ is $R^{11B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10B}$ is $R^{11B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10B}$ is $R^{11B}$-substituted or unsubstituted aryl (e.g., $C_6$-$C_{10}$ aryl, $C_{10}$ aryl, or phenyl). In embodiments, $R^{10B}$ is $R^{11B}$-substituted or unsubstituted heteroaryl (e.g., 5 to 10 membered heteroaryl, 5 to 9 membered heteroaryl, or 5 to 6 membered heteroaryl).

$R^{11B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{11B}$ is unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 17embered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), R unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^2$ is independently hydrogen, halogen, —$CX^2_3$, —$CHX^2_2$, —$CH_2X^2$, —$OCX^2_3$, —$OCHX^2_2$, —$OCH_2X^2$, —CN, —$S(O)_n R^{2A}$, —$SR^{2A}$, —$S(O)R^{2A}$, —$SO_2NR^{2A}R^{2B}$, —NHC(O)$NR^{2A}R^{2B}$, —$N(O)_2$, —$NR^{2A}R^{2B}$, —$NHNR^{2A}R^{2B}$, —$C(O)R^{2A}$, —C(O)—$OR^{2A}$, —C(O)$NR^{2A}R^{2B}$, —C(O)NHNR^{2A}R^{2B}$, —$OR^{2A}$, —$NR^{2A}SO_2R^{2B}$, —$NR^{2A}C(O)R^{2B}$, —$NR^{2A}C(O)OR^{2B}$, —$NR^{2A}OR^{2B}$, —$N_3$, (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^2$ is halogen or substituted or unsubstituted alkyl. In embodiments, $R^2$ is halogen. In embodiments, $R^2$ is Cl or Br. In embodiments, $R^2$ is substituted or unsubstituted $C_1$-$C_2$ alkyl. In embodiments, $R^2$ is methyl.

In embodiments, $R^{2A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{2A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{2B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{2B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{2A}$ and $R^{2B}$ may optionally be joined to form a substituted or unsubstituted heterocycloalkyl or substituted or unsubstituted heteroaryl.

In embodiments, $R^{2A}$ and $R^{2B}$ may optionally be joined to form a substituted (e.g., substituted with a substituent group, a size-limited substituent group, or lower substituent group) or unsubstituted heterocycloalkyl (e.g., 3 to 8 membered, 3 to 6 membered, or 5 to 6 membered) or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^3$ is independently halogen, —$CX^3{}_3$, —$CHX^3{}_2$, —$CH_2X^3$, —$OCX^3{}_3$, —$OCHX^3{}_2$, —$OCH_2X^3$, —CN, —S(O)$_2R^{3A}$, —$SR^{3A}$, —S(O)$R^{3A}$, —$SO_2NR^{3A}R^{3B}$, —NHC(O)NR$^{3A}$R$^{3B}$, —N(O)$_2$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —C(O)NHNR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^3$ is halogen (e.g., —F, —Cl, Br, —I), —CX$^3{}_3$, —CHX$^3{}_2$, —CH$_2$X$_3$, —OCX$^3{}_3$, —OCHX$^3{}_2$, —OCH$_2$X$^3$, —CN, —S(O)$_2$R$^{3A}$, —SR$^{3A}$, —S(O)R$^{3A}$, —SO$_2$NR$^{3A}$R$^{3B}$, —NHC(O)NR$^{3A}$R$^{3B}$, —N(O)$_2$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —C(O)NHNR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^1$ is independently —F, —Cl, —Br, or —I.

In embodiments, R$^3$ is —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, R$^3$ is —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, R$^3$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{12}$-substituted or unsubstituted alkyl (e.g., C$_1$-C$_8$ alkyl, C$_1$-C$_6$ alkyl, or C$_1$-C$_4$ alkyl), R$^{12}$-substituted or unsubstituted heteroalkyl (e.g., 2 to 8 membered heteroalkyl, 2 to 6 membered heteroalkyl, or 2 to 4 membered heteroalkyl), R$^{12}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{12}$-substituted or unsubstituted heterocycloalkyl (e.g., 3 to 8 membered heterocycloalkyl, 3 to 6 membered heterocycloalkyl, or 5 to 6 membered heterocycloalkyl), R$^{12}$-substituted or unsubstituted aryl (e.g., C6-C$_{10}$ aryl, C$_{10}$ aryl, or phenyl), or R$^{12}$-substituted or unsubstituted heteroaryl (e.g., 5 to 10 membered heteroaryl, 5 to 9 membered heteroaryl, or 5 to 6 membered heteroaryl).

In embodiments, R$^3$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^3$ is R$^{12}$-substituted or unsubstituted alkyl (e.g., C$_1$-C$_8$ alkyl, C$_1$-C$_6$ alkyl, or C$_1$-C$_4$ alkyl). In embodiments, R$^3$ is R$^{12}$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^3$ is $R^{12}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{12}$-substituted or unsubstituted aryl (e.g., $C_6$-$C_{10}$ aryl, $C_{10}$ aryl, or phenyl). In embodiments, $R^3$ is $R^{12}$-substituted or unsubstituted heteroaryl (e.g., 5 to 10 membered heteroaryl, 5 to 9 membered heteroaryl, or 5 to 6 membered heteroaryl).

$R^{12}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{13}$-substituted or unsubstituted alkyl (e.g., $C_1$-$C_8$ alkyl, $C_1$-$C_6$ alkyl, or $C_1$-$C_4$ alkyl), $R^{13}$-substituted or unsubstituted heteroalkyl (e.g., 2 to 8 membered heteroalkyl, 2 to 6 membered heteroalkyl, or 2 to 4 membered heteroalkyl), $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{13}$-substituted or unsubstituted heterocycloalkyl (e.g., 3 to 8 membered heterocycloalkyl, 3 to 6 membered heterocycloalkyl, or 5 to 6 membered heterocycloalkyl), $R^{13}$-substituted or unsubstituted aryl (e.g., $C_6$-$C_{10}$ aryl, $C_{10}$ aryl, or phenyl), or $R^{13}$-substituted or unsubstituted heteroaryl (e.g., 5 to 10 membered heteroaryl, 5 to 9 membered heteroaryl, or 5 to 6 membered heteroaryl).

In embodiments, $R^{12}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{12}$ is $R^{13}$-substituted or unsubstituted alkyl (e.g., $C_1$-$C_8$ alkyl, $C_1$-$C_6$ alkyl, or $C_1$-$C_4$ alkyl). In embodiments, $R^{12}$ is $R^{13}$-substituted or unsubstituted heteroalkyl (e.g., 2 to 8 membered heteroalkyl, 2 to 6 membered heteroalkyl, or 2 to 4 membered heteroalkyl). In embodiments, $R^{12}$ is $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{12}$ is $R^{13}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{12}$ is $R^{13}$-substituted or unsubstituted aryl (e.g., $C_6$-$C_{10}$ aryl, $C_{10}$ aryl, or phenyl). In embodiments, $R^{12}$ is $R^{13}$-substituted or unsubstituted heteroaryl (e.g., 5 to 10 membered heteroaryl, 5 to 9 membered heteroaryl, or 5 to 6 membered heteroaryl).

$R^{13}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{14}$-substituted or unsubstituted alkyl (e.g., $C_1$-$C_8$ alkyl, $C_1$-$C_6$ alkyl, or $C_1$-$C_4$ alkyl), $R^{14}$-substituted or unsubstituted heteroalkyl (e.g., 2 to 8 membered heteroalkyl, 2 to 6 membered heteroalkyl, or 2 to 4 membered heteroalkyl), $R^{14}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14}$-substituted or unsubstituted aryl (e.g., $C_6$-$C_{10}$ aryl, $C_{10}$ aryl, or phenyl), or $R^{14}$-substituted or unsubstituted heteroaryl (e.g., 5 to 10 membered heteroaryl, 5 to 9 membered heteroaryl, or 5 to 6 membered heteroaryl).

In embodiments, $R^{13}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{13}$ is $R^{14}$-substituted or unsubstituted alkyl (e.g., $C_1$-$C_8$ alkyl, $C_1$-$C_6$ alkyl, or $C_1$-$C_4$ alkyl). In embodiments, $R^{13}$ is $R^{14}$-substituted or unsubstituted heteroalkyl (e.g., 2 to 8 membered heteroalkyl, 2 to 6 membered heteroalkyl, or 2 to 4 membered heteroalkyl). In embodiments, $R^{13}$ is $R^{14}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is $R^{14}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{13}$ is $R^{14}$-substituted or unsubstituted aryl (e.g., $C_6$-$C_{10}$ aryl, $C_{10}$ aryl, or phenyl). In embodiments, $R^{13}$ is $R^{14}$-substituted or unsubstituted heteroaryl (e.g., 5 to 10 membered heteroaryl, 5 to 9 membered heteroaryl, or 5 to 6 membered heteroaryl).

$R^{14}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{14}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{14}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{3A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$C_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{3A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{12A}$-substituted or unsubstituted alkyl (e.g., $C_1$-$C_8$ alkyl, $C_1$-$C_6$ alkyl, or $C_1$-$C_4$ alkyl), $R^{12A}$-substituted or unsubstituted heteroalkyl (e.g., 2 to 8 membered heteroalkyl, 2 to 6 membered heteroalkyl, or 2 to 4 membered heteroalkyl), $R^{12A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12A}$-substituted or unsubstituted aryl (e.g., $C_6$-$C_{10}$ aryl, $C_{10}$ aryl, or phenyl), or $R^{12A}$-substituted or unsubstituted heteroaryl (e.g., 5 to 10 membered heteroaryl, 5 to 9 membered heteroaryl, or 5 to 6 membered heteroaryl).

In embodiments, $R^{3A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{3A}$ is $R^{12A}$-substituted or unsubstituted alkyl (e.g., $C_1$-$C_8$ alkyl, $C_1$-$C_6$ alkyl, or $C_1$-$C_4$ alkyl). In embodiments, $R^{3A}$ is $R^{12A}$-substituted or unsubstituted heteroalkyl (e.g., 2 to 8 membered heteroalkyl, 2 to 6 membered heteroalkyl, or 2 to 4 membered heteroalkyl). In embodiments, $R^{3A}$ is $R^{12A}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{3A}$ is $R^{12A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is $R^{2A}$-substituted or unsubstituted aryl (e.g., $C_6$-$C_{10}$ aryl, $C_{10}$ aryl, or phenyl). In embodiments, $R^{3A}$ is $R^{12A}$-substituted or unsubstituted heteroaryl (e.g., 5 to 10 membered heteroaryl, 5 to 9 membered heteroaryl, or 5 to 6 membered heteroaryl).

$R^{12A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{13A}$-substituted or unsubstituted alkyl (e.g., $C_1$-$C_8$ alkyl, $C_1$-$C_6$ alkyl, or $C_1$-$C_4$ alkyl), $R^{13A}$-substituted or unsubstituted heteroalkyl (e.g., 2 to 8 membered heteroalkyl, 2 to 6 membered heteroalkyl, or 2 to 4 membered heteroalkyl), $R^{13A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{13A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{13A}$-substituted or unsubstituted aryl (e.g., $C_6$-$C_{10}$ aryl, $C_{10}$ aryl, or phenyl), or $R^{13A}$-substituted or unsubstituted heteroaryl (e.g., 5 to 10 membered heteroaryl, 5 to 9 membered heteroaryl, or 5 to 6 membered heteroaryl).

In embodiments, $R^{12A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, or —$OCH_2I$.

In embodiments, $R^{12A}$ is $R^{13A}$-substituted or unsubstituted alkyl (e.g., $C_1$-$C_8$ alkyl, $C_1$-$C_6$ alkyl, or $C_1$-$C_4$ alkyl). In embodiments, $R^{12A}$ is $R^{13A}$-substituted or unsubstituted heteroalkyl (e.g., 2 to 8 membered heteroalkyl, 2 to 6 membered heteroalkyl, or 2 to 4 membered heteroalkyl). In embodiments, $R^{12A}$ is $R^{13A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{12A}$ is $R^{13A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{12A}$ is $R^{13A}$-substituted or unsubstituted aryl (e.g., $C_6$-$C_{10}$ aryl, $C_{10}$ aryl, or phenyl). In embodiments, $R^{12A}$ is $R^{13A}$-substituted or unsubstituted heteroaryl (e.g., 5 to 10 membered heteroaryl, 5 to 9 membered heteroaryl, or 5 to 6 membered heteroaryl).

$R^{13A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{14A}$-substituted or unsubstituted alkyl (e.g., $C_1$-$C_8$ alkyl, $C_1$-$C_6$ alkyl, or $C_1$-$C_4$ alkyl), $R^{14A}$-substituted or unsubstituted heteroalkyl (e.g., 2 to 8 membered heteroalkyl, 2 to 6 membered heteroalkyl, or 2 to 4 membered heteroalkyl), $R^{14A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14A}$-substituted or unsubstituted aryl (e.g., $C_6$-$C_{10}$ aryl, $C_{10}$ aryl, or phenyl), or $R^{14A}$-substituted or unsubstituted heteroaryl (e.g., 5 to 10 membered heteroaryl, 5 to 9 membered heteroaryl, or 5 to 6 membered heteroaryl).

In embodiments, $R^{13A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{13A}$ is $R^{14A}$-substituted or unsubstituted alkyl (e.g., $C_1$-$C_8$ alkyl, $C_1$-$C_6$ alkyl, or $C_1$-$C_4$ alkyl). In embodiments, $R^{13A}$ is $R^{14A}$-substituted or unsubstituted heteroalkyl (e.g., 2 to 8 membered heteroalkyl, 2 to 6 membered heteroalkyl, or 2 to 4 membered heteroalkyl). In embodiments, $R^{13A}$ is $R^{14A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{13A}$ is $R^{14A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{13A}$ is $R^{14A}$-substituted or unsubstituted aryl (e.g., $C_6$-$C_{10}$ aryl, $C_{10}$ aryl, or phenyl). In embodiments, $R^{13A}$ is $R^{14A}$-substituted or unsubstituted heteroaryl (e.g., 5 to 10 membered heteroaryl, 5 to 9 membered heteroaryl, or 5 to 6 membered heteroaryl).

$R^{14A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{14A}$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{14A}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{3B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3B}$ is hydrogen, —F, —Cl, Br, —I, —$CF_3$, —$CHF_2$, —$CH_2F$, —$CCl_3$, —$CHCl_2$, —$CH_2Cl$, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_1$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, R$^{3B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{12B}$-substituted or unsubstituted alkyl (e.g., C$_1$-C$_8$ alkyl, C$_1$-C$_6$ alkyl, or C$_1$-C$_4$ alkyl), R$^{12B}$-substituted or unsubstituted heteroalkyl (e.g., 2 to 8 membered heteroalkyl, 2 to 6 membered heteroalkyl, or 2 to 4 membered heteroalkyl), R$^{12B}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{12B}$-substituted or unsubstituted heterocycloalkyl (e.g., 3 to 8 membered heterocycloalkyl, 3 to 6 membered heterocycloalkyl, or 5 to 6 membered heterocycloalkyl), R$^{12B}$-substituted or unsubstituted aryl (e.g., C$_6$-C$_{10}$ aryl, C$_{10}$ aryl, or phenyl), or R$^{12B}$-substituted or unsubstituted heteroaryl (e.g., 5 to 10 membered heteroaryl, 5 to 9 membered heteroaryl, or 5 to 6 membered heteroaryl).

In embodiments, R$^{3B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, or —OCH$_2$I.

In embodiments, R$^{3B}$ is R$^{12B}$-substituted or unsubstituted alkyl (e.g., C$_1$-C$_8$ alkyl, C$_1$-C$_6$ alkyl, or C$_1$-C$_4$ alkyl). In embodiments, R$^{3B}$ is R$^{12B}$-substituted or unsubstituted heteroalkyl (e.g., 2 to 8 membered heteroalkyl, 2 to 6 membered heteroalkyl, or 2 to 4 membered heteroalkyl). In embodiments, R$^{3B}$ is R$^{12B}$-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, R$^{3B}$ is R$^{12B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{3B}$ is R$^{12B}$-substituted or unsubstituted aryl (e.g., C$_6$-C$_{10}$ aryl, C$_{10}$ aryl, or phenyl). In embodiments, R$^{3B}$ is R$^{2B}$-substituted or unsubstituted heteroaryl (e.g., 5 to 10 membered heteroaryl, 5 to 9 membered heteroaryl, or 5 to 6 membered heteroaryl).

R$^{12B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{13B}$-substituted or unsubstituted alkyl (e.g., C$_1$-C$_8$ alkyl, C$_1$-C$_6$ alkyl, or C$_1$-C$_4$ alkyl), R$^{13B}$-substituted or unsubstituted heteroalkyl (e.g., 2 to 8 membered heteroalkyl, 2 to 6 membered heteroalkyl, or 2 to 4 membered heteroalkyl), R$^{13B}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{13B}$-substituted or unsubstituted heterocycloalkyl (e.g., 3 to 8 membered heterocycloalkyl, 3 to 6 membered heterocycloalkyl, or 5 to 6 membered heterocycloalkyl), R$^{13B}$-substituted or unsubstituted aryl (e.g., C$_6$-C$_{10}$ aryl, C$_{10}$ aryl, or phenyl), or R$^{13B}$-substituted or unsubstituted heteroaryl (e.g., 5 to 10 membered heteroaryl, 5 to 9 membered heteroaryl, or 5 to 6 membered heteroaryl).

In embodiments, R$^{12B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{12B}$ is R$^{13B}$-substituted or unsubstituted alkyl (e.g., C$_1$-C$_8$ alkyl, C$_1$-C$_6$ alkyl, or C$_1$-C$_4$ alkyl). In embodiments, R$^{12B}$ is R$^{3B}$-substituted or unsubstituted heteroalkyl (e.g., 2 to 8 membered heteroalkyl, 2 to 6 membered heteroalkyl, or 2 to 4 membered heteroalkyl). In embodiments, R$^{12B}$ is R$^{13B}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{12B}$ is R$^{13B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{12B}$ is R$^{13B}$-substituted or unsubstituted aryl (e.g., C$_6$-C$_{10}$ aryl, C$_{10}$ aryl, or phenyl). In embodiments, R$^{12B}$ is R$^{13B}$-substituted or unsubstituted heteroaryl (e.g., 5 to 10 membered heteroaryl, 5 to 9 membered heteroaryl, or 5 to 6 membered heteroaryl).

R$^{13B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{14B}$-substituted or unsubstituted alkyl (e.g., C$_1$-C$_8$ alkyl, C$_1$-C$_6$ alkyl, or C$_1$-C$_4$ alkyl), R$^{14B}$-substituted or unsubstituted heteroalkyl (e.g., 2 to 8 membered heteroalkyl, 2 to 6 membered heteroalkyl, or 2 to 4 membered heteroalkyl), R$^{14B}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{14B}$-substituted or unsubstituted heterocycloalkyl (e.g., 3 to 8 membered heterocycloalkyl, 3 to 6 membered heterocycloalkyl, or 5 to 6 membered heterocycloalkyl), R$^{14B}$-substituted or unsubstituted aryl (e.g., C$_6$-C$_{10}$ aryl, C$_{10}$ aryl, or phenyl), or R$^{14B}$-substituted or unsubstituted heteroaryl (e.g., 5 to 10 membered heteroaryl, 5 to 9 membered heteroaryl, or 5 to 6 membered heteroaryl).

In embodiments, R$^{13B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)

—NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, $R^{13B}$ is $R^{14B}$-substituted or unsubstituted alkyl (e.g., C$_1$-C$_8$ alkyl, C$_1$-C$_6$ alkyl, or C$_1$-C$_4$ alkyl). In embodiments, $R^{3B}$ is $R^{14B}$-substituted or unsubstituted heteroalkyl (e.g., 2 to 8 membered heteroalkyl, 2 to 6 membered heteroalkyl, or 2 to 4 membered heteroalkyl). In embodiments, $R^{13B}$ is $R^{14B}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{3B}$ is $R^{14B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{13B}$ is $R^{14B}$-substituted or unsubstituted aryl (e.g., C6-C$_{10}$ aryl, C$_{10}$ aryl, or phenyl). In embodiments, $R^{3B}$ is $R^{14B}$-substituted or unsubstituted heteroaryl (e.g., 5 to 10 membered heteroaryl, 5 to 9 membered heteroaryl, or 5 to 6 membered heteroaryl).

$R^{14B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{14B}$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O) NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCH$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, $R^{14B}$ is independently unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{3A}$ and $R^{3B}$ may optionally be joined to form a substituted or unsubstituted heterocycloalkyl or substituted or unsubstituted heteroaryl.

In embodiments, $R^{3A}$ and $R^{3B}$ may optionally be joined to form a substituted (e.g., substituted with a substituent group, a size-limited substituent group, or lower substituent group) or unsubstituted heterocycloalkyl (e.g., 3 to 8 membered, 3 to 6 membered, or 5 to 6 membered) or substituted (e.g., substituted with a substituent group, a size-limited substituent group, or lower substituent group) or unsubstituted heteroaryl (e.g., 5 to 10 membered, 5 to 9 membered, or 5 to 6 membered).

In certain embodiments, the compounds are compounds of Formula (II):

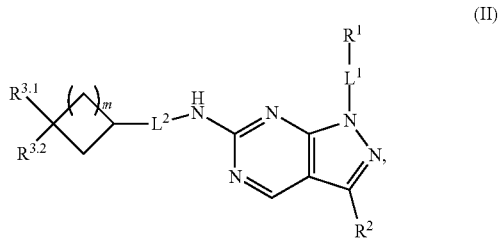

(II)

or a pharmaceutically acceptable salt thereof, wherein L$^1$, L$^2$, R$^1$, and R$^2$ are as defined above, including embodiments thereof, and wherein m is an integer from 1 to 4. In other embodiments, m is 2.

$R^{3.1}$ is independently hydrogen, halogen, —CX$^{3.1}_3$, —CHX$^{3.1}_2$, —CH$_2$X$_{3.1}$, —OCX$^{3.3}$, —OCHX$^{3.1}_2$, —OCH$_2$X$^{3.1}$, —CN, —S(O)$_2$R$^{3.1A}$, —SR$^{3.1A}$, —S(O)R$^{3.1A}$, —SO$_2$NR$^{3.1A}$R$^{3.1B}$, —NHC(O)NR$^{3.1A}$R$^{3.1B}$, —N(O)$_2$, —NR$^{3.1A}$R$^{3.1B}$, —NHNR$^{3.1A}$R$^{3.1B}$, —C(O)R$^{3.1A}$, —C(O)—OR$^{3.1A}$, —C(O)NR$^{3.1A}$R$^{3.1B}$, —P(O)R$^{3.1A}$R$^{3.1B}$, —C(O) NHNR$^{3.1A}$R$^{3.1B}$, —OR$^{3.1A}$, —NR$^{3.1}$SO$_2$R$^{3.1B}$, —NR$^{3.1A}$C(O)R$^{3.1B}$, —NR$^{3.1A}$C(O)OR$^{3.1B}$, —NR$^{3.1A}$OR$^{3.1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1}$ and $R^{3.2}$ may optionally be joined to form a substituted or unsubstituted heterocycloalkyl or substituted or unsubstituted heteroaryl.

In embodiments, $R^3$ is independently hydrogen, halogen, —CX$^{3.1}_3$, —CHX$^{3.1}_2$, —CH$_2$X$^{3.1}$, —OCX$^{3.1}_3$, —OCHX$^{3.1}_2$, —OCH$_2$X$^{3.1}$, —CN, —S(O)$_2$R$^{3.1A}$, —SR$^{3.1A}$, —S(O)$^{3.1A}$, —SO$_2$NR$^{3.1A}$R$^{3.1B}$, —NHC(O)NR$^{3.1A}$R$^{3.1B}$, —N(O)$_2$, —NR$^{3.1A}$R$^{3.1B}$, —NHNR$^{3.1A}$R$^{3.1B}$, —C(O)R$^{3.1A}$, —C(O)—O$^{3.1A}$, —C(O)N$^{3.1A}$R$^{3.1B}$, —P(O)R$^{3.1A}$R$^{3.1B}$, —C(O)NHNR$^{3.1A}$R$^{3.1B}$, —OR$^{3.1A}$, —NR$^{3.1A}$SO$_2$R$^{3.1B}$, —NR$^{3.1A}$C(O)R$^{3.1B}$, —NR$^{3.1A}$C(O)OR$^{3.1B}$, —N$^{3.1A}$OR$^{3.1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3.1}$ is independently hydrogen, halogen (e.g., —F, —Cl, Br, —I), —CX$^{3.1}_3$, —CHX$^{3.1}_2$, —CH$_2$X$^{3.1}$, —OCX$^{3.1}_2$, —OCHX$^{3.1}_2$, —OCH$_2$X$^{3.1}$, —CN, —S(O)$_2$R$^{3.1A}$, —SR$^{3.1A}$, —S(O)R$^{3.1A}$, —SO$_2$NR$^{3.1A}$R$^{3.1B}$, —NHC(O)NR$^{3.1A}$R$^{3.1B}$, —N(O)$_2$, —NR$^{3.1A}$R$^{3.1B}$, —NHNR$^{3.1A}$R$^{3.1B}$, —C(O)R$^{3.1A}$, —C(O)—OR$^{3.1A}$, —C(O) NR$^{3.1A}$R$^{3.1B}$, —P(O)R$^{3.1A}$R$^{3.1B}$, —C(O)NHNR$^{3.1A}$R$^{3.1B}$, —OR$^{3.1A}$, —NR$^{3.1A}$SO$_2$R$^{3.1B}$, —N$^{3.1A}$C(O)R$^{3.1B}$, —NR$^{3.1A}$C(O)OR$^{3.1B}$, —NR$^{3.1A}$OR$^{3.1B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —NHC(O)H, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, or —NCH₃OCH₃), substituted (e.g., substituted with a substituent group, a size-limited substituent group, or lower substituent group) or unsubstituted alkyl (e.g., $C_1$-$C_5$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X is independently —F, —Cl, —Br, or —I.

In embodiments, $R^{3.1}$ is independently hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{1a}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3.1}$ is independently hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O) NH₂, —C(O)NHCH₃, —OH, —OCH₃, —NHSO₂H, —NHSO₂CH₃, —NHC(O)H, —NCH₃C(O)H, —NHC(O) OH, —NCH₃C(O)OH, —NHOH, —NCH₃OH, —NCH₃OCH₃, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{3.1}$ is independently hydrogen, halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O) NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —OCH₂F, —OCH₂Cl, —OCH₂Br, —OCH₂I, $R^{12}$-substituted or unsubstituted alkyl (e.g., $C_1$-$C_8$ alkyl, $C_1$-$C_6$ alkyl, or $C_1$-$C_4$ alkyl), $R^{12}$-substituted or unsubstituted heteroalkyl (e.g., 2 to 8 membered heteroalkyl, 2 to 6 membered heteroalkyl, or 2 to 4 membered heteroalkyl), $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12}$-substituted or unsubstituted aryl (e.g., $C_6$-$C_{10}$ aryl, $C_{10}$ aryl, or phenyl), or $R^{12}$-substituted or unsubstituted heteroaryl (e.g., 5 to 10 membered heteroaryl, 5 to 9 membered heteroaryl, or 5 to 6 membered heteroaryl).

In embodiments, $R^{3.1}$ is independently hydrogen, halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O) NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —OCH₂F, —OCH₂Cl, —OCH₂Br, or —OCH₂I.

In embodiments, $R^{3.1}$ is $R^{12}$-substituted or unsubstituted alkyl (e.g., $C_1$-$C_8$ alkyl, $C_1$-$C_6$ alkyl, or $C_1$-$C_4$ alkyl). In embodiments, $R^{3.1}$ and $R^{3.2}$ is $R^{12}$-substituted or unsubstituted heteroalkyl (e.g., 2 to 8 membered heteroalkyl, 2 to 6 membered heteroalkyl, or 2 to 4 membered heteroalkyl). In embodiments, $R^{3.1}$ and $R^{3.2}$ is $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{3.1}$ and $R^{3.2}$ is $R^2$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.1}$ and $R^{3.2}$ is $R^{12}$-substituted or unsubstituted aryl (e.g., $C_6$-$C_{10}$ aryl, $C_{10}$ aryl, or phenyl). In embodiments, $R^{3.1}$ and $R^{3.2}$ is $R^{12}$-substituted or unsubstituted heteroaryl (e.g., 5 to 10 membered heteroaryl, 5 to 9 membered heteroaryl, or 5 to 6 membered heteroaryl).

In embodiments, $R^{12}$, $R^{13}$, and $R^{14}$ are as defined above. $R^{3.2}$ is independently hydrogen, halogen, —$CX^{3.2}_3$, —$CHX^{3.2}_2$, —$CH_2X^{3.2}$, —$OCX^{3.2}_3$, —$OCHX^{3.2}_2$, —$OCH_2X^{3.2}$, —CN, —$S(O)_2R^{3.2A}$, —$SR^{3.2A}$, —$S(O)R^{3.2A}$, —$O_2NR^{3.2A}R^{3.2B}$, —$NHC(O)N^{3.2A}R^{3.2B}$, —$N(O)_2$, —$NR^{3.2A}R^{3.2B}$, —$NHN^{3.2A}R^{3.2B}$, —$C(O)R^{3.2A}$, —$C(O)$—$OR^{3.2A}$, —$C(O)N^{3.2A}R^{3.2B}$, —$P(O)R^{3.2A}R^{3.2B}$, —$C(O)NHNR^{3.2A}R^{3.2B}$, —$OR^{3.2A}NR^{3.2A}SO_2R^{3.2B}$, —$NR^{3.2A}C(O)R^{3.2B}$, —$NR^{3.2A}C(O)OR^{3.2B}$, —$NR^{3.2A}OR^{3.2B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.1}$ and $R^{3.2}$ may optionally be joined to form a substituted or unsubstituted heterocycloalkyl or substituted or unsubstituted heteroaryl.

In embodiments, $R^{3.2}$ is independently hydrogen, halogen, $-CX^{3.2}_3$, $-CHX^{3.2}_2$, $-CH_2X^{3.2}$, $-OCX^{3.2}_3$, $-OCHX^{3.2}_2$, $-OCH_2X^{3.2}$, $-CN$, $-S(O)_2R^{3.2A}$, $R^{3.2A}$, $-S(O)R^{3.2A}$, $-SO_2NR^{3.2A}R^{3.2B}$, $-NHC(O)NR^{3.2A}R^{3.2B}$, $-N(O)_2$, $-NR^{3.2A}R^{3.2B}$, $-NHNR^{3.2A}R^{3.2B}$, $-(O)R^{3.2A}$, $-C(O)-OR^{3.2A}$, $-C(O)NR^{3.2A}R^{3.2B}$, $-P(O)R^{3.2A}R^{3.2B}$, $-C(O)NHNR^{3.2A}R^{3.2B}$, $-OR^{3.2A}$, $-NR^{3.2A}SO_2R^{3.2B}$, $-NR^{3.2A}C(O)R^{3.2B}$, $-NR^{3.2A}C(O)OR^{3.2}B$, $-NR^{3.2A}OR^{3.2B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3.2}$ is independently hydrogen, halogen (e.g., $-F$, $-Cl$, Br, $-I$), $-CX^{3.2}_3$, $-CHX^{3.2}_2$, $-CH_2X^{3.2}$, $-OCX^{3.2}_3$, $-OCHX^{3.2}_2$, $-OCH_2X^{3.2}$, $-CN$, $-S(O)_2R^{3.2A}$, $-SR^{3.2A}$, $-S(O)R^{3.2A}$, $-SO_2NR^{3.2A}R^{3.2B}$, $-NHC(O)NR^{3.2A}R^{3.2B}$, $-N(O)_2$, $-NR^{3.2A}R^{3.2B}$, $-NHNR^{3.2A}R^{3.2B}$, $-C(O)R^{3.2A}$, $-C(O)-OR^{3.2A}$, $-C(O)NR^{3.2A}R^{3.2B}$, $-P(O)R^{3.2A}R^{3.2B}$, $-C(O)NHNR^{3.2A}R^{3.2B}$, $-OR^{3.2A}$, $-NR^{3.2A}SO_2R^{3.2B}$, $-NR^{3.2A}C(O)R^{3.2B}$, $-NR^{3.2A}C(O)OR^{3.2B}$, $-NR^{3.2A}OR^{3.2B}$, $-N_3$, (e.g., $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, or $-NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently $-F$, $-Cl$, $-Br$, or $-I$.

In embodiments, $R^{3.2}$ is independently hydrogen, $-F$, $-Cl$, Br, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, $-NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3.2}$ is independently hydrogen, $-F$, $-Cl$, Br, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, $-NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{3.2}$ is independently hydrogen, halogen, $-CF_3$, $-CCl_3$, $-CBr_3$, $-CI_3$, $-OH$, $-NH_2$, $-COOH$, $-CONH_2$, $-NO_2$, $-N_3$, $-SH$, $-SO_3H$, $-SO_4H$, $-SO_2NH_2$, $-NHNH_2$, $-ONH_2$, $-NHC(O)NHNH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-OCH_2F$, $-OCH_2Cl$, $-OCH_2Br$, $-OCH_2I$, $R^{12}$-substituted or unsubstituted alkyl (e.g., $C_1$-$C_8$ alkyl, $C_1$-$C_6$ alkyl, or $C_1$-$C_4$ alkyl), $R^{12}$-substituted or unsubstituted heteroalkyl (e.g., 2 to 8 membered heteroalkyl, 2 to 6 membered heteroalkyl, or 2 to 4 membered heteroalkyl), $R^2$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12}$-substituted or unsubstituted aryl (e.g., $C_6$-$C_{10}$ aryl, $C_{10}$ aryl, or phenyl), or $R^{12}$-substituted or unsubstituted heteroaryl (e.g., 5 to 10 membered heteroaryl, 5 to 9 membered heteroaryl, or 5 to 6 membered heteroaryl).

In embodiments, $R^{3.2}$ is independently hydrogen, halogen, —CF$_3$, —CCl$_3$, —CBr$_3$, —C$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O) NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, $R^{3.2}$ is $R^{12}$-substituted or unsubstituted alkyl (e.g., C$_1$-C$_8$ alkyl, C$_1$-C$_6$ alkyl, or C$_1$-C$_4$ alkyl). In embodiments, $R^{3.2}$ is $R^{12}$-substituted or unsubstituted heteroalkyl (e.g., 2 to 8 membered heteroalkyl, 2 to 6 membered heteroalkyl, or 2 to 4 membered heteroalkyl). In embodiments, $R^{3.2}$ is $R^{12}$-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, $R^{3.2}$ is $R^{12}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.2}$ is $R^{12}$-substituted or unsubstituted aryl (e.g., C$_6$-C$_{10}$ aryl, C$_{10}$ aryl, or phenyl). In embodiments, $R^{3.2}$ is $R^{12}$-substituted or unsubstituted heteroaryl (e.g., 5 to 10 membered heteroaryl, 5 to 9 membered heteroaryl, or 5 to 6 membered heteroaryl).

In embodiments, $R^{12}$, $R^{13}$, and $R^{14}$ are as defined above. $R^{3.1A}$, $R^{3.1B}$, $R^{3.2A}$, and $R^{3.2B}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^{3.1A}$ and $R^{3.1B}$ may optionally be joined to form a substituted or unsubstituted heterocycloalkyl or substituted or unsubstituted heteroaryl; $R^{3.2A}$ and $R^{3.1B}$ may optionally be joined to form a substituted or unsubstituted heterocycloalkyl or substituted or unsubstituted heteroaryl; $R^{3.1A}$ and $R^{3.2B}$ may optionally be joined to form a substituted or unsubstituted heterocycloalkyl or substituted or unsubstituted heteroaryl; and $R^{3.2A}$ and $R^{3.1B}$ may optionally be joined to form a substituted or unsubstituted heterocycloalkyl or substituted or unsubstituted heteroaryl.

In embodiments, $R^{3.1A}$, $R^{3.1B}$, $R^{3.2A}$, and $R^{3.2B}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3.1A}$, $R^{3.1B}$, $R^{3.2A}$, and $R^{3.2B}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O) NHCH$_3$, —NO$_2$, —NH$_2$, —NHCH$_3$, —C(O)H, —C(O) CH$_3$, —C(O)OH, —C(O)OCH$_3$, —C(O)NH$_2$, —C(O) NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C (O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, $R^{3.1A}$, $R^{3.1B}$, $R^{3.2A}$, and $R^{3.2B}$ are independently hydrogen, halogen, —CF$_3$, —CCl$_3$, —CBr$_3$, —C$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC (O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, $R^{12A}$-substituted or unsubstituted alkyl (e.g., C1-C$_8$ alkyl, C$_1$-C$_6$ alkyl, or C$_1$-C$_4$ alkyl), $R^{12A}$-substituted or unsubstituted heteroalkyl (e.g., 2 to 8 membered heteroalkyl, 2 to 6 membered heteroalkyl, or 2 to 4 membered heteroalkyl), $R^{12A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{12A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12A}$-substituted or unsubstituted aryl (e.g., C$_6$-C$_{10}$ aryl, C$_{10}$ aryl, or phenyl), or $R^{12A}$-substituted or unsubstituted heteroaryl (e.g., 5 to 10 membered heteroaryl, 5 to 9 membered heteroaryl, or 5 to 6 membered heteroaryl).

In embodiments, $R^{3.1A}$, $R^{3.1B}$, $R^{3.2A}$, and $R^{3.2B}$ are independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC (O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, $R^{3.1A}$, $R^{3.1B}$, $R^{3.2A}$, and $R^{3.2B}$ is $R^{12A}$-substituted or unsubstituted alkyl (e.g., $C_1$-$C_8$ alkyl, $C_1$-$C_6$ alkyl, or $C_1$-$C_4$ alkyl). In embodiments, $R^{3.1A}$ is $R^{12A}$-substituted or unsubstituted heteroalkyl (e.g., 2 to 8 membered heteroalkyl, 2 to 6 membered heteroalkyl, or 2 to 4 membered heteroalkyl). In embodiments, $R^{3.1A}$ is $R^{12A}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{3.1A}$ is $R^{12A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.1A}$ is $R^{12A}$-substituted or unsubstituted aryl (e.g., C6-$C_{10}$ aryl, $C_{10}$ aryl, or phenyl). In embodiments, $R^{3.1A}$ and $R^{3.2A}$ are $R^{12A}$-substituted or unsubstituted heteroaryl (e.g., 5 to 10 membered heteroaryl, 5 to 9 membered heteroaryl, or 5 to 6 membered heteroaryl).

In embodiments, $R^{12A}$, $R^{13A}$, $R^{14A}$, $R^{12B}$, $R^{13B}$, and $R^{14B}$ are as defined above.

In embodiments, $R^{3.1A}$ and $R^{3.1B}$ may optionally be joined to form a substituted or unsubstituted heterocycloalkyl or substituted or unsubstituted heteroaryl. In embodiments, $R^{3.1A}$ and $R^{3.1B}$ may optionally be joined to form a substituted (e.g., substituted with a substituent group, a size-limited substituent group, or lower substituent group) or unsubstituted heterocycloalkyl (e.g., 3 to 8 membered, 3 to 6 membered, or 5 to 6 membered) or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3.2A}$ and $R^{3.2B}$ may optionally be joined to form a substituted or unsubstituted heterocycloalkyl or substituted or unsubstituted heteroaryl. In embodiments, $R^{3.2A}$ and $R^{3.2B}$ may optionally be joined to form a substituted (e.g., substituted with a substituent group, a size-limited substituent group, or lower substituent group) or unsubstituted heterocycloalkyl (e.g., 3 to 8 membered, 3 to 6 membered, or 5 to 6 membered) or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3.1A}$ and $R^{3.2B}$ may optionally be joined to form a substituted or unsubstituted heterocycloalkyl or substituted or unsubstituted heteroaryl. In embodiments, $R^{3.1A}$ and $R^{3.2B}$ may optionally be joined to form a substituted (e.g., substituted with a substituent group, a size-limited substituent group, or lower substituent group) or unsubstituted heterocycloalkyl (e.g., 3 to 8 membered, 3 to 6 membered, or 5 to 6 membered) or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{3.2A}$ and $R^{3.1B}$ may optionally be joined to form a substituted or unsubstituted heterocycloalkyl or substituted or unsubstituted heteroaryl. In embodiments, $R^{3.2A}$ and $R^{3.1B}$ may optionally be joined to form a substituted (e.g., substituted with a substituent group, a size-limited substituent group, or lower substituent group) or unsubstituted heterocycloalkyl (e.g., 3 to 8 membered, 3 to 6 membered, or 5 to 6 membered) or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, the compounds are compounds of Formula (II'):

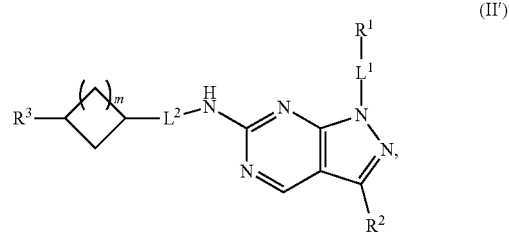

or a pharmaceutically acceptable salt thereof, wherein $L^1$, $L^2$, $R^1$, $R^2$ and $R^3$ are as defined above, including embodiments thereof, and wherein m is an integer from 1 to 4. In other embodiments, m is 2.

In embodiments, $L^1$ and $L^2$ are each bonds, providing compounds of Formula (III):

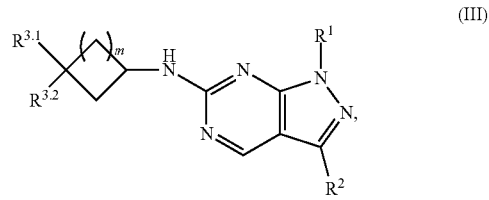

or a pharmaceutically acceptable salt thereof, wherein $L^1$, $L^2$, $R^1$, and $R^2$ are as defined above, including embodiments thereof, and wherein m is an integer from 1 to 4. In other embodiments, m is 2.

In certain embodiments, the compounds are compounds of Formula (III'):

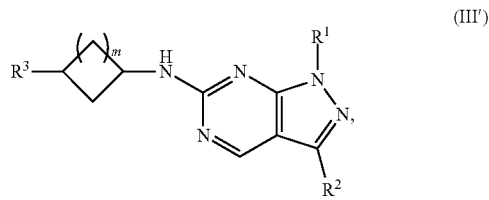

or a pharmaceutically acceptable salt thereof, wherein $R^1$, $R^2$ and $R^3$ are as defined above, including embodiments thereof.

In embodiments, the compounds are compounds of Formula (IV):

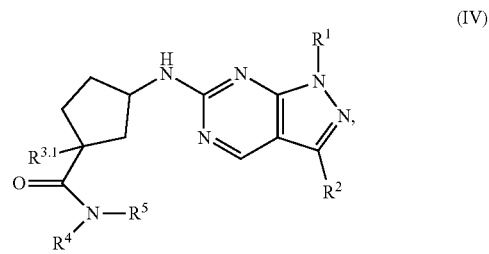

or a pharmaceutically acceptable salt thereof, wherein $R^1$, $R^2$, and $R^3$ are as defined above, including embodiments thereof.

In embodiments, the compounds are compounds of Formula (IV'):

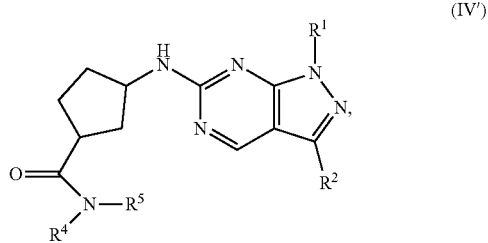

(IV')

wherein $R^1$ and $R^2$ are as defined above, including embodiments thereof.

In embodiments, $R^4$ is independently hydrogen, halogen, $-CX^4_3$, $-CHX^4_2$, $-CH_2X^4$, $-OCX^4_3$, $-OCHX^4_2$, $-OCH_2X^4$, $-CN$, $-S(O)_2R^{4A}$, $-SR^{4A}$, $-S(O)R^{4A}$, $-SO_2NR^{4A}R^{4B}$, $-NHC(O)NR^{4A}R^{4B}$, $-N(O)_2$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen, halogen (e.g., —F, —Cl, Br, —I), $-CX^4_3$, $-CHX^4_2$, $-CH_2X^4$, $-OCX^4_3$, $-OCHX^4_2$, $-OCH_2X^4$, $-CN$, $-S(O)_2R^{4A}$, $-SR^{4A}$, $-S(O)R^{4A}$, $-SO_2NR^{4A}R^{4B}$, $-NHC(O)NR^{4A}R^{4B}$, $-N(O)_2$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, (e.g., $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, or $-NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^4$ is hydrogen, —F, —Cl, Br, —I, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, $-NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^4$ is hydrogen, —F, —Cl, Br, —I, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, $-NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^4$ is independently halogen, $-CF_3$, $-CCl_3$, $-CBr_3$, $-CI_3$, $-OH$, $-NH_2$, $-COOH$, $-CONH_2$, $-NO_2$, $-N_3$, $-SH$, $-SO_3H$, $-SO_4H$, $-SO_2NH_2$, $-NHNH_2$, $-ONH_2$, $-NHC(O)NHNH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $R^{15}$-substituted or unsubstituted alkyl (e.g., $C_1$-$C_8$ alkyl, $C_1$-$C_6$ alkyl, or $C_1$-$C_4$ alkyl), $R^{15}$-substituted or unsubstituted heteroalkyl (e.g., 2 to 8 membered heteroalkyl, 2 to 6 membered heteroalkyl, or 2 to 4 membered heteroalkyl), $R^5$-substituted or unsubstituted cycloalkyl (e.g., $C_3$-$C_8$ cycloalkyl, $C_3$-$C_6$ cycloalkyl, or $C_5$-$C_6$ cycloalkyl), $R^{15}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15}$-substituted or unsubstituted aryl (e.g., $C_6$-$C_{10}$ aryl, $C_{10}$ aryl, or phenyl), or $R^{15}$-substituted or unsubstituted heteroaryl (e.g., 5 to 10 membered heteroaryl, 5 to 9 membered heteroaryl, or 5 to 6 membered heteroaryl).

In embodiments, $R^4$ is independently halogen, —$CF_3$, —$CCl_3$, —$CBr_3$, —$C_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^4$ is $R^{15}$-substituted or unsubstituted alkyl (e.g., $C_1$-$C_8$ alkyl, $C_1$-$C_6$ alkyl, or $C_1$-$C_4$ alkyl). In embodiments, $R^4$ is $R^{15}$-substituted or unsubstituted heteroalkyl (e.g., 2 to 8 membered heteroalkyl, 2 to 6 membered heteroalkyl, or 2 to 4 membered heteroalkyl). In embodiments, $R^4$ is $R^5$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^4$ is $R^{15}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is $R^{15}$-substituted or unsubstituted aryl (e.g., $C_6$-$C_{10}$ aryl, $C_{10}$ aryl, or phenyl). In embodiments, $R^4$ is $R^{15}$-substituted or unsubstituted heteroaryl (e.g., 5 to 10 membered heteroaryl, 5 to 9 membered heteroaryl, or 5 to 6 membered heteroaryl).

$R^{15}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{16}$-substituted or unsubstituted alkyl (e.g., $C_1$-$C_8$ alkyl, $C_1$-$C_6$ alkyl, or $C_1$-$C_4$ alkyl), $R^{16}$-substituted or unsubstituted heteroalkyl (e.g., 2 to 8 membered heteroalkyl, 2 to 6 membered heteroalkyl, or 2 to 4 membered heteroalkyl), $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16}$-substituted or unsubstituted aryl (e.g., $C_6$-$C_{10}$ aryl, $C_{10}$ aryl, or phenyl), or $R^{16}$-substituted or unsubstituted heteroaryl (e.g., 5 to 10 membered heteroaryl, 5 to 9 membered heteroaryl, or 5 to 6 membered heteroaryl).

In embodiments, $R^{15}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{15}$ is $R^{16}$-substituted or unsubstituted alkyl (e.g., $C_1$-$C_8$ alkyl, $C_1$-$C_6$ alkyl, or $C_1$-$C_4$ alkyl). In embodiments, $R^{15}$ is $R^{16}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is $R^{16}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is $R^{16}$-substituted or unsubstituted aryl (e.g., $C_6$-$C_{10}$ aryl, $C_{10}$ aryl, or phenyl). In embodiments, $R^{15}$ is $R^{16}$-substituted or unsubstituted heteroaryl (e.g., 5 to 10 membered heteroaryl, 5 to 9 membered heteroaryl, or 5 to 6 membered heteroaryl).

$R^{16}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{17}$-substituted or unsubstituted alkyl (e.g., $C_1$-$C_8$ alkyl, $C_1$-$C_6$ alkyl, or $C_1$-$C_4$ alkyl), $R^{17}$-substituted or unsubstituted heteroalkyl (e.g., 2 to 8 membered heteroalkyl, 2 to 6 membered heteroalkyl, or 2 to 4 membered heteroalkyl), $R^{17}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{17}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17}$-substituted or unsubstituted aryl (e.g., $C_6$-$C_{10}$ aryl, $C_{10}$ aryl, or phenyl), or $R^{17}$-substituted or unsubstituted heteroaryl (e.g., 5 to 10 membered heteroaryl, 5 to 9 membered heteroaryl, or 5 to 6 membered heteroaryl).

In embodiments, $R^{16}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{16}$ is $R^{17}$-substituted or unsubstituted alkyl (e.g., $C_1$-$C_8$ alkyl, $C_1$-$C_6$ alkyl, or $C_1$-$C_4$ alkyl). In embodiments, $R^{16}$ is $R^{17}$-substituted or unsubstituted heteroalkyl (e.g., 2 to 8 membered heteroalkyl, 2 to 6 membered heteroalkyl, or 2 to 4 membered heteroalkyl). In embodiments, $R^{16}$ is $R^{17}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16}$ is $R^{17}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16}$ is $R^{17}$-substituted or unsubstituted aryl (e.g., $C_6$-$C_{10}$ aryl, $C_{10}$ aryl, or phenyl). In embodiments, $R^{16}$ is $R^{17}$-substituted or unsubstituted heteroaryl (e.g., 5 to 10 membered heteroaryl, 5 to 9 membered heteroaryl, or 5 to 6 membered heteroaryl).

$R^{17}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{17}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{17}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{4A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{4A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{4A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$, $R^{15A}$-substituted or unsubstituted alkyl (e.g., $C_1$-$C_8$ alkyl, $C_1$-$C_6$ alkyl, or C1-$C_4$ alkyl), $R^{15A}$-substituted or unsubstituted heteroalkyl (e.g., 2 to 8 membered heteroalkyl, 2 to 6 membered heteroalkyl, or 2 to 4 membered heteroalkyl), $R^{15A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{15A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15A}$-substituted or unsubstituted aryl (e.g., $C_6$-$C_{10}$ aryl, $C_{10}$ aryl, or phenyl), or $R^{15A}$-substituted or unsubstituted heteroaryl (e.g., 5 to 10 membered heteroaryl, 5 to 9 membered heteroaryl, or 5 to 6 membered heteroaryl).

In embodiments, $R^{4A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{4A}$ is $R^{15A}$-substituted or unsubstituted alkyl (e.g., $C_1$-$C_8$ alkyl, $C_1$-$C_6$ alkyl, or $C_1$-$C_4$ alkyl). In embodiments, $R^{4A}$ is $R^{15A}$-substituted or unsubstituted heteroalkyl (e.g., 2 to 8 membered heteroalkyl, 2 to 6 membered heteroalkyl, or 2 to 4 membered heteroalkyl). In embodiments, $R^{4A}$ is $R^{15A}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{4A}$ is $R^{15A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is $R^{15A}$-substituted or unsubstituted aryl (e.g., $C_6$-$C_{10}$ aryl, $C_{10}$ aryl, or phenyl). In embodiments, $R^{4A}$ is $R^{15A}$-substituted or unsubstituted heteroaryl (e.g., 5 to 10 membered heteroaryl, 5 to 9 membered heteroaryl, or 5 to 6 membered heteroaryl).

$R^{15A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{6A}$-substituted or unsubstituted alkyl (e.g., $C_1$-$C_8$ alkyl, $C_1$-$C_6$ alkyl, or $C_1$-$C_4$ alkyl), $R^{16A}$-substituted or unsubstituted heteroalkyl (e.g., 2 to 8 membered heteroalkyl, 2 to 6 membered heteroalkyl, or 2 to 4 membered heteroalkyl), $R^{16A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16A}$-substituted or unsubstituted aryl (e.g., $C_6$-$C_{10}$ aryl, $C_{10}$ aryl, or phenyl), or $R^{16A}$-substituted or unsubstituted heteroaryl (e.g., 5 to 10 membered heteroaryl, 5 to 9 membered heteroaryl, or 5 to 6 membered heteroaryl).

In embodiments, $R^{15A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{15A}$ is $R^{16A}$-substituted or unsubstituted alkyl (e.g., $C_1$-$C_8$ alkyl, $C_1$-$C_6$ alkyl, or $C_1$-$C_4$ alkyl). In embodiments, $R^{15A}$ is $R^{16A}$-substituted or unsubstituted heteroalkyl (e.g., 2 to 8 membered heteroalkyl, 2 to 6 membered heteroalkyl, or 2 to 4 membered heteroalkyl). In embodiments, $R^{15A}$ is $R^{16A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15A}$ is $R^{16A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15A}$ is $R^{16A}$-substituted or unsubstituted aryl (e.g., $C_6$-$C_{10}$ aryl, $C_{10}$ aryl, or phenyl). In embodiments, $R^{5A}$ is $R^{16A}$-substituted or unsubstituted heteroaryl (e.g., 5 to 10 membered heteroaryl, 5 to 9 membered heteroaryl, or 5 to 6 membered heteroaryl).
I
$R^{16A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2C$, —$OCH_2Br$, —$OCH_2I$, $R^{17A}$-substituted or unsubstituted alkyl (e.g., $C_1$-$C_8$ alkyl, $C_1$-$C_6$ alkyl, or $C_1$-$C_4$ alkyl), $R^{17A}$-substituted or unsubstituted heteroalkyl (e.g., 2 to 8 17embered heteroalkyl, 2 to 6 membered heteroalkyl, or 2 to 4 membered heteroalkyl), $R^{17A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{17A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17A}$-substituted or unsubstituted aryl (e.g., $C_6$-$C_{10}$ aryl, $C_{10}$ aryl, or phenyl), or $R^{17A}$-substituted or unsubstituted heteroaryl (e.g., 5 to 10 membered heteroaryl, 5 to 9 membered heteroaryl, or 5 to 6 membered heteroaryl).

In embodiments, $R^{11A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{16A}$ is $R^{17A}$-substituted or unsubstituted alkyl (e.g., $C_1$-$C_8$ alkyl, $C_1$-$C_6$ alkyl, or $C_1$-$C_4$ alkyl). In embodiments, $R^{16A}$ is $R^{17A}$-substituted or unsubstituted heteroalkyl (e.g., 2 to 8 membered heteroalkyl, 2 to 6 membered heteroalkyl, or 2 to 4 membered heteroalkyl). In embodiments, $R^{16A}$ is $R^{17A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16A}$ is $R^{17A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16A}$ is $R^{17A}$-substituted or unsubstituted aryl (e.g., $C_6$-$C_{10}$ aryl, $C_{10}$ aryl, or phenyl). In embodiments, $R^{16A}$ is $R^{17A}$-substituted or unsubstituted heteroaryl (e.g., 5 to 10 membered heteroaryl, 5 to 9 membered heteroaryl, or 5 to 6 membered heteroaryl).

$R^{17A}$ is independently halogen, —$CF_3$, —$CCl_3$, —$CBr_3$, —$CI_3$, —OH, —N112, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C6-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{17A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OC_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{17A}$ is independently unsubstituted alkyl (e.g., $C_1$-$C_8$alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{4B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —NCH₃OCH₃, substituted (e.g., substituted with a substituent group, a size-limited substituent group, or lower substituent group) or unsubstituted alkyl (e.g., $C_1$-$C^8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{4B}$ is hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CH₁₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{4B}$ is independently halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O)NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —OCH₂F, —OCH₂Cl, —OCH₂Br, or —OCH₂I, $R^{15B}$-substituted or unsubstituted alkyl (e.g., $C_1$-$C_8$ alkyl, $C_1$-$C_6$ alkyl, or C1-$C_4$ alkyl), $R^{15B}$-substituted or unsubstituted heteroalkyl (e.g., 2 to 8 membered heteroalkyl, 2 to 6 membered heteroalkyl, or 2 to 4 membered heteroalkyl), $R^{15B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{15B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15B}$-substituted or unsubstituted aryl (e.g., $C_6$-$C_{10}$ aryl, $C_{10}$ aryl, or phenyl), or $R^{15B}$-substituted or unsubstituted heteroaryl (e.g., 5 to 10 membered heteroaryl, 5 to 9 membered heteroaryl, or 5 to 6 membered heteroaryl).

In embodiments, $R^{4B}$ is independently halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O)NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —OCH₂F, —OCH₂Cl, —OCH₂Br, or —OCH₂I.

In embodiments, $R^{4B}$ is $R^{15B}$-substituted or unsubstituted alkyl (e.g., $C_1$-$C_8$ alkyl, $C_1$-$C_6$ alkyl, or $C_1$-$C_4$ alkyl). In embodiments, $R^{4B}$ is $R^{15B}$-substituted or unsubstituted heteroalkyl (e.g., 2 to 8 membered heteroalkyl, 2 to 6 membered heteroalkyl, or 2 to 4 membered heteroalkyl). In embodiments, $R^{4B}$ is $R^{15B}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{4B}$ is $R^{15B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is $R^{15B}$-substituted or unsubstituted aryl (e.g., C6-$C_{10}$ aryl, $C_{10}$ aryl, or phenyl). In embodiments, $R^{4B}$ is $R^{15B}$-substituted or unsubstituted heteroaryl (e.g., 5 to 10 membered heteroaryl, 5 to 9 membered heteroaryl, or 5 to 6 membered heteroaryl).

$R^{15B}$ is independently halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O)NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —OCH₂F, —OCH₂Cl, —OCH₂Br, —OCH₂I, $R^{16B}$ substituted or unsubstituted alkyl (e.g., $C_1$-$C_8$ alkyl, $C_1$-$C_6$ alkyl, or $C_1$-$C_4$ alkyl), $R^{16B}$-substituted or unsubstituted heteroalkyl (e.g., 2 to 8 membered heteroalkyl, 2 to 6 membered heteroalkyl, or 2 to 4 membered heteroalkyl), $R^{16B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16B}$-substituted or unsubstituted aryl (e.g., $C_6$-$C_{10}$ aryl, $C_{10}$ aryl, or phenyl), or $R^{16B}$-substituted or unsubstituted heteroaryl (e.g., 5 to 10 membered heteroaryl, 5 to 9 membered heteroaryl, or 5 to 6 membered heteroaryl).

In embodiments, $R^{15B}$ is independently halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O)NHNH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —OCH₂F, —OCH₂Cl, —OCH₂Br, or —OCH₂I.

In embodiments, $R^{15B}$ is $R^{16B}$-substituted or unsubstituted alkyl(e.g., $C_1$-$C_8$ alkyl, $C_1$-$C_6$ alkyl, or $C_1$-$C_4$ alkyl). In embodiments, $R^{15B}$ is $R^{16B}$-substituted or unsubstituted heteroalkyl (e.g., 2 to 8 membered heteroalkyl, 2 to 6 membered heteroalkyl, or 2 to 4 membered heteroalkyl). In embodiments, $R^{15B}$ is $R^{16B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15B}$ is $R^{16B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15B}$ is $R^{16B}$-substituted or unsubstituted aryl (e.g., $C_6$-$C_{10}$ aryl, $C_{10}$ aryl, or phenyl). In embodiments, $R^{15B}$ is $R^{16B}$-substituted or unsubstituted heteroaryl (e.g., 5 to 10 membered heteroaryl, 5 to 9 membered heteroaryl, or 5 to 6 membered heteroaryl).

$R^{16B}$ is independently halogen, —CF₃, —CCl₃, —CBr₃, —CI₃, —OH, —NH₂, —COOH, —CONH₂, —NO₂, —N₃, —SH, —SO₃H, —SO₄H, —SO₂NH₂, —NHNH₂, —ONH₂, —NHC(O)NHNH₂, —NHSO₂H, —NHC(O)H, —NHC (O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{17B}$-substituted or unsubstituted alkyl (e.g., C$_1$-C$_8$ alkyl, C$_1$-C$_6$ alkyl, or C$_1$-C$_4$ alkyl), R$^{7B}$-substituted or unsubstituted heteroalkyl (e.g., 2 to 8 membered heteroalkyl, 2 to 6 membered heteroalkyl, or 2 to 4 membered heteroalkyl), R$^{17B}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{17B}$-substituted or unsubstituted heterocycloalkyl (e.g., 3 to 8 membered heterocycloalkyl, 3 to 6 membered heterocycloalkyl, or 5 to 6 membered heterocycloalkyl), R$^{17B}$-substituted or unsubstituted aryl (e.g., C$_6$-C$_{10}$ aryl, C$_{10}$ aryl, or phenyl), or R$^{17B}$-substituted or unsubstituted heteroaryl (e.g., 5 to 10 membered heteroaryl, 5 to 9 membered heteroaryl, or 5 to 6 membered heteroaryl).

In embodiments, R$^{16B}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{16B}$ is R$^{17B}$-substituted or unsubstituted alkyl (e.g., C$_1$-C$_8$ alkyl, C$_1$-C$_6$ alkyl, or C$_1$-C$_4$ alkyl). In embodiments, R$^{16B}$ is R$^{17B}$-substituted or unsubstituted heteroalkyl (e.g., 2 to 8 membered heteroalkyl, 2 to 6 membered heteroalkyl, or 2 to 4 membered heteroalkyl). In embodiments, R$^{16B}$ is R$^{17B}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{16B}$ is R$^{17B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{16B}$ is R$^{17B}$-substituted or unsubstituted aryl (e.g., C$_6$-C$_{10}$ aryl, C$_{10}$ aryl, or phenyl). In embodiments, R$^{16B}$ is R$^{17B}$-substituted or unsubstituted heteroaryl (e.g., 5 to 10 membered heteroaryl, 5 to 9 membered heteroaryl, or 5 to 6 membered heteroaryl).

R$^{17B}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C6-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{17B}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{17B}$ is independently unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^5$ is independently hydrogen, halogen, —CX$^5_3$, —CHX$^5_2$, —CH$_2$X$^5$, —OCX$^5_3$, —OCHX$^5_2$, —OCH$_2$X$^5$, —CN, —S(O)$_2$R$^{5A}$, —SR$^{5A}$, —S(O)R$^{5A}$, —SO$_2$NR$^{5A}$R$^{5B}$, —NHC(O)NR$^{5A}$R$^{5B}$, —N(O)$_2$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^5$ is hydrogen, halogen (e.g., —F, —Cl, Br, —I), —CX$^5_3$, —CHX$^5_2$, —CH$_2$X$_5$, —OCX$^5_3$, —OCHX$^5_2$, —OCH$_2$X$^5$, —CN, —S(O)$_2$R$^{5A}$, —SR$^{5A}$, —S(O)R$^{5A}$, —SO$_2$NR$^{5A}$R$^{5B}$, —NHC(O)NR$^{5A}$R$^{5B}$, —N(O)$_2$, —NR$^{5A}$R$^{5B}$, —NHNR$^{5A}$R$^{5B}$, —C(O)R$^{5A}$, —C(O)—OR$^{5A}$, —C(O)NR$^{5A}$R$^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O) OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_8$, C$_1$-C$_6$, or C$_1$-C$_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., C$_3$-C$_8$, C$_3$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., C$_6$-C$_{10}$, C$_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X$^1$ is independently —F, —Cl, —Br, or —I.

In embodiments, $R^5$ is hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted (e.g., substituted with a substituent group, a size-limited substituent group, or lower substituent group) or unsubstituted alkyl (e.g., $C_1$-$C^8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^5$ is hydrogen, —F, —Cl, Br, —I, —CF$_3$, —CHF$_2$, —CH$_2$F, —CCl$_3$, —CHCl$_2$, —CH$_2$C, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^5$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, $R^{18}$-substituted or unsubstituted alkyl (e.g., $C_1$-$C_8$ alkyl, $C_1$-$C_6$ alkyl, or $C_1$-$C_4$ alkyl), $R^{18}$-substituted or unsubstituted heteroalkyl (e.g., 2 to 8 membered heteroalkyl, 2 to 6 membered heteroalkyl, or 2 to 4 membered heteroalkyl), $R^{18}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{18}$-substituted or unsubstituted heterocycloalkyl (e.g., 3 to 8 membered heterocycloalkyl, 3 to 6 membered heterocycloalkyl, or 5 to 6 membered heterocycloalkyl), $R^{18}$-substituted or unsubstituted aryl (e.g., $C_6$-$C_{10}$ aryl, $C_{10}$ aryl, or phenyl), or $R^{18}$-substituted or unsubstituted heteroaryl (e.g., 5 to 10 membered heteroaryl, 5 to 9 membered heteroaryl, or 5 to 6 membered heteroaryl).

In embodiments, $R^5$ is $R^{18}$-substituted or unsubstituted alkyl (e.g., $C_1$-$C_8$ alkyl, $C_1$-$C_6$ alkyl, or $C_1$-$C_4$ alkyl). In embodiments, $R^5$ is $R^{18}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is $R^{18}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^5$ is $R^{18}$ substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^{18}$-substituted or unsubstituted aryl (e.g., $C_6$-$C_{10}$ aryl, $C_{10}$ aryl, or phenyl). In embodiments, $R^5$ is $R^8$-substituted or unsubstituted heteroaryl (e.g., 5 to 10 membered heteroaryl, 5 to 9 membered heteroaryl, or 5 to 6 membered heteroaryl).

$R^{18}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —S4H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, $R^{19}$-substituted or unsubstituted alkyl (e.g., $C_1$-$C_8$ alkyl, $C_1$-$C_6$ alkyl, or $C_1$-$C_4$ alkyl), $R^{19}$-substituted or unsubstituted heteroalkyl (e.g., 2 to 8 membered heteroalkyl, 2 to 6 membered heteroalkyl, or 2 to 4 membered heteroalkyl), $R^{19}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19}$-substituted or unsubstituted heterocycloalkyl (e.g., 3 to 8 membered heterocycloalkyl, or 5 to 6 membered heterocycloalkyl), $R^{19}$-substituted or unsubstituted aryl (e.g., $C_6$-$C_{10}$ aryl, $C_{10}$ aryl, or phenyl), or $R^{19}$-substituted or unsubstituted heteroaryl (e.g., 5 to 10 membered heteroaryl, 5 to 9 membered heteroaryl, or 5 to 6 membered heteroaryl).

In embodiments, $R^{18}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, $R^{18}$ is $R^{19}$-substituted or unsubstituted alkyl (e.g., $C_1$-$C_8$ alkyl, $C_1$-$C_6$ alkyl, or $C_1$-$C_4$ alkyl). In embodiments, $R^{18}$ is $R^{19}$-substituted or unsubstituted heteroalkyl (e.g., 2 to 8 membered heteroalkyl, 2 to 6 membered heteroalkyl, or 2 to 4 membered heteroalkyl). In embodiments, $R^{18}$ is $R^{19}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is $R^{19}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18}$ is $R^{19}$-substituted or unsubstituted aryl (e.g., $C_6$-$C_{10}$ aryl, $C_{10}$ aryl, or phenyl). In embodiments, $R^{18}$ is $R^{19}$-substituted or unsubstituted heteroaryl (e.g., 5 to 10 membered heteroaryl, 5 to 9 membered heteroaryl, or 5 to 6 membered heteroaryl).

$R^{19}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

In embodiments, $R^{19}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2C$, —$OCH_2Br$, —$OCH_2I$, —$OCH_2F$, —$OCH_2Cl$, —$OCH_2Br$, or —$OCH_2I$.

In embodiments, $R^{19}$ is $R^{20}$-substituted or unsubstituted alkyl (e.g., $C_1$-$C_8$ alkyl, $C_1$-$C_6$ alkyl, or $C_1$-$C_4$ alkyl). In embodiments, $R^{19}$ is $R^{20}$-substituted or unsubstituted heteroalkyl (e.g., 2 to 8 membered heteroalkyl, 2 to 6 membered heteroalkyl, or 2 to 4 membered heteroalkyl). In embodiments, $R^{19}$ is $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{19}$ is $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{19}$ is $R^{20}$-substituted or unsubstituted aryl (e.g., $C_6$-$C_{10}$ aryl, $C_{10}$ aryl, or phenyl). In embodiments, $R^{19}$ is $R^{20}$-substituted or unsubstituted heteroaryl (e.g., 5 to 10 membered heteroaryl, 5 to 9 membered heteroaryl, or 5 to 6 membered heteroaryl).

$R^{20}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{20}$ is independently halogen, —$CF_3$, —$CCl_3$, —$CBr_3$, —$C_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{20}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{5A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{5A}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)

OH, —NCH$_3$C(O)OH, —NHOH, —NCH$_3$OH, —NCH$_3$OCH$_3$, unsubstituted alkyl (e.g., C$_1$-C$_8$, C$_1$-C$_6$, or C$_1$-C$_4$), unsubstituted heteroalkyl (e.g., 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_6$, or phenyl), or unsubstituted heteroaryl (e.g., 5 to 10 membered, 5 to 9 membered, or 5 to 6 membered).

In embodiments, R$^{5A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$, R$^{18A}$-substituted or unsubstituted alkyl (e.g., C$_1$-C$_8$ alkyl, C$_1$-C$_6$ alkyl, or C$_1$-C$_4$ alkyl), R$^{ISA}$-substituted or unsubstituted heteroalkyl (e.g., 2 to 8 membered heteroalkyl, 2 to 6 membered heteroalkyl, or 2 to 4 membered heteroalkyl), R$^{18A}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{18A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{18A}$-substituted or unsubstituted aryl (e.g., C$_6$-C$_{10}$ aryl, C$_{10}$ aryl, or phenyl), or R$^{18A}$-substituted or unsubstituted heteroaryl (e.g., 5 to 10 membered heteroaryl, 5 to 9 membered heteroaryl, or 5 to 6 membered heteroaryl).

In embodiments, R$^{5A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{5A}$ is R$^{8A}$-substituted or unsubstituted alkyl (e.g., C$_1$-C$_8$ alkyl, C$_1$-C$_6$ alkyl, or C$_1$-C$_4$ alkyl). In embodiments, R$^{5A}$ is R$^{18A}$-substituted or unsubstituted heteroalkyl (e.g., 2 to 8 membered heteroalkyl, 2 to 6 membered heteroalkyl, or 2 to 4 membered heteroalkyl). In embodiments, R$^{5A}$ is R$^{18A}$-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, R$^{5A}$ is R$^{18A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{5A}$ is R$^{18A}$-substituted or unsubstituted aryl (e.g., C$_6$-C$_{10}$ aryl, C$_{10}$ aryl, or phenyl). In embodiments, R$^{17A}$ is R$^{18A}$-substituted or unsubstituted heteroaryl (e.g., 5 to 10 membered heteroaryl, 5 to 9 membered heteroaryl, or 5 to 6 membered heteroaryl).

R$^{18A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{19A}$-substituted or unsubstituted alkyl (e.g., C$_1$-C$_8$ alkyl, C$_1$-C$_6$ alkyl, or C$_1$-C$_4$ alkyl), R$^{19A}$-substituted or unsubstituted heteroalkyl (e.g., 2 to 8 membered heteroalkyl, 2 to 6 membered heteroalkyl, or 2 to 4 membered heteroalkyl), R$^{19A}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{19A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{19A}$-substituted or unsubstituted aryl (e.g., C6-C$_{10}$ aryl, C$_{10}$ aryl, or phenyl), or R$^{19A}$-substituted or unsubstituted heteroaryl (e.g., 5 to 10 membered heteroaryl, 5 to 9 membered heteroaryl, or 5 to 6 membered heteroaryl).

In embodiments, R$^{18A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{18A}$ is R$^{19A}$-substituted or unsubstituted alkyl (e.g., C$_1$-C$_8$ alkyl, C1-C$_6$ alkyl, or C$_1$-C$_4$ alkyl). In embodiments, R$^{18A}$ is R$^{19A}$-substituted or unsubstituted heteroalkyl (e.g., 2 to 8 membered heteroalkyl, 2 to 6 membered heteroalkyl, or 2 to 4 membered heteroalkyl). In embodiments, R$^{18A}$ is R$^{19A}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{18A}$ is R$^{19A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{18A}$ is R$^{19A}$ substituted or unsubstituted aryl (e.g., C$_6$-C$_{10}$ aryl, C$_{10}$ aryl, or phenyl). In embodiments, R$^{18A}$ is R$^{19A}$-substituted or unsubstituted heteroaryl (e.g., 5 to 10 membered heteroaryl, 5 to 9 membered heteroaryl, or 5 to 6 membered heteroaryl). I R$^{19A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{20A}$-substituted or unsubstituted alkyl (e.g., C$_1$-C$_8$ alkyl, C$_1$-C$_6$ alkyl, or C$_1$-C$_4$ alkyl), R$^{20A}$-substituted or unsubstituted heteroalkyl (e.g., 2 to 8 17embered heteroalkyl, 2 to 6 membered heteroalkyl, or 2 to 4 membered heteroalkyl), R$^{20A}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{20A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{20A}$-substituted or unsubstituted aryl (e.g., C$_6$-C$_{10}$ aryl, C$_{10}$ aryl, or phenyl), or R$^{20A}$-substituted or unsubstituted heteroaryl (e.g., 5 to 10 membered heteroaryl, 5 to 9 membered heteroaryl, or 5 to 6 membered heteroaryl).

In embodiments, R$^{19A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{19A}$ is R$^{20A}$-substituted or unsubstituted alkyl (e.g., C$_1$-C$_8$ alkyl, C$_1$-C$_6$ alkyl, or C$_1$-C$_4$ alkyl). In embodiments, R$^{9A}$ is R$^{20A}$-substituted or unsubstituted heteroalkyl (e.g., 2 to 8 membered heteroalkyl, 2 to 6 membered heteroalkyl, or 2 to 4 membered heteroalkyl). In embodiments, $R^{9A}$ is $R^{20A}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{19A}$ is $R^{20A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{9A}$ is $R^{20A}$-substituted or unsubstituted aryl (e.g., $C_6$-$C_{10}$ aryl, $C_{10}$ aryl, or phenyl). In embodiments, $R^{19A}$ is $R^{20A}$-substituted or unsubstituted heteroaryl (e.g., 5 to 10 membered heteroaryl, 5 to 9 membered heteroaryl, or 5 to 6 membered heteroaryl).

$R^{20A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{20A}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{20A}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{5B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{5B}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{5B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{18B}$-substituted or unsubstituted alkyl (e.g., $C_1$-$C_8$ alkyl, $C_1$-$C_6$ alkyl, or $C_1$-$C_4$ alkyl), $R^{18B}$-substituted or unsubstituted heteroalkyl (e.g., 2 to 8 membered heteroalkyl, 2 to 6 membered heteroalkyl, or 2 to 4 membered heteroalkyl), $R^{18B}$-substituted or unsubstituted cycloalkyl (e.g., $C_3$-$C_8$ cycloalkyl, $C_3$-$C_6$ cycloalkyl, or $C_1$-$C_6$ cycloalkyl), $R^{18B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{1B}$-substituted or unsubstituted aryl (e.g., $C_6$-$C_{10}$ aryl, $C_{10}$ aryl, or phenyl), or $R^B$-substituted or unsubstituted heteroaryl (e.g., 5 to 10 membered heteroaryl, 5 to 9 membered heteroaryl, or 5 to 6 membered heteroaryl).

In embodiments, $R^{5B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{5B}$ is $R^{18B}$-substituted or unsubstituted alkyl (e.g., $C_1$-$C_8$ alkyl, $C_1$-$C_6$ alkyl, or $C_1$-$C_4$ alkyl). In embodiments, $R^{5B}$ is $R^{18B}$-substituted or unsubstituted heteroalkyl (e.g., 2 to 8 membered heteroalkyl, 2 to 6 membered heteroalkyl, or 2 to 4 membered heteroalkyl). In embodiments, $R^{5B}$ is $R^{18B}$-substituted or unsubstituted cycloalkyl (e.g., $C_3$-$C_8$ cycloalkyl, $C_3$-$C_6$ cycloalkyl, or $C_5$-$C_6$ cycloalkyl 1). In embodiments, $R^{5B}$ is $R^{18B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5B}$ is $R^{18B}$-substituted or unsubstituted aryl (e.g., $C_6$-$C_{10}$ aryl, $C_{10}$ aryl, or phenyl). In embodiments, $R^{5B}$ is $R^{18B}$-substituted or unsubstituted heteroaryl (e.g., 5 to 10 membered heteroaryl, 5 to 9 membered heteroaryl, or 5 to 6 membered heteroaryl).

$R^{18B}$ is independently halogen, —$CF_3$, —$CCl_3$, —$CBr_3$, —$C_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{19B}$-substituted or unsubstituted alkyl (e.g., $C_1$-$C_8$ alkyl, $C_1$-$C_6$ alkyl, or $C_1$-$C_4$ alkyl), $R^{19B}$-substituted or unsubstituted heteroalkyl (e.g., 2 to 8 membered heteroalkyl, 2 to 6 membered heteroalkyl, or 2 to 4 membered heteroalkyl), $R^{19B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19B}$-substituted or unsubstituted aryl (e.g., $C_6$-$C_{10}$ aryl, $C_{10}$ aryl, or phenyl), or $R^{19B}$-substituted or unsubstituted heteroaryl (e.g., 5 to 10 membered heteroaryl, 5 to 9 membered heteroaryl, or 5 to 6 membered heteroaryl).

In embodiments, $R^{18B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{18B}$ is $R^{19B}$-substituted or unsubstituted alkyl (e.g., $C_1$-$C_8$ alkyl, $C_1$-$C_6$ alkyl, or $C_1$-$C_4$ alkyl). In embodiments, $R^{18B}$ is $R^{19B}$-substituted or unsubstituted heteroalkyl (e.g., 2 to 8 membered heteroalkyl, 2 to 6 membered heteroalkyl, or 2 to 4 membered heteroalkyl). In embodiments, $R^{18B}$ is $R^{19B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18B}$ is $R^{19B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18B}$ is $R^{19B}$-substituted or unsubstituted aryl (e.g., $C_6$-$C_{10}$ aryl, $C_{10}$ aryl, or phenyl). In embodiments, $R^{18B}$ is $R^{19B}$-substituted or unsubstituted heteroaryl (e.g., 5 to 10 membered heteroaryl, 5 to 9 membered heteroaryl, or 5 to 6 membered heteroaryl).

$R^{19B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{20B}$-substituted or unsubstituted alkyl (e.g., $C_1$-$C_8$ alkyl, $C_1$-$C_6$ alkyl, or $C_1$-$C_4$ alkyl), $R^{20B}$-substituted or unsubstituted heteroalkyl (e.g., 2 to 8 membered heteroalkyl, 2 to 6 membered heteroalkyl, or 2 to 4 membered heteroalkyl), $R^{20B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20B}$-substituted or unsubstituted aryl (e.g., $C_6$-$C_{10}$ aryl, $C_{10}$ aryl, or phenyl), or $R^{20B}$-substituted or unsubstituted heteroaryl (e.g., 5 to 10 membered heteroaryl, 5 to 9 membered heteroaryl, or 5 to 6 membered heteroaryl).

In embodiments, $R^{19B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2C$, —$OCH_2Br$, —$OCH_2I$, —$OCH_2F$, —$OCH_2Cl$, —$OCH_2Br$, or —$OCH_2I$.

In embodiments, $R^{19B}$ is $R^{20B}$-substituted or unsubstituted alkyl (e.g., $C_1$-$C_8$ alkyl, $C_1$-$C_6$ alkyl, or $C_1$-$C_4$ alkyl). In embodiments, $R^{9B}$ is $R^{20B}$-substituted or unsubstituted heteroalkyl (e.g., 2 to 8 membered heteroalkyl, 2 to 6 membered heteroalkyl, or 2 to 4 membered heteroalkyl). In embodiments, $R^{19B}$ is $R^{20B}$-substituted or unsubstituted cycloalkyl (e.g., $C_3$-$C_8$ cycloalkyl, $C_3$-$C_6$ cycloalkyl, or $C_1$-$C_6$ cycloalkyl). In embodiments, $R^{19B}$ is $R^{20B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{19B}$ is $R^{20B}$-substituted or unsubstituted aryl (e.g., $C_6$-$C_{10}$ aryl, $C_{10}$ aryl, or phenyl). In embodiments, $R^{9B}$ is $R^{20B}$-substituted or unsubstituted heteroaryl (e.g., 5 to 10 membered heteroaryl, 5 to 9 membered heteroaryl, or 5 to 6 membered heteroaryl).

$R^{20B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2CL$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{20B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, —$OC_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{20B}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^4$ and $R^5$ are independently hydrogen, substituted (e.g., substituted with a substituent group, a size-limited substituent group, or lower substituent group) or unsubstituted $C_1$-$C_8$ alkyl, substituted (e.g., substituted with a substituent group, a size-limited substituent group, or lower substituent group) or unsubstituted 2 to 8 membered heteroalkyl, substituted (e.g., substituted with a substituent group, a size-limited substituent group, or lower substituent group) or unsubstituted $C_3$-$C_8$ cycloalkyl, or substituted (e.g., substituted with a substituent group, a size-limited substituent group, or lower substituent group) or unsubstituted 3 to 7 membered heterocycloalkyl;

In embodiments, $R^4$ and $R^5$ may optionally be joined to form a substituted (e.g., substituted with a substituent group, a size-limited substituent group, or lower substituent group) or unsubstituted $C_3$-$C_8$ cycloalkyl, substituted (e.g., substituted with a substituent group, a size-limited substituent group, or lower substituent group) or unsubstituted 3 to 7 membered heterocycloalkyl or substituted (e.g., substituted with a substituent group, a size-limited substituent group, or lower substituent group) or unsubstituted 5 or 6 membered heteroaryl. In embodiments, $R^4$ and $R^5$ may optionally be joined to form a substituted (e.g., substituted with a substituent group, a size-limited substituent group, or lower substituent group) or unsubstituted 3 to 7 membered heterocycloalkyl or substituted or unsubstituted 5 or 6 membered heteroaryl.

In certain embodiments of the compounds of Formula (IV) or (IV'), the moieties $R^4$ and $R^5$ are independently hydrogen or substituted (e.g., substituted with a substituent group, a size-limited substituent group, or lower substituent group) or unsubstituted $C_1$-$C_4$ alkyl. In other embodiments, the moieties $R^4$ and $R^5$ are independently hydrogen, methyl, ethyl, propyl, isopropyl, butyl, isobutyl, tert-butyl, propan-1-ol, 2,2-difluorobutane, or 2-fluorobutane.

In other embodiments, $R^4$ and $R^5$ are independently hydrogen or substituted (e.g., substituted with a substituent group, a size-limited substituent group, or lower substituent group) or unsubstituted 2 to 4 membered heteroalkyl. In other embodiments, $R^4$ and $R^5$ are independently hydrogen, 1-methoxypropane, 1-methoxy-2-methylpropane, N,N-dimethylpropan-1-amine, 1-(methylsulfonyl)propane, (2,2-difluorobutyl)-1-oxidane, 1-(1-azaneyl)-2,2-difluoropropan-1-one, methyl(methylimino)(propyl)-6-sulfanone, or 2-methoxy-2-methylbutane.

In other embodiments, $R^4$ and $R^5$ are independently hydrogen or substituted (e.g., substituted with a substituent group, a size-limited substituent group, or lower substituent group) or unsubstituted $C_3$-$C_5$ cycloalkyl. In other embodiments, $R^4$ and $R^5$ are independently hydrogen, cyclobutyl or cyclopentyl.

In other embodiments, $R^4$ and $R^5$ are independently hydrogen, or substituted (e.g., substituted with a substituent group, a size-limited substituent group, or lower substituent group) or unsubstituted $C_3$-$C_7$ heterocycloalkyl. In other embodiments, $R^4$ and $R^5$ are independently hydrogen, pyrrolidinyl, morpholinyl, piperazinyl, azetidinyl, 1,4-piperazin-2-one, piperidinyl, 1,3-imidazolidin-4-one, 1,3-imidazolidine, 6-oxa-2-azaspiro[4.5]decane, tetrahydropyranyl, 2-oxa-5,2-azabicyclo[2.2.1]heptane, (1R,5S)-3-oxa-8-azabicyclo[3.2.1]octane, 2,6-diazaspiro[3,4]octane, 4-thiomorpholine-1,1-dioxide, 4-thiomorpholine-1-oxide, tetrahydro-2H-thiopyran-1,1-oxide, 1-oxa-8-azaspiro[4,5]decane, 1-pyrrolidin-2-one, 1-imidazolidin-4-one, 2,7-diazaspiro[4.4]nolan-1-one, tetrahydro-1H-8-pyrazino[3,4-c][1,4]oxazin-4(3H)-one, or hexahydro-1H-8-pyrazino[3,4-c][1,4]oxazine.

In other embodiments, the moieties $R^4$ and $R^5$ are independently hydrogen, unsubstituted methyl, unsubstituted ethyl, unsubstituted propyl, unsubstituted isopropyl, unsubstituted butyl, unsubstituted isobutyl, unsubstituted tert-butyl, unsubstituted propan-1-ol, unsubstituted 2,2-difluorobutane, or unsubstituted 2-fluorobutane.

In other embodiments, $R^4$ and $R^5$ are independently hydrogen, unsubstituted 1-methoxypropane, unsubstituted 1-methoxy-2-methylpropane, unsubstituted N,N-dimethylpropan-1-amine, unsubstituted 1-(methylsulfonyl)propane, unsubstituted (2,2-difluorobutyl)-1-oxidane, unsubstituted 1-(1-azaneyl)-2,2-difluoropropan-1-one, unsubstituted methyl(methylimino)(propyl)-6-sulfanone, or unsubstituted 2-methoxy-2-methylbutane.

In other embodiments, $R^4$ and $R^5$ are independently hydrogen, unsubstituted cyclobutyl or unsubstituted cyclopentyl.

In other embodiments, $R^4$ and $R^5$ are independently hydrogen, unsubstituted pyrrolidinyl, unsubstituted morpholinyl, unsubstituted piperazinyl, unsubstituted azetidinyl, unsubstituted 1,4-piperazin-2-one, unsubstituted piperidinyl, unsubstituted 1,3-imidazolidin-4-one, unsubstituted 1,3-imidazolidine, unsubstituted 6-oxa-2-azaspiro[4.5]decane, unsubstituted tetrahydropyranyl, unsubstituted 2-oxa-5,2-azabicyclo[2.2.1]heptane, unsubstituted (R,5S)-3-oxa-8-azabicyclo[3.2.1]octane, unsubstituted 2,6-diazaspiro[3,4]octane, unsubstituted 4-thiomorpholine-1,1-dioxide, unsubstituted 4-thiomorpholine-1-oxide, unsubstituted tetrahydro-2H-thiopyran-1,1-oxide, unsubstituted 1-oxa-8-azaspiro[4,5]decane, 1-pyrrolidin-2-one, unsubstituted 1-imidazolidin-4-one, unsubstituted 2,7-diazaspiro[4.4]nolan-1-one, unsubstituted tetrahydro-1H-8-pyrazino[3,4-c][1,4]oxazin-4(3H)-one, or unsubstituted hexahydro-1H-8-pyrazino[3,4-c][1,4]oxazine.

z is an integer from 0 to 6. In embodiments, z is 0. In embodiments, z is 1. In embodiments, z is 2. In embodiments, z is 3. In embodiments, z is 4. In embodiments, z is 5. In embodiments, z is 6.

m is an integer from 0 to 4. In embodiments, m is 0. In embodiments, m is 1. In embodiments, m is 2. In embodiments, m is 3. In embodiments, m is 4.

$X^2$ is halogen. In embodiments, halogen is —F, —Cl, —Br, —I. In embodiments, $X^2$ is —F.
In embodiments, $X^2$ is —Cl. In embodiments, $X^2$ is —Br. In embodiments, $X^2$ is —I.

$X^3$ is halogen. In embodiments, halogen is —F, —Cl, —Br, —I. In embodiments, $X^3$ is —F. In embodiments, $X^3$ is —Cl. In embodiments, $X^3$ is —Br. In embodiments, $X^3$ is —I.

$X^4$ is halogen. In embodiments, halogen is —F, —Cl, —Br, —I. In embodiments, $X^4$ is —F. In embodiments, $X^4$ is —Cl. In embodiments, $X^4$ is —Br. In embodiments, $X^4$ is —I.

$X^5$ is halogen. In embodiments, halogen is —F, —Cl, —Br, —I. In embodiments, $X^5$ is —F. In embodiments, $X^5$ is —Cl. In embodiments, $X^5$ is —Br. In embodiments, $X^5$ is —I.

$X^6$ is halogen. In embodiments, halogen is —F, —Cl, —Br, —I. In embodiments, $X^6$ is —F. In embodiments, $X^6$ is —Cl. In embodiments, $X^6$ is —Br. In embodiments, $X^6$ is —I.

$X^7$ is halogen. In embodiments, halogen is —F, —Cl, —Br, —I. In embodiments, $X^7$ is —F. In embodiments, $X^7$ is —Cl. In embodiments, $X^7$ is —Br. In embodiments, $X^7$ is —I.

In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) or unsubstituted alkyl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) alkyl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently unsubstituted alkyl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted or unsubstituted alkyl (e.g., $C_1$-$C_8$ alkyl, $C_1$-$C_6$ alkyl, or $C_1$-$C_4$ alkyl). In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted alkyl alkyl (e.g., $C_1$-$C_8$ alkyl, $C_1$-$C_6$ alkyl, or $C_1$-$C_4$ alkyl).

In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently unsubstituted alkyl alkyl (e.g., $C_1$-$C_8$ alkyl, $C_1$-$C_6$ alkyl, or $C_1$-$C_4$ alkyl).

In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) or unsubstituted heteroalkyl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) heteroalkyl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently unsubstituted heteroalkyl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted or unsubstituted heteroalkyl (e.g., 2 to 8 membered, 2 to 6 membered, 4 to 6 membered, 2 to 3 membered, or 4 to 5 membered). $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted heteroalkyl (e.g., 2 to 8 membered, 2 to 6 membered, or 2 to 4 membered). In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently an unsubstituted heteroalkyl (e.g., 2 to 8 membered, 2 to 6 membered, or 2 to 4 membered).

In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted (e.g., substituted with a substituent group, a size-limited substituent group, or lower substituent group) or unsubstituted cycloalkyl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted (e.g., substituted with a substituent group, a size-limited substituent group, or lower substituent group) cycloalkyl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently an unsubstituted cycloalkyl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted cycloalkyl (e.g., C$_3$-C$_8$ cycloalkyl, C$_3$-C$_6$ cycloalkyl, or C$_5$-C$_6$ cycloalkyl). In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently unsubstituted cycloalkyl (e.g., C$_3$-C$_8$ cycloalkyl, C$_3$-C$_6$ cycloalkyl, or C$_5$-C$_6$ cycloalkyl).

In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted (e.g., substituted with a substituent group, a size-limited substituent group, or lower substituent group) or unsubstituted heterocycloalkyl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted (e.g., substituted with a substituent group, a size-limited substituent group, or lower substituent group) heterocycloalkyl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently an unsubstituted heterocycloalkyl.

In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted or unsubstituted heterocycloalkyl (e.g., 3 to 8 membered, 3 to 6 membered, or 5 to 6 membered).

In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted heterocycloalkyl (e.g., 3 to 8 membered, 3 to 6 membered, or 5 to 6 membered).

In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently an unsubstituted heterocycloalkyl (e.g., 3 to 8 membered, 3 to 6 membered, or 5 to 6 membered).

In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted (e.g., substituted with a substituent group, a size-limited substituent group, or lower substituent group) or unsubstituted aryl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently substituted (e.g., substituted with a substituent group, a size-limited substituent group, or lower substituent group) aryl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, R$^{9A}$, R$^{9B}$, R$^{10}$, R$^{10A}$, R$^{10B}$, R$^{11}$, R$^{11A}$, R$^{11B}$, R$^{12}$, R$^{12A}$, R$^{12B}$, R$^{13}$, R$^{13A}$, R$^{13B}$, R$^{14}$, R$^{14A}$, R$^{14B}$, R$^{15}$, R$^{5A}$, R$^{15B}$, R$^{16}$, R$^{16A}$, R$^{16B}$, R$^{17}$, R$^{17A}$, R$^{17B}$, R$^{18}$, R$^{18A}$, R$^{18B}$, R$^{19}$, R$^{19A}$, R$^{19B}$, R$^{20}$, R$^{20A}$, R$^{20B}$, R$^{21}$ and R$^{22}$ are independently an unsubstituted aryl. In embodiments, R$^1$, R$^2$, R$^{2A}$, R$^{2B}$, R$^3$, R$^{3A}$, R$^{3B}$, R$^{3.1}$, R$^{3.1A}$, R$^{3.1B}$, R$^{3.2}$, R$^{3.2A}$, R$^{3.2B}$, R$^4$, R$^{4A}$, R$^{4A}$, R$^5$, R$^{5A}$, R$^{5B}$, R$^6$, R$^{6A}$, R$^{6B}$, R$^7$, R$^{7A}$, R$^{7B}$, R$^8$, R$^{8A}$, R$^{8B}$, R$^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted or unsubstituted aryl (e.g., $C_6$-$C_{10}$ aryl, $C_{10}$ aryl, or phenyl). In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted aryl (e.g., $C_6$-$C_{10}$ aryl, $C_{10}$ aryl, or phenyl). $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently an unsubstituted aryl (e.g., $C_6$-$C_{10}$ aryl, $C_{10}$ aryl, or phenyl).

In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) or unsubstituted heteroaryl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted (e.g., substituted with a substituent group, a size-limited substituent group, or lower substituent group) heteroaryl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently an unsubstituted heteroaryl. In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted or unsubstituted heteroaryl (e.g., 5 to 10 membered heteroaryl, 5 to 9 membered heteroaryl, or 5 to 6 membered heteroaryl). In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently substituted heteroaryl (e.g., 5 to 10 membered heteroaryl, 5 to 9 membered heteroaryl, or 5 to 6 membered heteroaryl). In embodiments, $R^1$, $R^2$, $R^{2A}$, $R^{2B}$, $R^3$, $R^{3A}$, $R^{3B}$, $R^{3.1}$, $R^{3.1A}$, $R^{3.1B}$, $R^{3.2}$, $R^{3.2A}$, $R^{3.2B}$, $R^4$, $R^{4A}$, $R^{4A}$, $R^5$, $R^{5A}$, $R^{5B}$, $R^6$, $R^{6A}$, $R^{6B}$, $R^7$, $R^{7A}$, $R^{7B}$, $R^8$, $R^{8A}$, $R^{8B}$, $R^9$, $R^{9A}$, $R^{9B}$, $R^{10}$, $R^{10A}$, $R^{10B}$, $R^{11}$, $R^{11A}$, $R^{11B}$, $R^{12}$, $R^{12A}$, $R^{12B}$, $R^{13}$, $R^{13A}$, $R^{13B}$, $R^{14}$, $R^{14A}$, $R^{14B}$, $R^{15}$, $R^{5A}$, $R^{15B}$, $R^{16}$, $R^{16A}$, $R^{16B}$, $R^{17}$, $R^{17A}$, $R^{17B}$, $R^{18}$, $R^{18A}$, $R^{18B}$, $R^{19}$, $R^{19A}$, $R^{19B}$, $R^{20}$, $R^{20A}$, $R^{20B}$, $R^{21}$ and $R^{22}$ are independently an unsubstituted heteroaryl (e.g., 5 to 10 membered heteroaryl, 5 to 9 membered heteroaryl, or 5 to 6 membered heteroaryl).

Pharmaceutical Compositions

In an aspect, there is provided a pharmaceutical composition, including a compound as described herein, including embodiments (e.g., structural Formulae (I), (II), (II'), (III), (III'), (IV) or (IV')) and a pharmaceutically acceptable excipient. In embodiments, the pharmaceutical compositions are for use in treating a disorder modulated by general control nonderepressable 2 (GCN2) kinase inhibitors. In embodiments, the disorder is cancer.

The compounds as described herein of the present disclosure may be in the form of compositions suitable for administration to a subject. In general, such compositions are "pharmaceutical compositions" comprising a compound (e.g., compounds described herein) and one or more pharmaceutically acceptable or physiologically acceptable excipients (e.g., acceptable diluents or carriers). In certain embodiments, the compounds are present in a therapeutically effective amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of Wnt/catenin signaling pathway, or a compound described herein) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients that are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound described herein contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form.

In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a Wnt/catenin signaling pathway inhibitor, including implants (e.g., implantable pumps) and catheter systems, slow injection pumps and devices, all of which are well known to the skilled artisan.

Depot injections, which are generally administered subcutaneously or intramuscularly, may also be utilized to release a compound disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compounds described herein in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compounds described herein contemplated by the present disclosure may be in the form of any other suitable pharmaceutical composition (e.g., sprays for nasal or inhalation use) currently known or developed in the future.

Methods of Use

In an aspect provided are methods of treating or preventing a disease or disorder mediated by GCN2, including administering to a subject in need thereof a therapeutically effective amount of a compound of Formula (I), (II), (II'), (III), (III'), (IV) or (IV'), or a pharmaceutically acceptable salts thereof. In embodiments of such treatment methods, the disease or disorder is cancer.

In an aspect, there is provided a method of treating or preventing a disease or disorder mediated by GCN2, including administering to a subject in need thereof a therapeutically effective amount of a compound of Formula (I), (II), (II'), (III), (III'), (IV) or (IV'), or pharmaceutically acceptable salts thereof or a pharmaceutical composition as described herein, including embodiments (e.g., structural Formulae (I), (II), (II'), (III), (III'), (IV) or (IV') or a pharmaceutically acceptable salt thereof). In embodiments of such treatment methods, the disease or disorder is cancer.

In accordance with the present disclosure, a compound (e.g., a compound described herein) or pharmaceutical salt thereof can be used to treat or prevent a proliferative condition or disorder, including a cancer, for example, brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In some embodiments, the tumor or cancer is breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma. The use of the term(s) cancer-related diseases, disorders and conditions is meant to refer broadly to conditions that are associated, directly or indirectly, with cancer, and includes, e.g., angiogenesis and precancerous conditions such as dysplasia. In embodiments, the cancer is breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma.

In some embodiments, the present disclosure provides methods for treating a proliferative condition, cancer, tumor, or precancerous condition with a compound described herein and at least one additional therapeutic or diagnostic agent, examples of which are set forth elsewhere herein.

The present disclosure provides methods for treating and/or preventing a proliferative condition, cancer, tumor, or precancerous disease, disorder or condition with a compound described herein.

In embodiments, a disease or disorder mediated by GCN2 is cancer. In certain embodiments, cancer includes, but is not limited to, brain tumor, melanoma, non-small cell lung cancer, bladder cancer, pancreatic cancer, or head and neck cancer.

In embodiments, a method of treating cancer mediated by GCN2 comprises administering to a patient in need thereof a therapeutically effective amount of a compound or pharmaceutical composition as described herein, including embodiments (e.g., structural Formulae (I), (II), (II'), (III), (III'), (IV) or (IV'), or a pharmaceutically acceptable salt thereof).

The present disclosure contemplates the administration of the compounds described herein, and compositions (e.g., pharmaceutical salts, pharmaceutical composition) thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the compounds disclosed herein over a defined period of time. In embodiments, the administration is oral administration. In embodiments, the administration is parenteral administration.

The compounds of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

The GCN2 inhibitors and other immune modulators disclosed herein can be administered by any acceptable route, such oral, intraadiposal, intraarterial, intraarticular, intracranial, intradermal, intralesional, intramuscular, intranasal, intraocular, intrapericardial, intraperitoneal, intrapleural, intraprostatical, intrarectal, intrathecal, intratracheal, intratumoral, intraumbilical, intravaginal, intravenous, intravesicular, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The GCN2 inhibitors disclosed herein may be administered once daily until study reached endpoint. The immune modulator disclosed herein may be administered at least three times but in some studies four or more times depending on the length of the study and/or the design of the study.

The methods disclosed herein may be used in combination with additional cancer therapy. In some embodiments, the distinct cancer therapy comprises surgery, radiotherapy, chemotherapy, toxin therapy, immunotherapy, cryotherapy or gene therapy. In some embodiments, the cancer is a chemotherapy-resistant or radio-resistant cancer.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors.

Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the compounds of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the compounds contemplated by the present disclosure may be administered (e.g., orally) at dosage levels of about 0.01 mg/kg to about 50 mg/kg, or about 1 mg/kg to about 25 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient.

A pharmaceutically acceptable carrier(s), diluent(s) and/or excipient(s) may be present in an amount of from about 0.1 g to about 2.0 g.

In embodiments, the dosage of the desired compound is contained in a "unit dosage form". The phrase "unit dosage form" refers to physically discrete units, each unit including a predetermined amount of a compound (e.g., a compound described herein), sufficient to produce the desired effect. It will be appreciated that the parameters of a unit dosage form will depend on the particular agent and the effect to be achieved.

KITS

In another aspect, provided herein is a kit including a compound described herein or pharmaceutical compositions thereof. The kits are generally in the form of a physical structure housing various components, as described below, and may be utilized, for example, in practicing the methods described above.

A kit may include one or more of the compounds disclosed herein (e.g., provided in a sterile container), which may be in the form of a pharmaceutical composition suitable for administration to a subject. In embodiments, the compound has the structure of Formulae(I), (II), (II'), (III), (III'), (IV) or (IV'), or a pharmaceutically acceptable salt thereof. The compounds described herein can be provided in a form that is ready for use (e.g., a tablet or capsule) or in a form requiring, for example, reconstitution or dilution (e.g., a powder) prior to administration. When the compound is in a form that needs to be reconstituted or diluted by a user, the kit may also include diluents (e.g., sterile water), buffers, pharmaceutically acceptable excipients, and the like, packaged with, or separately from, the compound. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EMBODIMENTS

Embodiment 1. A compound of formula (I):

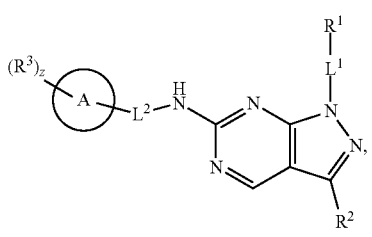

(I)

or a pharmaceutically acceptable salt thereof;
wherein:
z is an integer from 0 to 6;
ring A is substituted or unsubstituted cycloalkyl, or substituted or unsubstituted heterocycloalkyl;
$L^1$ and $L^2$ are independently a bond, substituted or unsubstituted alkylene, or substituted or unsubstituted heteroalkylene;
$R^1$ is substituted or unsubstituted aryl or substituted or unsubstituted heteroaryl;
$R^2$ is independently hydrogen, halogen, $-CX^2_3$, $-CHX^2_2$, $-CH_2X^2$, $-OCX^2_3$, $-OCHX^2_2$, $-OCH_2X2$, $-CN$, $-S(O)_2R^{2A}$, $-SR^{2A}$, $-S(O)R^{2A}$, $-SO_2NR^{2A}R^{2B}$, $-NHC(O)NR^{2A}R^{2B}$, $-N(O)_2$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently halogen, $-CX^3_3$, $-CHX^3_2$, $-CH_2X_3$, $-OCX^3_3$, $-OCHX^3_2$, $-OCH_2X^3$, $-CN$, $-S(O)_2R^{3A}$, $-SR^{3A}$, $-S(O)R^{3A}$, $SO_2NR^{3A}R^{3B}$, $-NHC(O)NR^{3A}R^{3B}$, $-N(O)_2$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-P(O)R^{3A}R^{3B}$, $-C(O)NHNR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ may optionally be joined to form a substituted or unsubstituted heterocycloalkyl or substituted or unsubstituted heteroaryl;

$R^{2A}$, $R^{2B}$, $R^{3A}$, and $R^{3B}$ are independently hydrogen, $-F$, $-Cl$, $Br$, $-I$, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $-CN$, $-SH$, $-SCH_3$, $-SO_2H$, $-SO_2CH_3$, $-SO_2NH_2$, $-SO_2NHCH_3$, $-NHC(O)NH_2$, $-NHC(O)NHCH_3$, $-NO_2$, $-NH_2$, $-NHCH_3$, $-C(O)H$, $-C(O)CH_3$, $-C(O)OH$, $-C(O)OCH_3$, $-C(O)NH_2$, $-C(O)NHCH_3$, $-OH$, $-OCH_3$, $-NHSO_2H$, $-NHSO_2CH_3$, $-NHC(O)H$, $-NCH_3C(O)H$, $-NHC(O)OH$, $-NCH_3C(O)OH$, $-NHOH$, $-NCH_3OH$, $-NCH_3OCH_3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^{2A}$ and $R^{2B}$ may optionally be joined to form a substituted or unsubstituted heterocycloalkyl or substituted or unsubstituted heteroaryl; $R^{3A}$ and $R^{3B}$ may optionally be joined to form a substituted or unsubstituted heterocycloalkyl or substituted or unsubstituted heteroaryl; and $X^2$ and $X^3$ are independently halogen;
with the proviso that when ring A is cyclohexyl, then $R^3$ is not an ortho-substituted $-NH_2$ or $-HNC=(O)t-BuO$, or para-substituted $-NHSO_2CH_2CH_2CF_3$, $-NHSO_2CH_3$, or $-OH$.

Embodiment 2. The compound of embodiment 1, wherein $R^3$ is not a substituted or unsubstituted amine attached to ring A at the ortho position.

Embodiment 3. The compound of embodiment 1, wherein $R^3$ is not attached to ring A at the ortho position.

Embodiment 4. The compound of any one of embodiments 1 to 3, wherein $L^1$ and L2 are a bond.

Embodiment 5. The compound of any one of embodiments 1 to 4, wherein $L^1$ and $L^2$ are independently substituted or unsubstituted $C_1$-$C_8$ alkylene or substituted or unsubstituted 2 to 8 membered heteroalkylene.

Embodiment 6. The compound of any one of embodiments 1 to 5, wherein $L^1$ and $L^2$ are independently unsubstituted $C_1$-$C_8$ alkylene or unsubstituted 2 to 8 membered heteroalkylene.

Embodiment 7. The compound of any one of embodiments 1 to 6, having the formula:

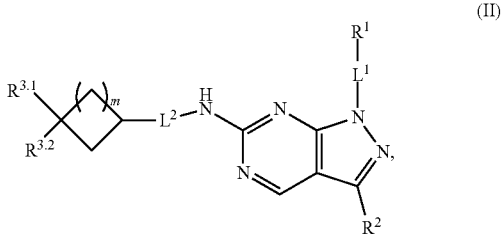

(II)

or a pharmaceutically acceptable salt thereof;
wherein:
m is an integer from 1 to 4;
$R^{3.1}$ is independently hydrogen, halogen, $-CX^{3.1}_3$, $-CHX^{3.1}_2$, $-CH_2X^{3.1}$, $-OCX^{3.1}_3$, $-OCHX^{3.1}_2$, $-OCH_2X^{3.1}$, $-CN$, $-S(O)_2R^{3.1A}$, $-SR^{3.1A}$, $-S(O)R^{3.1A}$, —SO$_2$NR$^{3.1A}$R$^{3.1B}$, —NHC(O)NR$^{3.1A}$R$^{3.1B}$, —N(O)$_2$, —NR$^{3.1A}$R$^{3.1B}$, —NHNR$^{3.1A}$R$^{3.1B}$, —C(O)R$^{3.1A}$, —C(O)OR$^{3.1A}$, —C(O)NR$^{3.1A}$R$^{3.1B}$, —P(O)R$^{3.1A}$R$^{3.1B}$, —C(O)NHNR$^{3.1A}$R$^{3.1B}$, —OR$^{3.1A}$, —NR$^{3.1A}$SO$_2$R$^{3.1B}$, —NR$^{3.1A}$C(O)R$^{3.1B}$, —NR$^{3.1A}$C(O)OR$^{3.1B}$, —NR$^{3.1A}$OR$^{3.1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.1}$ and R$^{3.2}$ may optionally be joined to form a substituted or unsubstituted heterocycloalkyl or substituted or unsubstituted heteroaryl;

R$^{3.2}$ is independently hydrogen, halogen, —CX$^{3.2}_3$, —CHX$^{3.2}_2$, —CH$_2$X$^{3.2}$, —OCX$^{3.2}_3$, —OCHX$^{3.2}_2$, —OCH$_2$X$^{3.2}$, —CN, —S(O)$_2$R$^{3.2A}$, —SR$^{3.2A}$, —S(O)R$^{3.2A}$, —SO$_2$NR$^{3.2A}$R$^{3.2B}$, —NHC(O)NR$^{3.2A}$R$^{3.2B}$, —N(O)$_2$, —NR$^{3.2A}$R$^{3.2B}$, —NHNR$^{3.2A}$R$^{3.2B}$, —C(O)R$^{3.2A}$, —C(O)OR$^{3.2A}$, —C(O)NR$^{3.2A}$R$^{3.2B}$, —P(O)R$^{3.2A}$R$^{3.2B}$, —C(O)NHNR$^{3.2A}$R$^{3.2B}$, —OR$^{3.2A}$, —NR$^{3.2A}$SO$_2$R$^{3.2B}$, —NR$^{3.2A}$C(O)R$^{3.2B}$, —NR$^{3.2A}$C(O)OR$^{3.2B}$, —NR$^{3.2A}$OR$^{3.2B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.1}$ and R$^{3.2}$ may optionally be joined to form a substituted or unsubstituted heterocycloalkyl or substituted or unsubstituted heteroaryl; and R$^{3.1A}$, R$^{3.1B}$, R$^{3.2A}$, and R$^{3.2B}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; R$^{3.1A}$ and R$^{3.1B}$ may optionally be joined to form a substituted or unsubstituted heterocycloalkyl or substituted or unsubstituted heteroaryl; R$^{3.2A}$ and R$^{3.2B}$ may optionally be joined to form a substituted or unsubstituted heterocycloalkyl or substituted or unsubstituted heteroaryl.

Embodiment 8. The compound of any one of embodiments 1 to 7 having the formula:

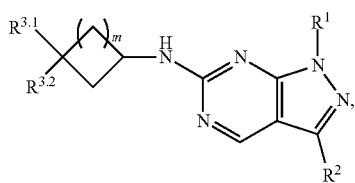

(III)

or a pharmaceutically acceptable salt thereof.

Embodiment 9. The compound of any one of embodiments 1 to 8, wherein: ring A is R$^6$-substituted or unsubstituted C$_4$-C$_7$ cycloalkyl, or R$^6$-substituted or unsubstituted 4- to 7-membered heterocycloalkyl; R$^6$ is independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl.

Embodiment 10. The compound of any one of embodiments 1 to 7, having the formula:

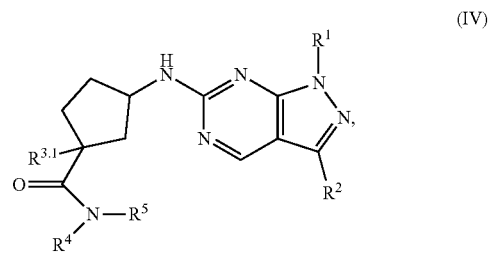

(IV)

wherein:

R$^4$ and R$^5$ are independently hydrogen, substituted or unsubstituted C$_1$-C$_8$ alkyl, substituted or unsubstituted 2 to 8 membered heteroalkyl, substituted or unsubstituted C$_3$-C$_8$ cycloalkyl, or substituted or unsubstituted 3 to 8 membered heterocycloalkyl;

wherein R$^4$ and R$^5$ may optionally be joined to form a substituted or unsubstituted C$_3$-C$_8$ cycloalkyl, substituted or unsubstituted 3 to 8 membered heterocycloalkyl or substituted or unsubstituted 5 or 6 membered heteroaryl.

Embodiment 11. The compound of any one of embodiments 1 to 10, wherein R$^4$ and R$^5$ are independently hydrogen or substituted or unsubstituted C$_1$-C$_4$ alkyl.

Embodiment 12. The compound of any one of embodiments 1 to 11, wherein R$^4$ and R$^5$ are independently hydrogen, methyl, ethyl, propyl, isopropyl, butyl, isobutyl, tert-butyl, propan-1-ol, 2,2-difluorobutane, or 2-fluorobutane.

Embodiment 13. The compound of any one of embodiments 1 to 12, wherein R$^4$ and R$^5$ are independently hydrogen or substituted or unsubstituted 2 to 4 membered heteroalkyl.

Embodiment 14. The compound of any one of embodiments 1 to 13, wherein R$^4$ and R$^5$ are independently hydrogen, 1-methoxypropane, 1-methoxy-2-methylpropane, N,N-dimethylpropan-1-amine, 1-(methylsulfonyl)propane, (2,2-difluorobutyl)-1-oxidane, 1-(1-azaneyl)-2,2-difluoropropan-1-one, methyl(methylimino)(propyl)-6-sulfanone, or 2-methoxy-2-methylbutane.

Embodiment 15. The compound of any one of embodiments 1 to 10, wherein R$^4$ and R$^5$ are independently hydrogen or substituted or unsubstituted C$_3$-C$_5$ cycloalkyl.

Embodiment 16. The compound of any one of embodiments 1 to 15, wherein R$^4$ and R$^5$ are independently hydrogen, cyclobutyl or cyclopentyl.

Embodiment 17. The compound of any one of embodiments 1 to 10, wherein $R^4$ and $R^5$ are independently hydrogen, or substituted or unsubstituted $C_3$-$C_7$ heterocycloalkyl.

Embodiment 18. The compound of any one of embodiments 1 to 17, wherein $R^4$ and $R^5$ are independently hydrogen, pyrrolidinyl, morpholinyl, piperazinyl, azetidinyl, 1,4-piperazin-2-one, piperidinyl, 1,3-imidazolidin-4-one, 1,3-imidazolidine, 6-oxa-2-azaspiro[4.5]decane, tetrahydropyranyl, 2-oxa-5,2-azabicyclo[2.2.1]heptane, (1R,5S)-3-oxa-8-azabicyclo[3.2.1]octane, 2,6-diazaspiro[3,4]octane, 4-thiomorpholine-1,1-dioxide, 4-thiomorpholine-1-oxide, tetrahydro-2H-thiopyran-1,1-oxide, 1-oxa-8-azaspiro[4,5]decane, 1-pyrrolidin-2-one, 1-imidazolidin-4-one, 2,7-diazaspiro[4.4]nolan-1-one, tetrahydro-1H-8-pyrazino[3,4-c][1,4]oxazin-4(3H)-one, or hexahydro-1H-8-pyrazino[3,4-c][1,4]oxazine.

Embodiment 19. The compound of any one of embodiments 1 to 18, wherein:

$R^1$ is $R^7$-substituted or unsubstituted $C_6$-$C_{10}$ aryl or $R^7$-substituted or unsubstituted 5 to 10 membered heteroaryl;

$R^7$ is independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$ substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

Embodiment 20. The compound of any one of embodiments 1 to 19, wherein:

$R^1$ is $R^{7.4}$-substituted or unsubstituted phenyl or $R^{7.4}$-substituted or unsubstituted quinolone.

Embodiment 21. The compound of any one of embodiments 1 to 20, or a pharmaceutically acceptable salt thereof, wherein $R^2$ is halogen or substituted or unsubstituted $C_1$-$C_2$-alkyl.

Embodiment 22. The compound of any one of embodiments 1 to 21, wherein $R^2$ is halogen.

Embodiment 23. The compound of any one of embodiments 1 to 22, wherein halogen is Cl or Br.

Embodiment 24. The compound of any one of embodiments 1 to 21, wherein $R^2$ is substituted or unsubstituted $C_1$-$C_2$-alkyl.

Embodiment 25. The compound of any one of embodiments 1 to 24, wherein $R^2$ is methyl.

Embodiment 26. A pharmaceutical composition comprising a compound of any one of embodiments 1 to 25, and a pharmaceutically acceptable excipient.

Embodiment 27. The pharmaceutical composition of embodiment 26 for use in treating a disorder modulated by general control nonderepressable 2 (GCN2) kinase inhibitors.

Embodiment 28. The pharmaceutical composition of embodiment 26 or 27, wherein the disorder is cancer.

Embodiment 29. A method of treating or preventing a disease or disorder mediated by GCN2, comprising administering to a subject in need thereof a therapeutically effective amount of a compound of any one of embodiments 1 to 25.

Embodiment 30. A method of treating or preventing a disease or disorder mediated by GCN2, comprising administering to a subject in need thereof a therapeutically effective amount of a pharmaceutical composition of embodiment 26.

Embodiment 31. The method of embodiment 29 or 30, comprising administering a compound of Formula (I).

Embodiment 32. The method of embodiment 31, comprising administering a compound of Formula (II).

Embodiment 33. The method of embodiment 31, comprising administering a compound of Formula (III).

Embodiment 34. The method of embodiment 31, comprising administering a compound of Formula (IV).

Embodiment 35. The method of any one of embodiments 29 to 34, wherein the disease or disorder is cancer.

Embodiment 36. The method of embodiment 35, wherein the cancer is melanoma, non-small cell lung cancer, bladder cancer, pancreatic cancer, head and neck cancer or brain tumor.

VI. General Synthetic Methods

Synthesis of Precursor I:

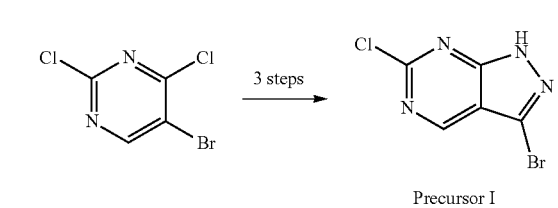 [SMILES: Clc1ncc(Br)c(Cl)n1 ; Clc1ncc2c(Br)n[nH]c2n1]

Precursor I

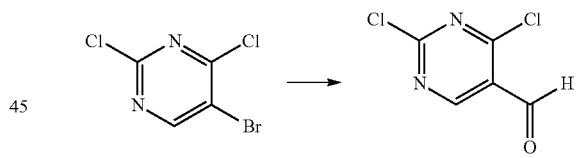

To a solution of 5-bromo-2,4-dichloropyrimidine (30.0 g, 132 mmol) in THF (310 mL) was added iPrMgC—LiCl complex (1.3 M in THF, 112 mL, 1.1 eq) dropwise, over 30 minutes, at −78° C. The reaction mixture was stirred for 15 minutes at −78° C. after addition completed and then warmed to −42° C. for 30 minutes. The reaction mixture was cooled to −78° C. again and a solution of N-formylmorpholine (46.2 g, 3 eq) in THF (180 mL) was added dropwise, over 45 minutes, at −78° C. The reaction was stirred at −78° C. for 10 minutes, warmed to −42° C., and stirred for 3 hours, monitoring by NMR. When most of the starting material was consumed, the reaction was poured into a flask containing 1N aq HCl (750 mL) at 0° C., 500 mL of $Et_2O$ was added and the layers were separated. The aqueous phase was extracted with $Et_2O$ (500 mL) then the combined organic phase was dried over $Na_2SO_4$, filtered, and concentrated via rotary evaporation. The crude product was purified by normal-phase column chromatography on silica gel (dichloromethane) to afford 2,4-dichloropyrimidine-5-carbaldehyde as a white solid (20.2 g, 87% yield). ¹HNMR (400 MHz, CDCl₃) δ (ppm): 10.38 (s, 1H), 9.03 (s, 1H).
Step 2.

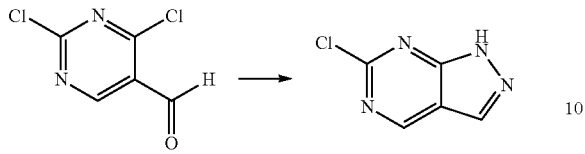

To a solution of 2,4-dichloropyrimidine-5-carbaldehyde (20.2 g, 114 mmol) in THF (530 mL) at 0° C. was added a chilled solution of hydrazine hydrate (11.5 g, 2 eq) in THF (230 mL) over 5 minutes. The reaction mixture was stirred 10 minutes at 0° C. and 1 hour at room temperature. It was then diluted with EtOAc and H₂O and the layers were separated. The aqueous layer was extracted with EtOAc then the combined organic phase was dried over Na₂SO₄, filtered, and concentrated. The crude product was purified by normal-phase column chromatography on silica gel (50% EtOAc/hexanes) to afford 6-chloro-H-pyrazolo[3,4-d]pyrimidine as a light-yellow solid (8.8 g, 50% yield). 1HNMR (400 MHz, CD₃OD) δ (ppm): 9.17 (s, 1H), 8.30 (s, 1H).
Step 3.

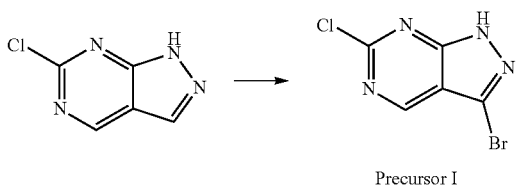 [SMILES: Clc1ncc2cn[nH]c2n1 ; Clc1ncc2c(Br)n[nH]c2n1]

Precursor I

To a solution of 6-chloro-1H-pyrazolo[3,4-d]pyrimidine (8.8 g, 56.9 mmol) in DMF (190 mL) was added NBS (12.2 g, 1.2 eq) and stirred overnight at room temperature. Most of the DMF was removed under vacuum and the crude mixture was diluted with EtOAc (500 mL) then washed with H₂O. The aqueous layer was extracted with EtOAc (250 mL) then the combined organic phase was dried over Na₂SO₄, filtered, and concentrated. The crude product was purified by normal-phase column chromatography on silica gel (20% EtOAc/hexanes) to afford 3-bromo-6-chloro-1H-pyrazolo[3,4-d]pyrimidine (Precursor I) as a light-yellow solid (11.1 g, 50% yield). 1HNMR (400 MHz, CD₃OD) δ (ppm): 9.01 (s, 1H).

Synthesis of Precursor II and III:

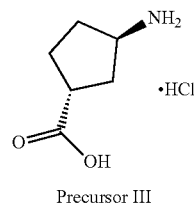

Precursor III

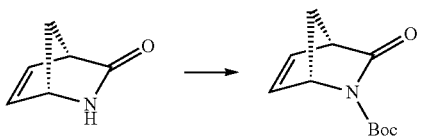 [SMILES: O=C1N[C@@H]2C=C[C@@H]1C2 ; CC(C)(C)OC(=O)N1C(=O)[C@@H]2C=C[C@@H]1C2]

To a solution of (1S,4R)-2-azabicyclo[2.2.1]hept-5-en-3-one (100 g, 916 mmol) in pyridine (240 mL) was added DMAP (117.5 g, 962 mmol) and (Boc)₂O (240 g, 1.1 mol) in pyridine (100 mL). The reaction mixture was stirred at room temperature for 3 hours. The pyridine was removed under reduced pressure and the residue was diluted with EtOAc then neutralized with a 1 N aqueous HCL solution to pH=7. The two layers were separated and the aqueous layer was extracted with EtOAc. The combined organic extracts were washed with brine, dried over Na₂SO₄, filtered, and concentrated. The crude residue was purified by column chromatography (20% EtOAc/hexanes) to afford tert-butyl (S,4R)-3-oxo-2-azabicyclo[2.2.1]hept-5-ene-2-carboxylate as a solid (194.7 g, 100%).
Step 2.

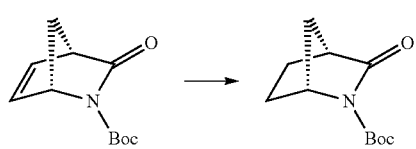 [SMILES: CC(C)(C)OC(=O)N1C(=O)[C@@H]2C=C[C@@H]1C2 ; CC(C)(C)OC(=O)N1C(=O)[C@@H]2CC[C@@H]1C2]

To a suspension of tert-butyl (S,4R)-3-oxo-2-azabicyclo [2.2.1]hept-5-ene-2-carboxylate (194.7 g, 916 mmol) in MeOH (1.5 L) was added Pd/C (10%, 6.5 g). The mixture was stirred under an atmosphere of hydrogen at room temperature until TLC and LC-MS revealed complete conversion of the starting material. The mixture was filtered over celite, and the filtrate was concentrated to give the crude tert-butyl (1R,4S)-3-oxo-2-azabicyclo[2.2.1]heptane-2-carboxylate (194.6 g, 100%).
Step 3.

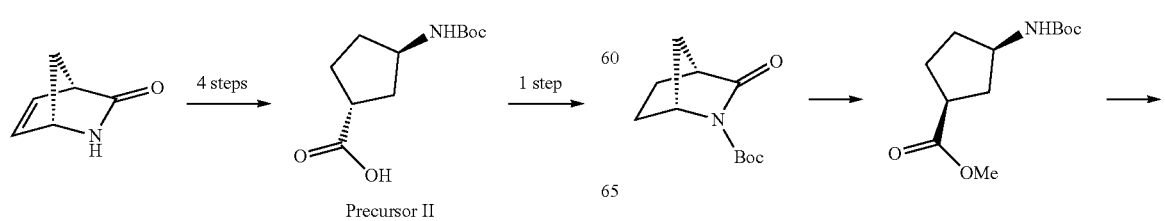

Precursor II

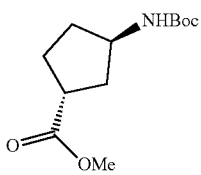

Tert-butyl (1R,4S)-3-oxo-2-azabicyclo[2.2.1]heptane-2-carboxylate (194.6 g, 916 mmol) was dissolved in dry MeOH (750 mL). To the suspension was added NaOMe (42 mL, 25 wt % in MeOH, 183 mmol) under N$_2$, and the reaction mixture was stirred at room temperature for 3 hours. Both TLC and LC-MS revealed the complete conversion of the starting material. More NaOMe (80 mL, 352 mmol) was added, and the mixture was stirred at 50° C. overnight to result an equilibrium mixture of cis- and trans-ester. The MeOH was removed under reduced pressure, the residue was diluted with EtOAc, cooled to 0° C. and neutralized to pH 6-7 with 1.0 M aqueous HCl solution. The two layers were separated and the aqueous layer was extracted with EtOAc. The combined organic extracts were washed with brine, dried over Na$_2$SO$_4$, and concentrated by rotary evaporation. The crude product was purified by normal-phase column chromatography on silica gel (7.5% acetone in hexanes) to afford the pure product methyl (1R,3R)-3-((tert-butoxycarbonyl)amino)cyclopentane-1-carboxylate (59.7 g, 27% yield).

Step 4.

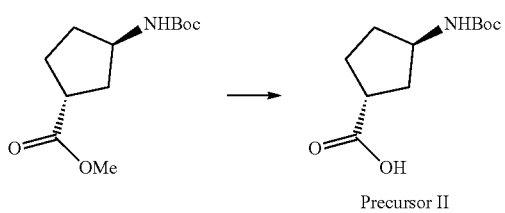

Precursor II

To a solution of methyl (1R,3R)-3-((tert-butoxycarbonyl)amino)cyclopentane-1-carboxylate (59.7 g, 245.6 mmol) in MeOH (600 mL) was added a 2 N aqueous NaOH solution (245.5 mL, 491 mmol). The reaction mixture was stirred at room temperature for 2 hours. TLC and LC-MS revealed complete hydrolysis of the ester. MeOH was removed under reduced pressure then the residue was diluted with EtOAc, cooled to 0° C., and carefully acidified to pH 2-3 with 1 N aqueous HCl. The two layers were separated and the aqueous layer was extracted with EtOAc. The combined organic extracts were washed with brine, dried over Na$_2$SO$_4$, filtered, and concentrated under rotary evaporation to afford (R,3R)-3-((tert-butoxycarbonyl)amino)cyclopentane-1-carboxylic acid (Precursor II) as a white solid (54.2 g, 96%).

Step 5.

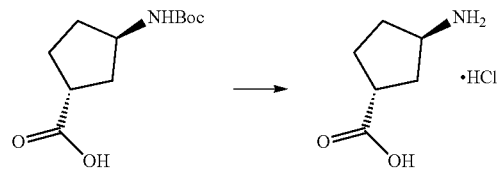

Precursor III (1R,3R)-3-((tert-butoxycarbonyl)amino)cyclopentane-1-carboxylic acid (30.0 g, 131 mmol) was dissolved in TFA/CH$_2$Cl2 (150 mL, 1:1 (v/v)) and the mixture was stirred at room temperature for 2 hours. TLC and LC-MS revealed the complete conversion of the starting material. The reaction was concentrated under rotary evaporation. The TFA salt of the amino acid was converted to its HCl salt by treatment with HCl in dioxane. The resulting mixture was filtered, the solid was washed with ether, and dried to afford (1R,3R)-3-aminocyclopentane-1-carboxylic acid (Precursor III) hydrochloride (20.7 g, 95%).

Synthesis of Precursor IV:

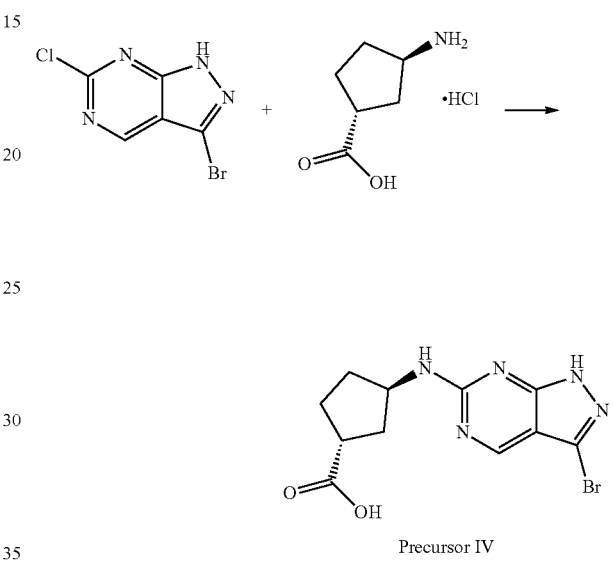

Precursor IV

To a suspension of 3-bromo-6-chloro-1H-pyrazolo[3,4-d]pyrimidine (10 g, 42.84 mmol) and (1R,3R)-3-amino-cyclopentanecarboxylic acid hydrochloride (7.8 g, 47.12 mmol) in ethanol (70 mL) was added diisopropyletheylamine (22.43 mL, 128.51 mmol). The resulting mixture was stirred at 70° C. for 18 hours. The reaction was concentrated via rotary evaporation and to the vicious oil was added water and acidified to pH 5 with 1 M aqueous HCl solution. A white solid precipitated out and was filtered, washed with water, washed with DCM and allowed to dry in the open air to afford (1R,3R)-3-[(3-bromo-H-pyrazolo[3,4-d]pyrimidin-6-yl)amino]cyclopentanecarboxylic acid (Precursor IV) as a light-yellow solid as (10.8 g, 33.11 mmol, 77% yield).

Synthesis of Precursor V:

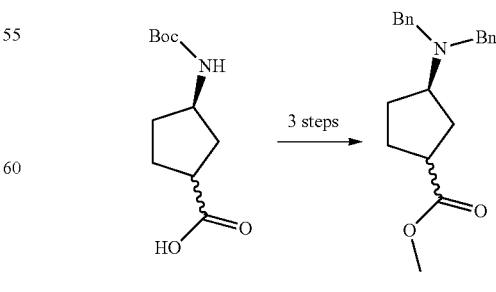

Precursor V

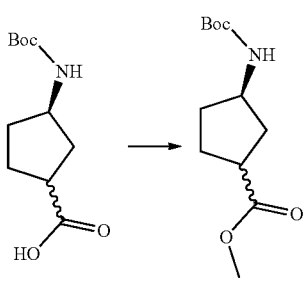 [SMILES: CC(C)(C)OC(=O)N[C@@H]1CCC(C(=O)O)C1 ; COC(=O)C1CC[C@@H](NC(=O)OC(C)(C)C)C1]

To a 50-mL round bottom flask was added Boc-3-aminocyclopentane carboxylic acid (1.5 g, 6.5 mmol). The material was dissolved in DCM (26.3 mL) and methanol (6.4 mL), cooled to 0° C. and then (trimethylsilyl)diazomethane (3.3 mL, 6.5 mmol) was added dropwise. The reaction mixture was slowly warmed and stirred for 1 h. The crude mixture was concentrated in vacuo to get a colorless oil and taken forward without further purification.
Step 2:

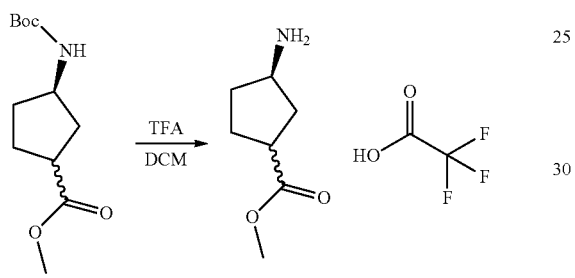

To a vial of methyl 3-(tert-butoxycarbonylamino)cyclopentanecarboxylate (1.6 g, 6.6 mmol) was added DCM (21.9 mL) and then trifluoroacetic acid (2.52 mL, 32.9 mmol). The mixture was stirred for 1 h then concentrated in vacuo 3 times with DCM as rinse to remove excess TFA. The crude material was taken forward without further purification.
Step 3:

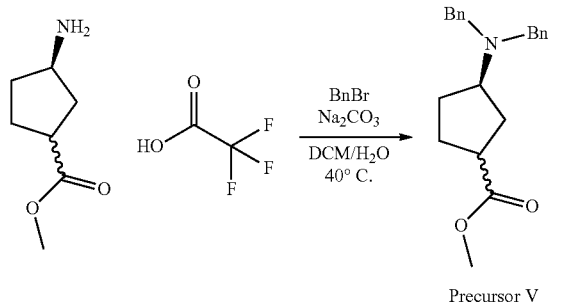

To a 50-mL round bottom flask containing 2,2,2-trifluoroacetic acid salt of methyl 3-aminocyclopentanecarboxylate (3.0 g, 11.7 mmol) was added DCM (29 mL) then sodium carbonate (3.1 g, 29.2 mmol) in water (9 mL). To this mixture was added benzyl bromide (2.77 mL, 23.3 mmol) and then heated to reflux and stirred for 6 h. The reaction mixture was cooled, diluted with water (50 mL), and extracted with EtOAc (3×20 mL). The combined organic extracts were dried over anhydrous Na₂SO₄, filtered, concentrated in vacuo, adsorbed onto silica gel and purified by flash chromatography using 0-20% EtOAc/hexanes gradient. The desired product (Precursor V) was obtained in 41% yield over 3 steps (1.5 g).

Synthesis of (2-methyl-5-(4-(4,4,5,5-tetramethyl-1,3,2-dioxaborolan-2-yl)phenyl)-1,3,4-thiadiazole) (Precursor VI) and ([4-(5-methyl-1,3,4-thiadiazol-2-yl)phenyl]boronic acid (Precursor VII)

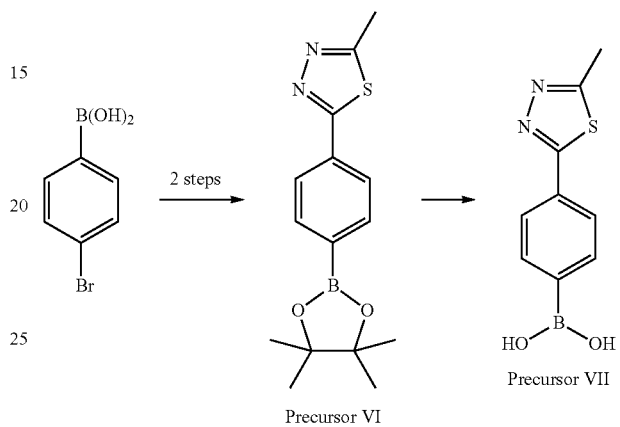

Step 1: N—

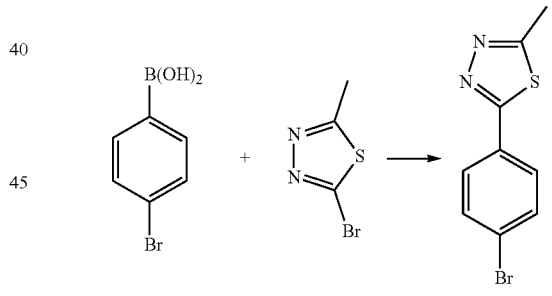

10 g (49.8 mmol) of 4-Bromophenylboronic acid was mixed with 8.92 g (49.8 mmol) of 2-bromo-5-methyl-1,3,4-thiadiazole, and 3.64 g (4.98 mmol) of 1,1'-bis(diphenylphosphino)ferrocene-palladium(II) dichloride. 200 mL of toluene/ethanol mixture was added to the reaction mixture, followed by 100 mL of 1M sodium carbonate. Reaction mixture was heated at 90° C. for 18 hours. After the reaction was complete (followed by LCMS) additional 100 mL of water and 300 mL of Ethyl acetate were added and partitioned. Aqueous layer was washed two more times with 150 mL of ethyl acetate. Combined organic layer was dried with magnesium sulfate, filtered through celite, concentrated and purified on silica using hexanes/ethyl acetate. 12.7 g of 2-(4-bromophenyl)-5-methyl-1,3,4-thiadiazole was isolated in 78% yield. If needed additional crystallization step can be performed using ethanol as a solvent.

Step 2:

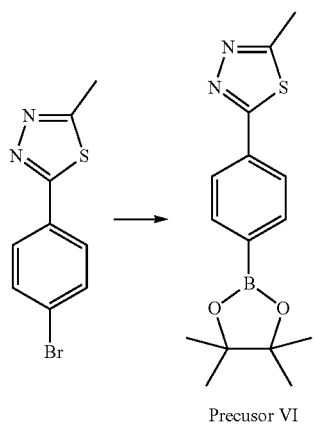

Precusor VI 4.4 (17.2 mmol) g of 2-(4-bromophenyl)-5-methyl-1,3,4-thiadiazole was placed in a pressure vial followed by 6.57 g (25.9 mmol) of bis(pinacolato)diboron, 1.26 g (1.72 mmol) of Pd(dppf)Cl$_2$, and 5.08 g (51.7 mmol) of anhydrous potassium acetate. 100 mL of anhydrous 1,4-dioxane was added to the mixture, the vial was sealed and heated at 90° C. for 18 hrs. Then the solvent was removed under reduced pressure and residue purified on silica using ethyl acetate hexanes. 4 g of 2-methyl-5-(4-(4,4,5,5-tetramethyl-1,3,2-dioxaborolan-2-yl)phenyl)-1,3,4-thiadiazole (Precursor VI) was obtained (76% yield).

Hydrolysis of 2-methyl-5-(4-(4,4,5,5-tetramethyl-1,3,2-dioxaborolan-2-yl)phenyl)-1,3,4-thiadiazole

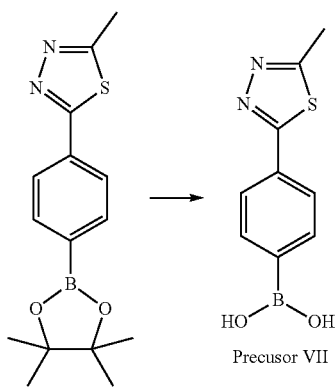

Precusor VII 2-methyl-5-[4-(4,4,5,5-tetramethyl-1,3,2-dioxaborolan-2-yl)phenyl]-1,3,4-thiadiazole (9.44 g, 31.22 mmol), sodium periodate (16.86 g, 78.05 mmol), and ammonium acetate (8.59 mL, 109.28 mmol) were dissolved in acetone (85 mL) and water (8.5 mL). The reaction mixture was stirred overnight at ambient temperature. The reaction mixture was acidified with concentrated hydrochloric acid, and the precipitate was filtered and collected to provide [4-(5-methyl-1,3,4-thiadiazol-2-yl)phenyl]boronic acid (Precursor VII) (2.751 g, 12.501 mmol, 40% yield) as a brown solid. $^1$H NMR (400 MHz, CD$_3$OD): δ 7.91 (m, 2H), 7.75 (m, 2H), 3.35 (s, 2H), 2.82 (s, 3H) ppm.

Synthesis of 3-(2-(5-methyl-1,3,4-thiadiazol-2-yl)-5-(4,4,5,5-tetramethyl-1,3,2-dioxaborolan-2-yl)phenyl)propanenitrile (Precursor VIII)

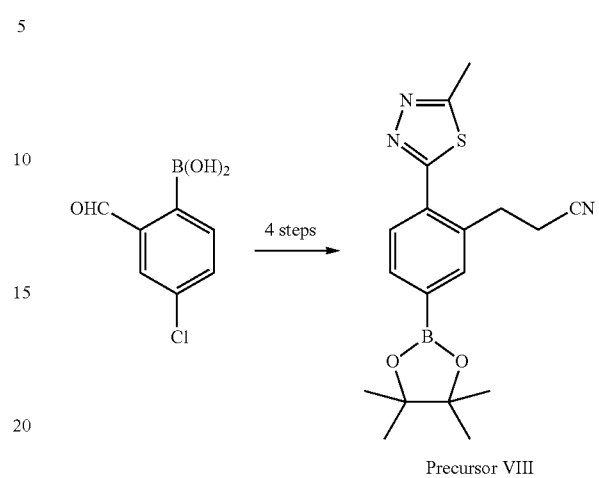

Precursor VIII

Step 1:

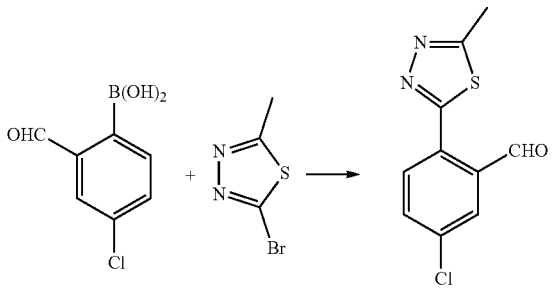

10 g (54.2 mmol) of (4-chloro-2-formylphenyl)boronic acid was mixed with 9.71 g (54.2 mmol) of 2-bromo-5-methyl-1,3,4-thiadiazole, 3.97 g (5.42 mmol) of 1,1'-bis(diphenylphosphino)ferrocene-palladium(II) dichloride, and 17.2 g (163 mmol) of sodium carbonate. 150 mL of 1,4-dioxane and 30 mL of water was added. The reaction mixture was heated at 80° C. until LCMS showed complete conversion. The mixture was diluted with additional 20 mL of water and extracted with ethyl acetate 3 times. Combined organic layer was dried over magnesium sulfate, filtered through celite, and purified on silica using ethyl acetate and hexanes. 5-Chloro-2-(5-methyl-1,3,4-thiadiazol-2-yl)benzaldehyde was isolated as yellow solid (6.6 g, 51% yield).

Step 2:

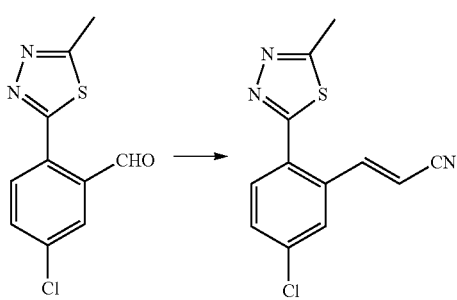 [SMILES: Cc1nnc(-c2ccc(Cl)cc2C=O)s1 ; Cc1nnc(-c2ccc(Cl)cc2/C=C/C#N)s1]

Sodium hydride (4.53 g, 113.2 mmol) was suspended in THF (250 mL) and cooled to 0° C. under nitrogen. Diethyl cyanomethyl phosphonate (15.77 mL, 97.03 mmol) was added dropwise and stirred 15 minutes. 5-chloro-2-(5-methyl-1,3,4-thiadiazol-2-yl)benzaldehyde (19.3 g, 80.86 mmol) was dissolved in THF (350 mL) and was cannulated into the reaction mixture. The reaction was stirred at 0° C. for 15 min and warmed to room temperature. After TLC (50% EtOAc/hexanes) showed no more starting material left and two new UV active spots (E/Z isomers) the reaction was quenched by the addition of saturated aqueous ammonium chloride solution and extracted with EtOAc (×3). The combined organic phase was washed with brine solution, dried over anhydrous sodium sulfate, and concentrated under reduced pressure. The crude product was used in the next step without purification.

Step 3:

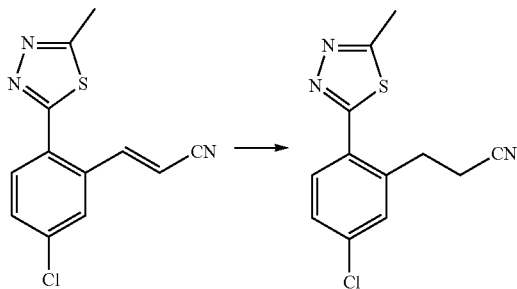 [SMILES: Cc1nnc(-c2ccc(Cl)cc2/C=C/C#N)s1 ; Cc1nnc(-c2ccc(Cl)cc2CCC#N)s1]

12.9 (49.29 mmol) g of E/Z mixture of 5-chloro-2-(5-methyl-1,3,4-thiadiazol-2-yl)phenyl)acrylonitrile was suspended in THF (250 mL) and cooled to −78° C. Super-Hydride (54.22 mL, 54.22 mmol) was added over 5 mins and stirred for additional 5 min. LCMS shows a new peak corresponding to the desired product mass and no starting material. The reaction was warmed to 0° C. and carefully quenched with water. A solution of 1M aqueous NaOH was added until pH=12 and the mixture was extracted with dichloromethane (×3). The combined organic phase was washed with brine solution, dried over anhydrous sodium sulfate, and concentrated under reduced pressure. The crude product was purified by flash chromatography using ethyl acetate and hexanes yielding 3-[5-chloro-2-(5-methyl-1,3,4-thiadiazol-2-yl)phenyl]propanenitrile (7.7 g, 29.194 mmol, 59.233% yield).

Step 4:

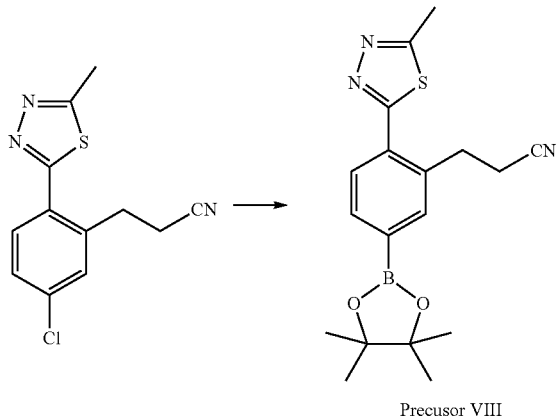 [SMILES: Cc1nnc(-c2ccc(Cl)cc2CCC#N)s1 ; Cc1nnc(-c2ccc(B3OC(C)(C)C(C)(C)O3)cc2CCC#N)s1]

Precusor VIII

Bis(dibenzylideneacetone) palladium(0) (336 mg, 0.5800 mmol) and XPhos (1.11 g, 2.34 mmol) were added to a mixture of 3-[5-chloro-2-(5-methyl-1,3,4-thiadiazol-2-yl)phenyl]propanenitrile (7.7 g, 29.19 mmol), bis(pinacolato) diboron (8.9 g, 35.03 mmol), and potassium acetate (8.6 g, 87.58 mmol) in 1,4-Dioxane (265.5172 mL) under nitrogen gas. The reaction was started at room temperature and heated at 90° C. for 2.5 h. The crude product was loaded directly onto silica gel and purified by flash chromatography (using hexanes and ethyl acetate yielding 3-[2-(5-methyl-1,3,4-thiadiazol-2-yl)-5-(4,4,5,5-tetramethyl-1,3,2-dioxaborolan-2-yl)phenyl]propanenitrile (8.4 g, 23.645 mmol, 81% yield). $^1$H NMR (400 MHz, Chloroform-d): δ 7.85 (s, 1H), 7.78 (d, J=7.7, 1H), 7.55 (d, J=7.7 Hz, 1H), 3.32 (t, J=7.4 Hz, 2H), 2.84 (s, 3H), 2.83 (t, J=7.4 Hz, 2H), 1.37 (s, 12H) ppm.

Synthesis of 3-Methyl-6-(4,4,5,5-tetramethyl-1,3,2-dioxaborolan-2-yl)quinazolin-4(3H)-one (Precursor IX)

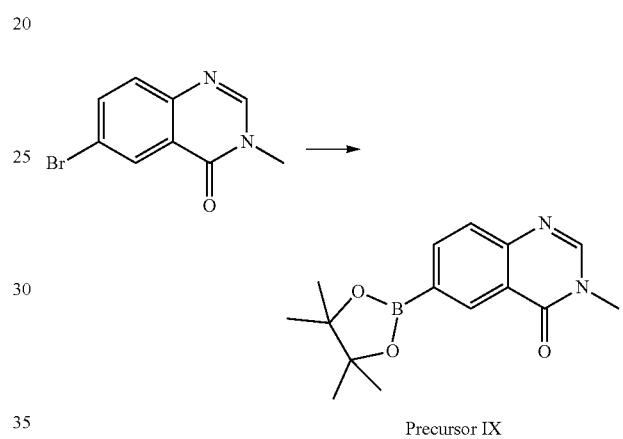

Precursor IX

To the 500 mL round-bottom flask were added 6-bromo-3-methylquinazolin-4(3H)-one (10 grams, 41 mmol), bis (pinacolato)diboron (12.7 grams, 50 mmol), Pd(dppf) Cl$_2$.DCM (1.7 grams, 2 mmol), potassium acetate (12.3 grams, 12 mmol) and 1,4-dioxane (236 mL). After being briefly stirred for several minutes, the reaction mixture was degassed using sonicator, subject to vacuum and then purged with nitrogen. This vacuum/nitrogen cycle was performed for three times. The reaction mixture was then heated at 100° C. Reaction is complete after 1 hour and no starting material remained according to LCMS. The reaction mixture was filtered through sand using filter paper, concentrated and purified on silica using ethyl acetate and hexanes. The product was obtained in 85% yield. $^1$H NMR (400 MHz, Chloroform-d): δ 8.78 (d, J=1.5 Hz, 1H), 8.12 (dd, J=8.1, 1.5 Hz, 1H), 8.07 (s, 1H), 7.66 (d, J=8.1 Hz, 1H), 3.59 (s, 3H), 1.36 (s, 12H) ppm.

Synthesis of 2-(Azetidin-1-yl)-6-(4,4,5,5-tetramethyl-1,3,2-dioxaborolan-2-yl)quinazoline (Precursor X)

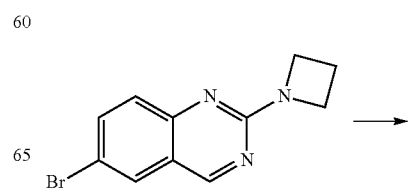

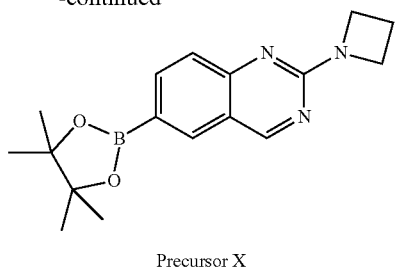

Precursor X

Step 1:

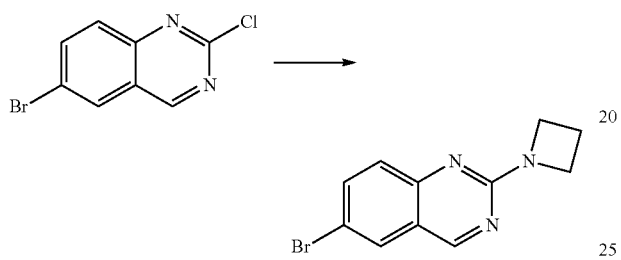

6-Bromo-2-chloroquinazoline (300 mg, 1.2 mmol), azetidine HCl salt (173 mg, 1.85 mmol), triethylamine (1.72 mL, 12.3 mmol) and 1,4-dioxane (10 mL) were added to the 25 mL microwave vial. The reaction mixture was heated in microwave reactor at 120° C. for 40 minutes. By LCMS targeted molecule was formed while some unreacted starting material was still remaining (the ratio between targeted molecule and starting material is about 2:1 by LCMS). The reaction mixture was concentrated and purified on silica using ethyl acetate and hexanes. 2-(Azetidin-1-yl)-6-bromoquinazoline was obtained in 14% yield. 1H NMR (400 MHz, Chloroform-d): δ 8.87 (s, 1H), 7.75 (d, J=2.3 Hz, 1H), 7.67 (dd, J=9.1, 2.3 Hz, 1H), 7.44 (d, J=9.0 Hz, 1H), 4.24 (t, J=7.5 Hz, 4H), 2.40 (p, J=7.5 Hz, 2H) ppm.

Step 2:

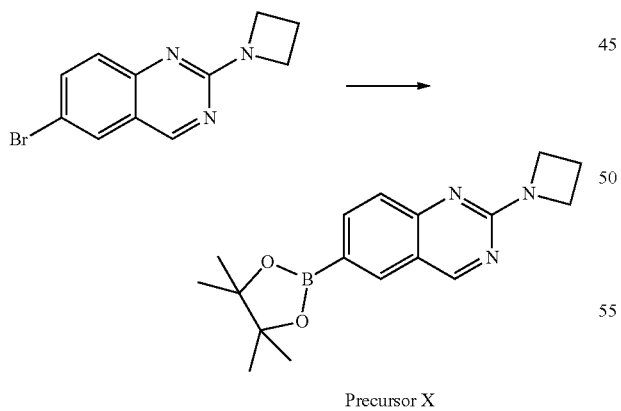

Precursor X

To the 10 mL reaction vial were added 2-(azetidin-1-yl)-6-bromoquinazoline (47 mg, 0.18 mmol), bis(pinacolato)diboron (54 mg, 0.21 mmol), Pd(dppf)Cl2.DCM (7 mg, 0.01 mmol), potassium acetate (52 mg, 0.53 mmol) and 1,4-dioxane (2 mL). After brief stirring for 1 minute, the reaction mixture was degassed using sonicator, subject to vacuum and then purged with nitrogen. This vacuum/nitrogen cycle was performed for three times. The reaction mixture was then heated at 100° C. After 40 minutes, targeted molecule was formed, and no starting material remained when analyzed by LCMS. After filtering through Celite, the reaction mixture was concentrated and purified on silica using ethyl acetate and hexanes. 2-(Azetidin-1-yl)-6-(4,4,5,5-tetramethyl-1,3,2-dioxaborolan-2-yl)quinazoline (Precursor X) was obtained in quantitative yield. 1H NMR (400 MHz, Chloroform-d): δ 9.01 (s, 1H), 8.16 (s, 1H), 8.02 (dd, J=8.6, 1.5 Hz, 1H), 7.57 (d, J=8.5 Hz, 1H), 4.30 (t, J=7.5 Hz, 4H), 2.42 (p, J=7.5 Hz, 2H), 1.36 (s, 12H) ppm.

Synthesis of (1R,3R)-3-amino-1-methylcyclopentan-1-ol (Precursor XI)

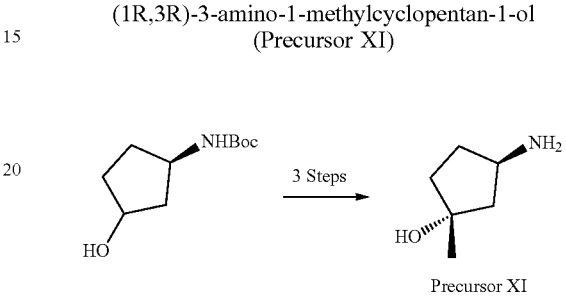

Precursor XI

Step 1:

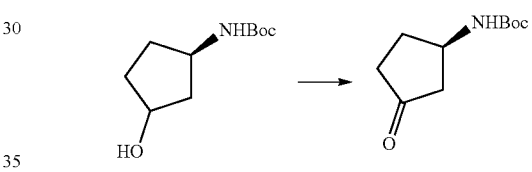

To a solution of tert-butyl ((R)-3-hydroxycyclopentyl)carbamate (10.0 g, 49.7 mmol) in 250 mL of DCM was added DMP (31.8 g, 1.5 eq) at 0° C., slowly warmed up to ambient temperature and stirred for 18 hrs. The reaction was quenched with saturated NaHCO₃ and saturated Na₂SO₃, extracted with dichloromethane (3 times) and dried over Na₂SO₄, filtered, and concentrated. Purification on silica using ethyl acetate/hexanes provided 9.60 g (96% yield) of tert-butyl (R)-(3-oxocyclopentyl)carbamate as a white solid.

Step 2:

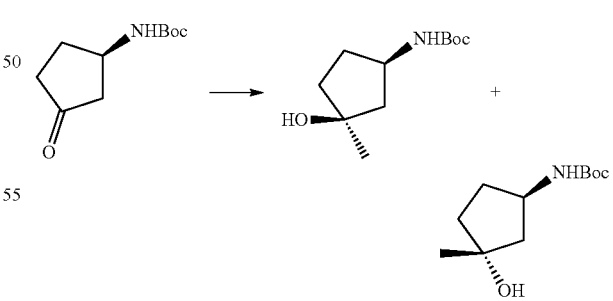

CeCl₃.7H₂O (14.1 g, 1.5 eq) was dried at 150° C. under vacuum for 14 hrs and filled with dry nitrogen gas while hot. Anhydrous THF (125 mL) was added to dry CeCl₃ and stirred for 3 hrs. The mixture was then cooled to 0° C. and MeMgBr (3 M in THF, 25.2 mL, 3 eq) was added dropwise. After stirring for 1.5 hrs at 0° C., a solution of tert-butyl (R)-(3-oxocyclopentyl)carbamate (5.03 g, 25.1 mmol) in THF (95 mL) was added over 5 min. The mixture was stirred at 0° C. for 2.5 hrs, quenched with 10% aqueous acetic acid (50 mL), extracted 2 times with ethyl acetate, washed with brine, and dried over Na₂SO₄. The resulting organic layer was filtrated and concentrated. Purification on silica suing hexanes/ethyl acetate provided 3.37 g of tert-butyl ((1R,3S)-3-hydroxy-3-methylcyclopentyl)carbamate (62% yield) and 1.09 g of tert-butyl ((1R,3R)-3-hydroxy-3-methylcyclopentyl)carbamate (20% yield), both as light yellow oil.
Step 3:

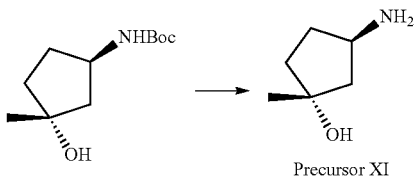

5 g (23.2 mmol) of tert-butyl ((1R,3R)-3-hydroxy-3-methylcyclopentyl)carbamate was dissolved in 50 mL of dry DCM and 20 mL of trifluoroacetic acid was slowly added to the reaction mixture. Progress of the reaction was followed by LCMS, and when all starting material converted to product, all solvent was rotovaped and oily residue was dried on high vac. If excess TFA is still present compound can be triturated from DCM/hexanes. (1R,3R)-3-amino-1-methylcyclopentan-1-ol (Precursor XI) was obtained in quantitative yield (2.67 g).

Synthesis of (S)-(3-(1-((tert-butoxycarbonyl)amino)ethyl)-5-chlorophenyl)boronic acid (Precursor XII)

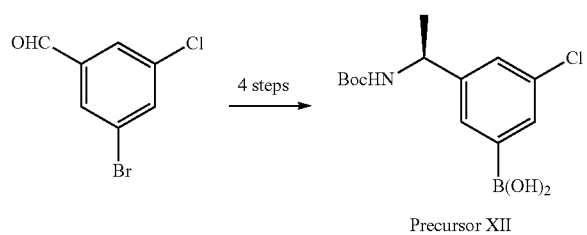 [SMILES: O=Cc1cc(Cl)cc(Br)c1 ; C[C@H](NC(=O)OC(C)(C)C)c1cc(Cl)cc(B(O)O)c1]

Step 1:

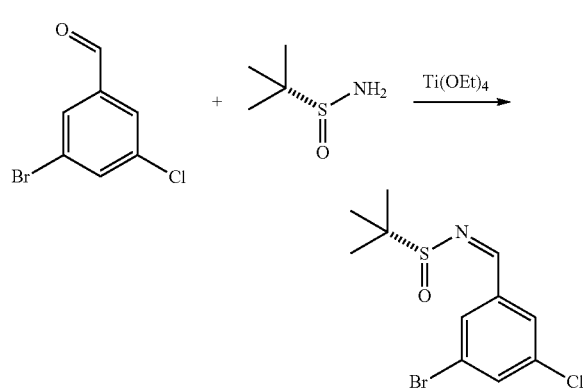

To a solution of substituted benzaldehyde (2.28 mmol) and (R)-(+)-2-methyl-2-propanesulfinamide (248 mg, 2.05 mmol) in THF (7.5 mL) was added Titanium(IV) ethoxide (0.95 mL, 4.56 mmol). The reaction mixture was stirred at room temperature overnight. Quench with brine, filter over a pad of Celite, wash through with ethyl acetate (100 mL). Dry filtrate with sodium sulfate, filter and concentrate to yield crude sulfinimine.
Step 2:

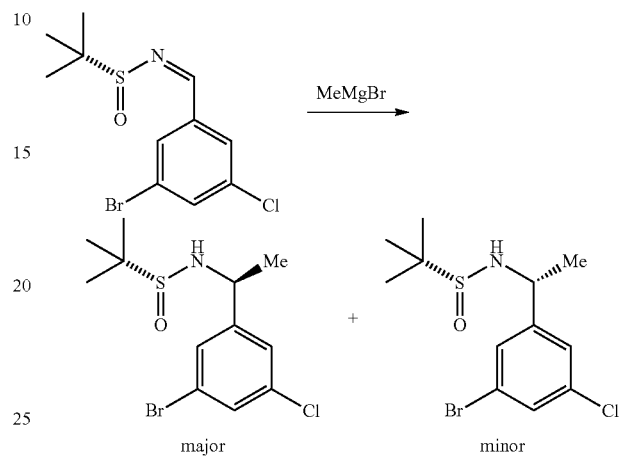

The crude sulfinimine (2.05 mmol) was dissolved in THF (15 mL) and cooled to −78 C, then MeMgBr (3 M, 0.91 mL, 2.73 mmol) was added. After stirring for 30 min at −78, the ice bath was allowed to expire and slowly warm to room temp over the course of 1 hour. The reaction mixture was quenched with saturated aqueous solution of NH₄Cl, extracted with ethyl acetate, dried with sodium sulfate, filtered, and concentrated. The residue was purified on silica using ethyl acetate/hexanes to separate the two sulfinamide diastereomers, with the desired major diastereomer coming out last (41% yield).
Step 3:

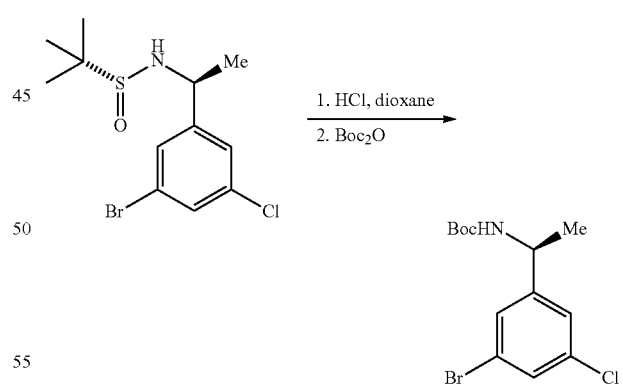

The sulfinamide (1 mmol) was dissolved in 1,4-dioxane (5 mL) and 4N HCl in dioxane (1 mL, 4 mmol) was added. The reaction mixture was stirred vigorously for 1 hour, then concentrated to yield the free amine as an HCl salt. Then, the residue was dissolved along with di-tert-butyl dicarbonate (308 mg, 1.41 mmol), 4-dimethylaminopyridine (23 mg, 0.19 mmol), and N,N-diisopropylethylamine (0.82 mL, 4.71 mmol) in THF (10 mL). The reaction was carried out at room temperature for 2 hours. Then solvent was removed under reduced pressure and the residue was purified directly by column chromatography using ethyl acetate/hexanes to give tert-butyl (S)-(1-(3-bromo-5-chlorophenyl)ethyl)carbamate.

Step 4:

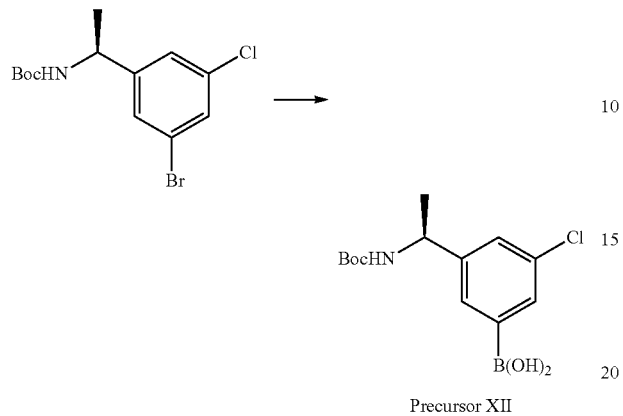

Precursor XII

Dissolved tert-butyl (S)-(1-(3-bromo-5-chlorophenyl)ethyl)carbamate (0.94 mmol) and bis(pinacolato)diboron (477.93 mg, 1.88 mmol), 1,1'-bis(diphenylphosphino)ferrocene-palladium(II) dichloride (68.86 mg, 0.0900 mmol), and potassium acetate (277.06 mg, 2.82 mmol) in 1,4-dioxane (4.705 mL) and heated to 100° C. for 1 hour. The crude reaction was purified by column chromatography using ethyl acetate/hexane, yielding the boronic acid ester. This was dissolved in acetone/water (1:1) and sodium acetate (3 equiv) and sodium periodate (3 equiv) were added and stirred at room temp overnight. After that the reaction mixture was extracted with ethylacetate, organic phase dried over sodium sulfate, filtered and concentrated. (S)-(3-(1-((tert-butoxycarbonyl)amino)ethyl)-5-chlorophenyl)boronic acid (Precursor XH) was obtained in 71% yield (200 mg).

General Synthesis Procedure A: Amide Coupling with Precursor IV.

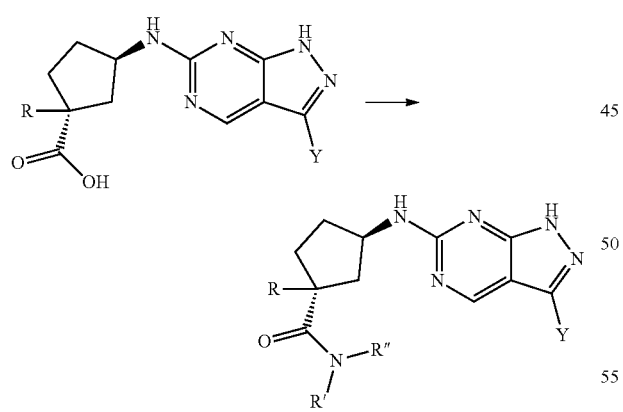

To a solution of diisopropylethylamine (3 eq), (1R,3R)-3-[(3-bromo-H-pyrazolo[3,4-d]pyrimidin-6-yl)amino]cyclopentanecarboxylic acid (Precursor IV, 61 mmol), and the amine R'R"NH (2 eq) in DMF (40 mL) was added HATU (1.5 eq). The resulting mixture was stirred at room temperature for 2 hours. (a) The crude solution was diluted in water and acidified to pH=5. A precipitate formed which was filtered and allowed to dry in the open air to afford the desired amide. (b) Crude reaction mixture was purified by reverse phase HPLC.

General Synthesis Procedure B: Chan-Lam Coupling

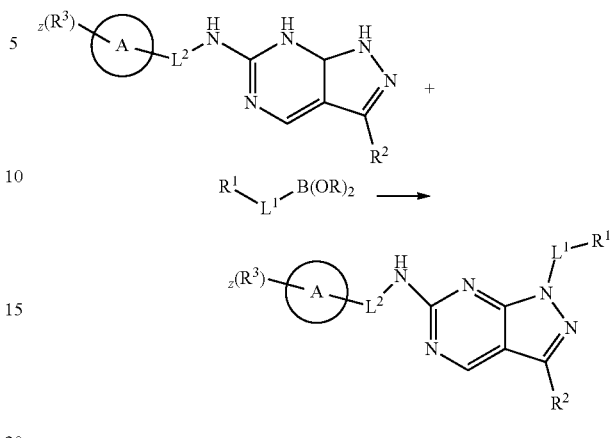

Using the above reaction scheme, in certain embodiments, $R^2$ is a halide such as Br, F, Cl or I.

Optionally substituted with R' at 6-position 3-bromo-H-pyrazolo[3,4-d]pyrimidin (0.3 mmol), boronic acid (1.2 eq), copper (II) acetate (0.3 eq), N,N-diisopropylethylamine (5 eq) and DMF (1.2 mL) were put in 2 dram vial and an $O_2$ balloon was attached. The reaction was heated under oxygen atmosphere at 60-90° C. for 1-15 hours and conversion was followed by LCMS and/or TLC. The crude reaction mixture was concentrated and purified by reverse-phase HPLC (5% to 100% MeCN/water with 0.1% TFA gradient over 30 minutes) to afford the desired product. If a pinacol ester was used instead of boronic acid, then loading of copper (II) acetate was increased to 1.5 equivalents, and no N,N-diisopropylethylamine was added.

General Synthesis Procedure C: Amide Coupling with Cycloalkyl Carboxylic Acids.

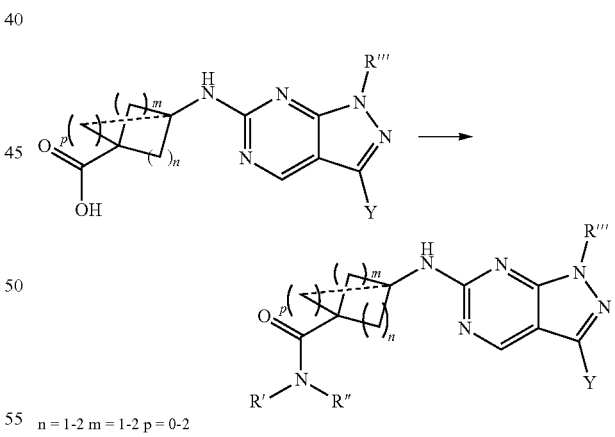

n = 1-2 m = 1-2 p = 0-2

HATU (1.2 eq) or T3P (3 eq) was added to a solution of optionally substituted at N1 3-bromo-1H-pyrazolo[3,4-d]pyrimidin-6-yl)amino)cycloalkylcarboxylic acid (0.2 mmol), the amine R'R"NH (3 eq), and N,N-Diisopropylethylamine (3 eq) in DMF (2 mL). The reaction was stirred at 23° C. (HATU) or 50° C. overnight. After concentrating, the crude product was purified by reverse-phase HPLC (20% to 100% MeCN/water with 0.1% TFA gradient over 30 minutes) to afford the desired product as the TFA salt.

General Synthesis Procedure D: Nucleophilic Aromatic Substitution

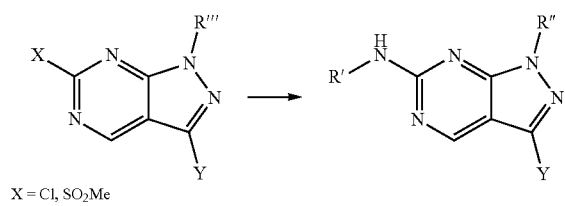

X = Cl, SO₂Me

To a suspension of optionally substituted at N1 and C6 3-bromo-pyrazolo[3,4-d]pyrimidine (4.27 mmol) and primary amine R'NH2 (4.27 mmol) in DMSO (4 mL) was added N,N-diisopropylethylamine (2.24 mL, 12.81 mmol). The resulting mixture was stirred at 100° C. for 3-5 hours. The suspension became homogeneous as the reaction proceeded and was complete by LCMS. Water was added, and the mixture was neutralized to pH 7 using 4 M aqueous HCl solution. (a) A precipitate formed which was filtered and washed with DCM and hexanes. The solid was dried in the open air to afford the desired product. (b) The solution was further acidified until homogeneous and injected onto reverse-phase HPLC for purification (c) Solvent was removed and residue purified using normal phase chromatography with DCM/MeOH as eluent.

General Synthesis Procedure E: Amide Coupling with Precursor II and Deprotection of the Boc Group.

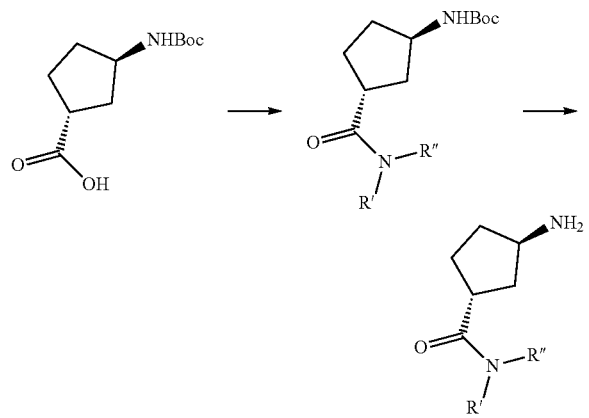

HATU (1.2 eq) was added to a solution of the amine R'R"NH (9 mmol, 1.0 eq) and (1R,3R)-3-(tert-butoxycarbonylamino)cyclopentanecarboxylic acid (Precursor II, 9 mmol, 1 eq) in DMF (15 mL) and N,N-diisopropylethylamine (27 mmol, 3 eq) cooled in an ice bath. After two minutes, the reaction was warmed to 23° C. and stirred for at least 2 hours until LCMS showed complete conversion. The crude reaction was concentrated and loaded directly onto silica gel and purified by normal-phase column chromatography on silica gel (0 to 20% 7N NH₃ in MeOH/DCM) to afford the Boc-protected product.

Hydrochloric acid (5 eq, 4 M in 1,4-dioxane) was added to a solution of the Boc-protected product in DCM (15 mL) and stirred at 23° C. overnight when LCMS showed the disappearance of the starting material. The crude reaction mixture was concentrated and (a) material was loaded directly onto silica gel and was purified by normal phase column chromatography on silica gel (0 to 20% 7N NH₃ in MeOH/DCM) to afford the free amine, or (b) crude material was used directly in the next step without purification.

General Synthesis Procedure F: Alkylation of Precursor V and Deprotection

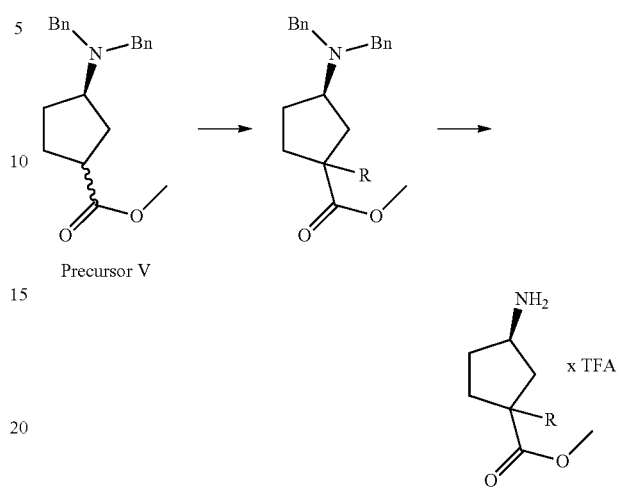

Precursor V

To a dry 25-mL round bottom flask under nitrogen was added THF (11.9 mL) and diisopropylamine (2.2 mL, 15.7 mmol, 3.3 eq). The flask was cooled to 0° C. followed by the dropwise addition of n-butyllithium (5.7 mL, 14.3 mmol, 3 eq). The reaction mixture was stirred for 15 min then cooled to −78° C. Precursor V (1.5 g, 4.8 mmol) dissolved in THF (6 mL) and the resulting mixture was stirred for 80 min at −78° C. The necessary alkylating reagent RX (28.57 mmol, 6 eq) was added in a solution of THF (6 mL) and the reaction mixture was stirred for 20 min at −78° C. The cooling bath was removed, and the flask was warmed to ambient temperature and then stirred overnight. The next day, the reaction was poured into sat. NH₄Cl (20 mL) and diluted with water (10 mL), then extracted with EtOAc (3×10 mL). The combined organic extracts were washed with water and brine, then dried over anhydrous Na₂SO₄, filtered, concentrated in vacuo, adsorbed crude onto silica gel, and purified by flash chromatography.

The product (4.3 mmol) was dissolved in 100 mL of methanol and placed in a 250-mL high-pressure vessel. 10% Pd/C (2 g) and trifluoroacetic acid (0.25 mL, 4.33 mmol, 1 eq) were added. The flask was attached to a Parr shaker and pressurized with hydrogen gas to 48 psi. The reaction was monitored until complete removal of both Bn groups (12-24 hrs, checked by LCMS). Upon completion, the reaction vessel was flushed with nitrogen, the reaction mixture was filtered through a pad of celite to afford crude product, which was used without further purification.

General Synthesis Procedure G: Preparation of (1R,3R)-3-aminocyclopentane-1-sulfonamides

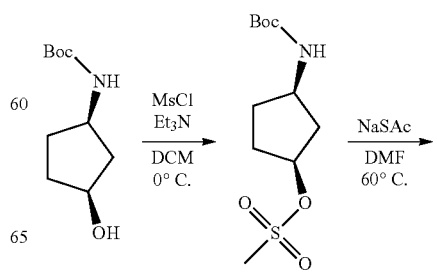

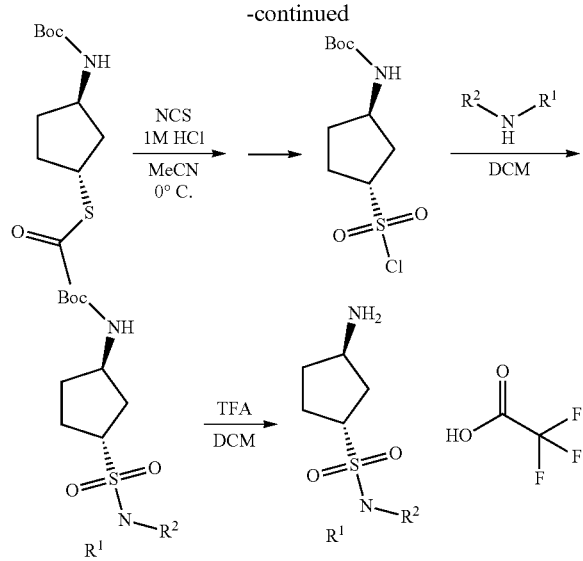

Step 1.

Tert-butyl N-[(1R,3S)-3-hydroxycyclopentyl]carbamate (350 mg, 1.7 mmol) was added to a reaction vial and dissolved in dichloromethane (3.5 mL) under a nitrogen atmosphere. The resulting solution was cooled to 0° C. Methanesulfonyl chloride (0.2 mL, 2.6 mmol) and triethylamine (0.5 mL, 3.5 mmol) were added dropwise and the reaction mixture was warmed to ambient temperature and stirred overnight. The reaction was quenched with water and extracted with dichloromethane (3×5 mL). The combined organic extracts were dried over anhydrous $Na_2SO_4$, filtered, and concentrated in vacuo and used without further purification, (480 mg, 98% yield).

Step 2.

[(1S,3R)-3-(tert-butoxycarbonylamino)cyclopentyl] methanesulfonate (950 mg, 3.4 mmol) was dissolved in DMF (11.3 mL) and potassium thioacetate (582.6 mg, 5.1 mmol) was added. The reaction mixture was sealed and heated at 60° C. overnight. Upon completion, the reaction mixture was diluted with cold water then extracted with ethyl acetate (3×25 mL). The combined organic extracts were dried over anhydrous $Na_2SO_4$, filtered, concentrated In vacuo, adsorbed onto silica gel, and purified by flash chromatography using 0-20% EtOAc/hexanes gradient. The major (second) peak was collected and concentrated, and the residue solidified into an orange solid (649 mg, 73% yield). It was taken forward without further purification.

Step 3.

To a reaction vial was added acetonitrile (12.5 mL), hydrochloric acid (2.6 mL, 2.6 mmol), and N-chlorosuccinimide (1338.6 mg, 10.0 mmol). The mixture was then cooled to 5° C. and S-[(1R,3R)-3-(tert-butoxycarbonylamino)cyclopentyl] ethanethioate (650 mg, 2.5 mmol) in 4.2 mL of acetonitrile was added to the solution. A small amount of white precipitate formed over 10 min and the reaction turned in color from brown to colorless as time progressed. The mixture was stirred for 1 h then diluted with water (10 mL) and extracted with ethyl acetate (3×3 mL). The combined organic extracts were dried over $MgSO_4$, filtered, and concentrated in vacuo to give a colorless oil that solidified to a white solid on high-vac. The product was taken forward without further purification.

Step 4.

Tert-butyl N-[(1R,3R)-3-chlorosulfonylcyclopentyl]carbamate (80 mg, 0.28 mmol) from the previous step was added to a reaction vial and dissolved in dichloromethane (1.4 mL). The amine R'R"NH (1.4 mmol, 5 eq) was added to the solution and the resulting reaction mixture was stirred for 1 h at ambient temperature. Upon completion, water was added (2 mL) followed by 1 M HCl to acidify mixture to pH<3. The mixture was extracted with dichloromethane (3×1 mL) and the combined organic extracts were dried over anhydrous $Na_2SO_4$, filtered, and concentrated in vacuo. The crude product was purified by flash chromatography, 0-100% EtOAc/hexanes to afford the desired product.

Step 5.

Tert-butylcarbamate protected amine (0.36 mmol) was dissolved in dichloromethane (3.6 mL) then trifluoroacetic acid (0.14 mL, 1.8 mmol, 5 eq) was added and the reaction mixture was stirred until complete deprotection was observed (followed by LCMS and/or TLC). Upon completion the reaction mixture was concentrated in vacuo to remove TFA and DCM and used in the next step without purification.

COMPOUND EXAMPLES

Example 1

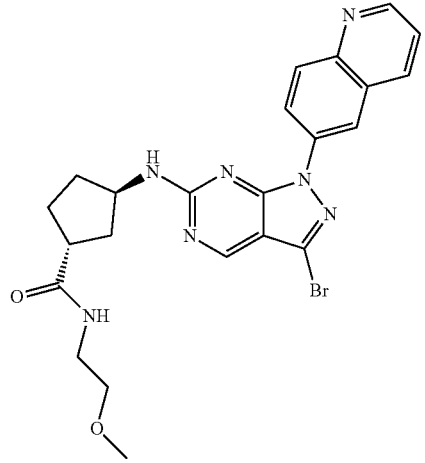 [SMILES: COCCNC(=O)[C@@H]1CC[C@@H](Nc2ncc3c(Br)nn(-c4ccc5ncccc5c4)c3n2)C1]

(1R,3R)-3-((3-bromo-1-(quinolin-6-yl)-1H-pyrazolo[3,4-d]pyrimidin-6-yl)amino)-N-(2-methoxyethyl)cyclopentane-1-carboxamide was prepared employing general synthesis procedure B using Precursor I (R'=Cl) and quinoline-6-boronic acid, general synthesis procedure E(b) using 2-methoxyethan-1-amine, and general synthesis procedure D(b) using products from the previous steps (X=Cl, R"=quinolin-6-yl). $^1$H NMR (400 MHz, DMSO-d6, HCl salt) δ 8.95 (d, J=15.5 Hz, 2H), 8.74 (d, J=9.7 Hz, 1H), 8.64 (s, 1H), 8.27-8.12 (m, 2H), 7.75 (s, 1H), 4.44-4.09 (m, 1H), 3.19-3.11 (m, 2H), 3.12-3.03 (m, 2H), 3.02 (s, 3H), 2.74-2.63 (m, 1H), 2.17-2.00 (m, 1H), 1.97-1.75 (m, 1H), 1.65-1.46 (m, 4H) ppm. LCMS [M+H]510.0.

Example 2

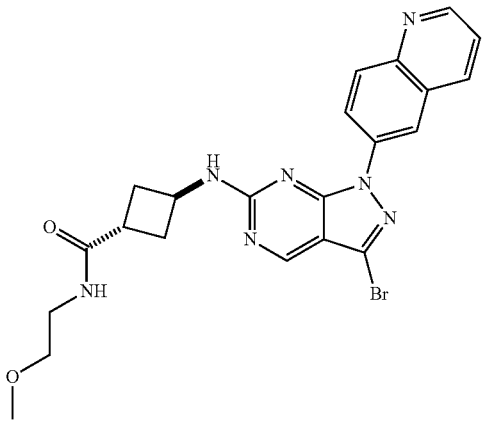

(1r,3r)-3-((3-bromo-1-(quinolin-6-yl)-1H-pyrazolo[3,4-d]pyrimidin-6-yl)amino)-N-(2-methoxyethyl)cyclobutane-1-carboxamide was prepared employing general synthesis procedure B using Precursor I (R'=Cl) and quinoline-6-boronic acid, general synthesis procedure D(a) using product from the previous step (X=Cl, R''=quinolin-6-yl) and (1r,3r)-3-aminocyclobutane-1-carboxylic acid, general synthesis procedure C using HATU with product from the previous step (trans, n=1, m=1, p=0) and 2-methoxyethan-1-amine. $^1$H NMR (400 MHz, DMSO-d6, HCl salt) 9.26-9.06 (m, 1H), 9.00 (d, J=8.5 Hz, 1H), 8.83-8.70 (m, 2H), 8.59 (s, 1H), 8.34 (d, J=9.3 Hz, 1H), 7.90-7.77 (m, 1H), 4.69-4.57 (m, 1H), 3.36 (t, J=5.6 Hz, 2H), 3.31-3.24 (m, 2H), 3.21-3.11 (m, 3H), 3.01-2.89 (m, 1H), 2.51 (s, 2H), 2.32-2.18 (m, 2H) ppm. LCMS [M+H] 496.0.

Example 3

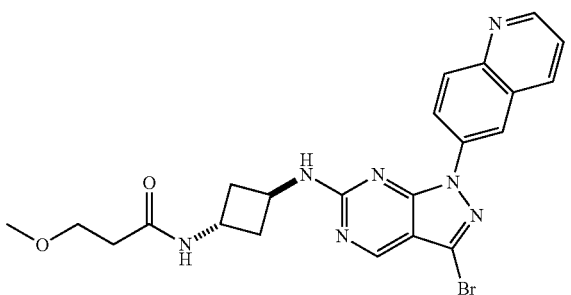

N-((1r,3r)-3-((3-bromo-1-(quinolin-6-yl)-1H-pyrazolo[3,4-d]pyrimidin-6-yl)amino)cyclobutyl)-3-methoxypropanamide was prepared employing general synthesis procedure B using Precursor I (R'=Cl) and quinoline-6-boronic acid. N-((1Rr,3R)-3-aminocyclobutyl)-3-methoxypropanamide was prepared as follows: to a solution of 3-methoxypropanoic acid (111.79 mg, 1.07 mmol) in DMF (1 mL) was added N,N-diisopropylethylamine (0.37 mL, 2.15 mmol), HATU (489.96 mg, 1.29 mmol) and trans-tert-butyl 3-aminocyclobutylcarbamate (200 mg, 1.07 mmol), the resulting mixture was stirred at ambient temperature for 18 hours, water was added and the mixture was extracted with ethyl acetate 3 times, organic phase was washed with brine, dried over sodium sulfate, solvent was removed, and the crude was purified by normal phase column chromatography on silica gel eluting with ethyl acetate/hexanes to afford N-((1Rr,3Rr)-3-aminocyclobutyl)-3-methoxypropanamide in 71% yield. General synthesis procedure D(b) was employed to afford the final compound using product from the general synthesis procedure B (X=Cl, R''=quinoline-6-yl) and N-((1r,3r)-3-aminocyclobutyl)-3-methoxypropanamide. $^1$H NMR (400 MHz, DMSO-d6, HCl salt) δ 9.12 (d, J=4.8 Hz, 1H), 9.04-8.80 (m, 2H), 8.64 (d, J=5.7 Hz, 1H), 8.36 (t, J=7.5 Hz, 2H), 7.88 (dd, J=8.4 Hz, J=4.8 Hz, 1H), 4.58-4.41 (m, 1H), 4.41-4.16 (m, 1H), 3.52 (t, J=6.4 Hz, 2H), 3.23-3.13 (m, 5H), 2.45-2.19 (m, 4H) ppm. LCMS [M+H] 496.0.

Example 4

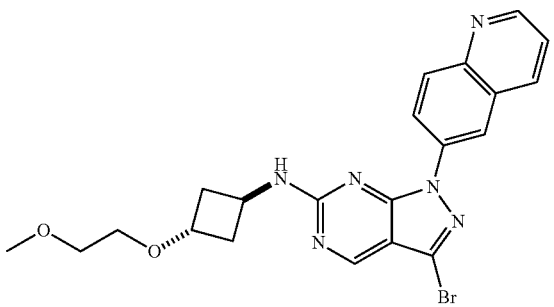

3-bromo-N-((1r,3r)-3-(2-methoxyethoxy)cyclobutyl)-1-(quinolin-6-yl)-1H-pyrazolo[3,4-d]pyrimidin-6-amine was prepared employing general synthesis procedure B using Precursor I (R'=Cl) and quinoline-6-boronic acid, and general synthesis procedure D(b) using product from the previous step (X=Cl, R''=quinolin-6-yl) and commercial (1r,3r)-3-(2-methoxyethoxy)cyclobutan-1-amine. $^1$H NMR (400 MHz, Methanol-d4, HCl salt) δ 9.10-8.93 (m, 4H), 8.52 (s, 1H), 8.20 (d, J=9.0 Hz, 1H), 8.06-7.86 (m, 1H), 4.43 (t, J=9.7 Hz, 2H), 4.17-3.98 (m, 2H), 3.97 (s, 1H), 3.46-3.35 (m, 3H), 3.23-3.20 (m, 1H), 2.49-2.31 (m, 2H), 2.31-2.10 (m, 2H) ppm. LCMS [M+H] 469.0.

Example 5

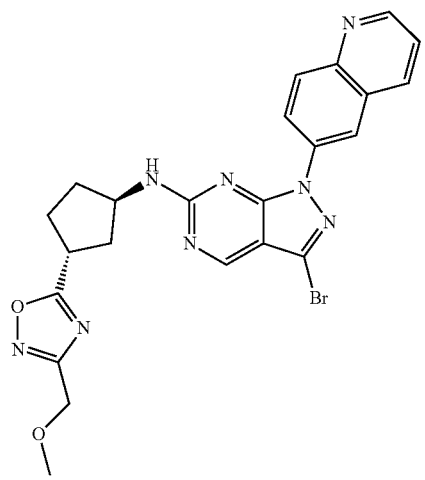 [SMILES: COCc1noc([C@@H]2CC[C@@H](Nc3ncc4c(Br)nn(-c5ccc6ncccc6c5)c4n3)C2)n1]

3-bromo-N-((1R,3R)-3-(3-(methoxymethyl)-1,2,4-oxadiazol-5-yl)cyclopentyl)-1-(quinolin-6-yl)-1H-pyrazolo[3,4-d]pyrimidin-6-amine was prepared employing general synthesis procedure B using Precursor I (R'=Cl) and quinoline-6-boronic acid, followed by general synthesis procedure D(b) with products from the previous steps (X=Cl, R'''=quinoline-6-yl) and (1R,3R)-3-(3-(Methoxymethyl)-1,2,4-oxadiazol-5-yl)cyclopentan-1-amine. ¹H NMR (400 MHz, Methanol-d4, HCl salt) δ 9.28 (s, 1H), 9.27-9.21 (m, 2H), 9.15 (d, J=9.7 Hz, 1H), 8.81 (d, J=1.6 Hz, 1H), 8.42 (d, J=9.4 Hz, 1H), 8.17 (dd, J=8.3, 5.2 Hz, 1H), 4.74-4.60 (m, 1H), 4.56 (s, 2H), 3.86-3.70 (m, 1H), 3.42 (d, J=4.0 Hz, 3H), 2.68 (d, J=17.2 Hz, 1H), 2.41 (d, J=12.9 Hz, 2H), 2.29 (d, J=9.5 Hz, 1H), 2.18-2.03 (m, 1H), 2.01-1.85 (m, 1H) ppm. LCMS [M+H] 521.0. (1R,3R)-3-(3-(Methoxymethyl)-1,2,4-oxadiazol-5-yl)cyclopentan-1-amine was prepared as follows: to a solution of (R,3R)-3-(tert-butoxycarbonylamino)cyclopentanecarboxylic acid (0.1 g, 0.4400 mmol) in DMF (2 mL) was added N'-hydroxy-2-methoxy-acetamidine hydrochloride (0.06 g, 0.4400 mmol), N,N-diisopropylethylamine (0.15 mL, 0.8700 mmol) and HATU (0.2 g, 0.5200 mmol). The resulting mixture was stirred at ambient temperature for 12 hours, water was added and resulting mixture was extracted with ethyl acetate 3 times, solvent was removed in vacuo, the crude was purified using flash chromatography eluting with EtOAc/hexanes to afford the intermediate used in general synthesis procedure D(b).

Example 6

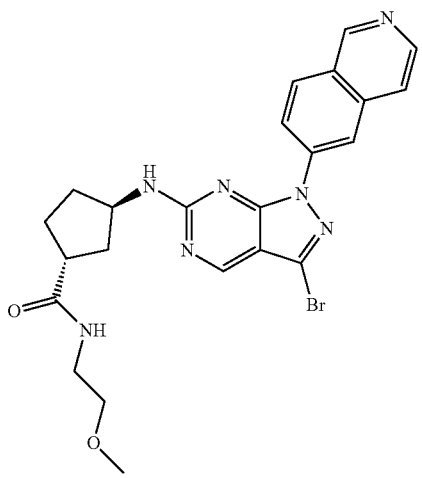 [SMILES: COCCNC(=O)[C@@H]1CC[C@@H](Nc2ncc3c(Br)nn(-c4ccc5cnccc5c4)c3n2)C1]

(1R,3R)-3-((3-bromo-1-(isoquinolin-6-yl)-1H-pyrazolo[3,4-d]pyrimidin-6-yl)amino)-N-(2-methoxyethyl)cyclopentane-1-carboxamide was prepared employing general synthesis procedure E(b) with Precursor II and 2-methoxyethan-1-amine, followed by general synthesis procedure D(c) with the product from previous step and Precursor I (X=Cl, R'''=H), followed by general synthesis procedure B with the product from previous step and isoquinolin-6-ylboronic acid. ¹H NMR (400 MHz, Methanol-d4, HCl salt) δ 9.67 (s, 1H), 9.20 (s, 1H), 8.90 (d, J=8.3 Hz, 1H), 8.70-8.45 (m, 4H), 4.65-4.32 (m, 1H), 3.46 (t, J=4.9 Hz, 3H), 3.44-3.36 (m, 4H), 2.98-2.82 (m, 1H), 2.63-2.05 (m, 3H), 1.81-1.64 (m, 3H) ppm. LCMS [M+H]510.0.

Example 7

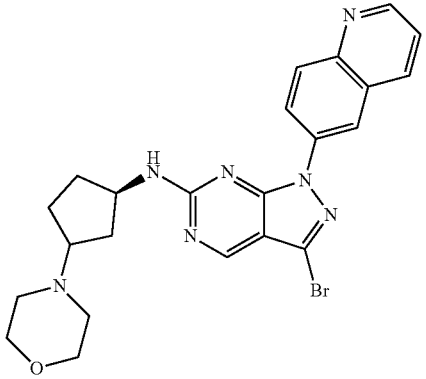 [SMILES: Brc1nn(-c2ccc3ncccc3c2)c2nc(N[C@@H]3CCC(N4CCOCC4)C3)ncc12]

3-bromo-N-(3-morpholinocyclopentyl)-1-(quinolin-6-yl)-1H-pyrazolo[3,4-d]pyrimidin-6-amine (as a mixture of diastereomers). (1R)-3-morpholinocyclopentanamine was prepared via the following procedure: to a solution of 2-Methyl-2-propanyl [(1R)-3-oxocyclopentyl]carbamate (200 mg, 1 mmol) in 1,2-dichloroethane (2 mL) was added morpholine (174.9 mg, 2.01 mmol). The resulting mixture was stirred at ambient temperature for 3 hours and then sodium triacetoxyborohydride (638.18 mg, 3.01 mmol) was added to the mixture and continued stirring at ambient temperature for 18 hours. The reaction mixture was quenched with saturated sodium bicarbonate solution, extracted with dichloromethane 3 times, and the solvent was removed via rotary evaporation and the crude residue was purified by flash chromatography using 0-6% MeOH/DCM with ammonia to afford a yellow solid. To this was added 4 M HCl in dioxane (5 mL) and sonicated for 10 min. The solvent was removed to afford (1R)-3-morpholinocyclopentanamine hydrochloride (103.4 mg, 49% yield). To prepare the title compound general synthesis procedure B was used with Precursor I and quinoline-6-boronic acid, followed by general synthesis procedure D(b) with the product from previous step and (1R)-3-morpholinocyclopentanamine hydrochloride. ¹H NMR (400 MHz, Methanol-d4, HCl salt) δ 9.49 (s, 1H), 9.38 (d, J=8.5 Hz, 1H), 9.13-8.99 (m, 2H), 8.53-8.39 (m, 2H), 8.18 (s, 1H), 4.87-4.81 (m, 1H), 4.76-4.61 (m, 1H), 4.23-3.81 (m, 6H), 3.58 (t, J=13.9 Hz, 2H), 2.54-2.36 (m, 2H), 2.29-2.06 (m, 2H), 2.23-1.98 (m, 2H) ppm. LCMS [M+H] 494.0.

Example 8

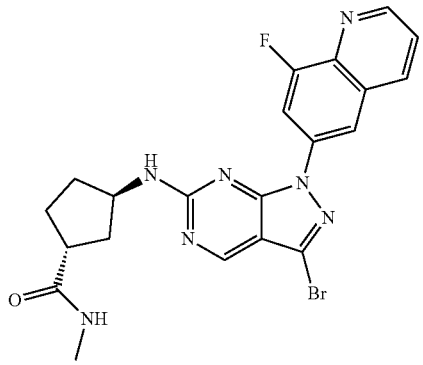 [SMILES: CNC(=O)[C@@H]1CC[C@@H](Nc2ncc3c(Br)nn(-c4cc(F)c5ncccc5c4)c3n2)C1]

(1R,3R)-3-((3-bromo-1-(8-fluoroquinolin-6-yl)-1H-pyrazolo[3,4-d]pyrimidin-6-yl)amino)-N-methylcyclopentane-1-carboxamide was prepared employing general synthesis procedure B with precursor I and 8-fluoroquinoline-6-boronic acid, followed by general synthesis procedure D(a) with product from the previous step and Precursor III, followed by general synthesis procedure C using HATU with product from the previous step and methylamine. ¹H NMR (400 MHz, Methanol-d4, HCl salt) δ 9.34 (s, 1H), 9.07 (s, 2H), 8.89-8.54 (m, 1H), 8.06 (s, 1H), 7.62 (s, 1H), 4.61-4.30 (m, 1H), 2.98-2.67 (m, 1H), 2.70-2.42 (m, 3H), 2.31 (m, 1H), 2.23-2.08 (m, 1H), 2.07-1.90 (m, 1H), 1.90-1.50 (m, 3H) ppm. LCMS [M+H] 484.0.

Example 9

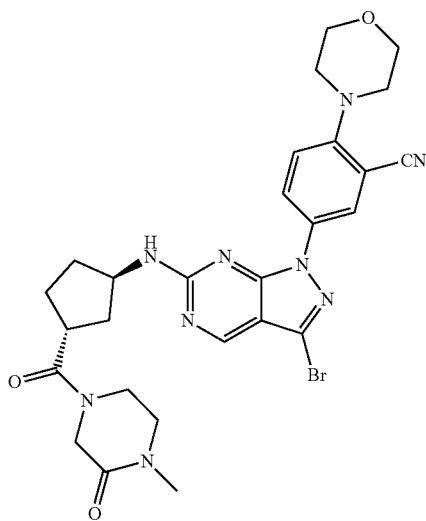 [SMILES: CN1CCN(C(=O)[C@@H]2CC[C@@H](Nc3ncc4c(Br)nn(-c5ccc(N6CCOCC6)c(C#N)c5)c4n3)C2)CC1=O]

5-(3-bromo-6-(((1R,3R)-3-(4-methyl-3-oxopiperazine-1-carbonyl)cyclopentyl)amino)-1H-pyrazolo[3,4-d]pyrimidin-1-yl)-2-morpholinobenzonitrile was prepared employing general synthesis procedure E(a) with 1-methylpiperazin-2-one, followed by general synthesis procedure D(a) with the product from previous step and Precursor I (workup: mixture was acidified to pH 3 instead of pH 7), followed by general synthesis procedure B with the product from previous step and (3-cyano-4-morpholinophenyl)boronic acid. ¹H NMR (400 MHz, Methanol-d4, TFA salt) δ 8.26 (s, 1H), 8.14 (s, 1H), 8.04 (s, 1H), 6.93 (d, J=8.8 Hz, 1H), 4.17-3.98 (m, 1H), 3.87-3.60 (m2H), 3.54-3.45 (m, 3H), 3.11 (s, 2H), 3.06 (s, 2H), 2.92-2.88 (m, 4H), 2.86-2.79 (m, 2H), 2.64 (s, 3H), 2.12-1.93 (m, 1H), 1.93-1.72 (m, 2H), 1.72-1.30 (m, 3H) ppm. LCMS [M+H]608.0.

Example 10

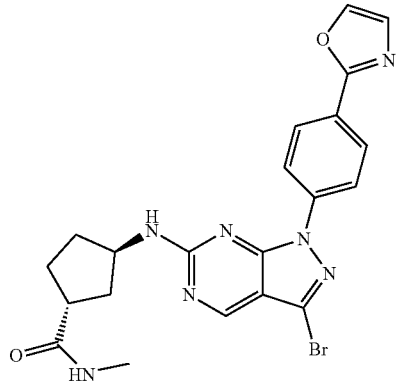 [SMILES: CNC(=O)[C@@H]1CC[C@@H](Nc2ncc3c(Br)nn(-c4ccc(-c5ncco5)cc4)c3n2)C1]

(1R,3R)-3-((3-bromo-1-(4-(oxazol-2-yl)phenyl)-1H-pyrazolo[3,4-d]pyrimidin-6-yl)amino)-N-methylcyclopentane-1-carboxamide was prepared employing general synthesis procedure A(a) with Precursor IV and methylamine, followed by general synthesis procedure B with product from the previous step and (4-(oxazol-2-yl)phenyl)boronic acid. ¹H NMR (400 MHz, Methanol-d4, HCl salt) δ 8.58 (s, 1H), 8.21-8.01 (m, 2H), 7.91 (s, 1H), 7.79-7.64 (m, 1H), 7.49 (s, 1H), 7.07 (d, J=2.8 Hz, 1H), 4.36-4.21 (m, 1H), 2.77-2.59 (m, 1H), 2.49 (s, 3H), 2.21-1.98 (m, 2H), 1.95-1.77 (m, 1H), 1.68-1.55 (m, 2H), 1.49 (dd, J=10.2 Hz, J=5.9 Hz, 1H) ppm. LCMS [M+H] 482.0.

Example 11

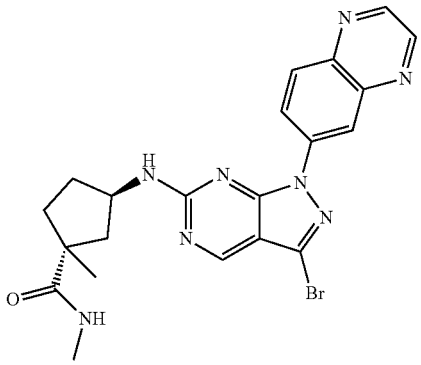 [SMILES: CNC(=O)[C@]1(C)CC[C@@H](Nc2ncc3c(Br)nn(-c4ccc5nccnc5c4)c3n2)C1]

(1R,3R)-3-((3-bromo-1-(quinoxalin-6-yl)-1H-pyrazolo[3,4-d]pyrimidin-6-yl)amino)-N,1-dimethylcyclopentane-1-carboxamide was prepared employing general synthesis procedure F and methyl iodide as alkylating reagent, followed by general synthesis procedure D(c) with product from the previous step and Precursor I (X=Cl, R'''=H), followed by general synthesis procedure B with product from the previous step and isoquinolin-6-ylboronic acid. Active diastereomer was separated at the final step by reverse phase HPLC and come as a second peak. ¹H NMR (400 MHz, Methanol-d4, HCl salt) δ 8.98 (s, 1H), 8.94-8.79 (m, 3H), 8.70 (d, J=8.9 Hz, 1H), 8.19 (d, J=9.3 Hz, 1H), 4.66-4.52 (m, 1H), 2.72 (s, 3H), 2.38-2.12 (m, 3H), 2.13-1.97 (m, 1H), 1.93-1.75 (m, 1H), 1.75-1.59 (m, 1H), 1.35 (s, 3H). LCMS [M+H] 481.0.

Example 12

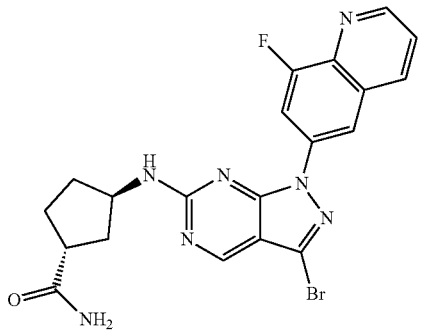 [SMILES: NC(=O)[C@@H]1CC[C@@H](Nc2ncc3c(Br)nn(-c4cc(F)c5ncccc5c4)c3n2)C1]

(1R,3R)-3-((3-bromo-1-(8-fluoroquinolin-6-yl)-1H-pyrazolo[3,4-d]pyrimidin-6-yl)amino)cyclopentane-1-carboxamide was prepared employing general synthesis procedure B using Precursor I (R'=Cl) and 8-fluoroquinoline-6-boronic acid, general synthesis procedure D(b) using product from the previous step (X=Cl, R''=8-fluoroquinolin-6-yl) and Precursor III, followed by general synthesis procedure C using HATU with product from the previous step and ammonia. $^1$H NMR (400 MHz, Methanol-d4, HCl salt) δ 8.57 (s, 1H), 8.31-8.05 (m, 2H), 7.46-7.27 (m, 3H), 4.25 (s, 1H), 2.76-2.62 (m, 1H), 2.26-1.91 (m, 2H), 1.91-1.71 (m, 1H), 1.75-1.54 (m, 2H), 1.54-1.39 (m, 1H) ppm. LCMS [M+H] 470.0.

Example 13

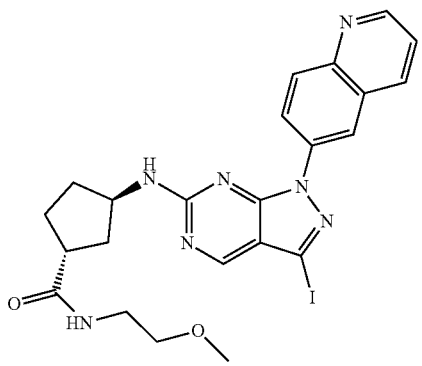 [SMILES: COCCNC(=O)[C@@H]1CC[C@@H](Nc2ncc3c(I)nn(-c4ccc5ncccc5c4)c3n2)C1]

(1R,3R)-3-((3-iodo-1-(quinolin-6-yl)-1H-pyrazolo[3,4-d]pyrimidin-6-yl)amino)-N-(2-methoxyethyl)cyclopentane-1-carboxamide was prepared employing general synthesis procedure E(a) with Precursor II and 2-methoxyethan-1-amine, followed by general synthesis procedure D(c) with product from the previous step and 6-chloro-3-iodo-H-pyrazolo[3,4-d]pyrimidine (X=Cl, Y=I, R'''=H), followed by general synthesis procedure B with product from the previous step and quinoline-6-boronic acid. $^1$H NMR (400 MHz, Methanol-d4, HCl salt) δ 9.56-9.44 (m, 1H), 9.31 (d, J=2.3 Hz, 1H), 9.25 (dd, J=5.4 Hz, J=1.4 Hz, 1H), 9.14 (dd, J=9.4 Hz, J=2.3 Hz, 1H), 8.79 (s, 1H), 8.47 (d, J=9.4 Hz, 1H), 8.19 (dd, J=8.5 Hz, J=5.4 Hz, 1H), 4.76-4.61 (m, 1H), 3.50-3.45 (m, 2H), 3.45-3.39 (m, 2H), 3.33 (s, 3H), 3.10-2.96 (m, 1H), 2.59-2.41 (m, 1H), 2.40-2.25 (m, 1H), 2.25-2.10 (m, 1H), 1.98-1.74 (m, 3H) ppm. LCMS [M+H]588.0.

Example 14

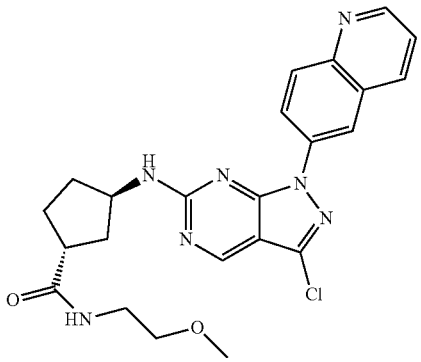 [SMILES: COCCNC(=O)[C@@H]1CC[C@@H](Nc2ncc3c(Cl)nn(-c4ccc5ncccc5c4)c3n2)C1]

(1R,3R)-3-((3-chloro-1-(quinolin-6-yl)-1H-pyrazolo[3,4-d]pyrimidin-6-yl)amino)-N-(2-methoxyethyl)cyclopentane-1-carboxamide was prepared employing general synthesis procedure E(a) with Precursor II and 2-methoxyethan-1-amine, followed by general synthesis procedure D(c) with product from the previous step and 3,6-dichloro-1H-pyrazolo[3,4-d]pyrimidine (X=Cl, Y=Cl, R'''=H), followed by general synthesis procedure B with product from the previous step and quinoline-6-boronic acid. $^1$H NMR (400 MHz, Methanol-d4, HCl salt) δ 9.55-9.43 (m, 1H), 9.34 (d, J=2.3 Hz, 1H), 9.24 (dd, J=5.4 Hz, J=1.4 Hz, 1H), 9.14 (dd, J=9.4, J=2.4 Hz, 1H), 9.01 (s, 1H), 8.46 (d, J=9.4 Hz, 1H), 8.19 (dd, J=8.5 Hz, J=5.4 Hz, 1H), 4.75-4.60 (m, 1H), 3.52-3.45 (m, 2H), 3.45-3.38 (m, 2H), 3.33 (s, 3H), 3.07-2.95 (m, 1H), 2.58-2.41 (m, 1H), 2.37-2.25 (m, 1H), 2.25-2.12 (m, 1H), 1.98-1.74 (m, 3H) ppm. LCMS [M+H] 466.0.

Example 15

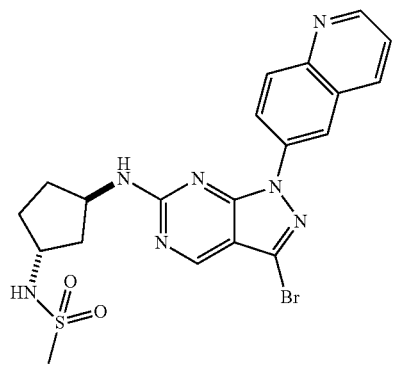

N-(trans-3-((3-bromo-1-(quinolin-6-yl)-1H-pyrazolo[3,4-d]pyrimidin-6-yl)amino)cyclopentyl)methanesulfonamide (as a mixture of enantiomers). N-(trans-3-aminocyclopentyl)methanesulfonamide was prepared via the following sequence: Tert-butyl N-[trans-3-aminocyclopentyl]carbamate (75 mg, 0.37 mmol) was dissolved in dichloromethane (0.75 mL) and cooled to 0° C. Methanesulfonyl chloride (0.04 mL, 0.56 mmol) and triethylamine (0.11 mL, 0.75 mmol) were added dropwise. The reaction mixture was slowly warmed to ambient temperature, stirred overnight, quenched with water, and extracted with DCM (3×5 mL). The combined organic extracts were dried over anhydrous Na₂SO₄, filtered, and concentrated in vacuo. The crude product was dissolved in dichloromethane (3.6 mL, 0.1 M) and trifluoroacetic acid (0.14 mL, 1.8 mmol, 5 eq) was added. The reaction mixture was stirred for 1 h, concentrated in vacuo, and taken forward to the next step. N-(trans-3-aminocyclopentyl)methanesulfonamide was used in general synthesis procedure D(b) with 6-(3-bromo-6-chloro-1H-pyrazolo[3,4-d]pyrimidin-1-yl)quinoline, which was prepared employing general synthesis procedure B with Precursor I and quinoline-6-boronic acid (product was purified using normal phase chromatography with dichloromethane/methanol as eluent). ¹H NMR (400 MHz, Methanol-d4, TFA salt) δ 9.18-8.86 (m, 4H), 8.64 (s, 1H), 8.27 (d, J=9.4 Hz, 1H), 7.94 (dd, J=8.4, J=5.2 Hz, 1H), 4.63-4.42 (m, 1H), 4.08-3.93 (m, 1H), 2.99 (s, 3H), 2.44-2.22 (m, 3H), 2.10-1.94 (m, 1H), 1.86-1.62 (m, 2H) ppm. LCMS [M+H] 502.0.

Example 16

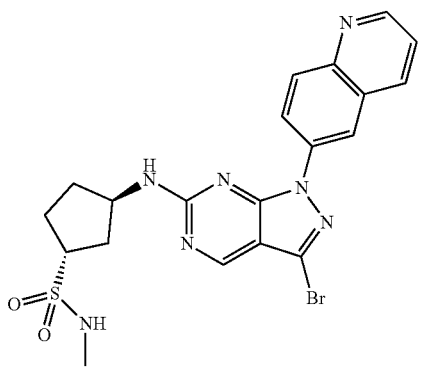 [SMILES: CNS(=O)(=O)[C@@H]1CC[C@@H](Nc2ncc3c(Br)nn(-c4ccc5ncccc5c4)c3n2)C1]

(1R,3R)-3-((3-bromo-1-(quinolin-6-yl)-1H-pyrazolo[3,4-d]pyrimidin-6-yl)amino)-N-methylcyclopentane-1-sulfonamide was prepared as described in Example 65. The title compound was the first eluting peak on reverse phase HPLC. ¹H NMR (400 MHz, Methanol-d4, TFA salt) δ 9.52-9.40 (m, 1H), 9.31 (d, J=15.9 Hz, 2H), 9.22-9.13 (m, 1H), 8.75 (s, 1H), 8.45 (d, J=9.2 Hz, 1H), 8.13 (t, J=7.0 Hz, 1H), 4.69 (t, J=7.9 Hz, 1H), 3.97-3.84 (m, 1H), 3.79-3.55 (m, 5H), 2.74 (s, 3H), 2.38-2.24 (m, 2H), 2.03-1.79 (m, 1H) ppm. LCMS [M+H] 502.0.

Example 17

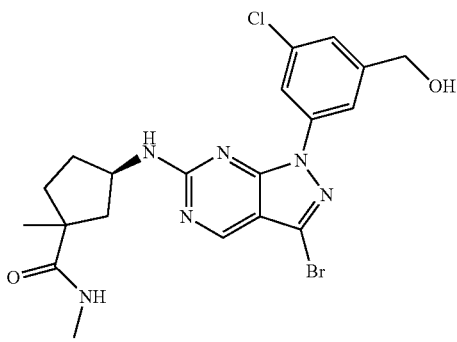 [SMILES: CNC(=O)C1(C)CC[C@@H](Nc2ncc3c(Br)nn(-c4cc(Cl)cc(CO)c4)c3n2)C1]

(3R)-3-((3-bromo-1-(3-chloro-5-(hydroxymethyl)phenyl)-1H-pyrazolo[3,4-d]pyrimidin-6-yl)amino)-N,1-dimethylcyclopentane-1-carboxamide (mixture of diastereomers) was prepared employing general synthesis procedure F and methyl iodide as alkylating reagent, followed by general synthesis procedure D(c) with product from the previous step and Precursor I, followed by ester hydrolysis (0.07M) with 3 equiv. of LiOH in THF/water (2:1) at 70° C. until full conversion was achieved (conversion analysis was carried out by LCMS), followed by acidification and extraction with EtOAc, followed by solvent removal and general synthesis procedure A (R=Me) using crude material from the previous step and methylamine and 0-100% EtOAc/hexanes gradient for purification on silica gel. The title compound was obtained by using product from the last step and general synthesis procedure B with (3-chloro-5-(hydroxymethyl)phenyl)boronic acid. H NMR (400 MHz, Methanol-d4) δ 8.58 (s, 1H), 8.35 (s, 1H), 7.97 (s, 1H), 7.19 (s, 1H), 4.68 (s, 2H), 4.45-4.43 (m, 1H), 2.81-2.69 (m, 1H), 2.73 (s, 3H), 2.33-2.20 (m, 1H), 2.17-2.03 (m, 1H), 1.78-1.62 (m, 2H), 1.45-1.37 (m, 1H), 1.31 (s, 3H) ppm. LCMS [M+H] 493.1.

Example 18

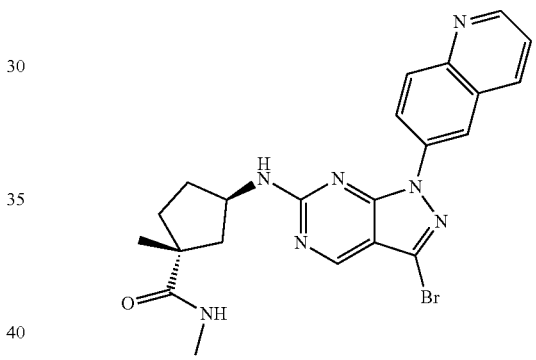

(1R,3R)-3-((3-bromo-1-(quinolin-6-yl)-1H-pyrazolo[3,4-d]pyrimidin-6-y)amino)-N,1-dimethylcyclopentane-1-carboxamide was prepared employing general synthesis procedure F and methyl iodide as alkylating reagent, followed by general synthesis procedure D(c) with product from the previous step and Precursor I (X=Cl, R'''=H), followed by general synthesis procedure B with product from the previous step and quinoline-6-boronic acid, followed by ester hydrolysis in THF/water mixture at ambient temperature with 10 equivalents of LiOH until complete conversion was reached, followed by acidification with trifluoroacetic acid to pH 3 and isolation of the carboxylic acid compound by reverse phase HPLC. Final amide coupling was performed employing general synthesis procedure C using HATU and methylamine. Title diastereomer was separated at the final step by reverse phase HPLC and comes out as the first peak. ¹H NMR (400 MHz, Methanol-d4, TFA salt) δ 9.37-9.19 (m, 2H), 9.16-8.97 (m, 2H), 8.64 (s, 1H), 8.32 (d, J=9.3 Hz, 1H), 8.09-7.93 (m, 1H), 4.60-4.47 (m, 1H), 3.01-2.88 (m, 1H), 2.83 (s, 3H), 2.36-2.12 (m, 2H), 1.93-1.69 (m, 2H), 1.54-1.41 (m, 1H), 1.39 (s, 3H) ppm. LCMS [M+H] 480.0.

Example 19

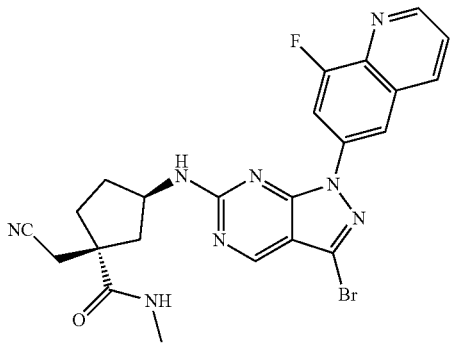 [SMILES: CNC(=O)[C@]1(CC#N)CC[C@@H](Nc2ncc3c(Br)nn(-c4cc(F)c5ncccc5c4)c3n2)C1]

(1R,3R)-3-((3-bromo-1-(8-fluoroquinolin-6-yl)-1H-pyrazolo[3,4-d]pyrimidin-6-yl)amino)-1-(cyanomethyl)-N-methylcyclopentane-1-carboxamide was prepared employing general synthesis procedure F and 2-bromoacetonitrile as alkylating reagent, followed by general synthesis procedure D(c) with product from the previous step and Precursor I (X=Cl, R'''=H), followed by general synthesis procedure B with product from the previous step and 8-fluoroquinoline-6-boronic acid, followed by ester hydrolysis in THF/water mixture at ambient temperature with 10 equivalents of LiOH until complete conversion was reached, followed by acidification with trifluoroacetic acid to pH 3 and isolation of the carboxylic acid compound by reverse phase HPLC. Final amide coupling was performed employing general synthesis procedure C using HATU and methylamine. Title diastereomer was separated at the final step by reverse phase HPLC and comes out as the first peak. $^1$H NMR (400 MHz, Methanol-d4, HC salt) δ 8.93-8.82 (m, 1H), 8.81-8.63 (m, 1H), 8.61-8.47 (m, 3H), 8.43-8.33 (m, 1H), 7.77-7.59 (m, 1H), 4.49 (s, 1H), 2.91 (s, 2H), 2.85 (s, 1H), 2.84-2.71 (m, 2H), 2.42-2.12 (m, 4H), 2.05-1.80 (m, 2H), 1.76-1.66 (m, 1H) ppm. LCMS [M+H] 523.1.

Example 20

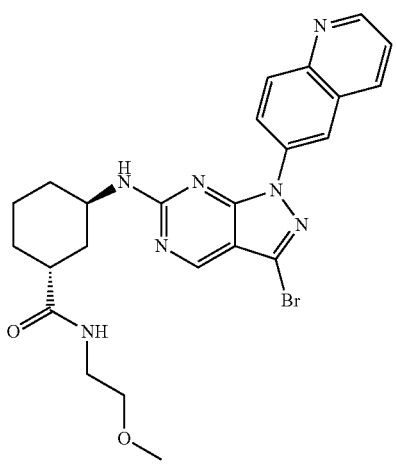 [SMILES: COCCNC(=O)[C@@H]1CCC[C@@H](Nc2ncc3c(Br)nn(-c4ccc5ncccc5c4)c3n2)C1]

(1R,3R)-3-((3-bromo-1-(quinolin-6-yl)-1H-pyrazolo[3,4-d]pyrimidin-6-yl)amino)-N-(2-methoxyethyl)cyclohexane-1-carboxamide was prepared employing general synthesis procedure B with Precursor I and quinoline-6-boronic acid, followed by general synthesis procedure D(b) with the product from previous step and (R,3R)-3-aminocyclohexane-1-carboxylic acid, followed by general synthesis procedure C using T3P, product from the previous step and 2-methoxyethan-1-amine. $^1$H NMR (400 MHz, Methanol-d4, TFA salt) δ 9.36 (d, J=8.4 Hz, 1H), 9.28 (s, 1H), 9.17 (dd, J=5.2 Hz, J=1.5 Hz, 1H), 9.14-9.09 (m, 1H), 8.70 (s, 1H), 8.36 (d, J=9.4 Hz, 1H), 8.08 (dd, J=8.4 Hz, J=5.2 Hz, 1H), 4.70-4.57 (m, 1H), 3.51-3.45 (m, 2H), 3.46-3.38 (m, 2H), 3.32 (s, 3H), 2.80-2.67 (m, 1H), 2.26-2.13 (m, 1H), 2.04-1.91 (m, 2H), 1.89-1.72 (m, 5H) ppm. LCMS [M+H] 524.1.

Example 21

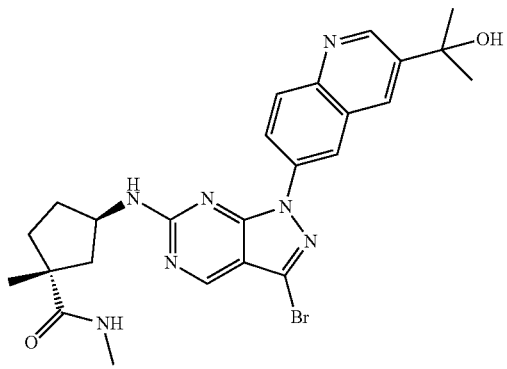 [SMILES: CNC(=O)[C@]1(C)CC[C@@H](Nc2ncc3c(Br)nn(-c4ccc5ncc(C(C)(C)O)cc5c4)c3n2)C1]

(1R,3R)-3-((3-bromo-1-(3-(2-hydroxypropan-2-yl)quinolin-6-yl)-1H-pyrazolo[3,4-d]pyrimidin-6-yl)amino)-N,1-dimethylcyclopentane-1-carboxamide was prepared employing general synthesis procedure F and methyl iodide as alkylating reagent, followed by general synthesis procedure D(c) with product from the previous step and Precursor I, followed by ester hydrolysis (0.07M) with 3 equiv. of LiOH in THF/water (2:1) at 70° C. until full conversion was achieved (conversion analysis was carried out by LCMS), followed by acidification and extraction with EtOAc, followed by solvent removal and general synthesis procedure A (R=Me) using crude material from the previous step and methylamine. The title compound was obtained by using product from the last step and general synthesis procedure B with (3-(2-hydroxypropan-2-yl)quinolin-6-yl)boronic acid. $^1$H NMR (400 MHz, Methanol-d4, HCl salt) δ 9.41 (s, 1H), 9.37-9.32 (m, 2H), 9.19 (d, J=9.4 Hz, 1H), 8.77 (s, 1H), 8.41 (d, J=9.6 Hz, 1H), 4.60-4.48 (m, 1H), 2.99 (s, 1H), 2.79 (s, 3H), 2.35-2.13 (m, 2H), 1.76 (s, 9H), 1.47 (dd, J=13.0, 8.5 Hz, 1H), 1.41-1.32 (m, 5H) ppm. LCMS [M+H] 538.1.

Example 22

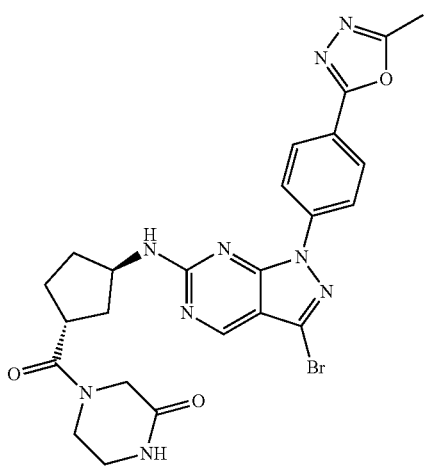 [SMILES: Cc1nnc(-c2ccc(-n3nc(Br)c4cnc(N[C@@H]5CC[C@@H](C(=O)N6CCNC(=O)C6)C5)nc43)cc2)o1]

4-((1R,3R)-3-((3-bromo-1-(4-(5-methyl-1,3,4-oxadiazol-2-yl)phenyl)-1H-pyrazolo[3,4-d]pyrimidin-6-yl)amino)cyclopentane-1-carbonyl)piperazin-2-one was prepared employing general synthesis procedure E(a) using piperazin-2-one, followed by general synthesis procedure D(a) using product from the previous step and Precursor I (at the workup step the mixture was acidified to pH 3 instead of pH 7), followed by general synthesis procedure B with product from the previous step and (4-(5-methyl-1,3,4-oxadiazol-2-yl)phenyl)boronic acid. $^1$H NMR (400 MHz, DMSO-d6) δ 8.78 (s, 1H), 8.55-8.45 (m, 2H), 8.13 (d, J=8.3 Hz, 2H), 4.39-4.30 (m, 1H), 4.10 (s, 1H), 3.98 (s, 1H), 3.71-3.57 (m, 2H), 3.23-3.13 (m, 2H), 2.58 (s, 3H), 2.12-1.94 (m, 3H), 1.85-1.63 (m, 3H) ppm. LCMS [M+H] 566.1.

Example 23

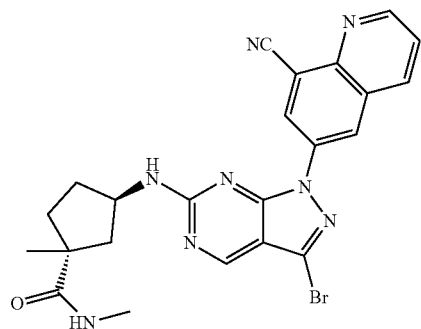 [SMILES: CNC(=O)[C@]1(C)CC[C@@H](Nc2ncc3c(Br)nn(-c4cc(C#N)c5ncccc5c4)c3n2)C1]

(1R,3R)-3-((3-bromo-1-(8-cyanoquinolin-6-yl)-1H-pyrazolo[3,4-d]pyrimidin-6-yl)amino)-N,1-dimethylcyclopentane-1-carboxamide was prepared employing general synthesis procedure F and methyl iodide as alkylating reagent, followed by general synthesis procedure D(c) with product from the previous step and Precursor I (for purification 0-50% EtOAc/hexanes gradient was used instead of methanol/dichloromethane), followed by ester hydrolysis (0.07M) with 3 equiv. of LiOH in THF/water (2:1) at 70° C. until full conversion was achieved (followed by LCMS), followed by acidification and extraction with EtOAc, followed by solvent removal and general synthesis procedure A (R=Me) using crude material from the previous step and methylamine and 0-100% EtOAc/hexanes gradient for purification on silica gel. The title compound was obtained by using product from the last step and general synthesis procedure B with 8-cyanoquinoline-6-boronic acid. The title diastereomer was separated on reverse phase HPLC and comes out as the first peak. $^1$H NMR (400 MHz, Methanol-d4, TFA salt) δ 9.21 (s, 1H), 9.13 (s, 1H), 8.98 (s, 1H), 8.65-8.59 (m, 2H), 7.71-7.61 (m, 1H), 4.57-4.43 (m, 1H), 2.91-2.81 (m, 1H), 2.78 (s, 3H), 2.43-2.29 (m, 1H), 2.28-2.13 (m, 1H), 1.90-1.70 (m, 2H), 1.61-1.49 (m, 1H), 1.37 (s, 3H) ppm. LCMS [M+H] 505.1.

Example 24

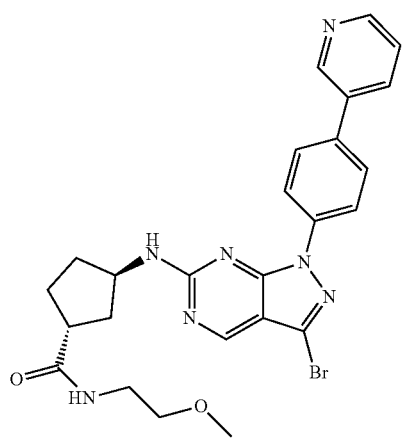 [SMILES: COCCNC(=O)[C@@H]1CC[C@@H](Nc2ncc3c(Br)nn(-c4ccc(-c5cccnc5)cc4)c3n2)C1]

(1R,3R)-3-((3-bromo-1-(4-(pyridin-3-yl)phenyl)-1H-pyrazolo[3,4-d]pyrimidin-6-yl)amino)-N-(2-methoxyethyl)cyclopentane-1-carboxamide was prepared employing general synthesis procedure E(b) with Precursor II and 2-methoxyethan-1-amine, followed by general synthesis procedure D(c) with the product from previous step and Precursor I (X=Cl, R'''=H), followed by general synthesis procedure B with the product from previous step and (4-(pyridin-3-yl)phenyl)boronic acid. $^1$H NMR (400 MHz, Methanol-d4, TFA salt): d 9.10-9.25 (bs, 1H), 8.75-8.85 (m, 2H), 8.60 (s, 1H), 8.45 (d, J=8.7 Hz, 2H), 8.03-8.11 (m, 1H), 7.92 (d, J=8.3 Hz, 2H), 4.43-4.53 (m, 1H), 3.43-3.48 (m, 2H), 3.35-3.40 (m, 2H), 3.31 (s, 3H), 2.89-3.00 (m, 1H), 2.20-2.40 (m, 2H), 2.04-2.16 (m, 1H), 1.80-1.95 (m, 2H), 1.67-1.80 (m, 1H) ppm. LCMS [M+H]536.0.

Example 25

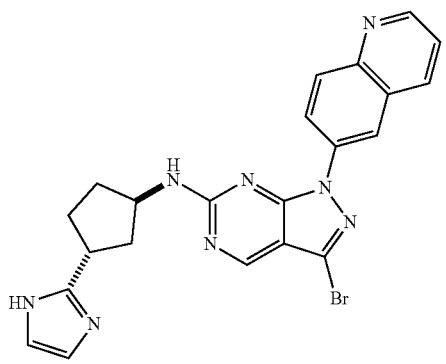

N-((1R,3R)-3-(1H-imidazol-2-yl)cyclopentyl)-3-bromo-1-(quinolin-6-yl)-1H-pyrazolo[3,4-d]pyrimidin-6-amine. Trans-3-(1H-imidazol-2-yl)cyclopentan-1-amine was prepared via reaction steps 1-3 described in Example 154, followed by deprotection in dichloromethane/TFA mixture (1:1) at 40° C. for 30 min (0.1M). The title compound was prepared using general synthesis procedure B using Precursor I and quinoline-6-boronic acid, followed by general synthesis procedure D(b) using crude trans-3-(1H-imidazol-2-yl)cyclopentan-1-amine trifluoroacetate. $^1$H NMR (400 MHz, Methanol-d4, TFA salt): d 8.89.8.95 (bs, 1H), 8.1-8.81 (bm, 2H), 8.48-8.68 (bm, 2H), 8.07-8.14 (m, 1H), 7.68-7.76 (bm, 1H), 7.47 (s, 2H), 4.53-4.68 (bm, 1H), 3.69-3.80 (m, 1H), 2.27-2.56 (m, 4H), 1.87-2.08 (m, 2H) ppm. LCMS [M+H] 475.0

Example 26

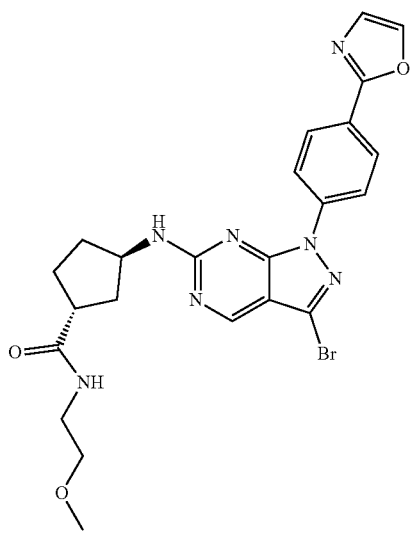 [SMILES: COCCNC(=O)[C@@H]1CC[C@@H](Nc2ncc3c(Br)nn(-c4ccc(-c5ncco5)cc4)c3n2)C1]

(1R,3R)-3-((3-bromo-1-(4-(oxazol-2-yl)phenyl)-1H-pyrazolo[3,4-d]pyrimidin-6-yl)amino)-N-(2-methoxyethyl)cyclopentane-1-carboxamide was prepared employing general synthesis procedure E(b) with Precursor II and 2-methoxyethan-1-amine, followed by general synthesis procedure D(c) with the product from previous step and Precursor I, followed by general synthesis procedure B with the product from previous step and (4-(oxazol-2-yl)phenyl) boronic acid. $^1$H NMR (400 MHz, Methanol-d4, TFA salt): d 8.61-8.68 (bm, 1H), 8.39-8.47 (m, 2H), 8.10-8.19 (m, 2H), 7.99-8.04 (m, 1H), 7.30-7.34 (bs, 1H), 4.45-4.55 (bs, 1H), 3.34-3.49 (m, 4H), 3.31 (s, 3H), 2.88-2.98 (m, 1H), 2.20-2.38 (m, 2H), 2.02-2.14 (m, 1H), 1.68-2.00 (m, 3H) ppm. LCMS [M+H] 526.0.

Example 27

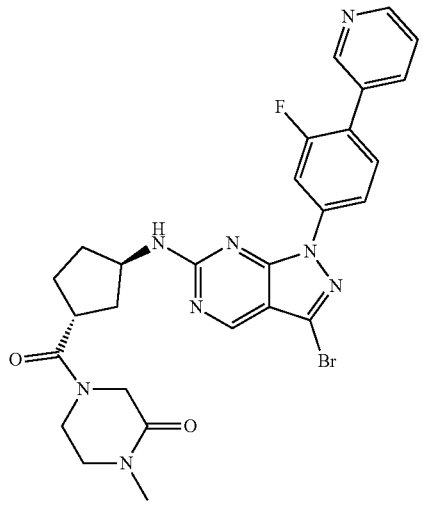 [SMILES: CN1CCN(C(=O)[C@@H]2CC[C@@H](Nc3ncc4c(Br)nn(-c5ccc(-c6cccnc6)c(F)c5)c4n3)C2)CC1=O]

4-((1R,3R)-3-((3-bromo-1-(3-fluoro-4-(pyridin-3-yl)phenyl)-1H-pyrazolo[3,4-d]pyrimidin-6-yl)amino)cyclopentane-1-carbonyl)-1-methylpiperazin-2-one was prepared employing general synthesis procedure E(b) with Precursor II and 1-methylpiperazin-2-one, followed by general synthesis procedure D(c) with the product from previous step and Precursor I, followed by general synthesis procedure B with the product from previous step and (3-fluoro-4-(pyridin-3-yl)phenyl)boronic acid. $^1$H NMR (400 MHz, Methanol-d4, TFA salt): d 8.97-9.10 (bs, 1H), 8.72-8.82 (bm, 1H), 8.56-8.67 (m, 2H), 8.20-8.44 (m, 2H), 7.93-8.06 (m, 1H), 7.73-7.85 (m, 1H), 4.41-4.51 (bm, 1H), 4.11-4.28 (m, 2H), 3.82-3.92 (m, 2H), 3.34-3.50 (m, 3H), 2.94-3.00 (m, 3H), 2.06-2.50 (m, 3H), 1.70-2.06 (m, 3H) ppm. LCMS [M+H] 593.0.

Example 28

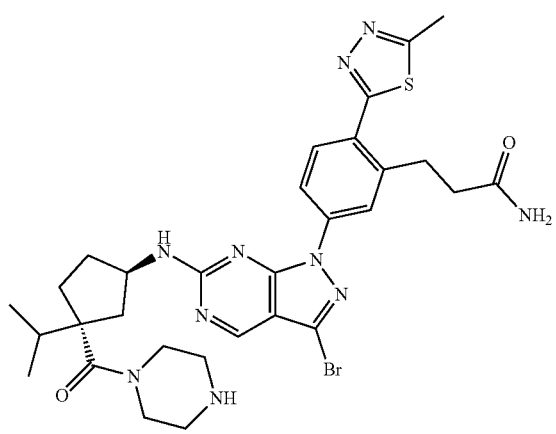 [SMILES: Cc1nnc(-c2ccc(-n3nc(Br)c4cnc(N[C@@H]5CC[C@](C(=O)N6CCNCC6)(C(C)C)C5)nc43)cc2CCC(N)=O)s1]

3-(5-(3-bromo-6-((((1R,3R)-3-isopropyl-3-(piperazine-1-carbonyl)cyclopentyl)amino)-1H-pyrazolo[3,4-d]pyrimidin-1-yl)-2-(5-methyl-1,3,4-thiadiazol-2-yl)phenyl)propanamide; 2,2,2-trifluoroacetic acid was prepared using one or more synthetic methods described earlier herein.

Example 29

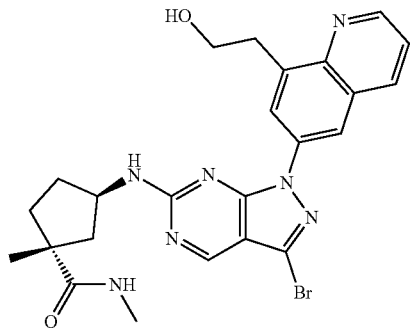 [SMILES: CNC(=O)[C@]1(C)CC[C@@H](Nc2ncc3c(Br)nn(-c4cc(CCO)c5ncccc5c4)c3n2)C1]

(1R,3R)-3-((3-bromo-1-(8-(2-hydroxyethyl)quinolin-6-yl)-1H-pyrazolo[3,4-d]pyrimidin-6-yl)amino)-N,1-dimethylcyclopentane-1-carboxamide hydrochloride was prepared using general procedure A(a), followed by general procedure B with (8-(2-hydroxyethyl)quinolin-6-yl)boronic acid. $^1$H NMR (400 MHz, Methanol-d4): δ 8.96-8.84 (m, 1H), 8.82 (s, 1H), 8.76-8.57 (m, 3H), 7.71 (s, 1H), 4.62-4.50 (m, 1H), 4.01 (t, J=6.4 Hz, 2H), 3.55 (t, J=6.4 Hz, 2H), 2.90-2.65 (m, 4H), 2.42-2.04 (m, 2H), 1.87-1.64 (m, 1H), 1.52 (dd, J=13.2, 8.2 Hz, 1H), 1.42-1.17 (m, 4H) ppm. LCMS [M+H] 524.1.

Example 31

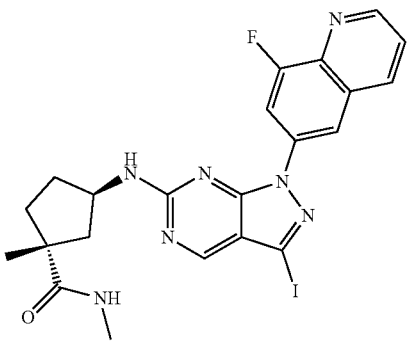

(1R,3R)-3-((1-(8-fluoroquinolin-6-yl)-3-iodo-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (8-fluoroquinolin-6-yl)boronic acid. $^1$H NMR (400 MHz, Methanol-d4) δ 9.58 (s, 1H), 9.23 (dd, J=5.2, 1.4 Hz, 1H), 9.22-9.15 (m, 1H), 8.95-8.85 (m, 1H), 8.78 (s, 1H), 8.21 (dd, J=8.5, 5.3 Hz, 1H), 4.72-4.55 (m, 1H), 2.98-2.86 (m, 1H), 2.81 (s, 3H), 2.36-2.25 (m, 1H), 2.25-2.15 (m, 1H), 1.96-1.76 (m, 2H), 1.50 (dd, J=13.0, 8.7 Hz, 1H), 1.40 (s, 3H). LCMS [M+H] 545.9.

Example 30

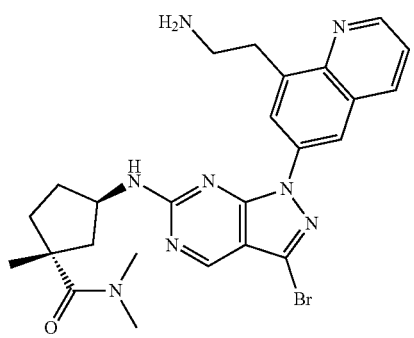 [SMILES: CN(C)C(=O)[C@]1(C)CC[C@@H](Nc2ncc3c(Br)nn(-c4cc(CCN)c5ncccc5c4)c3n2)C1]

(1R,3R)-3-((1-(8-(2-aminoethyl)quinolin-6-yl)-3-bromo-1H-pyrazolo[3,4-d]pyrimidin-6-yl)amino)-N,N,1-trimethylcyclopentane-1-carboxamide; 2,2,2-trifluoroacetic acid was prepared using general procedure A(a), followed by general procedure B with (8-(2-((tert-butoxycarbonyl)amino)ethyl)quinolin-6-yl)boronic acid. Final compound was afforded by deprotection with trifluoroacetic acid in dichloromethane. $^1$H NMR (400 MHz, Methanol-d4) δ 8.91 (dd, J=4.3, 1.7 Hz, 1H), 8.78-8.65 (m, 2H), 8.60 (s, 1H), 8.48 (d, J=5.6 Hz, 1H), 7.59 (dt, J=8.2, 3.9 Hz, 1H), 4.34 (p, J=8.2 Hz, 1H), 3.62 (t, J=7.1 Hz, 2H), 3.41 (t, J=7.2 Hz, 2H), 3.21-2.91 (m, 7H), 2.38-2.27 (m, 1H), 2.21 (p, J=6.7 Hz, 1H), 1.90 (t, J=8.9 Hz, 1H), 1.85-1.72 (m, 1H), 1.59 (dd, J=13.0, 8.4 Hz, 1H), 1.46 (s, 3H). LCMS [M+H] 537.0.

Example 32

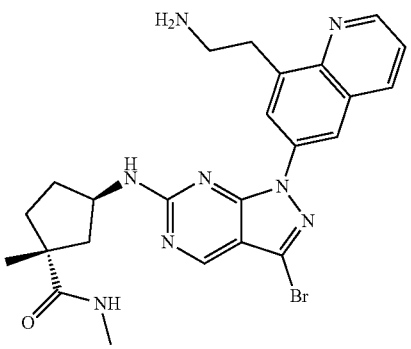 [SMILES: CNC(=O)[C@]1(C)CC[C@@H](Nc2ncc3c(Br)nn(-c4cc(CCN)c5ncccc5c4)c3n2)C1]

(1R,3R)-3-((1-(8-(2-aminoethyl)quinolin-6-yl)-3-bromo-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (8-(2-((tert-butoxycarbonyl)amino)ethyl)quinolin-6-yl)boronic acid. Final compound was afforded by deprotection with trifluoroacetic acid in dichloromethane. $^1$H NMR (400 MHz, Methanol-d4; TFA salt) δ 8.89 (dd, J=4.4, 1.7 Hz, 1H), 8.76 (s, 1H), 8.51 (s, 2H), 8.44 (d, J=8.2 Hz, 1H), 7.59 (dd, J=8.3, 4.4 Hz, 1H), 4.41 (q, J=7.8 Hz, 1H), 3.65-3.53 (m, 2H), 3.41 (t, J=7.1 Hz, 2H), 2.86 (q, J=9.9, 9.3 Hz, 1H), 2.80 (s, 3H), 2.34-2.12 (m, 2H), 1.86-1.69 (m, 2H), 1.46 (dd, J=13.1, 8.5 Hz, 1H), 1.39 (s, 3H). LCMS [M+H] 523.2.

Example 33

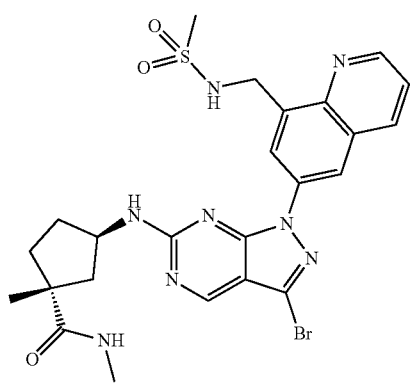 [SMILES: CNC(=O)[C@]1(C)CC[C@@H](Nc2ncc3c(Br)nn(-c4cc(CNS(C)(=O)=O)c5ncccc5c4)c3n2)C1]

(1R,3R)-3-((3-bromo-1-(8-(methylsulfonamidomethyl)quinolin-6-yl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with ((8-(((tert-butyldimethylsilyl)oxy)methyl)quinolin-6-yl)boronic acid. Final compound was afforded by: 1) deprotection with 1M TBAF in THF at ambient temperature, 2) mesylation of the alcohol in dichloromethane in the presence of 3 eq of N,N-diisopropylethylamine, 3) displacement of mesylate with tert-butyl (methylsulfonyl)carbamate in the presence of ceaesium carbonate in acetonitrile, 4) acidic deprotection of Boc protecting group. Final compound was purified by reverse phase HPLC. $^1$H NMR (400 MHz, Methanol-d4) δ 8.99 (s, 1H), 8.93 (d, J=4.5 Hz, 1H), 8.77 (s, 1H), 8.70 (d, J=8.1 Hz, 1H), 8.60 (s, 1H), 7.71 (dd, J=8.2, 4.6 Hz, 1H), 4.96 (s, 2H), 4.57 (p, J=7.5 Hz, 1H), 3.03 (s, 3H), 2.93-2.83 (m, 1H), 2.78 (s, 3H), 2.34-2.16 (m, 2H), 1.86-1.69 (m, 2H), 1.46 (dd, J=13.3, 8.0 Hz, 1H), 1.37 (s, 3H). LCMS [M+H] 587.1.

Example 34

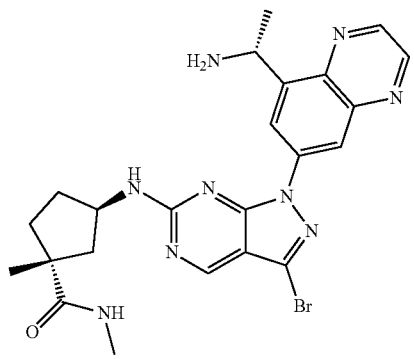 [SMILES: CNC(=O)[C@]1(C)CC[C@@H](Nc2ncc3c(Br)nn(-c4cc([C@@H](C)N)c5nccnc5c4)c3n2)C1]

(1R,3R)-3-((1-(8-((R)-1-aminoethyl)quinoxalin-6-yl)-3-bromo-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (R)-(8-(1-((tert-butoxycarbonyl)amino)ethyl)quinoxalin-6-yl)boronic acid. Final compound was afforded by deprotection with trifluoroacetic acid in dichloromethane. $^1$H NMR (400 MHz, Chloroform-d) δ 8.99 (s, 1H), 8.94 (s, 1H), 8.84 (s, 1H), 8.76 (s, 1H), 8.62 (s, 1H), 5.40 (q, J=5.4 Hz, 1H), 4.52 (p, J=7.0 Hz, 1H), 2.81 (t, J=10.1 Hz, 1H), 2.69 (s, 3H), 2.26 (q, J=13.0, 9.8, 8.2 Hz, 1H), 2.14-2.01 (m, 1H), 1.90 (d, J=7.0 Hz, 3H), 1.76-1.67 (m, 2H), 1.30 (s, 3H), 1.28-1.19 (m, 1H). LCMS [M+H] 524.1.

Example 35

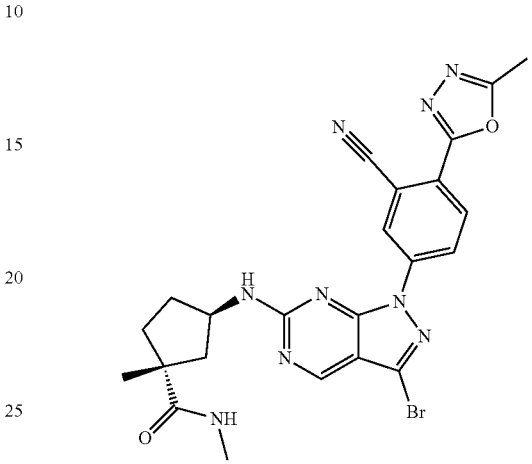

(1R,3R)-3-((3-bromo-1-(3-cyano-4-(5-methyl-1,3,4-oxadiazol-2-yl)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (3-cyano-4-(5-methyl-1,3,4-oxadiazol-2-yl)phenyl)boronic acid. $^1$H NMR (400 MHz, Methanol-d4; TFA salt) δ 8.93 (s, 1H), 8.85 (d, J=8.6 Hz, 1H), 8.64 (s, 1H), 8.35 (d, J=8.4 Hz, 1H), 4.49-4.33 (m, 1H), 2.83-2.75 (m, 1H), 2.77 (s, 3H), 2.68 (s, 3H), 2.38-2.25 (m, 1H), 2.24-2.12 (m, 2H), 1.85-1.66 (m, 2H), 1.62-1.47 (m, 1H), 1.36 (s, 3H). LCMS [M+H]536.1.

Example 36

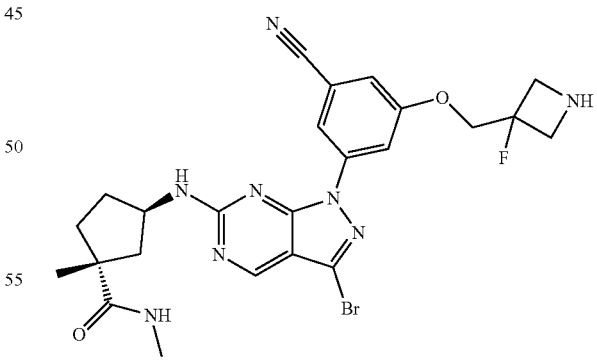

(1R,3R)-3-((3-bromo-1-(3-cyano-5-((3-fluoroazetidin-3-yl)methoxy)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (tert-butyl 3-((3-cyano-5-(4,4,5,5-tetramethyl-1,3,2-dioxaborolan-2-yl)phenoxy)methyl)-3-fluoroazetidine-1-carboxylate. LCMS [M+H] 557.0.

Example 37

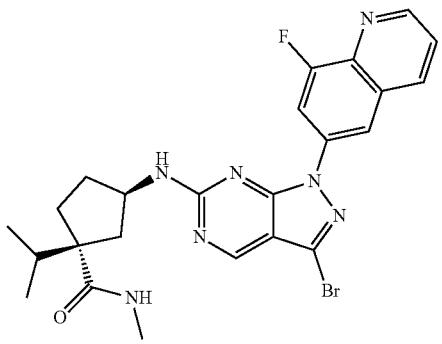 [SMILES: CNC(=O)[C@]1(C(C)C)CC[C@@H](Nc2ncc3c(Br)nn(-c4cc(F)c5ncccc5c4)c3n2)C1]

(1R,3R)-3-((3-bromo-1-(8-fluoroquinolin-6-yl)-1H-pyrazolo[3,4-d]pyrimidin-6-yl)amino)-1-isopropyl-N-methylcyclopentane-1-carboxamide hydrochloride was prepared using general procedure A(a), followed by general procedure B with 8-fluoroquinoline-6-boronic acid. $^1$H NMR (400 MHz, Methanol-d4): δ 9.53-9.39 (m, 1H), 9.22-9.07 (m, 2H), 8.92-8.78 (m, 1H), 8.73 (s, 1H), 8.09 (dd, J=8.5, 5.1 Hz, 1H), 4.52-4.35 (m, 1H), 2.84 (s, 3H), 2.26-2.08 (m, 2H), 2.02 (p, J=6.8 Hz, 1H), 1.97-1.85 (m, 1H), 1.78-1.62 (m, 1H), 1.51 (t, J=11.3 Hz, 1H), 1.37 (dd, J=6.7, 4.1 Hz, 1H), 0.98 (d, J=6.8 Hz, 3H), 0.91 (d, J=6.8 Hz, 3H) ppm. LCMS [M+H] 526.1.

Example 38

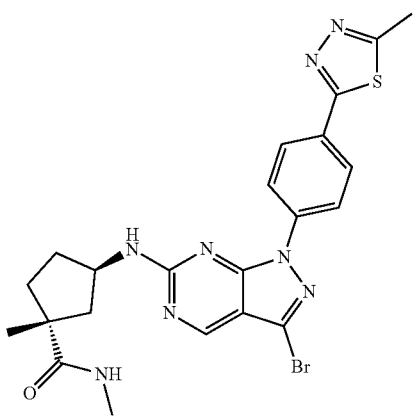

(1R,3R)-3-((3-bromo-1-(4-(5-methyl-1,3,4-thiadiazol-2-yl)phenyl)-1H-pyrazolo[3,4-d]pyrimidin-6-yl)amino)-N,1-dimethylcyclopentane-1-carboxamide was prepared using general procedure A(a), followed by general procedure B with 2-methyl-5-(4-(4,4,5,5-tetramethyl-1,3,2-dioxaborolan-2-yl)phenyl)-1,3,4-oxadiazole. $^1$H NMR (400 MHz, Chloroform-d, mesylate): δ 9.62 (d, J=6.2 Hz, 1H), 8.52 (s, 1H), 8.35 (d, J=8.0 Hz, 2H), 8.16 (d, J=8.0 Hz, 2H), 5.77 (s, 1H), 4.58 (h, J=7.4 Hz, 1H), 2.93 (s, 3H), 2.92-2.89 (m, 1H), 2.89 (d, J=4.1 Hz, 3H), 2.86 (s, 3H), 2.36-2.24 (m, 1H), 2.17 (dt, J=12.8, 7.7 Hz, 1H), 1.92 (dq, J=12.3, 7.9 Hz, 1H), 1.80 (ddd, J=13.3, 8.4, 5.0 Hz, 1H), 1.51 (dd, J=13.2, 7.7 Hz, 1H), 1.40 (s, 3H) ppm. LCMS [M+H] 527.0.

Example 39

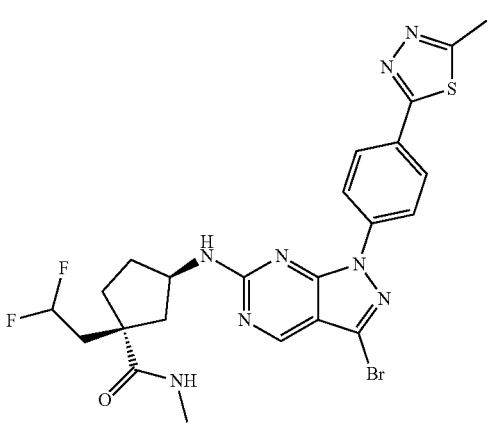 [SMILES: CNC(=O)[C@]1(CC(F)F)CC[C@@H](Nc2ncc3c(Br)nn(-c4ccc(-c5nnc(C)s5)cc4)c3n2)C1]

(1R,3R)-3-((3-bromo-1-(4-(5-methyl-1,3,4-thiadiazol-2-yl)phenyl)-1H-pyrazolo[3,4-d]pyrimidin-6-yl)amino)-1-(2,2-difluoroethyl)-N-methylcyclopentane-1-carboxamide; 2,2,2-trifluoroacetic acid was prepared using general procedure A(a), followed by general procedure B with 2-methyl-5-(4-(4,4,5,5-tetramethyl-1,3,2-dioxaborolan-2-yl)phenyl)-1,3,4-oxadiazole. $^1$H NMR (400 MHz, Methanol-d4; TFA salt) δ 8.66 (s, 1H), 8.42 (d, J=8.7 Hz, 2H), 8.08 (d, J=8.4 Hz, 2H), 5.85 (tt, J=56.1, 4.8 Hz, 1H), 4.50-4.35 (m, 1H), 2.92-2.82 (m, 1H), 2.82 (s, 3H), 2.81 (s, 3H), 2.39-2.18 (m, 4H), 1.95-1.85 (m, 1H), 1.83-1.72 (m, 1H), 1.63 (dd, J=13.3, 8.6 Hz, 1H). LCMS [M+H] 577.1.

Example 40

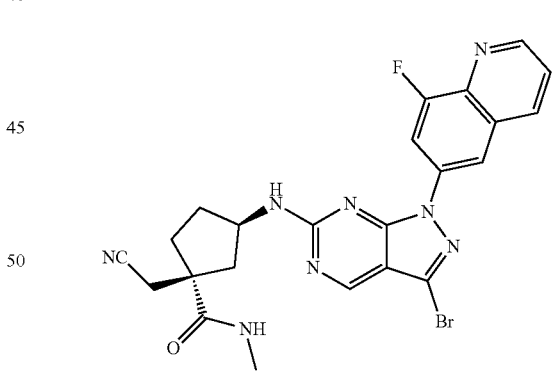

(1R,3R)-3-((3-bromo-1-(8-fluoroquinolin-6-yl)-1H-pyrazolo[3,4-d]pyrimidin-6-yl)amino)-1-(cyanomethyl)-N-methylcyclopentane-1-carboxamide hydrochloride was prepared using general procedure A(a), followed by general procedure B with 8-fluoroquinoline-6-boronic acid. $^1$H NMR (400 MHz, Methanol-d4): δ 8.92-8.82 (m, 1H), 8.79-8.63 (m, 1H), 8.61-8.35 (m, 3H), 7.71 (td, J=9.1, 4.5 Hz, 1H), 4.63-4.34 (m, 1H), 2.91 (s, 3H), 2.79 (s, 2H), 2.47-2.19 (m, 3H), 2.06-1.79 (m, 2H), 1.71 (dd, J=16, 8 Hz, 1H) ppm. LCMS [M+H] 523.1.

Example 41

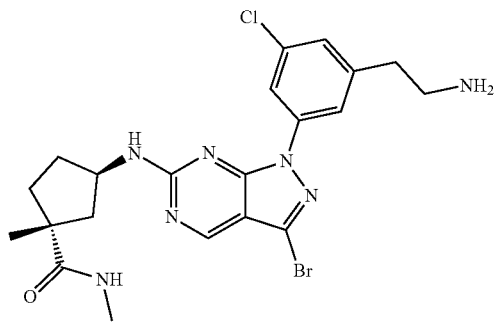 [SMILES: CNC(=O)[C@]1(C)CC[C@@H](Nc2ncc3c(Br)nn(-c4cc(Cl)cc(CCN)c4)c3n2)C1]

(1R,3R)-3-((1-(3-(2-aminoethyl)-5-chlorophenyl)-3-bromo-1H-pyrazolo[3,4-d]pyrimidin-6-yl)amino)-N,1-dimethylcyclopentane-1-carboxamide hydrochloride was prepared using general procedure A(a), followed by general procedure B with tert-butyl (3-chloro-5-(4,4,5,5-tetramethyl-1,3,2-dioxaborolan-2-yl)phenethyl)carbamate, followed by acidic deprotection of the Boc group. $^1$H NMR (400 MHz, Methanol-d4 and CDCl3; HCl salt) δ 8.90 (s, 1H), 8.32 (s, 1H), 7.96 (s, 1H), 7.29 (s, 1H), 4.42-4.53 (m, 1H), 3.09-3.28 (m, 4H), 2.82 (dd, J=8.1 Hz, J=13.2 Hz, 1H), 2.73 (s, 3H), 2.22-2.34 (m, 1H), 2.09-2.19 (m, 1H), 1.70-1.90 (m, 2H), 1.51 (dd, J=8.4 Hz, J=13.1 Hz, 1H), 1.37 (s, 3H) ppm. LCMS [M+H] 506.1.

Example 42

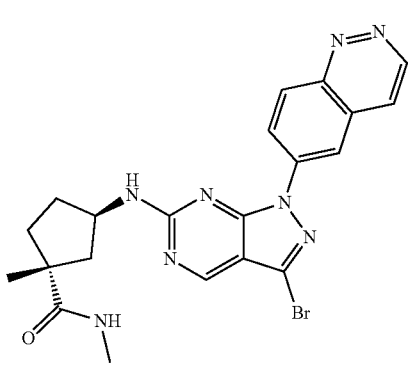 [SMILES: CNC(=O)[C@]1(C)CC[C@@H](Nc2ncc3c(Br)nn(-c4ccc5nnccc5c4)c3n2)C1]

(1R,3R)-3-((3-bromo-1-(cinnolin-6-yl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with cinnolin-6-ylboronic acid. $^1$H NMR (400 MHz, Methanol-d4; TFA salt) δ 9.34 (d, J=4.9 Hz, 1H), 9.15 (s, 1H), 9.03 (d, J=9.8 Hz, 1H), 8.85 (d, J=5.3 Hz, 1H), 8.61 (s, 1H), 8.58 (d, J=9.6 Hz, 1H), 4.51 (p, J=8.6, 7.9 Hz, 1H), 2.97-2.88 (m, 1H), 2.82 (s, 3H), 2.33-2.11 (m, 2H), 1.96-1.67 (m, 2H), 1.47-1.39 (m, 1H), 1.37 (s, 3H). LCMS [M+H] 481.1.

Example 43

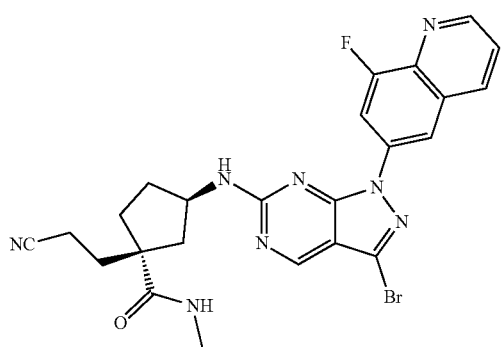 [SMILES: CNC(=O)[C@]1(CCC#N)CC[C@@H](Nc2ncc3c(Br)nn(-c4cc(F)c5ncccc5c4)c3n2)C1]

(1S,3R)-3-((3-bromo-1-(8-fluoroquinolin-6-yl)-1H-pyrazolo[3,4-d]pyrimidin-6-yl)amino)-1-(2-cyanoethyl)-N-methylcyclopentane-1-carboxamide hydrochloride was prepared using general procedure A(b), followed by general procedure B with (8-fluoroquinolin-6-yl)boronic acid. LCMS [M+H] 537.1.

Example 44

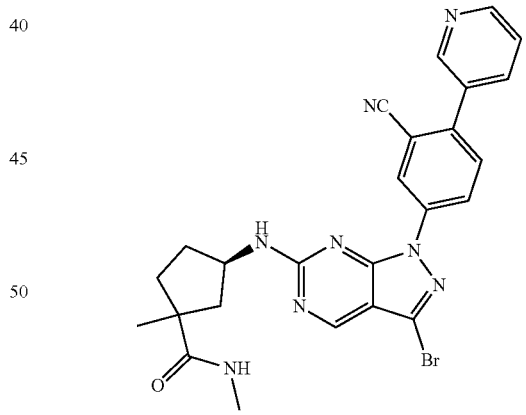

(3R)-3-((3-bromo-1-(3-cyano-4-(pyridin-3-yl)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (3-cyano-4-(pyridin-3-yl)phenyl)boronic acid. LCMS [M+H] 517.1.

Example 45

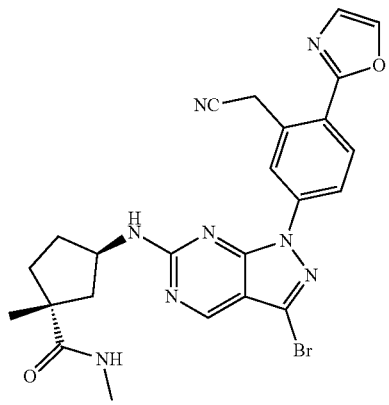 [SMILES: CNC(=O)[C@]1(C)CC[C@@H](Nc2ncc3c(Br)nn(-c4ccc(-c5ncco5)c(CC#N)c4)c3n2)C1]

(1R,3R)-3-((3-bromo-1-(3-(cyanomethyl)-4-(oxazol-2-yl)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with 2-(2-(oxazol-2-yl)-5-(4,4,5,5-tetramethyl-1,3,2-dioxaborolan-2-yl)phenyl)acetonitrile. $^1$H NMR (400 MHz, Chloroform-d) δ 8.73 (s, 1H), 8.59 (s, 1H), 8.23 (dd, J=8.7, 2.2 Hz, 1H), 8.16 (d, J=8.8 Hz, 1H), 7.75 (d, J=0.8 Hz, 1H), 7.27 (d, J=0.8 Hz, 1H), 4.65-4.50 (m, 3H), 2.78 (s, 3H), 2.77-2.71 (m, 1H), 2.29 (q, J=6.5 Hz, 1H), 2.19-2.06 (m, 1H), 1.74-1.64 (m, 2H), 1.46 (dd, J=13.6, 7.1 Hz, 1H), 1.32 (s, 3H). LCMS [M+H] 535.1.

Example 46

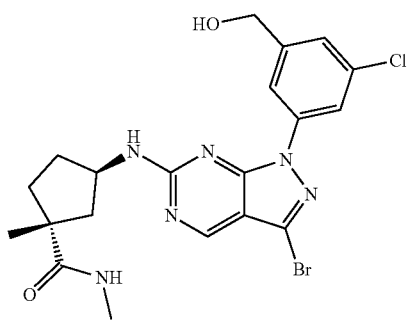 [SMILES: CNC(=O)[C@]1(C)CC[C@@H](Nc2ncc3c(Br)nn(-c4cc(Cl)cc(CO)c4)c3n2)C1]

(1R,3R)-3-((3-bromo-1-(3-chloro-5-(hydroxymethyl)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (3-chloro-5-(hydroxymethyl)phenyl)boronic acid. $^1$H NMR (400 MHz, Methanol-d4; TFA salt) δ 8.59 (s, 1H), 8.30 (s, 1H), 8.08 (t, J=2.0 Hz, 1H), 7.23 (td, J=1.3, 0.7 Hz, 1H), 4.46 (m, 1H), 2.81-2.73 (m, 1H), 2.74 (s, 3H), 2.36-2.22 (m, 1H), 2.20-2.08 (m, 1H), 1.80-1.63 (m, 2H), 1.48 (dd, J=13.4, 7.7 Hz, 1H), 1.33 (s, 3H). LCMS [M+H] 493.1.

Example 47

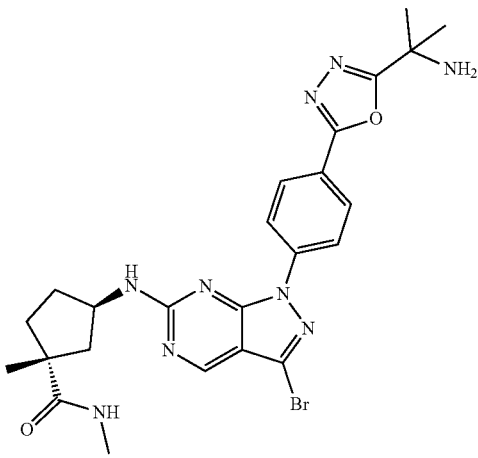 [SMILES: CNC(=O)[C@]1(C)CC[C@@H](Nc2ncc3c(Br)nn(-c4ccc(-c5nnc(C(C)(C)N)o5)cc4)c3n2)C1]

(1R,3R)-3-((1-(4-(5-(2-aminopropan-2-yl)-1,3,4-oxadiazol-2-yl)phenyl)-3-bromo-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with tert-butyl (2-(5-(4-(4,4,5,5-tetramethyl-1,3,2-dioxaborolan-2-yl)phenyl)-1,3,4-oxadiazol-2-yl)propan-2-yl)carbamate, followed by acidic deprotection of the Boc group. $^1$H NMR (400 MHz, Methanol-d4 and CDCl3; TFA salt) δ 8.52-5.58 (bs, 1H), 8.38-8.48 (bm, 2H), 8.07-8.18 (bm, 2H), 4.32-4.44 (bm, 1H), 2.68-2.82 (bs, 3H), 2.04-2.34 (m, 2H), 1.86 (s, 6H), 1.63-1.78 (m, 2H), 1.36-1.48 (m, 1H), 1.33 (s, 3H) ppm. LCMS [M+H] 554.1.

Example 48

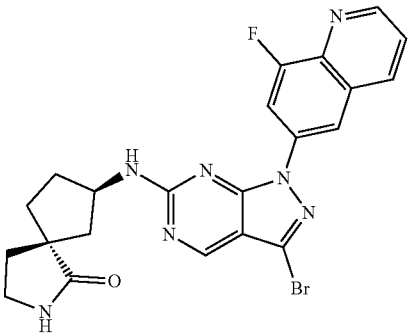 [SMILES: O=C1NCC[C@]12CC[C@@H](Nc1ncc3c(Br)nn(-c4cc(F)c5ncccc5c4)c3n1)C2]

(5S,7R)-7-((3-bromo-1-(8-fluoroquinolin-6-yl)-1H-pyrazolo[3,4-d]pyrimidin-6-yl)amino)-2-azaspiro[4.4]nonan-1-one hydrochloride was prepared using general procedure D(b) with (5S,7R)-7-amino-2-azaspiro[4.4]nonan-1-one. LCMS [M+H] 498.1.

Example 49

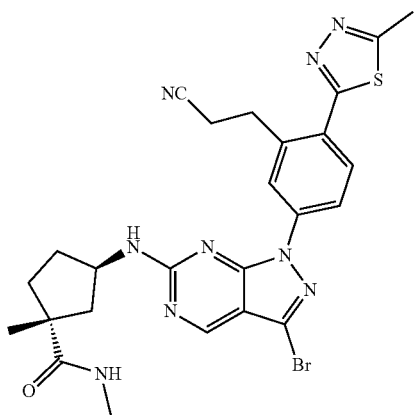

(1R,3R)-3-((3-bromo-1-(3-(2-cyanoethyl)-4-(5-methyl-1,3,4-thiadiazol-2-yl)phenyl)-1H-pyrazolo[3,4-d]pyrimidin-6-yl)amino)-N,1-dimethylcyclopentane-1-carboxamide was prepared using general procedure A(a), followed by general procedure B with 3-(2-(5-methyl-1,3,4-thiadiazol-2-yl)-5-(4,4,5,5-tetramethyl-1,3,2-dioxaborolan-2-yl)phenyl)propanenitrile. ¹H NMR (400 MHz, Chloroform-d, mesylate) δ 9.64 (d, J=6.5 Hz, 1H), 8.51 (s, 1H), 8.44 (d, J=2.3 Hz, 1H), 8.26 (dd, J=8.6, 2.4 Hz, 1H), 7.80 (d, J=8.6 Hz, 1H), 5.77 (bs, 1H), 4.66 (h, J=7.7 Hz, 1H), 3.47 (t, J=6.9 Hz, 2H), 2.96 (t, J=6.9 Hz, 2H), 2.92 (s, 3H), 2.92-2.83 (m, 1H), 2.86 (s, 3H), 2.83 (d, J=4.3 Hz, 3H), 2.37-2.24 (m, 1H), 2.16 (dt, J=12.8, 7.7 Hz, 1H), 1.97-1.86 (m, 1H), 1.84-1.73 (m, 1H), 1.52 (dd, J=13.2, 8.0 Hz, 1H), 1.39 (s, 3H) ppm. LCMS [M+H] 580.1.

Example 50

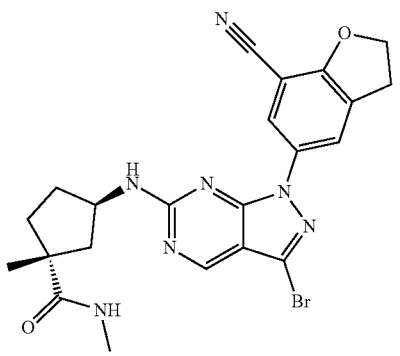 [SMILES: CNC(=O)[C@]1(C)CC[C@@H](Nc2ncc3c(Br)nn(-c4cc(C#N)c5c(c4)CCO5)c3n2)C1]

(1R,3R)-3-((3-bromo-1-(7-cyano-2,3-dihydrobenzofuran-5-yl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (7-cyano-2,3-dihydrobenzofuran-5-yl)boronic acid. ¹H NMR (400 MHz, Methanol-d4; TFA salt) δ 8.56 (s, 1H), 8.19 (s, 1H), 8.10 (s, 1H), 4.77 (t, J=8.8 Hz, 2H), 4.36-4.21 (m, 1H), 3.37 (t, J=8.8 Hz, 2H), 2.74 (s, 3H), 2.73-2.66 (m, 1H), 2.34-2.18 (m, 1H), 2.17-2.02 (m, 1H), 1.78-1.63 (m, 2H), 1.48 (dd, J=12.4, 6.7 Hz, 1H), 1.32 (s, 3H). LCMS [M+H] 493.1.

Example 51

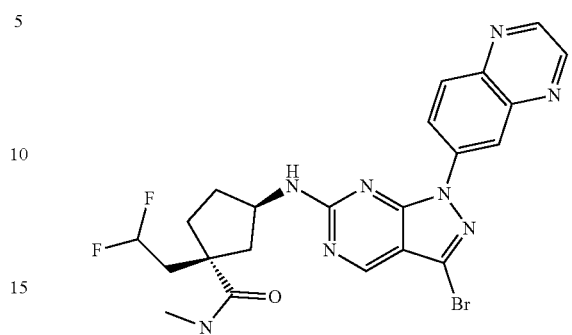

(1R,3R)-3-((3-bromo-1-(quinoxalin-6-yl)-1H-pyrazolo[3,4-d]pyrimidin-6-yl)amino)-1-(2,2-difluoroethyl)-N-methylcyclopentane-1-carboxamide; 2,2,2-trifluoroacetic acid was prepared using general procedure A(a), followed by general procedure B with quinoxalin-6-ylboronic acid. ¹H NMR (400 MHz, Methanol-d4; TFA salt) δ 9.04 (d, J=2.4 Hz, 1H), 8.87 (d, J=1.9 Hz, 1H), 8.83 (d, J=1.9 Hz, 1H), 8.76 (d, J=9.1 Hz, 1H), 8.62 (s, 1H), 8.19 (d, J=9.6 Hz, 1H), 5.81 (tt, J=55.8, 4.2 Hz, 1H), 4.47 (p, J=6.9 Hz, 1H), 2.91-2.81 (m, 1H), 2.78 (s, 3H), 2.41-2.11 (m, 4H), 1.95-1.83 (m, 1H), 1.83-1.64 (m, 2H). LCMS [M+H] 531.1.

Example 52

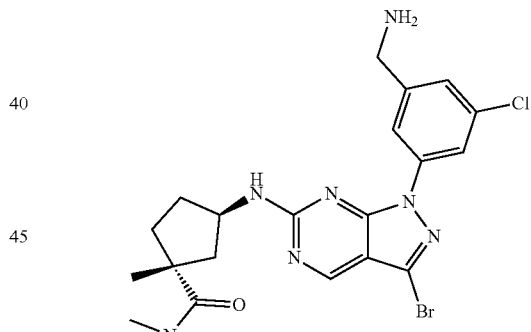

(1R,3R)-3-((1-(3-(aminomethyl)-5-chlorophenyl)-3-bromo-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (3-(((tert-butoxycarbonyl)amino)methyl)-5-chlorophenyl)boronic acid. Final compound was afforded by deprotection with trifluoroacetic acid in dichloromethane. ¹H NMR (400 MHz, Chloroform-d) δ 8.55 (s, 1H), 8.41 (s, 1H), 8.09 (s, 1H), 7.34 (s, 1H), 4.45 (p, J=8.0 Hz, 1H), 4.12 (q, J=9.7 Hz, 2H), 2.82-2.73 (m, 1H), 2.68 (s, 3H), 2.20 (q, J=8.1 Hz, 1H), 2.09-1.99 (m, 1H), 1.74-1.62 (m, 2H), 1.28 (s, 3H), 1.26-1.17 (m, 1H). LCMS [M+H] 492.0.

Example 53

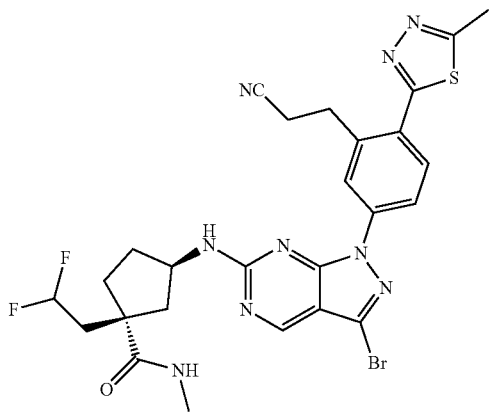 [SMILES: CNC(=O)[C@]1(CC(F)F)CC[C@@H](Nc2ncc3c(Br)nn(-c4ccc(-c5nnc(C)s5)c(CCC#N)c4)c3n2)C1]

(1R,3R)-3-((3-bromo-1-(3-(2-cyanoethyl)-4-(5-methyl-1,3,4-thiadiazol-2-yl)phenyl)-1H-pyrazolo[3,4-d]pyrimidin-6-yl)amino)-1-(2,2-difluoroethyl)-N-methylcyclopentane-1-carboxamide; 2,2,2-trifluoroacetic acid was prepared using general procedure A(a), followed by general procedure B with 3-(2-(5-methyl-1,3,4-thiadiazol-2-yl)-5-(4,4,5,5-tetramethyl-1,3,2-dioxaborolan-2-yl)phenyl)propanenitrile. $^1$H NMR (400 MHz, Chloroform-d; TFA salt) δ 8.63 (s, 1H), 8.47 (s, 1H), 8.22 (d, J=8.5 Hz, 1H), 7.79 (d, J=8.6 Hz, 1H), 6.04 (s, 1H), 5.84 (tt, J=55.9, 4.6 Hz, 1H), 4.68-4.52 (m, 1H), 3.54-3.32 (m, 2H), 3.07-2.94 (m, 3H), 2.88 (s, 3H), 2.87 (d, J=4.7 Hz, 3H), 2.41-2.15 (m, 5H), 2.05-1.84 (m, 2H), 1.69 (dd, J=13.6, 7.5 Hz, 1H). LCMS [M+H] 630.1.

Example 54

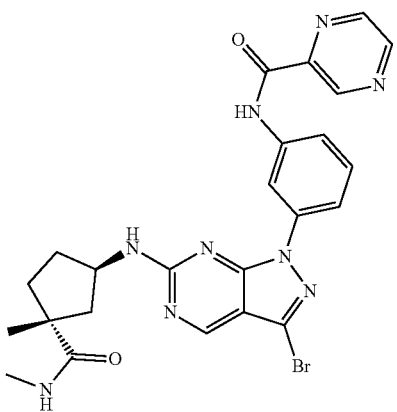 [SMILES: CNC(=O)[C@]1(C)CC[C@@H](Nc2ncc3c(Br)nn(-c4cccc(NC(=O)c5cnccn5)c4)c3n2)C1]

N-(3-(3-bromo-6-(((1R,3R)-3-methyl-3-(methylcarbamoyl)cyclopentyl)amino)-1H-pyrazolo[3,4-d]pyrimidin-1-yl)phenyl)pyrazine-2-carboxamide was prepared using general procedure A(a), followed by general procedure B with (3-((tert-butoxycarbonyl)amino)phenyl)boronic acid. Next, Boc group was removed under acidic conditions (TFA/DCM), and the product was acylated with pyrazine-2-carbonyl chloride in DCM in the presence of N,N-diisopropylethylamine. $^1$H NMR (400 MHz, Methanol-d4) δ 9.32-9.22 (m, 3H), 8.80 (s, 1H), 8.61 (s, 1H), 8.00 (d, J=8.4 Hz, 1H), 7.63 (d, J=8.3 Hz, 1H), 7.50 (t, J=8.2 Hz, 1H), 4.64-4.39 (m, 1H), 2.89-2.50 (m, 4H), 2.33-2.19 (m, 1H), 2.18-2.07 (m, 1H), 1.86-1.59 (m, 2H), 1.53-1.37 (m, 1H), 1.31 (s, 3H), 1.29-1.23 (m, 1H). LCMS [M+H] 550.1.

Example 55

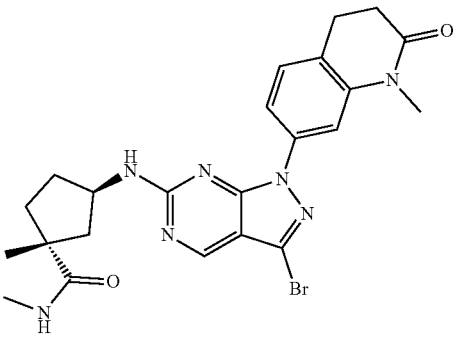 [SMILES: CNC(=O)[C@]1(C)CC[C@@H](Nc2ncc3c(Br)nn(-c4ccc5c(c4)N(C)C(=O)CC5)c3n2)C1]

(1R,3R)-3-((3-bromo-1-(1-methyl-2-oxo-1,2,3,4-tetrahydroquinolin-6-yl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with 1-methyl-6-(4,4,5,5-tetramethyl-1,3,2-dioxaborolan-2-yl)-3,4-dihydroquinolin-2(1H)-one. $^1$H NMR (400 MHz, MeOH-d4, TFA salt) δ 8.63 (s, 1H), 8.11 (m, 2H), 7.28-7.26 (d, J=8 Hz, 1H), 4.41 (m, 1H), 3.40 (s, 3H), 3.04-3.00 (m, 2H), 2.75 (s, 3H), 2.70-2.66 (m, 2H), 2.23 (m, 1H), 2.15 (m, 1H), 1.74 (m, 2H), 1.52-1.48 (m, 2H) 1.35-1.33 (s, 3H) ppm. LCMS [M+H] 512.0.

Example 56

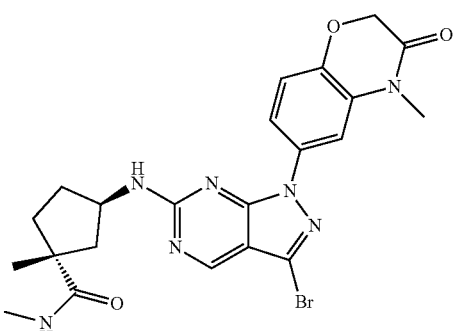

(1R,3R)-3-((3-bromo-1-(4-methyl-3-oxo-3,4-dihydro-2H-benzo[b][1,4]oxazin-7-yl)-1H-pyrazolo[3,4-d]pyrimidin-6-yl)amino)-N,1-dimethylcyclopentane-1-carboxamide was prepared using general procedure A(a), followed by general procedure B with 4-methyl-7-(4,4,5,5-tetramethyl-1,3,2-dioxaborolan-2-yl)-2H-benzo[b][1,4]oxazin-3(4H)-one. $^1$H NMR (400 MHz, MeOH-d4) 8.61 (s, 1H), 7.98 (m, 1H), 7.88 (m, 1H), 7.29 (m, 1H), 4.68 (s, 2H), 4.59 (m, 1H), 3.43-3.41 (s, 3H), 2.76-2.73 (s, 3H), 2.25 (m, 1H), 2.16 (m, 1H), 1.74 (m, 1H), 1.53 (m, 1H), 1.43-1.20) (m, 5H) ppm. LCMS [M+H] 514.0.

Example 57

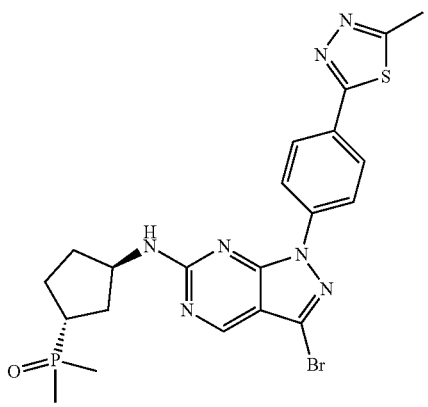 [SMILES: Cc1nnc(-c2ccc(-n3nc(Br)c4cnc(N[C@@H]5CC[C@@H](P(C)(C)=O)C5)nc43)cc2)s1]

(((1R,3R)-3-((3-bromo-1-(4-(5-methyl-1,3,4-thiadiazol-2-yl)phenyl)-1H-pyrazolo[3,4-d]pyrimidin-6-yl)amino)cyclopentyl)dimethylphosphine oxide was prepared as follows. ((1R,3R)-3-aminocyclopentyl)dimethylphosphine oxide was prepared as follows: 1) commercially available (1R,3R)-3-aminocyclopentane-1-carboxylic acid was treated with red HgO and Br2 in DCM at 50 C in the presence of MgSO$_4$ to afford (R)-3-bromocyclopentan-1-amine in 13% yield; 2) the resulting bromide was treated with with NaI in butatnone at reflux to afford (1R)-3-iodocyclopentan-1-amine; 3) the crude iodide was exposed to 2.2 eq of Na HMDS and dimethylphosphine oxide at ambient temperature for 18 hrs. The final compound was assembled using general procedure D(b), followed by general procedure B with 2-methyl-5-(4-(4,4,5,5-tetramethyl-1,3,2-dioxaborolan-2-yl)phenyl)-1,3,4-thiadiazole. LCMS [M+H] 532.0.

Example 58

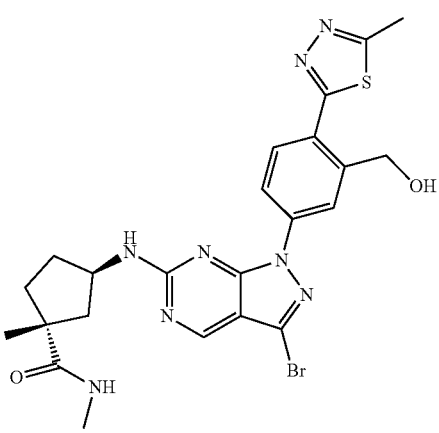 [SMILES: CNC(=O)[C@]1(C)CC[C@@H](Nc2ncc3c(Br)nn(-c4ccc(-c5nnc(C)s5)c(CO)c4)c3n2)C1]

(1R,3R)-3-((3-bromo-1-(3-(hydroxymethyl)-4-(5-methyl-1,3,4-oxadiazol-2-yl)phenyl)-1H-pyrazolo[3,4-d]pyrimidin-6-yl)amino)-N,1-dimethylcyclopentane-1-carboxamide was prepared using general procedure A(a), followed by general procedure B with 2-(2-(((tert-butyldimethylsilyl)oxy)methyl)-4-(4,4,5,5-tetramethyl-1,3,2-dioxaborolan-2-yl)phenyl)-5-methyl-1,3,4-oxadiazole, followed by in-situ deprotection of TBS group with 2 equivalents of 1M TBAF in THF. LCMS [M+H] 541.1.

Example 59

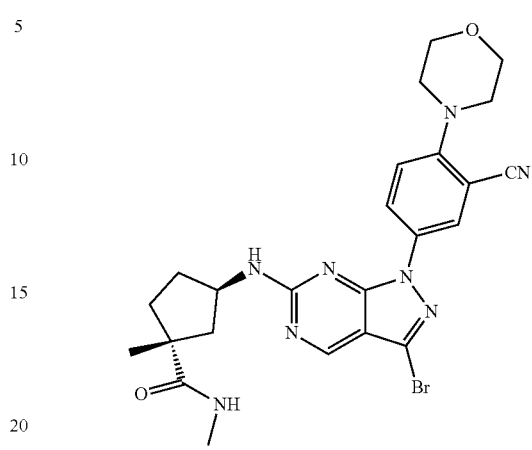

(1R,3R)-3-((3-bromo-1-(3-cyano-4-morpholinophenyl)-1H-pyrazolo[3,4-d]pyrimidin-6-yl)amino)-N,1-dimethylcyclopentane-1-carboxamide hydrochloride was prepared using general procedure A(a), followed by general procedure B with (3-cyano-4-morpholinophenyl)boronic acid. $^1$H NMR (400 MHz, Methanol-d4; HCl Salt) δ 8.50 (s, 1H), 8.16 (s, 1H), 8.11 (d, J=9.4 Hz, 1H), 7.07 (d, J=9.1 Hz, 1H), 4.17 (q, J=7.6 Hz, 1H), 3.72-3.60 (m, 4H), 3.12-3.05 (m, 3H), 3.06-2.98 (m, 4H), 2.55-2.47 (m, 1H), 2.10-1.88 (m, 2H), 1.66-1.48 (m, 2H), 1.31 (dd, J=13.4, 7.9 Hz, 1H), 1.15 (s, 3H). LCMS [M+H] 539.2.

Example 60

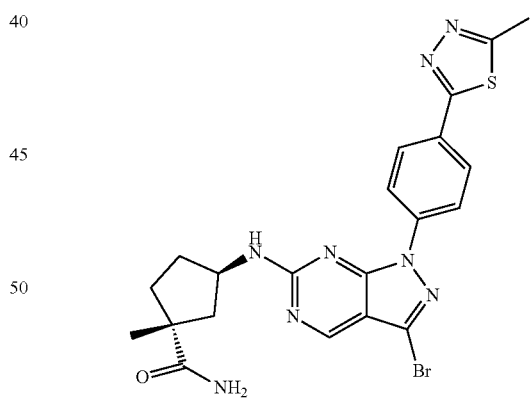

(1R,3R)-3-((3-bromo-1-(4-(5-methyl-1,3,4-thiadiazol-2-yl)phenyl)-1H-pyrazolo[3,4-d]pyrimidin-6-yl)amino)-1-methylcyclopentane-1-carboxamide was prepared using general procedure A(a), followed by general procedure B with 2-methyl-5-(4-(4,4,5,5-tetramethyl-1,3,2-dioxaborolan-2-yl)phenyl)-1,3,4-thiadiazole. $^1$H NMR (400 MHz, Methanol-d4): δ 8.45 (s, 1H), 8.08-7.91 (m, 2H), 7.73 (d, J=8.6 Hz, 1H), 7.64 (d, J=8.3 Hz, 2H), 4.35-4.18 (m, 1H), 2.73 (s, 3H), 2.29-1.95 (m, 3H), 1.84-1.57 (m, 2H), 1.52-1.39 (m, 1H), 1.32 (s, 3H). LCMS [M+H] 497.1.

Example 61

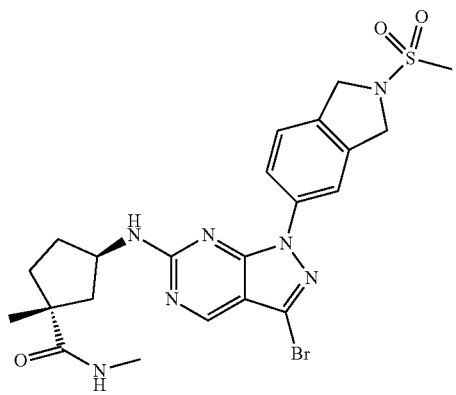

(1R,3R)-3-((3-bromo-1-(2-(methylsulfonyl)isoindolin-5-yl)-1H-pyrazolo[3,4-d]pyrimidin-6-yl)amino)-N,1-dimethylcyclopentane-1-carboxamide was prepared using general procedure A(a), followed by general procedure B with tert-butyl 5-(4,4,5,5-tetramethyl-1,3,2-dioxaborolan-2-yl)isoindoline-2-carboxylate, followed by acidic deprotection if the Boc group.

The resulting compound was treated with methanesulfonyl chloride in the presence of N,N-diisop[ropylethylamine and the final compound was purified using reverse phase HPLC. 1H NMR (400 MHz, Methanol-d4): 8.53 (s, 1H), 8.17 (s, 1H), 8.04 (d, 1H, J=8.5 Hz), 7.39 (d, 1H, J=8.5 Hz), 4.72 (s, 2H), 4.64 (s, 2H), 4.31 (m, 1H), 2.87 (s, 3H), 2.73 (m, 1H), 2.67 (s, 3H), 2.16-2.01 (m, 2H), 1.73-1.59 (m, 2H), 1.36 (m, 1H), 1.25 (s, 3H) ppm. LCMS [M+H] 548.0.

Example 62

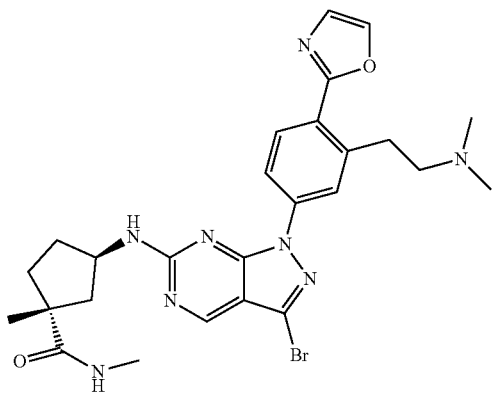

(1R,3R)-3-((3-bromo-1-(3-(2-(dimethylamino)ethyl)-4-(oxazol-2-yl)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (3-(2-(dimethylamino)ethyl)-4-(oxazol-2-yl)phenyl)boronic acid. LCMS [M+H] 567.0.

Example 63

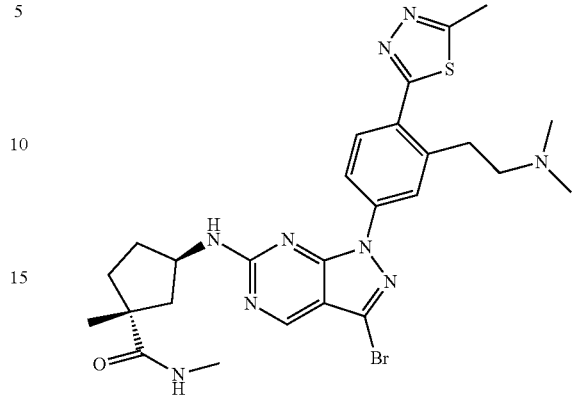

(1R,3R)-3-((3-bromo-1-(3-(2-(dimethylamino)ethyl)-4-(5-methyl-1,3,4-thiadiazol-2-yl)phenyl)-1H-pyrazolo[3,4-d]pyrimidin-6-yl)amino)-N,1-dimethylcyclopentane-1-carboxamide; 2,2,2-trifluoroacetic acid was prepared using general procedure A(a), followed by general procedure B with (3-(2-(dimethylamino)ethyl)-4-(5-methyl-1,3,4-thiadiazol-2-yl)phenyl)boronic acid. LCMS [M+H] 598.1.

Example 64

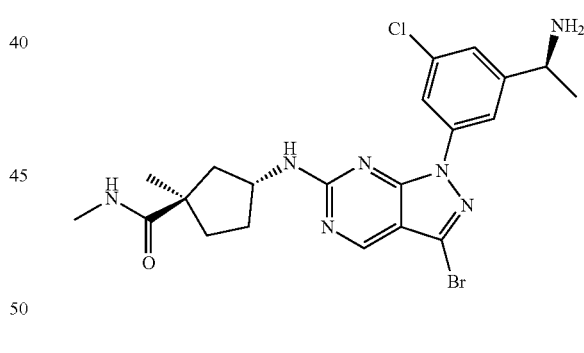

(1R,3R)-3-((1-(3-((S)-1-aminoethyl)-5-chlorophenyl)-3-bromo-1H-pyrazolo[3,4-d]pyrimidin-6-yl)amino)-N,1-dimethylcyclopentane-1-carboxamide was prepared using general procedure A(a), followed by general procedure B with Precursor XII, followed by deprotection of Boc group with mixture of dichloromethane/trifluoroacetic acid (1:1). 1H NMR (400 MHz, Chloroform-d) δ 8.53 (s, 1H), 8.41 (s, 1H), 8.11 (s, 1H), 7.31 (s, 1H), 4.54-4.38 (m, 2H), 2.73 (t, J=7.5 Hz, 1H), 2.67 (s, 3H), 2.20 (q, J=7.9 Hz, 1H), 2.02 (q, J=12.6, 11.5 Hz, 1H), 1.71-1.59 (m, 5H), 1.27 (s, 3H), 1.26-1.17 (m, 1H) ppm. LCMS [M+H] 506.1

Example 65

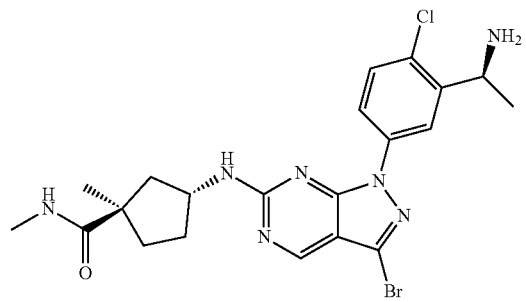 [SMILES: CNC(=O)[C@]1(C)CC[C@@H](Nc2ncc3c(Br)nn(-c4ccc(Cl)c([C@H](C)N)c4)c3n2)C1]

(1R,3R)-3-((1-(3-((S)-1-aminoethyl)-4-chlorophenyl)-3-bromo-1H-pyrazolo[3,4-d]pyrimidin-6-yl)amino)-N,1-dimethylcyclopentane-1-carboxamide was prepared using general procedure A(a), followed by general procedure B with (S)-(3-(1-((tert-butoxycarbonyl)amino)ethyl)-4-chlorophenyl)boronic acid, followed by deprotection of Boc group with mixture of dichloromethane/trifluoroacetic acid (1:1). 1H NMR (400 MHz, Chloroform-d) δ 8.63-8.55 (m, 2H), 8.00 (dd, J=8.8, 2.5 Hz, 1H), 7.55 (d, J=8.9 Hz, 1H), 4.95 (q, J=7.2 Hz, 1H), 4.62 (t, J=8.0 Hz, 1H), 2.79-2.65 (m, 4H), 2.19 (q, J=9.2 Hz, 1H), 2.03 (t, J=15.1 Hz, 1H), 1.76-1.62 (m, 5H), 1.29 (s, 3H), 1.18 (t, J=12.0 Hz, 1H) ppm. LCMS [M+H] 506.1

Example 67

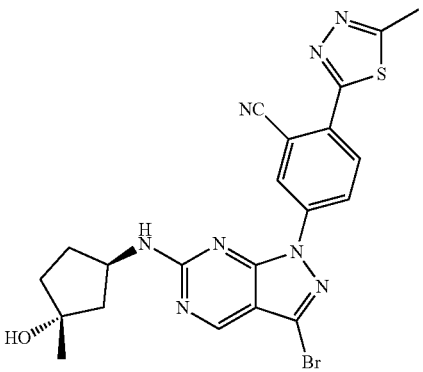

5-(3-bromo-6-(((1R,3R)-3-hydroxy-3-methylcyclopentyl)amino)-1H-pyrazolo[3,4-d]pyrimidin-1-yl)-2-(5-methyl-1,3,4-thiadiazol-2-yl)benzonitrile was prepared using general procedure D(c) with Precursor XI, followed by general procedure B with 2-(5-methyl-1,3,4-thiadiazol-2-yl)-5-(4,4,5,5-tetramethyl-1,3,2-dioxaborolan-2-yl)benzonitrile. 1H NMR (400 MHz, Methanol-d4/CDCl₃): δ 8.88 (s, 1H), 8.70-8.78 (m, 1H), 8.57 (s, 1H), 8.15-8.23 (m, 1H), 4.51-4.63 (m, 1H), 2.87 (s, 3H), 2.21-2.55 (m, 2H), 1.58-1.92 (m, 4H), 1.40 (s, 3H) ppm. LCMS [M+H] 511.0

Example 66

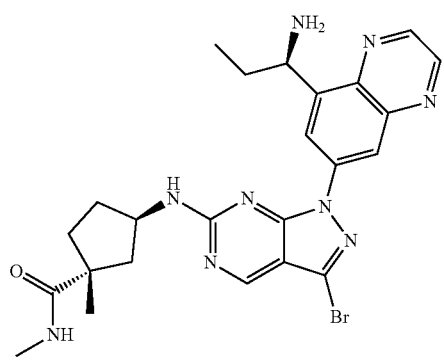 [SMILES: CC[C@@H](N)c1cc(-n2nc(Br)c3cnc(N[C@@H]4CC[C@@](C)(C(=O)NC)C4)nc32)cc2nccnc12]

(1R,3R)-3-((1-(8-((R)-1-aminopropyl)quinoxalin-6-yl)-3-bromo-1H-pyrazolo[3,4-d]pyrimidin-6-yl)amino)-N,1-dimethylcyclopentane-1-carboxamide was prepared using general procedure A(a), followed by general procedure B with (R)-(8-(1-((tert-butoxycarbonyl)amino)propyl)quinoxalin-6-yl)boronic acid, followed by deprotection of Boc group with mixture of dichloromethane/trifluoroacetic acid (1:1). 1H NMR (400 MHz, Chloroform-d) δ 8.95-8.87 (m, 2H), 8.84 (s, 1H), 8.80 (s, 1H), 8.60 (s, 1H), 5.08 (t, J=5.3 Hz, 1H), 4.47 (p, J=8.1 Hz, 1H), 2.77 (t, J=7.3 Hz, 1H), 2.69 (s, 3H), 2.35-2.17 (m, 3H), 2.09 (dd, J=11.0, 3.8 Hz, 1H), 1.77-1.64 (m, 2H), 1.36 (dd, J=13.0, 7.0 Hz, 1H), 1.29 (s, 3H), 0.89 (t, J=7.4 Hz, 3H) ppm. LCMS [M+H] 538.0

Example 68

(1R,3R)-3-((3-bromo-1-(4-(5-methyl-1,3,4-thiadiazol-2-yl)phenyl)-1H-pyrazolo[3,4-d]pyrimidin-6-yl)amino)-N-methylcyclopentane-1-sulfonamide was prepared using general procedure D(c) with (1R,3R)-3-amino-N-methylcyclopentane-1-sulfonamide, followed by general procedure B with 2-(5-methyl-1,3,4-thiadiazol-2-yl)-5-(4,4,5,5-tetramethyl-1,3,2-dioxaborolan-2-yl)benzonitrile. 1H NMR (400 MHz, 1:1 Chloroform-d3:Methanol-d4): δ 8.60 (s, 1H), 8.41 (d, J=8.5 Hz, 2H), 8.01 (d, J=8.3 Hz, 2H), 4.60-4.47 (m, 1H), 3.84-3.71 (m, 1H), 2.81 (s, 3H), 2.74 (s, 3H), 2.69-2.52 (m, 1H), 2.35-2.19 (m, 2H), 2.19-2.09 (m, 1H), 2.05 (ddd, J=14.6, 9.0, 5.8 Hz, 1H), 1.89-1.75 (m, 1H) ppm. LCMS [M+H] 549.0

Example 69

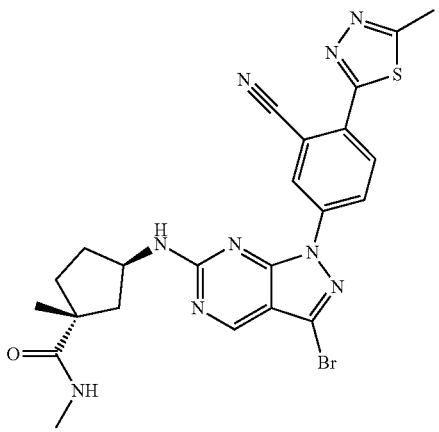 [SMILES: CNC(=O)[C@]1(C)CC[C@@H](Nc2ncc3c(Br)nn(-c4ccc(-c5nnc(C)s5)c(C#N)c4)c3n2)C1]

(1R,3R)-3-((3-bromo-1-(3-cyano-4-(5-methyl-1,3,4-thiadiazol-2-yl)phenyl)-1H-pyrazolo[3,4-d]pyrimidin-6-yl)amino)-N,1-dimethylcyclopentane-1-carboxamide was prepared using general procedure A(a), followed by general procedure B with 2-(5-methyl-1,3,4-thiadiazol-2-yl)-5-(4,4,5,5-tetramethyl-1,3,2-dioxaborolan-2-yl)benzonitrile. 1H NMR (400 MHz, Methanol-d4/CDCl3, Methanesulfonic acid salt): δ 8.90 (s, 1H), 8.70-8.80 (m, 2H), 8.26-8.35 (m, 1H), 4.47 (p, J=7.6 Hz, 1H), 2.88 (s, 3H), 2.76-2.85 (m, 7H), 2.23-2.35 (m, 1H), 2.10-2.21 (m, 1H), 1.72-1.90 (m, 2H), 1.52 (dd, J=7.8 Hz, J=13.4 Hz, 1H), 1.36 (s, 3H) ppm. LCMS [M+H] 552.1

Example 70

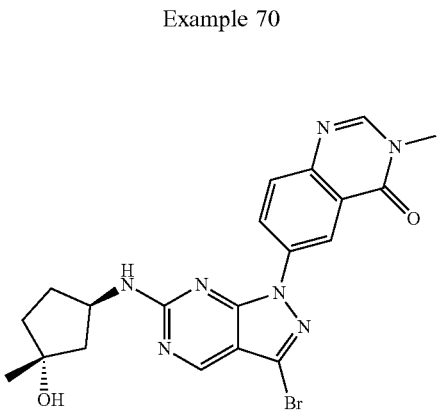

6-(3-bromo-6-(((1R,3R)-3-hydroxy-3-methylcyclopentyl)amino)-1H-pyrazolo[3,4-d]pyrimidin-1-yl)-3-methylquinazolin-4(3H)-one was prepared using general procedure D(c) with Precursor XI, followed by general procedure B with Precursor IX without the addition of N,N-diisopropylethylamine. 1H NMR (400 MHz, Chloroform-d; TFA salt) δ 9.56 (d, J=2.5 Hz, 1H), 8.82 (s, 1H), 8.72 (s, 1H), 8.56 (s, 1H), 8.43 (dd, J=8.9, 2.5 Hz, 1H), 8.20 (s, 1H), 7.84 (d, J=9.0 Hz, 1H), 4.66 (s, 1H), 3.65 (s, 3H), 2.91 (dd, J=12.8, 6.4 Hz, 1H), 2.55-2.39 (m, 1H), 2.01-1.88 (m, 2H), 1.87-1.78 (m, 1H), 1.56 (dd, J=12.7, 10.5 Hz, 1H), 1.49 (s, 3H) ppm. LCMS [M+H] 470.0

Example 71

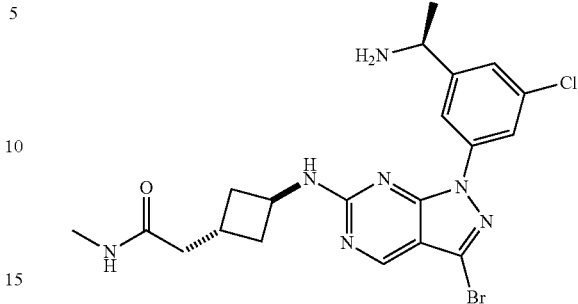

2-((1S,3r)-3-((1-(3-((S)-1-aminoethyl)-5-chlorophenyl)-3-bromo-1H-pyrazolo[3,4-d]pyrimidin-6-yl)amino)cyclobutyl)-N-methylacetamide was prepared using general procedure D(c) with 2-((1r,3r)-3-aminocyclobutyl)acetic acid, followed by general procedure A(b) with methylamine, followed by general procedure B with Precursor XII, followed by deprotection of Boc group with mixture of dichloromethane/trifluoroacetic acid (1:1). 1H NMR (400 MHz, Methanol-d4): δ 8.60 (s, 2H), 8.19 (s, 1H), 7.42 (s, 1H), 4.64-4.51 (m, 1H), 4.44 (m, 1H), 3.19 (s, 1H), 2.58 (s, 3H), 2.47 (m, 2H), 2.36-2.23 (m, 4H), 1.69 (d, J=6.9 Hz, 3H) ppm. LCMS [M+H] 492.1

Example 72

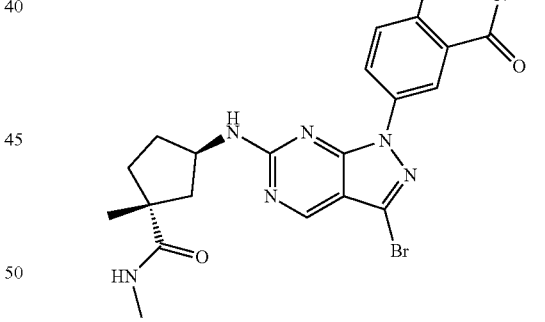

(1R,3R)-3-((3-bromo-1-(3-methyl-4-oxo-3,4-dihydroquinazolin-6-yl)-1H-pyrazolo[3,4-d]pyrimidin-6-yl)amino)-N,1-dimethylcyclopentane-1-carboxamide was prepared using general procedure A(a), followed by general procedure B with Precursor IX without the addition of N,N-diisopropylethylamine. 1H NMR (400 MHz, Chloroform-d; TFA salt) δ 9.43 (s, 1H), 8.60 (s, 1H), 8.54 (dd, J=8.9, 2.0 Hz, 1H), 8.15 (s, 1H), 7.87 (d, J=9.0 Hz, 1H), 7.52 (s, 1H), 6.77 (s, 1H), 4.40 (s, 1H), 3.65 (s, 3H), 3.03 (dd, J=13.7, 7.9 Hz, 1H), 2.86 (d, J=4.4 Hz, 3H), 2.48-2.25 (m, 2H), 1.87-1.66 (m, 3H), 1.40 (s, 3H) ppm. LCMS [M+H] 511.1

Example 73

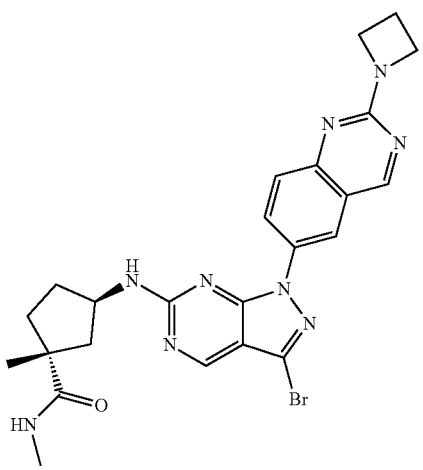 [SMILES: CNC(=O)[C@]1(C)CC[C@@H](Nc2ncc3c(Br)nn(-c4ccc5nc(N6CCC6)ncc5c4)c3n2)C1]

(1R,3R)-3-((1-(2-(azetidin-1-yl)quinazolin-6-yl)-3-bromo-1H-pyrazolo[3,4-d]pyrimidin-6-yl)amino)-N,1-dimethylcyclopentane-1-carboxamide was prepared using general procedure A(a), followed by general procedure B with Precursor X without the addition of N,N-diisopropylethylamine. 1H NMR (400 MHz, Chloroform-d; TFA salt) δ 9.68 (s, 1H), 8.99 (s, 1H), 8.72 (d, J=8.8 Hz, 1H), 8.58 (s, 1H), 8.04 (d, J=9.2 Hz, 1H), 6.94 (s, 1H), 5.79 (s, 1H), 4.64-4.45 (m, 4H), 3.01-2.90 (m, 1H), 2.87 (d, J=4.6 Hz, 3H), 2.61-2.46 (m, 2H), 2.38-2.25 (m, 1H), 2.23-2.10 (m, 1H), 1.86-1.67 (m, 2H), 1.38 (s, 3H), 1.35-1.15 (m, 2H) ppm. LCMS [M+H] 536.1

Example 74

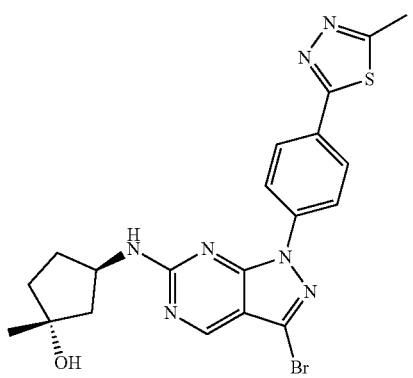

(1R,3R)-3-((3-bromo-1-(4-(5-methyl-1,3,4-thiadiazol-2-yl)phenyl)-1H-pyrazolo[3,4-d]pyrimidin-6-yl)amino)-1-methylcyclopentan-1-ol was prepared using general procedure D(c) with Precursor XI, followed by general procedure B with 2-(5-methyl-1,3,4-thiadiazol-2-yl)-5-(4,4,5,5-tetramethyl-1,3,2-dioxaborolan-2-yl)benzonitrile. 1H NMR (400 MHz, Methanol-d4/CDCl3, Methanesulfonic acid salt): δ 8.93 (s, 1H), 8.28-8.33 (m, 2H), 8.05-8.10 (m, 2H), 4.61-4.70 (m, 1H), 2.83 (s, 3H), 2.82 (s, 3H), 2.39-2.52 (m, 1H), 2.26-2.35 (m, 1H), 1.65-1.95 (m, 4H), 1.40 (s, 3H) ppm. LCMS [M+H] 486.1

Example 75

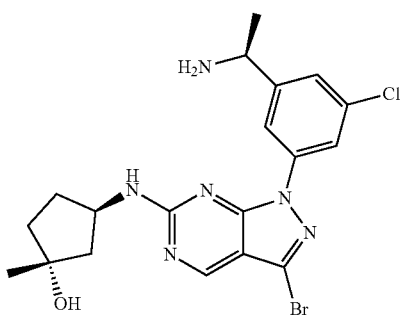 [SMILES: C[C@H](N)c1cc(Cl)cc(-n2nc(Br)c3cnc(N[C@@H]4CC[C@@](C)(O)C4)nc32)c1]

(1R,3R)-3-((1-(3-((S)-1-aminoethyl)-5-chlorophenyl)-3-bromo-1H-pyrazolo[3,4-d]pyrimidin-6-yl)amino)-1-methylcyclopentan-1-ol was prepared using general procedure D(c) with Precursor XI, followed by general procedure B with Precursor XII, followed by deprotection of Boc group with mixture of dichloromethane/trifluoroacetic acid (1:1). 1H NMR (400 MHz, Methanol-d4) δ 8.65 (s, 1H), 8.53 (s, 1H), 8.38 (s, 1H), 7.43 (s, 1H), 4.63 (t, J=8.0 Hz, 1H), 4.56 (q, J=6.8 Hz, 1H), 2.50-2.37 (m, 1H), 2.26 (q, J=8.6, 8.2 Hz, 1H), 1.89 (dt, J=13.0, 8.4 Hz, 1H), 1.80 (dd, J=12.7, 5.6 Hz, 1H), 1.72-1.65 (m, 2H), 1.70 (d, J=6.9 Hz, 3H), 1.40 (s, 3H) ppm. LCMS [M+H] 465.0

Example 76

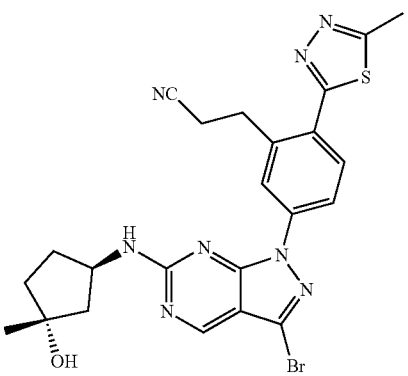

3-(5-(3-bromo-6-(((1R,3R)-3-hydroxy-3-methylcyclopentyl)amino)-1H-pyrazolo[3,4-d]pyrimidin-1-yl)-2-(5-methyl-1,3,4-thiadiazol-2-yl)phenyl)propanenitrile was prepared using general procedure D(c) with Precursor XI, followed by general procedure B with 3-(2-(5-methyl-1,3,4-thiadiazol-2-yl)-5-(4,4,5,5-tetramethyl-1,3,2-dioxaborolan-2-yl)phenyl)propanenitrile. 1H NMR (400 MHz, Methanol-d4/CDCl3, Methanesulfonic acid salt): δ 8.92 (s, 1H), 8.39-8.40 (m, 1H), 8.21-8.27 (m, 1H), 7.76-7.71 (m, 1H), 4.65-4.75 (m, 1H), 3.39 (t, J=7.1 Hz, 2H), 2.92 (t, J=7.1 Hz, 2H), 2.85 (s, 3H), 2.81 (s, 3H), 2.39-2.50 (m, 1H), 2.26-2.35 (m, 1H), 1.63-1.95 (m, 4H), 1.40 (s, 3H) ppm. LCMS [M+H] 539.0.

Example 77. Testing Compounds for Activity Against GCN2

The Enzymatic assay was run as an endpoint assay to quantify the activity of the serine/threonine GCN2 kinase by way of measuring phosphorylation of its natural substrate, eiF2α.

The enzymatic reaction was initiated by incubating with 2 μM ATP and 80 nM of GFP labeled eiF2a substrate at room temperature and then stopped after 90 minutes with EDTA. The amount of phosphorylated eIF2α is determined by TR-FRET (Lanthascreen). A terbium labeled antibody associates with the phosphorylated substrate resulting in an increased TR-FRET value. Activity was calculated as the ratio of the acceptor (fluorescein) signal at 520 nm wavelength to the donor (terbium) signal 495 nm. The amount of antibody that is bound to the tracer is directly proportional to the amount of phosphorylated substrate present, and in this manner, kinase activity can be detected and measured by an increase in the TR-FRET value.

Final Concentrations:
Hepes, pH 7.5 50 mM
$MgCl_2$ 10 mM
$MnCl_2$ 5 mM
DTT 1 mM
ATP 2 uM
Brij 35 0.005%
BSA 0.01%
GFP-eIF2α 80 nM
GCN2 4 nM
Assay Procedure
Compound addition by D300
5 μL enzyme solution in assay buffer
5 μL substrate/ATP mixture in assay buffer
Incubate 90 minutes RT
5 μL stop/detection mix in antibody dilution buffer
Incubate 60 min at RT
Readout Lanthascreen 340/495/520

The GCN2 biochemical $IC_{50}$ activity levels of the compounds of Examples 1-76 are shown in Table 2. A GCN2 activity of C means an $IC_{50}$ test compound concentration ranging from 1 μM to 0.5 μM; a GCN2 activity of B means an $IC_{50}$ test compound concentration ranging from 0.5 μM to 0.2 μM; a GCN2 activity of A means an $IC_{50}$ test compound concentration ranging from 0.2 μM to 25 nM; and a GCN2 activity of AA means an $IC_{50}$ test compound concentration of less than 25 nM.

TABLE 2

| Example | GCN2 activity |
| --- | --- |
| 1 | AA |
| 2 | A |
| 3 | C |
| 4 | A |
| 5 | C |
| 6 | A |
| 7 | A |
| 8 | A |
| 9 | B |
| 10 | A |
| 11 | A |
| 12 | A |
| 13 | AA |
| 14 | AA |
| 15 | B |
| 16 | A |
| 17 | A |
| 18 | A |
| 19 | A |
| 20 | C |
| 21 | A |
| 22 | A |
| 23 | AA |
| 24 | B |
| 25 | A |
| 26 | A |
| 27 | C |
| 28 | AA |
| 29 | AA |
| 30 | AA |
| 31 | AA |
| 32 | AA |
| 33 | AA |
| 34 | AA |
| 35 | AA |
| 36 | AA |
| 37 | AA |
| 38 | AA |
| 39 | AA |
| 40 | AA |
| 41 | AA |
| 42 | AA |
| 43 | AA |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | AA |
| 65 | AA |
| 66 | AA |
| 67 | AA |
| 68 | AA |
| 69 | AA |
| 70 | AA |
| 71 | A |
| 72 | A |
| 73 | A |
| 74 | A |
| 75 | A |
| 76 | A |

The compounds listed in the following Table 3, and/or a hydrochloride, dihydrochloride or a triflouroacetic acid salt thereof, were synthesized using the methods previously described herein and were tested for activity as described in Example 77.

TABLE 3

| Chemical Name | Chemical Structure | IC$_{50}$ Activity |
|---|---|---|
| (1R,3R)-3-((3-bromo-1-(1H-indazol-6-yl)-1H-pyrazolo[3,4-d]pyrimidin-6-yl)amino)-N-(2-methoxyethyl)cyclopentane-1-carboxamide | 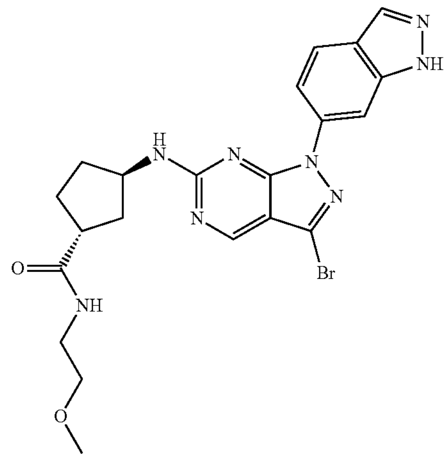 [SMILES: COCCNC(=O)[C@@H]1CC[C@@H](Nc2ncc3c(Br)nn(-c4ccc5cn[nH]c5c4)c3n2)C1] | C |
| (1R,3R)-3-((3-bromo-1-(isoquinolin-7-yl)-1H-pyrazolo[3,4-d]pyrimidin-6-yl)amino)-N-(2-methoxyethyl)cyclopentane-1-carboxamide | 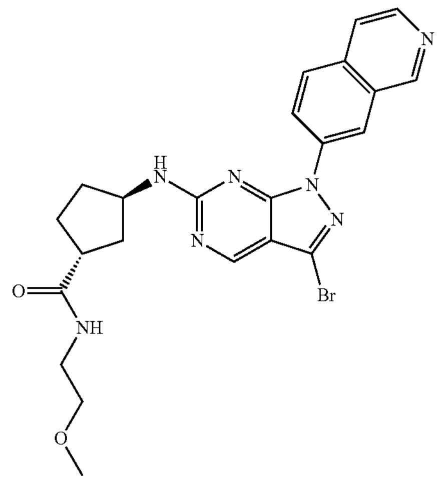 [SMILES: COCCNC(=O)[C@@H]1CC[C@@H](Nc2ncc3c(Br)nn(-c4ccc5ccncc5c4)c3n2)C1] | A |
| (1R,3R)-3-((3-bromo-1-(8-fluoroquinolin-6-yl)-1H-pyrazolo[3,4-d]pyrimidin-6-yl)amino)-N-(2-methoxyethyl)cyclopentane-1-carboxamide | 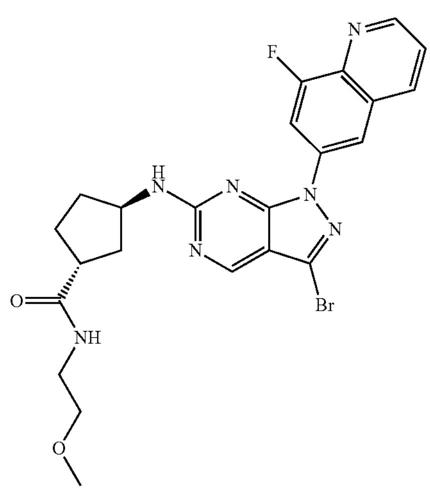 [SMILES: COCCNC(=O)[C@@H]1CC[C@@H](Nc2ncc3c(Br)nn(-c4cc(F)c5ncccc5c4)c3n2)C1] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(6-oxa-2-azaspiro[4.5]decan-2-yl)methanone | 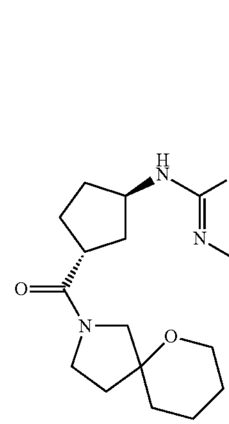 | B |
| ((1R,3R)-3-((3-bromo-1-(quinolin-6-yl)-1H-pyrazolo[3,4-d]pyrimidin-6-yl)amino)cyclopentyl)((R)-3-(2-methoxyethoxy)pyrrolidin-1-yl)methanone | 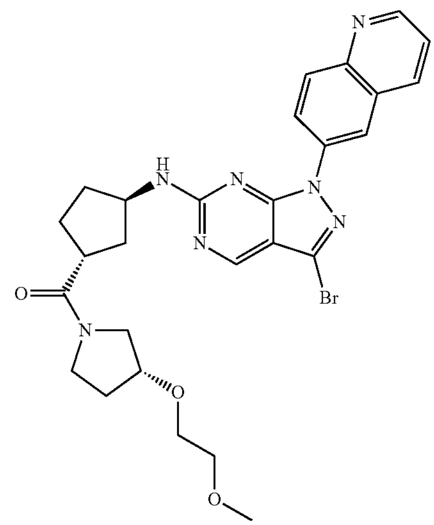 [SMILES: COCCO[C@@H]1CCN(C(=O)[C@@H]2CC[C@@H](Nc3ncc4c(Br)nn(-c5ccc6ncccc6c5)c4n3)C2)C1] | A |
| (1R,3R)-3-((3-bromo-1-(quinolin-6-yl)-1H-pyrazolo[3,4-d]pyrimidin-6-yl)amino)-N-(2-(dimethylamino)ethyl)cyclopentane-1-carboxamide | 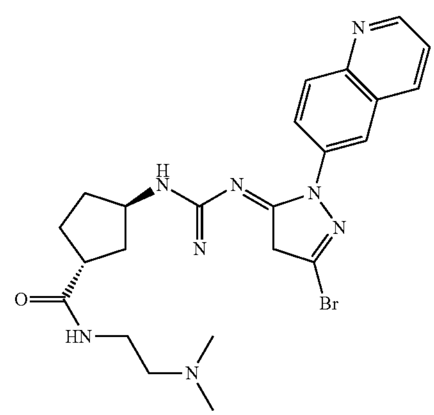 [SMILES: CN(C)CCNC(=O)[C@@H]1CC[C@@H](NC(=N)/N=C2\CC(Br)=NN2c2ccc3ncccc3c2)C1] | A |

TABLE 3-continued

| Chemical Name | Chemical Structure | IC$_{50}$ Activity |
|---|---|---|
| 4-((3-bromo-1-(quinolin-6-yl)-1H-pyrazolo[3,4-d]pyrimidin-6-yl)amino)-N-(2-methoxyethyl)bicyclo[2.2.1]heptane-1-carboxamide | 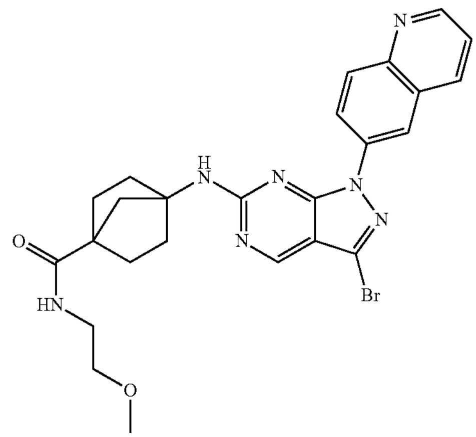 [SMILES: COCCNC(=O)C12CCC(Nc3ncc4c(Br)nn(-c5ccc6ncccc6c5)c4n3)(CC1)C2] | B |
| (1R,3R)-3-((3-bromo-1-(quinolin-6-yl)-1H-pyrazolo[3,4-d]pyrimidin-6-yl)amino)-N-((1r,3R)-3-hydroxy-1-methylcyclobutyl)cyclopentane-1-carboxamide | 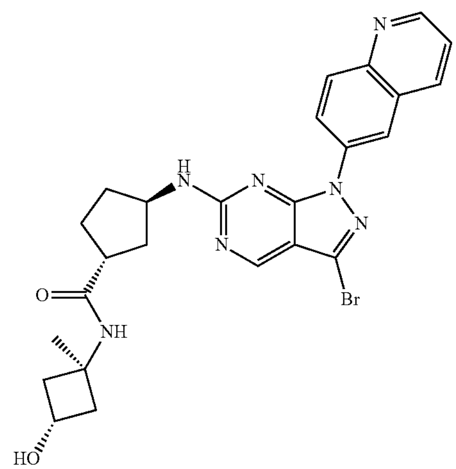 [SMILES: C[C@]1(NC(=O)[C@@H]2CC[C@@H](Nc3ncc4c(Br)nn(-c5ccc6ncccc6c5)c4n3)C2)C[C@H](O)C1] | A |
| (1R,3R)-3-((3-bromo-1-(6-fluoroquinolin-3-yl)-1H-pyrazolo[3,4-d]pyrimidin-6-yl)amino)-N-(2-methoxyethyl)cyclopentane-1-carboxamide | 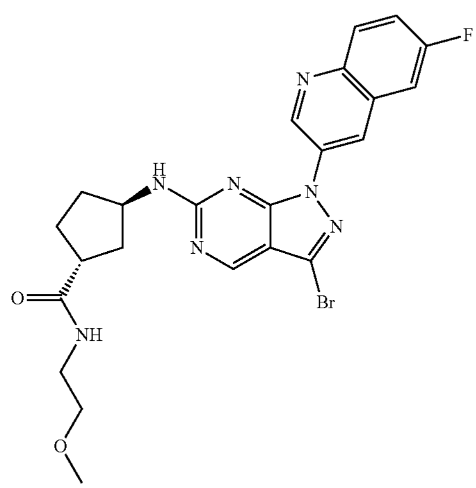 [SMILES: COCCNC(=O)[C@@H]1CC[C@@H](Nc2ncc3c(Br)nn(-c4cnc5ccc(F)cc5c4)c3n2)C1] | C |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-(2-isopropoxyethyl)cyclopentane-1-carboxamide | 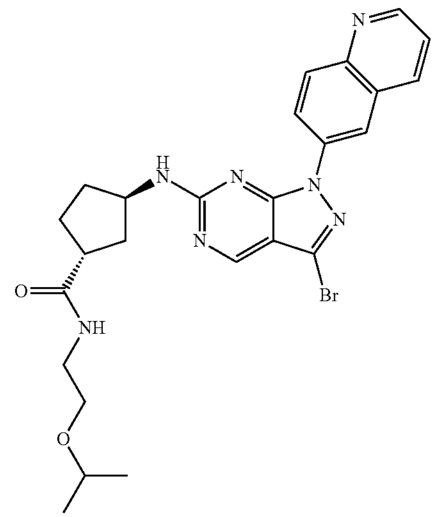 [SMILES: CC(C)OCCNC(=O)[C@@H]1CC[C@@H](Nc2ncc3c(Br)nn(-c4ccc5ncccc5c4)c3n2)C1] | B |
| (1R,3R)-3-((3-bromo-1-(quinolin-6-yl)-1H-pyrazolo[3,4-d]pyrimidin-6-yl)amino)-N-(2-(trifluoromethoxy)ethyl)cyclopentane-1-carboxamide | 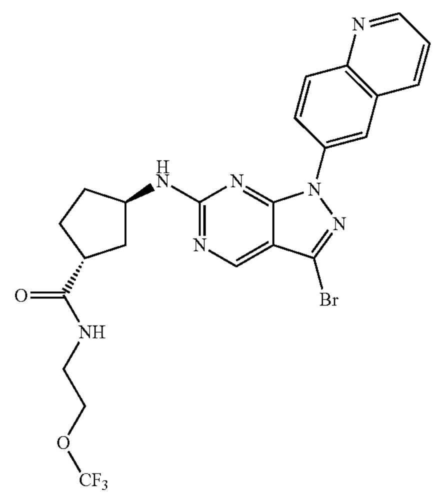 [SMILES: O=C(NCCOC(F)(F)F)[C@@H]1CC[C@@H](Nc2ncc3c(Br)nn(-c4ccc5ncccc5c4)c3n2)C1] | B |
| (1R,3R)-3-((3-bromo-1-(5-methoxypyridin-3-yl)-1H-pyrazolo[3,4-d]pyrimidin-6-yl)amino)-N-(2-methoxyethyl)cyclopentane-1-carboxamide | 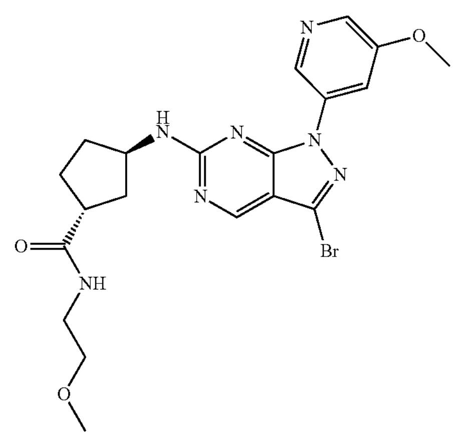 [SMILES: COCCNC(=O)[C@@H]1CC[C@@H](Nc2ncc3c(Br)nn(-c4cncc(OC)c4)c3n2)C1] | C |

TABLE 3-continued

| Chemical Name | Chemical Structure | IC$_{50}$ Activity |
|---|---|---|
| (1R,3R)-3-((3-bromo-1-(8-fluoroquinolin-6-yl)-1H-pyrazolo[3,4-d]pyrimidin-6-yl)amino)-N-((3-methyloxetan-3-yl)methyl)cyclopentane-1-carboxamide | 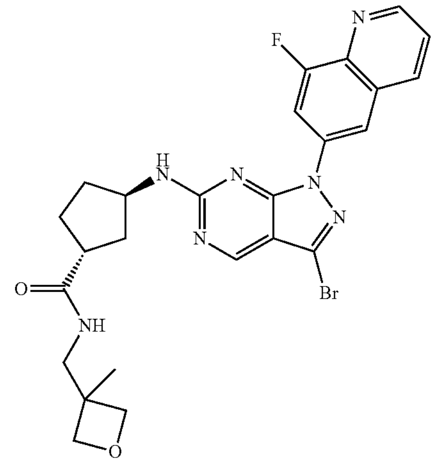 [SMILES: CC1(CNC(=O)[C@@H]2CC[C@@H](Nc3ncc4c(Br)nn(-c5cc(F)c6ncccc6c5)c4n3)C2)COC1] | A |
| (1R,3R)-3-((3-bromo-1-(quinolin-6-yl)-1H-pyrazolo[3,4-d]pyrimidin-6-yl)amino)-N-((3-methyloxetan-3-yl)methyl)cyclopentane-1-carboxamide | 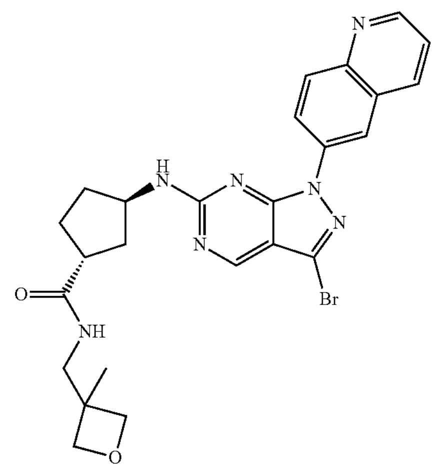 [SMILES: CC1(CNC(=O)[C@@H]2CC[C@@H](Nc3ncc4c(Br)nn(-c5ccc6ncccc6c5)c4n3)C2)COC1] | B |
| (1R,3R)-3-((3-bromo-1-(quinolin-6-yl)-1H-pyrazolo[3,4-d]pyrimidin-6-yl)amino)-N-(2-(pyrrolidin-1-yl)propyl)cyclopentane-1-carboxamide | 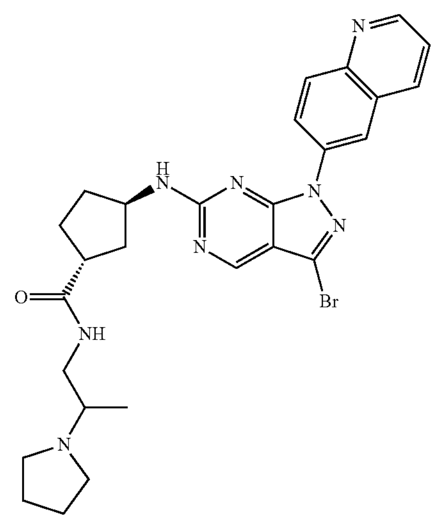 [SMILES: CC(CNC(=O)[C@@H]1CC[C@@H](Nc2ncc3c(Br)nn(-c4ccc5ncccc5c4)c3n2)C1)N1CCCC1] | A |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-((2-oxopiperidin-4-yl)methyl)cyclopentane-1-carboxamide | 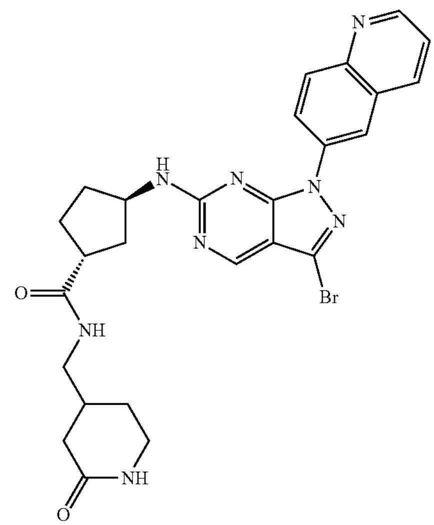 [SMILES: O=C1CC(CNC(=O)[C@@H]2CC[C@@H](Nc3ncc4c(Br)nn(-c5ccc6ncccc6c5)c4n3)C2)CCN1] | A |
| (1R,3R)-3-((3-bromo-1-(quinolin-6-yl)-1H-pyrazolo[3,4-d]pyrimidin-6-yl)amino)-N-(2-morpholinoethyl)cyclopentane-1-carboxamide | 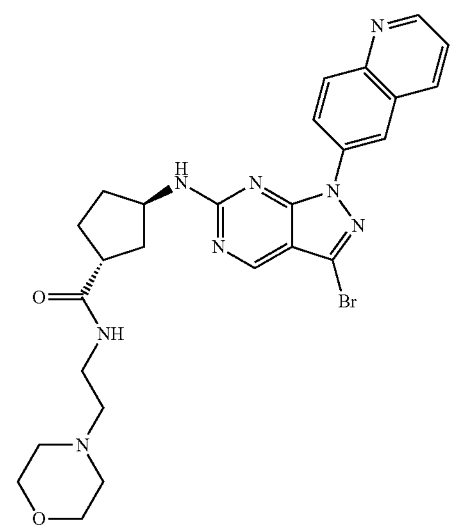 [SMILES: O=C(NCCN1CCOCC1)[C@@H]1CC[C@@H](Nc2ncc3c(Br)nn(-c4ccc5ncccc5c4)c3n2)C1] | A |
| (1R,3R)-3-((3-bromo-1-(quinolin-6-yl)-1H-pyrazolo[3,4-d]pyrimidin-6-yl)amino)-N-(1,1-dioxidotetrahydro-2H-thiopyran-4-yl)cyclopentane-1-carboxamide | 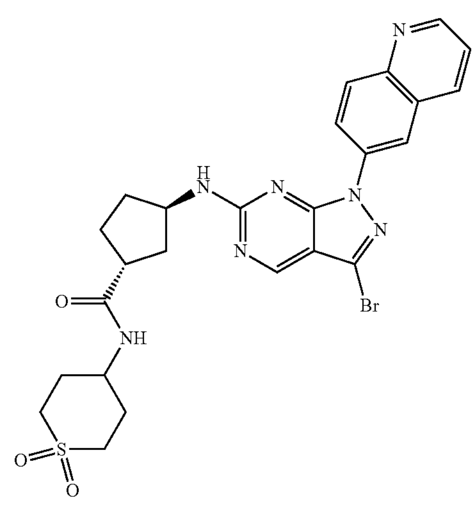 [SMILES: O=C(NC1CCS(=O)(=O)CC1)[C@@H]1CC[C@@H](Nc2ncc3c(Br)nn(-c4ccc5ncccc5c4)c3n2)C1] | A |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-(2-methyl-1-(pyrrolidin-1-yl)propan-2-yl)cyclopentane-1-carboxamide | 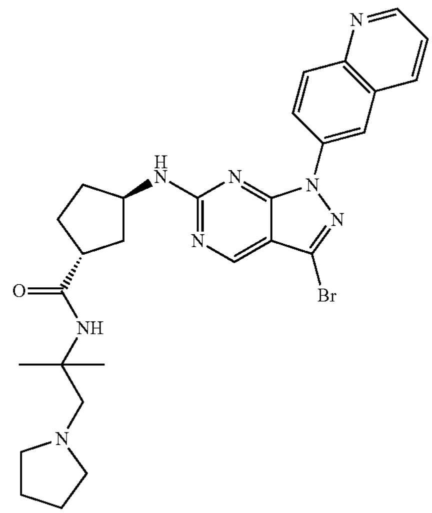 [SMILES: CC(C)(CN1CCCC1)NC(=O)[C@@H]1CC[C@@H](Nc2ncc3c(Br)nn(-c4ccc5ncccc5c4)c3n2)C1] | A |
| 1-(4-((1R,3R)-3-((3-bromo-1-(quinolin-6-yl)-1H-pyrazolo[3,4-d]pyrimidin-6-yl)amino)cyclopentane-1-carbonyl)piperazin-1-yl)-2-hydroxyethan-1-one | 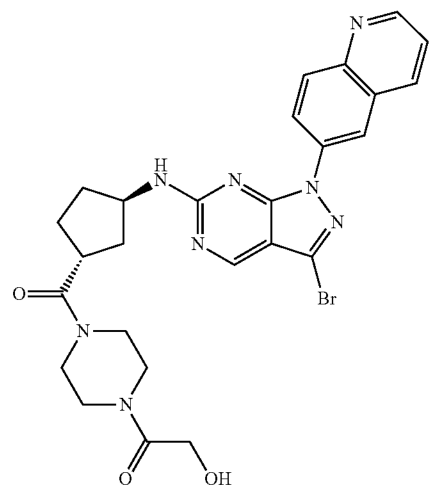 [SMILES: O=C(CO)N1CCN(C(=O)[C@@H]2CC[C@@H](Nc3ncc4c(Br)nn(-c5ccc6ncccc6c5)c4n3)C2)CC1] | A |
| (1R,3R)-3-((3-bromo-1-(quinolin-6-yl)-1H-pyrazolo[3,4-d]pyrimidin-6-yl)amino)-N-(2-(methylsulfonyl)ethyl)cyclopentane-1-carboxamide | 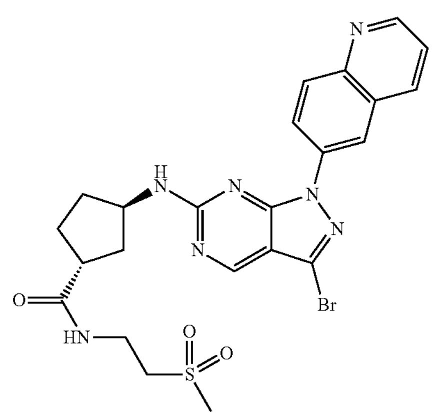 [SMILES: CS(=O)(=O)CCNC(=O)[C@@H]1CC[C@@H](Nc2ncc3c(Br)nn(-c4ccc5ncccc5c4)c3n2)C1] | B |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-(((R)-morpholin-3-yl)methyl)cyclopentane-1-carboxamide | 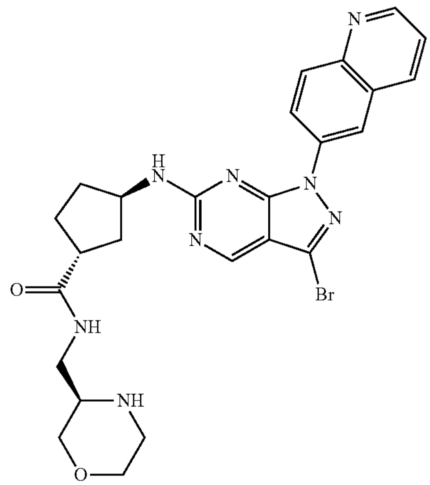 [SMILES: O=C(NC[C@@H]1COCCN1)[C@@H]1CC[C@@H](Nc2ncc3c(Br)nn(-c4ccc5ncccc5c4)c3n2)C1] | B |
| (1R,3R)-3-((3-bromo-1-(quinolin-6-yl)-1H-pyrazolo[3,4-d]pyrimidin-6-yl)amino)-N-(((S)-morpholin-3-yl)methyl)cyclopentane-1-carboxamide | 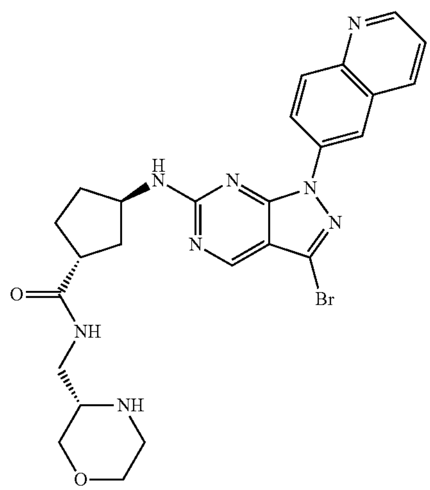 [SMILES: O=C(NC[C@H]1COCCN1)[C@@H]1CC[C@@H](Nc2ncc3c(Br)nn(-c4ccc5ncccc5c4)c3n2)C1] | A |
| (1R,3R)-3-((3-bromo-1-(quinolin-6-yl)-1H-pyrazolo[3,4-d]pyrimidin-6-yl)amino)-N-(3-methyltetrahydrofuran-3-yl)cyclopentane-1-carboxamide | 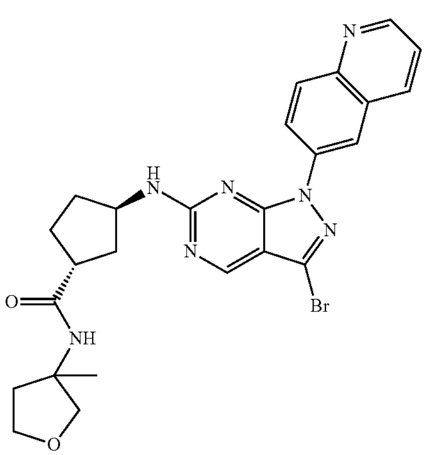 [SMILES: CC1(NC(=O)[C@@H]2CC[C@@H](Nc3ncc4c(Br)nn(-c5ccc6ncccc6c5)c4n3)C2)CCOC1] | A |

TABLE 3-continued

| Chemical Name | Chemical Structure | IC$_{50}$ Activity |
|---|---|---|
| (1R,3R)-N-(2-(1H-imidazol-5-yl)ethyl)-3-((3-bromo-1-(quinolin-6-yl)-1H-pyrazolo[3,4-d]pyrimidin-6-yl)amino)cyclopentane-1-carboxamide | 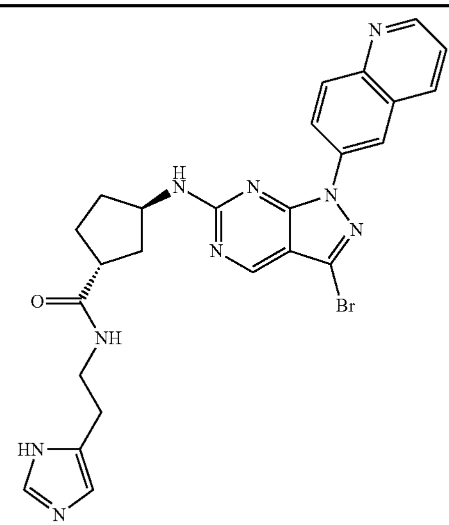 | B |
| (1R,3R)-3-((3-bromo-1-(4-(pyridin-3-yl)phenyl)-1H-pyrazolo[3,4-d]pyrimidin-6-yl)amino)-N-(1,1-dioxidotetrahydro-2H-thiopyran-4-yl)cyclopentane-1-carboxamide | 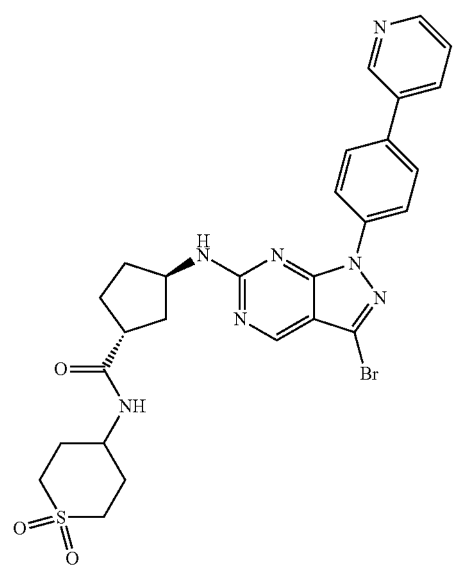 [SMILES: O=C(NC1CCS(=O)(=O)CC1)[C@@H]1CC[C@@H](Nc2ncc3c(Br)nn(-c4ccc(-c5cccnc5)cc4)c3n2)C1] | B |
| (1R,3R)-N-(2-(1H-imidazol-5-yl)ethyl)-3-((3-bromo-1-(8-fluoroquinolin-6-yl)-1H-pyrazolo[3,4-d]pyrimidin-6-yl)amino)cyclopentane-1-carboxamide | 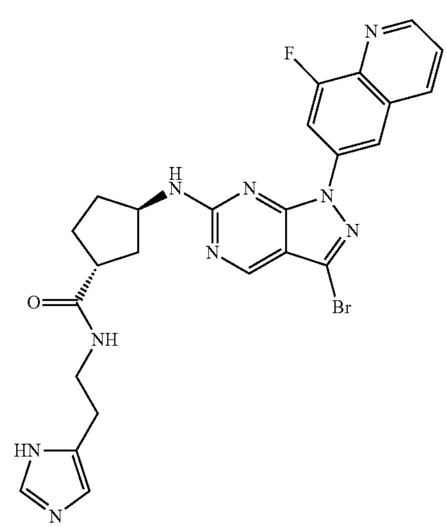 [SMILES: O=C(NCCc1cnc[nH]1)[C@@H]1CC[C@@H](Nc2ncc3c(Br)nn(-c4cc(F)c5ncccc5c4)c3n2)C1] | A |

TABLE 3-continued

| Chemical Name | Chemical Structure | IC$_{50}$ Activity |
|---|---|---|
| (1R,3R)-3-((3-bromo-1-(2-methoxypyridin-4-yl)-1H-pyrazolo[3,4-d]pyrimidin-6-yl)amino)-N-(2-(methylsulfonyl)ethyl)cyclopentane-1-carboxamide | 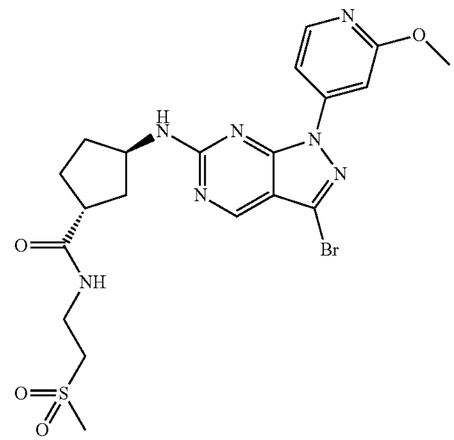 [SMILES: COc1cc(-n2nc(Br)c3cnc(N[C@@H]4CC[C@@H](C(=O)NCCS(C)(=O)=O)C4)nc32)ccn1] | C |
| (1R,3R)-3-((3-bromo-1-(8-fluoroquinolin-6-yl)-1H-pyrazolo[3,4-d]pyrimidin-6-yl)amino)-N-(((S)-morpholin-3-yl)methyl)cyclopentane-1-carboxamide | 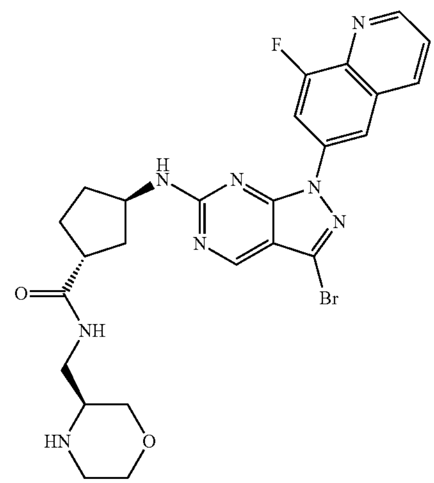 [SMILES: O=C(NC[C@H]1COCCN1)[C@@H]1CC[C@@H](Nc2ncc3c(Br)nn(-c4cc(F)c5ncccc5c4)c3n2)C1] | A |
| 1-(4-((1R,3R)-3-((3-bromo-1-(8-fluoroquinolin-6-yl)-1H-pyrazolo[3,4-d]pyrimidin-6-yl)amino)cyclopentane-1-carbonyl)piperazin-1-yl)-2-hydroxyethan-1-one | 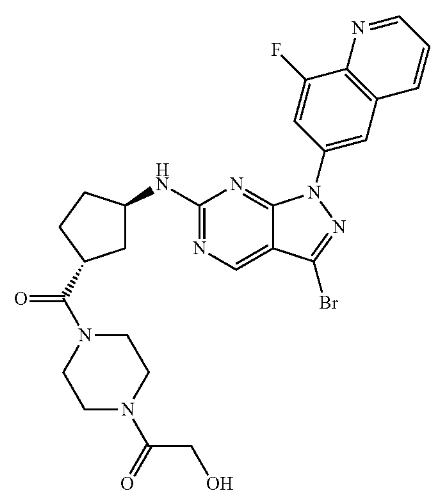 [SMILES: O=C(CO)N1CCN(C(=O)[C@@H]2CC[C@@H](Nc3ncc4c(Br)nn(-c5cc(F)c6ncccc6c5)c4n3)C2)CC1] | A |

TABLE 3-continued

| Chemical Name | Chemical Structure | IC$_{50}$ Activity |
|---|---|---|
| 5-(3-bromo-6-(((1R,3R)-3-(4-methyl-3-oxo-piperazine-1-carbonyl)cyclopentyl)amino)-1H-pyrazolo[3,4-d]pyrimidin-1-yl)-2-methoxybenzonitrile | 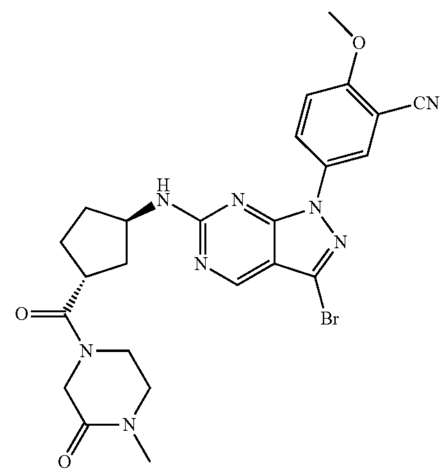 [SMILES: COc1ccc(-n2nc(Br)c3cnc(N[C@@H]4CC[C@@H](C(=O)N5CCN(C)C(=O)C5)C4)nc32)cc1C#N] | B |
| (1R,3R)-3-((3-bromo-1-(quinolin-6-yl)-1H-pyrazolo[3,4-d]pyrimidin-6-yl)amino)-N-(2-(isopropylamino)-2-oxoethyl)-N-methylcyclopentane-1-carboxamide | | A |
| (1R,3R)-3-((3-bromo-1-(quinolin-6-yl)-1H-pyrazolo[3,4-d]pyrimidin-6-yl)amino)-N-(oxazol-2-ylmethyl)cyclopentane-1-carboxamide | 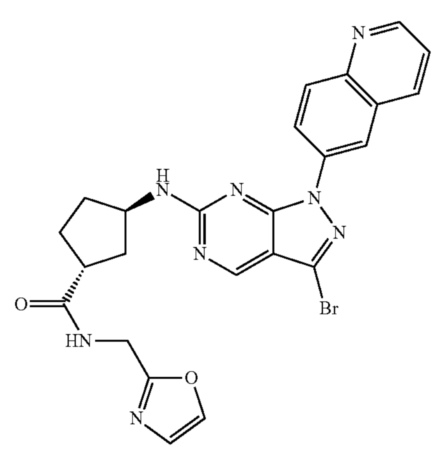 [SMILES: O=C(NCc1ncco1)[C@@H]1CC[C@@H](Nc2ncc3c(Br)nn(-c4ccc5ncccc5c4)c3n2)C1] | A |

TABLE 3-continued

| Chemical Name | Chemical Structure | IC$_{50}$ Activity |
|---|---|---|
| (1R,3R)-N-(2-(1H-imidazol-1-yl)ethyl)-3-((3-bromo-1-(quinolin-6-yl)-1H-pyrazolo[3,4-d]pyrimidin-6-yl)amino)cyclopentane-1-carboxamide | 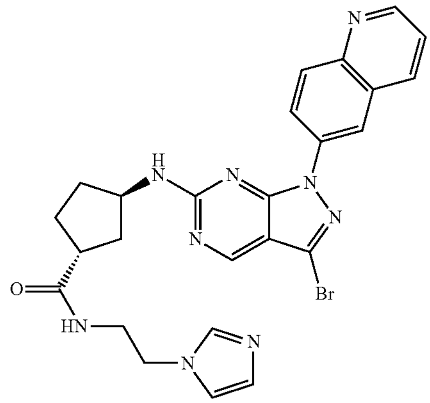 [SMILES: O=C(NCCn1ccnc1)[C@@H]1CC[C@@H](Nc2ncc3c(Br)nn(-c4ccc5ncccc5c4)c3n2)C1] | A |
| 1-(4-((1R,3R)-3-((3-bromo-1-(quinolin-6-yl)-1H-pyrazolo[3,4-d]pyrimidin-6-yl)amino)cyclopentane-1-carbonyl)piperazin-1-yl)-2-hydroxypropan-1-one | 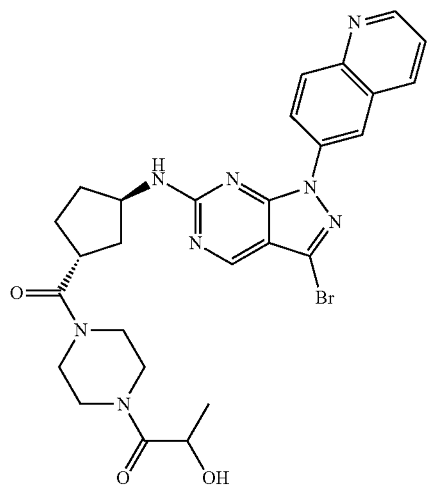 [SMILES: CC(O)C(=O)N1CCN(C(=O)[C@@H]2CC[C@@H](Nc3ncc4c(Br)nn(-c5ccc6ncccc6c5)c4n3)C2)CC1] | A |
| N-(2-((1R,3R)-3-((3-bromo-1-(quinolin-6-yl)-1H-pyrazolo[3,4-d]pyrimidin-6-yl)amino)cyclopentane-1-carboxamido)ethyl)-N-methylglycine | 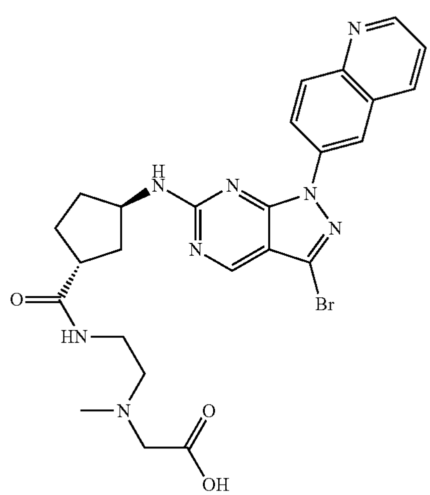 [SMILES: CN(CCNC(=O)[C@@H]1CC[C@@H](Nc2ncc3c(Br)nn(-c4ccc5ncccc5c4)c3n2)C1)CC(=O)O] | A |

TABLE 3-continued

| Chemical Name | Chemical Structure | IC$_{50}$ Activity |
|---|---|---|
| (1R,3R)-3-((3-bromo-1-(3-fluoro-2-methyl-quinolin-6-yl)-1H-pyrazolo[3,4-d]pyrimidin-6-yl)amino)-N-methylcyclopentane-1-carboxamide | 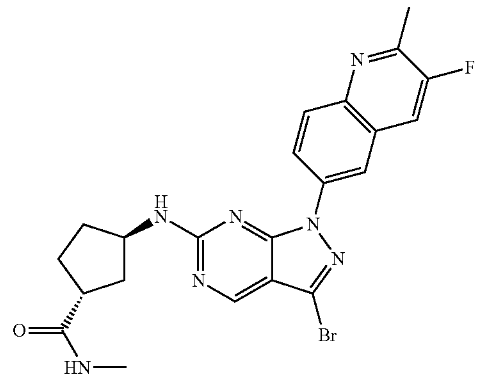 [SMILES: CNC(=O)[C@@H]1CC[C@@H](Nc2ncc3c(Br)nn(-c4ccc5nc(C)c(F)cc5c4)c3n2)C1] | A |
| (1R,3R)-3-((3-bromo-1-(3,8-difluoro-2-methyl-quinolin-6-yl)-1H-pyrazolo[3,4-d]pyrimidin-6-yl)amino)-N-methylcyclopentane-1-carboxamide | 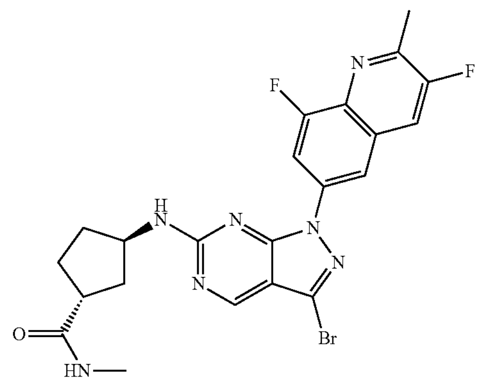 [SMILES: CNC(=O)[C@@H]1CC[C@@H](Nc2ncc3c(Br)nn(-c4cc(F)c5nc(C)c(F)cc5c4)c3n2)C1] | A |
| (1R,3R)-3-((3-bromo-1-(8-fluoro-2-methyl-quinolin-6-yl)-1H-pyrazolo[3,4-d]pyrimidin-6-yl)amino)-N-methylcyclopentane-1-carboxamide | 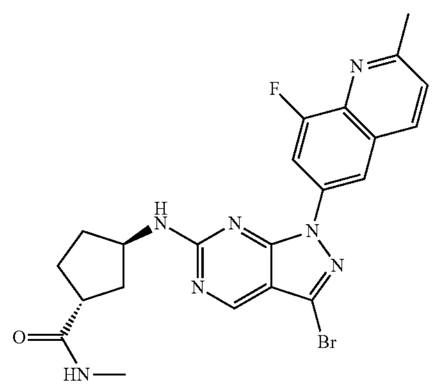 [SMILES: CNC(=O)[C@@H]1CC[C@@H](Nc2ncc3c(Br)nn(-c4cc(F)c5nc(C)ccc5c4)c3n2)C1] | A |
| (1R,3R)-3-((3-bromo-1-(3-cyano-4-morpholinophenyl)-1H-pyrazolo[3,4-d]pyrimidin-6-yl)amino)-N-methylcyclopentane-1-carboxamide | 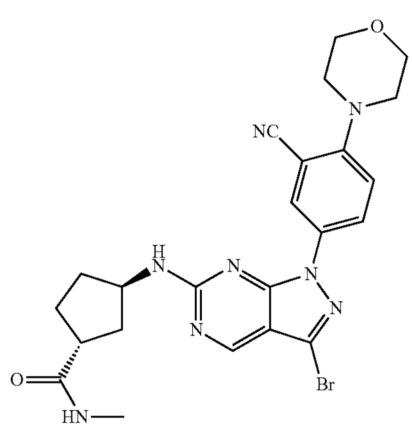 [SMILES: CNC(=O)[C@@H]1CC[C@@H](Nc2ncc3c(Br)nn(-c4ccc(N5CCOCC5)c(C#N)c4)c3n2)C1] | C |

TABLE 3-continued

| Chemical Name | Chemical Structure | IC$_{50}$ Activity |
|---|---|---|
| N-(2-(((1R,3R)-3-((3-bromo-1-(8-fluoroquinolin-6-yl)-1H-pyrazolo[3,4-d]pyrimidin-6-yl)amino)cyclopentane-1-carboxamido)ethyl)-N-methylglycine | | A |
| 1-((1R,3R)-3-((3-bromo-1-(8-fluoroquinolin-6-yl)-1H-pyrazolo[3,4-d]pyrimidin-6-yl)amino)cyclopentane-1-carbonyl)-3-hydroxy-pyrrolidine-3-carboxylic acid | 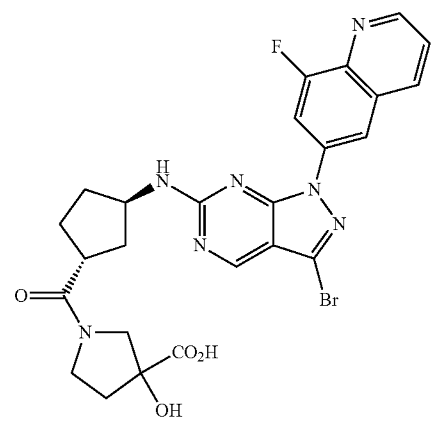 [SMILES: O=C([C@@H]1CC[C@@H](Nc2ncc3c(Br)nn(-c4cc(F)c5ncccc5c4)c3n2)C1)N1CCC(O)(C(=O)O)C1] | C |
| (3R)-3-((3-bromo-1-(isoquinolin-6-yl)-1H-pyrazolo[3,4-d]pyrimidin-6-yl)amino)-N,1-dimethylcyclopentane-1-carboxamide (as a mixture of diastereomers) | 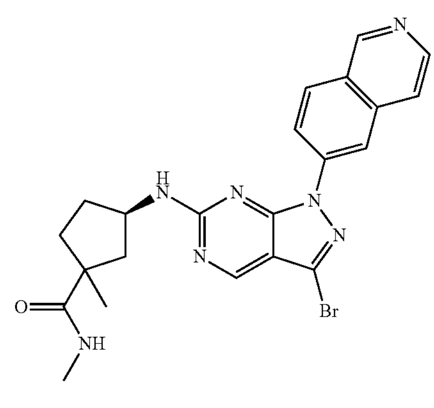 [SMILES: CNC(=O)C1(C)CC[C@@H](Nc2ncc3c(Br)nn(-c4ccc5cnccc5c4)c3n2)C1] | B |

TABLE 3-continued

| Chemical Name | Chemical Structure | IC$_{50}$ Activity |
|---|---|---|
| (1S,3R)-3-((3-bromo-1-(quinoxalin-6-yl)-1H-pyrazolo[3,4-d]pyrimidin-6-yl)amino)-N,1-dimethylcyclopentane-1-carboxamide | 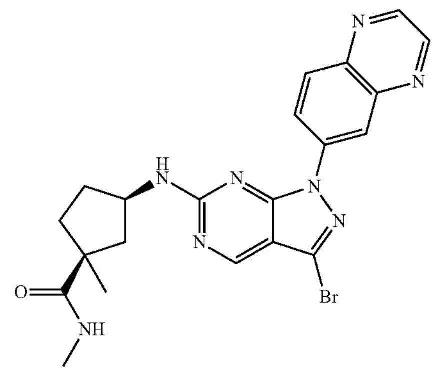 [SMILES: CNC(=O)[C@@]1(C)CC[C@@H](Nc2ncc3c(Br)nn(-c4ccc5nccnc5c4)c3n2)C1] | C |
| 8-((1R,3R)-3-((3-bromo-1-(8-fluoroquinolin-6-yl)-1H-pyrazolo[3,4-d]pyrimidin-6-yl)amino)cyclopentane-1-carbonyl)hexahydropyrazino[2,1-c][1,4]oxazin-4(3H)-one | 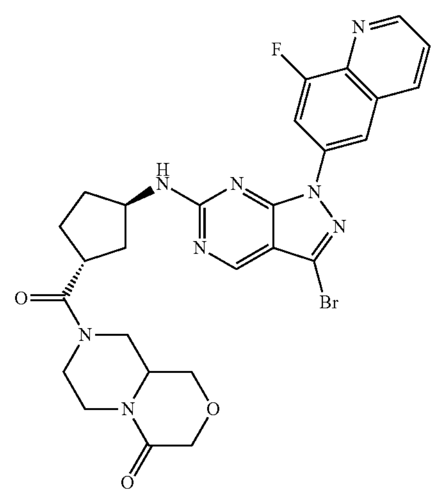 [SMILES: O=C([C@@H]1CC[C@@H](Nc2ncc3c(Br)nn(-c4cc(F)c5ncccc5c4)c3n2)C1)N1CCN2C(=O)COCC2C1] | A |
| ((1R,3R)-3-((3-bromo-1-(8-fluoroquinolin-6-yl)-1H-pyrazolo[3,4-d]pyrimidin-6-yl)amino)cyclopentyl)((S)-hexahydropyrazino[2,1-c][1,4]oxazin-8(1H)-yl)methanone | 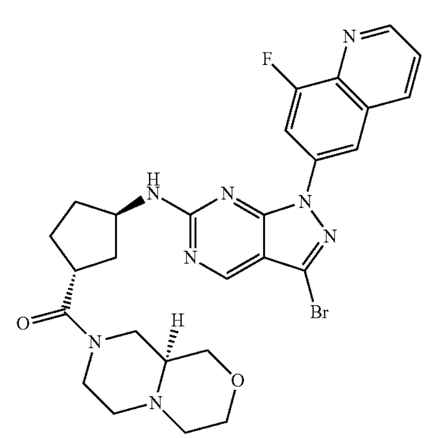 [SMILES: O=C([C@@H]1CC[C@@H](Nc2ncc3c(Br)nn(-c4cc(F)c5ncccc5c4)c3n2)C1)N1CCN2CCOC[C@@H]2C1] | A |

TABLE 3-continued

| Chemical Name | Chemical Structure | IC$_{50}$ Activity |
|---|---|---|
| (1R,3R)-N-(2-amino-2-oxoethyl)-3-((3-bromo-1-(8-fluoroquinolin-6-yl)-1H-pyrazolo[3,4-d]pyrimidin-6-yl)amino)-N-isopropylcyclopentane-1-carboxamide | 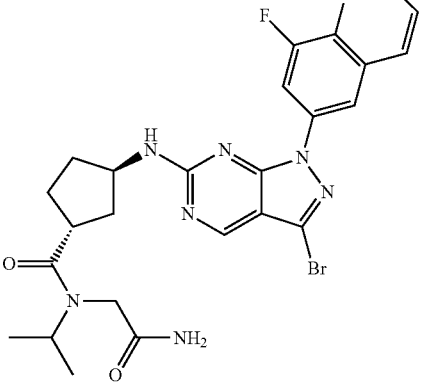 | A |
| (1R,3R)-N-(2-amino-2-oxoethyl)-3-((3-bromo-1-(8-fluoroquinolin-6-yl)-1H-pyrazolo[3,4-d]pyrimidin-6-yl)amino)-N-methylcyclopentane-1-carboxamide | 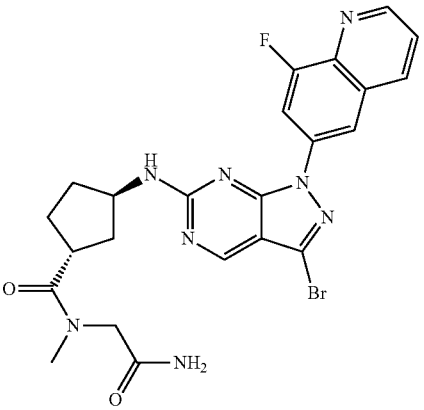 [SMILES: CN(CC(N)=O)C(=O)[C@@H]1CC[C@@H](Nc2ncc3c(Br)nn(-c4cc(F)c5ncccc5c4)c3n2)C1] | A |
| (1R,3R)-3-((3-bromo-1-(8-(trifluoromethyl)quinolin-6-yl)-1H-pyrazolo[3,4-d]pyrimidin-6-yl)amino)-N-(2-methoxyethyl)cyclopentane-1-carboxamide | 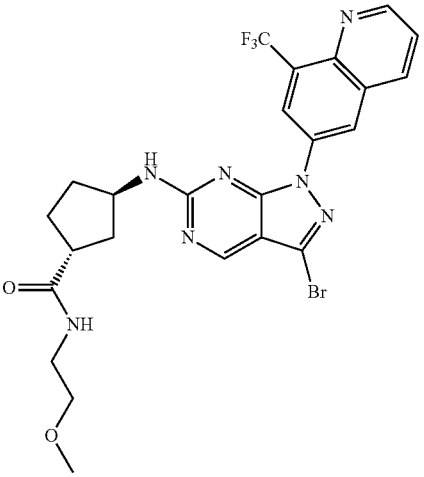 [SMILES: COCCNC(=O)[C@@H]1CC[C@@H](Nc2ncc3c(Br)nn(-c4cc(C(F)(F)F)c5ncccc5c4)c3n2)C1] | B |

TABLE 3-continued

| Chemical Name | Chemical Structure | IC$_{50}$ Activity |
|---|---|---|
| (1S,3R)-3-((3-bromo-1-(quinolin-6-yl)-1H-pyrazolo[3,4-d]pyrimidin-6-yl)amino)-N-methylcyclopentane-1-sulfonamide | 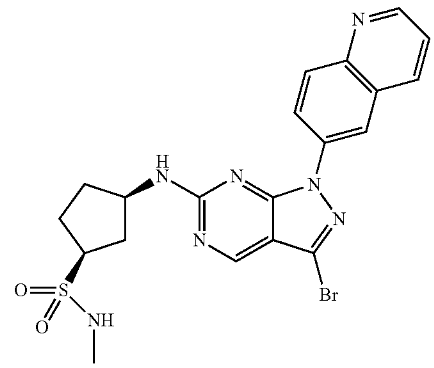 [SMILES: CNS(=O)(=O)[C@H]1CC[C@@H](Nc2ncc3c(Br)nn(-c4ccc5ncccc5c4)c3n2)C1] | C |
| (1R,3R)-3-((3-bromo-1-(quinolin-6-yl)-1H-pyrazolo[3,4-d]pyrimidin-6-yl)amino)-N,N-dimethylcyclopentane-1-sulfonamide | 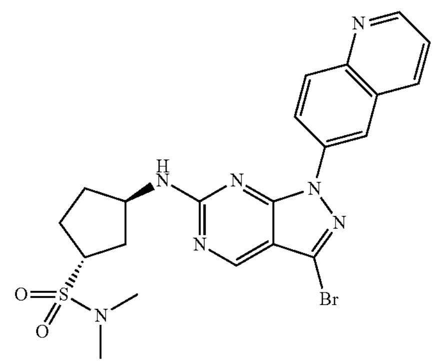 [SMILES: CN(C)S(=O)(=O)[C@@H]1CC[C@@H](Nc2ncc3c(Br)nn(-c4ccc5ncccc5c4)c3n2)C1] | A |
| 3-bromo-N-((1R,3R)-3-(morpholinosulfonyl)cyclopentyl)-1-(quinolin-6-yl)-1H-pyrazolo[3,4-d]pyrimidin-6-amine | 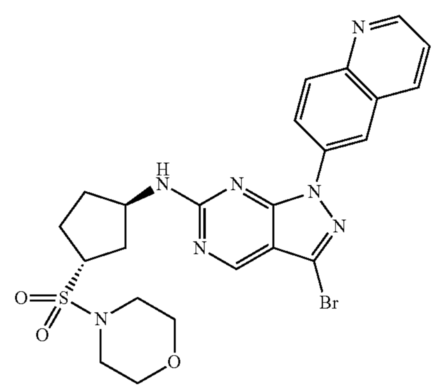 [SMILES: O=S(=O)([C@@H]1CC[C@@H](Nc2ncc3c(Br)nn(-c4ccc5ncccc5c4)c3n2)C1)N1CCOCC1] | B |
| (1R,3R)-3-((3-bromo-1-(quinolin-6-yl)-1H-pyrazolo[3,4-d]pyrimidin-6-yl)amino)-N-(2-methoxyethyl)cyclopentane-1-sulfonamide | 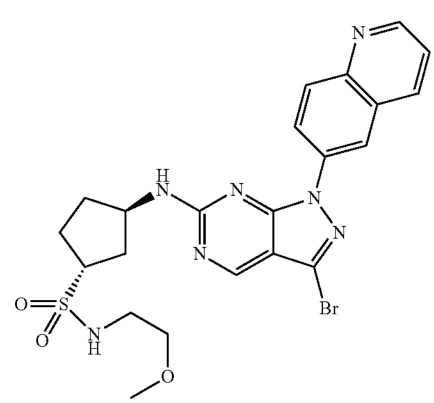 [SMILES: COCCNS(=O)(=O)[C@@H]1CC[C@@H](Nc2ncc3c(Br)nn(-c4ccc5ncccc5c4)c3n2)C1] | A |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-cyclopropylcyclopentane-1-sulfonamide | 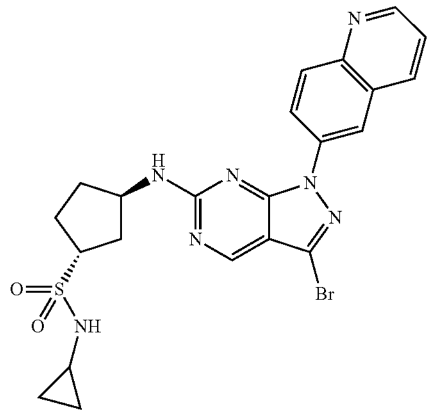 [SMILES: O=S(=O)(NC1CC1)[C@@H]1CC[C@@H](Nc2ncc3c(Br)nn(-c4ccc5ncccc5c4)c3n2)C1] | A |
| (1R,3R)-3-((3-bromo-1-(quinolin-6-yl)-1H-pyrazolo[3,4-d]pyrimidin-6-yl)amino)-N-(tetrahydro-2H-pyran-4-yl)cyclopentane-1-sulfonamide | 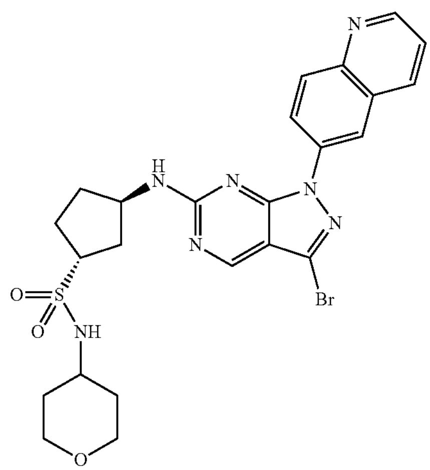 [SMILES: O=S(=O)(NC1CCOCC1)[C@@H]1CC[C@@H](Nc2ncc3c(Br)nn(-c4ccc5ncccc5c4)c3n2)C1] | B |
| (1R,3R)-3-((3-bromo-1-(quinolin-6-yl)-1H-pyrazolo[3,4-d]pyrimidin-6-yl)amino)-N-cyclobutylcyclopentane-1-sulfonamide | 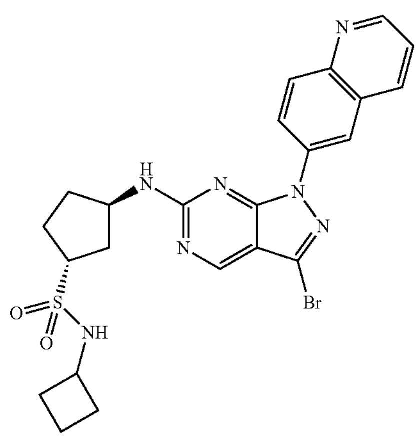 [SMILES: O=S(=O)(NC1CCC1)[C@@H]1CC[C@@H](Nc2ncc3c(Br)nn(-c4ccc5ncccc5c4)c3n2)C1] | C |

TABLE 3-continued

| Chemical Name | Chemical Structure | IC$_{50}$ Activity |
|---|---|---|
| (3R)-3-((3-bromo-1-(8-fluoroquinolin-6-yl)-1H-pyrazolo[3,4-d]pyrimidin-6-yl)amino)-N,N-dimethylcyclopentane-1-sulfonamide | 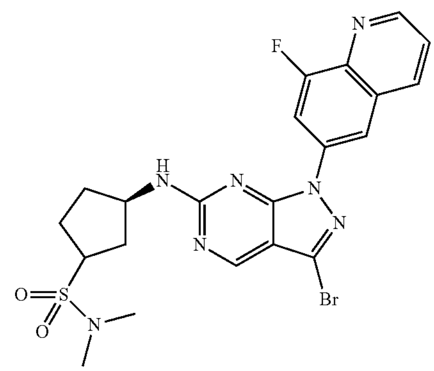 [SMILES: CN(C)S(=O)(=O)C1CC[C@@H](Nc2ncc3c(Br)nn(-c4cc(F)c5ncccc5c4)c3n2)C1] | A |
| (R)-3-bromo-N-(1-(methylsulfonyl)pyrrolidin-3-yl)-1-(quinolin-6-yl)-1H-pyrazolo[3,4-d]pyrimidin-6-amine | 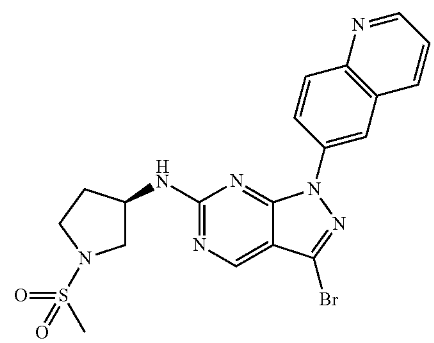 [SMILES: CS(=O)(=O)N1CC[C@@H](Nc2ncc3c(Br)nn(-c4ccc5ncccc5c4)c3n2)C1] | B |
| (R)-3-((3-bromo-1-(quinolin-6-yl)-1H-pyrazolo[3,4-d]pyrimidin-6-yl)amino)-N,N-dimethyl-pyrrolidine-1-carboxamide | 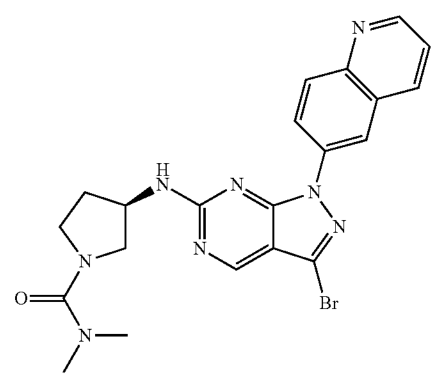 [SMILES: CN(C)C(=O)N1CC[C@@H](Nc2ncc3c(Br)nn(-c4ccc5ncccc5c4)c3n2)C1] | C |
| (3R)-3-((3-bromo-1-(2-methoxyquinolin-6-yl)-1H-pyrazolo[3,4-d]pyrimidin-6-yl)amino)-N,1-dimethylcyclopentane-1-carboxamide | 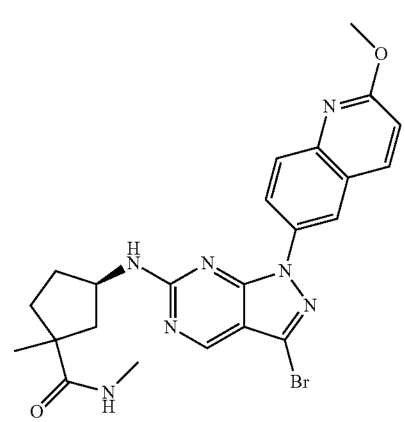 [SMILES: CNC(=O)C1(C)CC[C@@H](Nc2ncc3c(Br)nn(-c4ccc5nc(OC)ccc5c4)c3n2)C1] | A |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-(2-methoxyethyl)-1-methylcyclopentane-1-carboxamide | 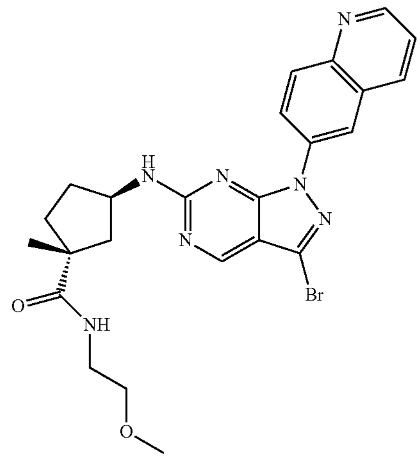 [SMILES: COCCNC(=O)[C@]1(C)CC[C@@H](Nc2ncc3c(Br)nn(-c4ccc5ncccc5c4)c3n2)C1] | A |
| (1S,3R)-3-((3-bromo-1-(quinolin-6-yl)-1H-pyrazolo[3,4-d]pyrimidin-6-yl)amino)-N-(2-methoxyethyl)-1-methylcyclopentane-1-carboxamide | 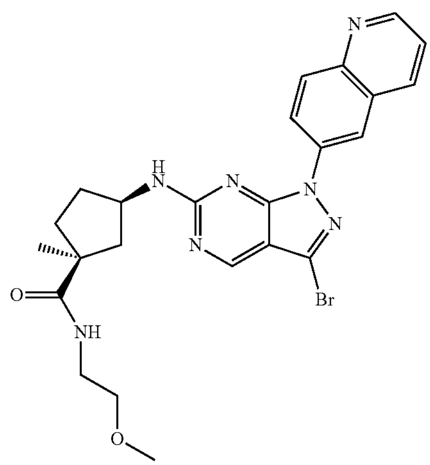 [SMILES: COCCNC(=O)[C@@]1(C)CC[C@@H](Nc2ncc3c(Br)nn(-c4ccc5ncccc5c4)c3n2)C1] | C |
| (1S,3R)-3-((3-bromo-1-(quinolin-6-yl)-1H-pyrazolo[3,4-d]pyrimidin-6-yl)amino)-N,1-dimethylcyclopentane-1-carboxamide | 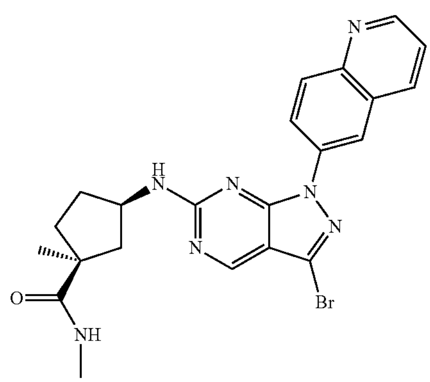 [SMILES: CNC(=O)[C@@]1(C)CC[C@@H](Nc2ncc3c(Br)nn(-c4ccc5ncccc5c4)c3n2)C1] | B |

TABLE 3-continued

| Chemical Name | Chemical Structure | IC$_{50}$ Activity |
|---|---|---|
| (1R,3R)-3-((3-bromo-1-(quinolin-7-yl)-1H-pyrazolo[3,4-d]pyrimidin-6-yl)amino)-N-(2-methoxyethyl)cyclopentane-1-carboxamide | 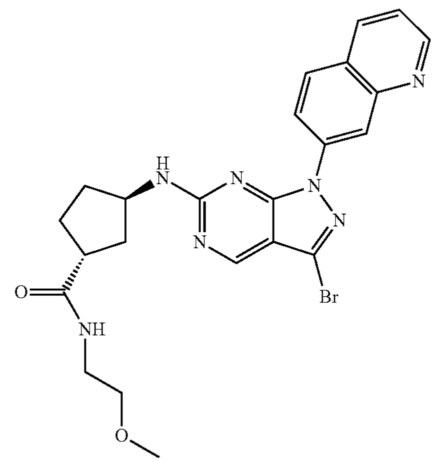 [SMILES: COCCNC(=O)[C@@H]1CC[C@@H](Nc2ncc3c(Br)nn(-c4ccc5cccnc5c4)c3n2)C1] | B |
| (1R,3R)-3-((3-bromo-1-(quinolin-6-yl)-1H-pyrazolo[3,4-d]pyrimidin-6-yl)amino)cyclohexane-1-carboxylic acid | 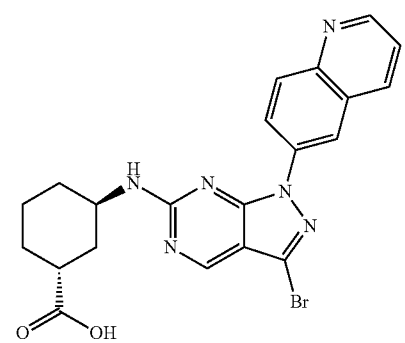 [SMILES: O=C(O)[C@@H]1CCC[C@@H](Nc2ncc3c(Br)nn(-c4ccc5ncccc5c4)c3n2)C1] | C |
| (1R,3R)-3-((3-bromo-1-(quinoxalin-6-yl)-1H-pyrazolo[3,4-d]pyrimidin-6-yl)amino)-N-(2-methoxyethyl)cyclopentane-1-carboxamide | 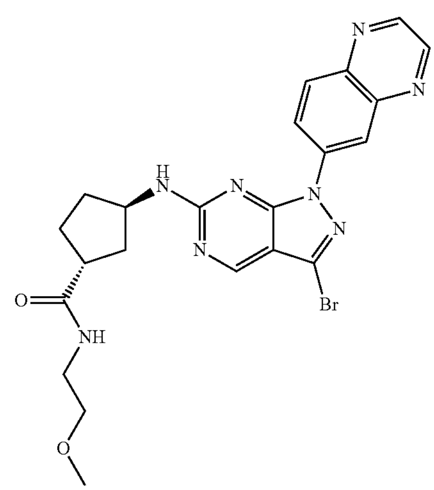 [SMILES: COCCNC(=O)[C@@H]1CC[C@@H](Nc2ncc3c(Br)nn(-c4ccc5nccnc5c4)c3n2)C1] | A |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-((R)-1-methoxypropan-2-yl)cyclohexane-1-carboxamide | 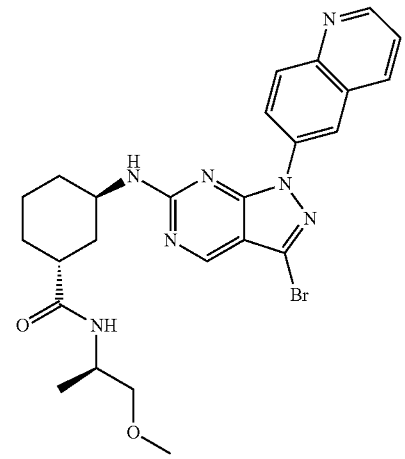 [SMILES: COC[C@@H](C)NC(=O)[C@@H]1CCC[C@@H](Nc2ncc3c(Br)nn(-c4ccc5ncccc5c4)c3n2)C1] | C |
| (1R,3R)-3-((3-bromo-1-(quinolin-6-yl)-1H-pyrazolo[3,4-d]pyrimidin-6-yl)amino)-N-((S)-1-methoxypropan-2-yl)cyclohexane-1-carboxamide | 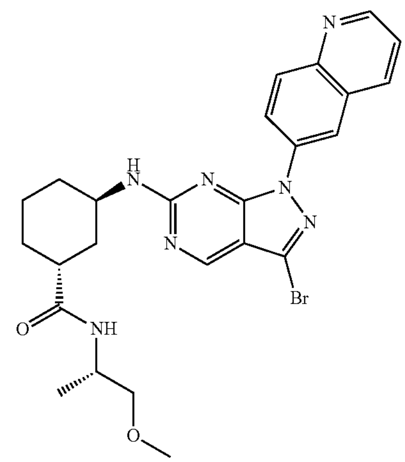 [SMILES: COC[C@H](C)NC(=O)[C@@H]1CCC[C@@H](Nc2ncc3c(Br)nn(-c4ccc5ncccc5c4)c3n2)C1] | C |
| (1R,3R)-3-((3-bromo-1-(quinolin-6-yl)-1H-pyrazolo[3,4-d]pyrimidin-6-yl)amino)-N-(2-hydroxyethyl)cyclopentane-1-carboxamide | 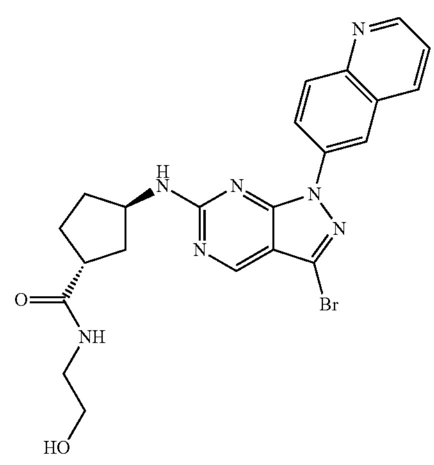 [SMILES: O=C(NCCO)[C@@H]1CC[C@@H](Nc2ncc3c(Br)nn(-c4ccc5ncccc5c4)c3n2)C1] | A |

TABLE 3-continued

| Chemical Name | Chemical Structure | IC₅₀ Activity |
|---|---|---|
| ((1R,4R)-2-oxa-5-azabicyclo[2.2.1]heptan-5-yl)((1R,3R)-3-((3-bromo-1-(quinolin-6-yl)-1H-pyrazolo[3,4-d]pyrimidin-6-yl)amino)cyclopentyl)methanone | | A |
| ((1R,3R)-3-((3-bromo-1-(quinolin-6-yl)-1H-pyrazolo[3,4-d]pyrimidin-6-yl)amino)cyclopentyl)((2S,6R)-2,6-dimethylmorpholino)methanone | 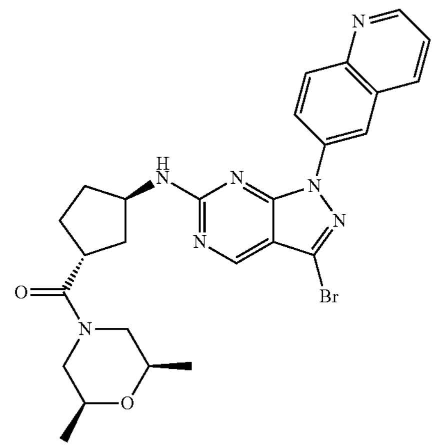 [SMILES: C[C@@H]1CN(C(=O)[C@@H]2CC[C@@H](Nc3ncc4c(Br)nn(-c5ccc6ncccc6c5)c4n3)C2)C[C@H](C)O1] | B |
| ((1R,3R)-3-((3-bromo-1-(quinolin-6-yl)-1H-pyrazolo[3,4-d]pyrimidin-6-yl)amino)cyclopentyl)(4-(2-hydroxyethyl)piperazin-1-yl)methanone | 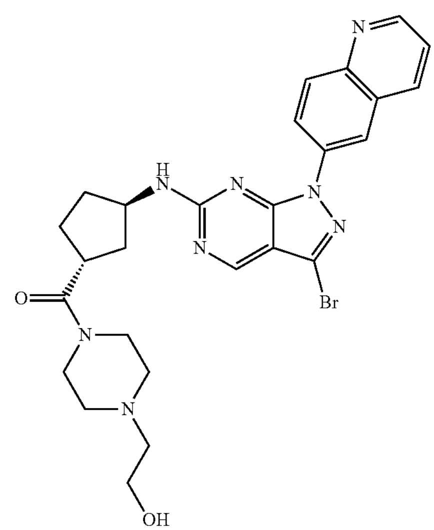 [SMILES: O=C([C@@H]1CC[C@@H](Nc2ncc3c(Br)nn(-c4ccc5ncccc5c4)c3n2)C1)N1CCN(CCO)CC1] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)((S)-3-methylmorpholino)methanone | 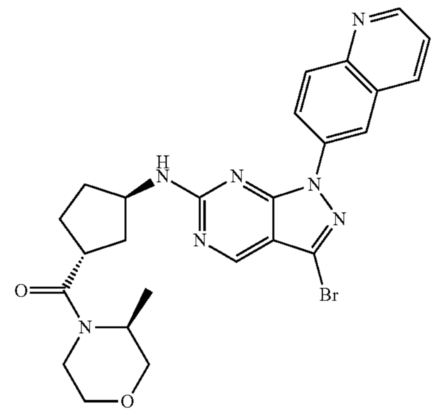 [SMILES: C[C@H]1COCCN1C(=O)[C@@H]1CC[C@@H](Nc2ncc3c(Br)nn(-c4ccc5ncccc5c4)c3n2)C1] | A |
| ((1R,3R)-3-((3-bromo-1-(quinolin-6-yl)-1H-pyrazolo[3,4-d]pyrimidin-6-yl)amino)cyclopentyl)((R)-2-methylmorpholino)methanone | 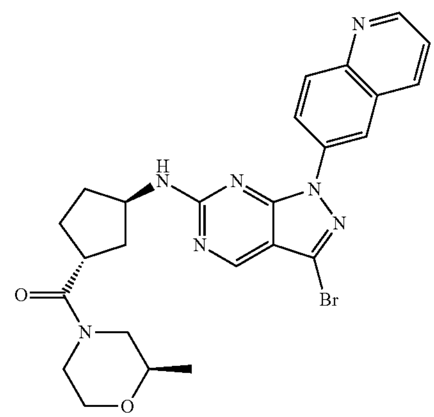 [SMILES: C[C@@H]1CN(C(=O)[C@@H]2CC[C@@H](Nc3ncc4c(Br)nn(-c5ccc6ncccc6c5)c4n3)C2)CCO1] | A |
| (8-oxa-3-azabicyclo[3.2.1]octan-3-yl)((1R,3R)-3-((3-bromo-1-(quinolin-6-yl)-1H-pyrazolo[3,4-d]pyrimidin-6-yl)amino)cyclopentyl)methanone | 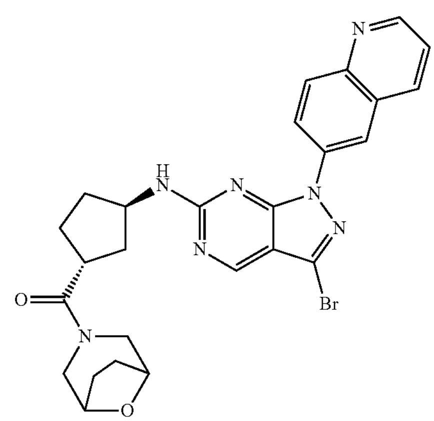 [SMILES: O=C([C@@H]1CC[C@@H](Nc2ncc3c(Br)nn(-c4ccc5ncccc5c4)c3n2)C1)N1CC2CCC(C1)O2] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(3-(1,1-dioxidothiomorpholino)azetidin-1-yl)methanone | 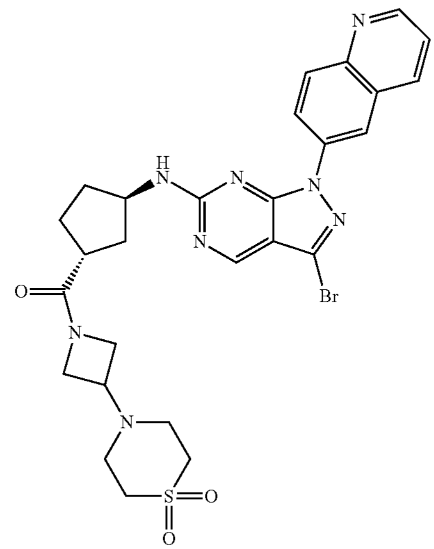 [SMILES: O=C([C@@H]1CC[C@@H](Nc2ncc3c(Br)nn(-c4ccc5ncccc5c4)c3n2)C1)N1CC(N2CCS(=O)(=O)CC2)C1] | A |
| ((1R,3R)-3-((3-bromo-1-(quinolin-6-yl)-1H-pyrazolo[3,4-d]pyrimidin-6-yl)amino)cyclopentyl)(piperazin-1-yl)methanone | 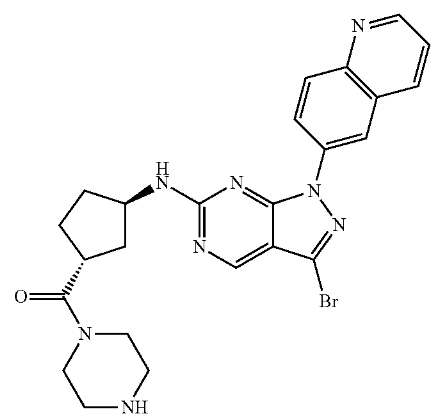 [SMILES: O=C([C@@H]1CC[C@@H](Nc2ncc3c(Br)nn(-c4ccc5ncccc5c4)c3n2)C1)N1CCNCC1] | A |
| (3-oxa-8-azabicyclo[3.2.1]octan-8-yl)((1R,3R)-3-((3-bromo-1-(quinolin-6-yl)-1H-pyrazolo[3,4-d]pyrimidin-6-yl)amino)cyclopentyl)methanone | 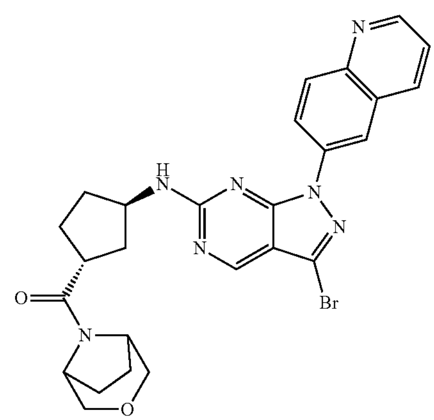 [SMILES: O=C([C@@H]1CC[C@@H](Nc2ncc3c(Br)nn(-c4ccc5ncccc5c4)c3n2)C1)N1C2CCC1COC2] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)((3S,5R)-3,5-dimethylpiperazin-1-yl)methanone | 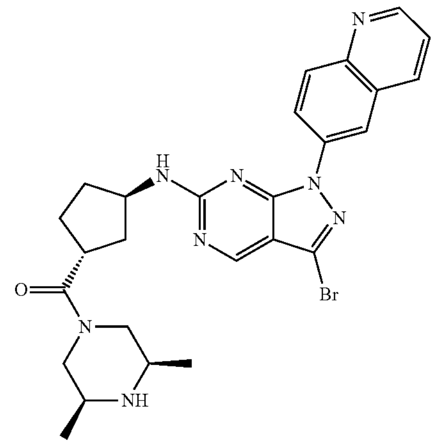 [SMILES: C[C@@H]1CN(C(=O)[C@@H]2CC[C@@H](Nc3ncc4c(Br)nn(-c5ccc6ncccc6c5)c4n3)C2)C[C@H](C)N1] | A |
| ((1R,3R)-3-((3-bromo-1-(quinolin-6-yl)-1H-pyrazolo[3,4-d]pyrimidin-6-yl)amino)cyclopentyl)((S)-3-(2-hydroxyethyl)piperazin-1-yl)methanone | 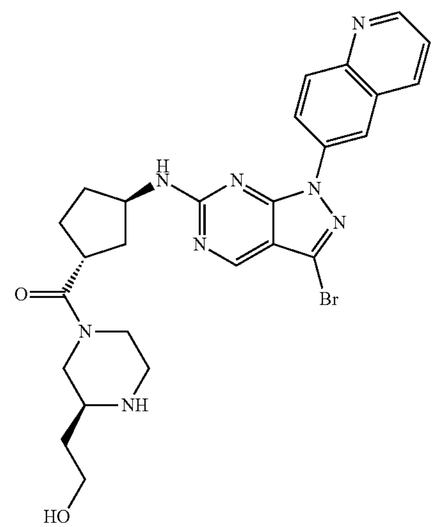 [SMILES: O=C([C@@H]1CC[C@@H](Nc2ncc3c(Br)nn(-c4ccc5ncccc5c4)c3n2)C1)N1CCN[C@@H](CCO)C1] | A |
| ((1R,3R)-3-((3-bromo-1-(quinolin-6-yl)-1H-pyrazolo[3,4-d]pyrimidin-6-yl)amino)cyclopentyl)((3S,5S)-3,5-dimethylpiperazin-1-yl)methanone | 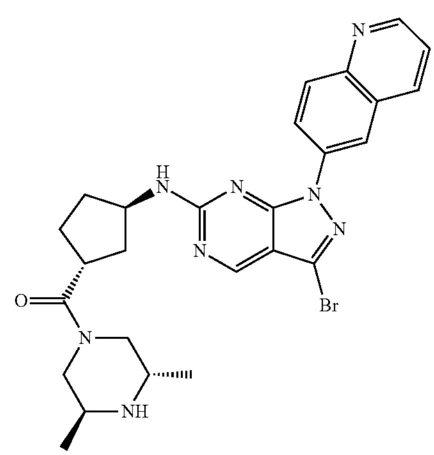 [SMILES: C[C@H]1CN(C(=O)[C@@H]2CC[C@@H](Nc3ncc4c(Br)nn(-c5ccc6ncccc6c5)c4n3)C2)C[C@H](C)N1] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(4-hydroxy-4-(hydroxymethyl)piperidin-1-yl)methanone | 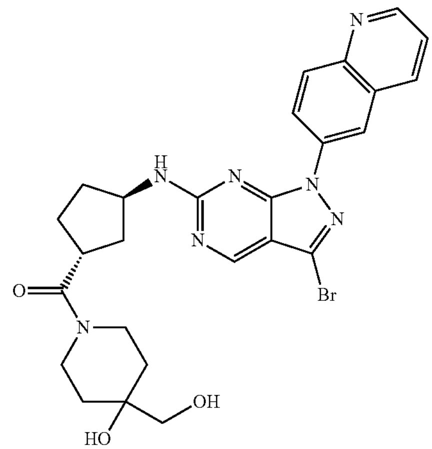 [SMILES: O=C([C@@H]1CC[C@@H](Nc2ncc3c(Br)nn(-c4ccc5ncccc5c4)c3n2)C1)N1CCC(O)(CO)CC1] | A |
| ((1R,3R)-3-((3-bromo-1-(quinolin-6-yl)-1H-pyrazolo[3,4-d]pyrimidin-6-yl)amino)cyclopentyl)((R)-3-methylmorpholino)methanone | 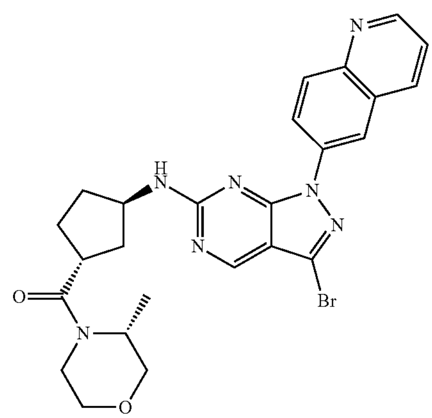 [SMILES: C[C@@H]1COCCN1C(=O)[C@@H]1CC[C@@H](Nc2ncc3c(Br)nn(-c4ccc5ncccc5c4)c3n2)C1] | A |
| ((1R,3R)-3-((3-bromo-1-(quinolin-6-yl)-1H-pyrazolo[3,4-d]pyrimidin-6-yl)amino)cyclopentyl)((S)-2-methylmorpholino)methanone | 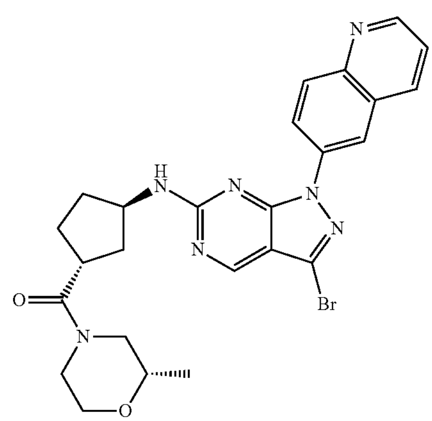 [SMILES: C[C@H]1CN(C(=O)[C@@H]2CC[C@@H](Nc3ncc4c(Br)nn(-c5ccc6ncccc6c5)c4n3)C2)CCO1] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)((2R,6R)-2,6-dimethylmorpholino)methanone | 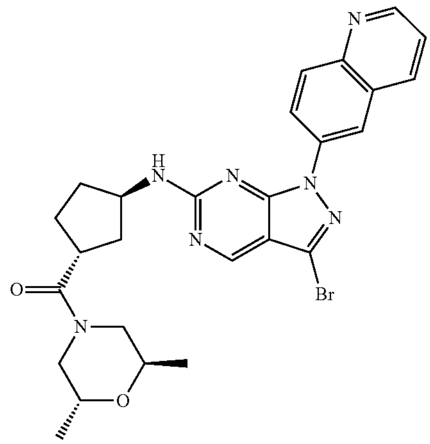 [SMILES: C[C@@H]1CN(C(=O)[C@@H]2CC[C@@H](Nc3ncc4c(Br)nn(-c5ccc6ncccc6c5)c4n3)C2)C[C@@H](C)O1] | A |
| ((1R,3R)-3-((3-bromo-1-(quinolin-6-yl)-1H-pyrazolo[3,4-d]pyrimidin-6-yl)amino)cyclopentyl)((2R,6S)-2,6-dimethylpiperazin-1-yl)methanone | 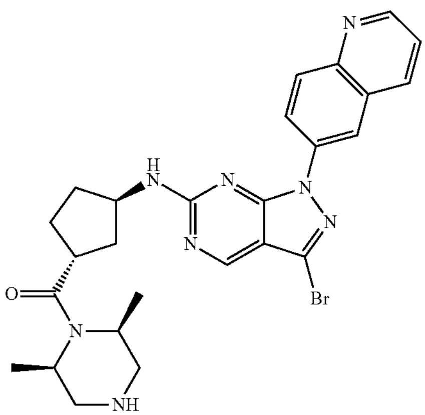 [SMILES: C[C@@H]1CNC[C@H](C)N1C(=O)[C@@H]1CC[C@@H](Nc2ncc3c(Br)nn(-c4ccc5ncccc5c4)c3n2)C1] | AA |
| ((1R,3R)-3-((3-bromo-1-(quinolin-6-yl)-1H-pyrazolo[3,4-d]pyrimidin-6-yl)amino)cyclopentyl)((2S,6S)-2,6-dimethylmorpholino)methanone | 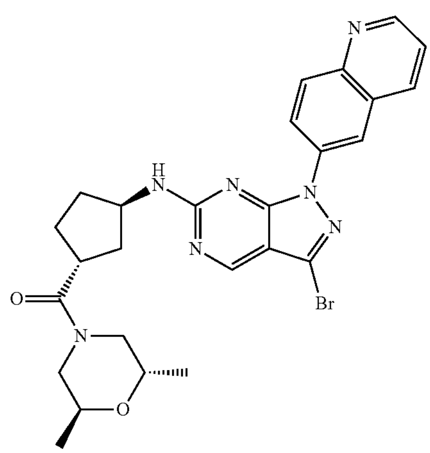 [SMILES: C[C@H]1CN(C(=O)[C@@H]2CC[C@@H](Nc3ncc4c(Br)nn(-c5ccc6ncccc6c5)c4n3)C2)C[C@H](C)O1] | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(2,6-diazaspiro[3.4]octan-2-yl)methanone | 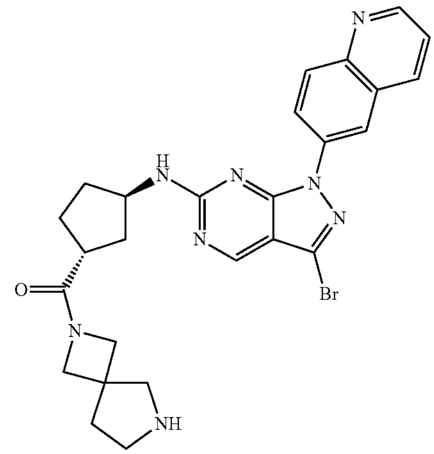 [SMILES: O=C([C@@H]1CC[C@@H](Nc2ncc3c(Br)nn(-c4ccc5ncccc5c4)c3n2)C1)N1CC2(CCNC2)C1] | A |
| ((1R,3R)-3-((3-bromo-1-(quinolin-6-yl)-1H-pyrazolo[3,4-d]pyrimidin-6-yl)amino)cyclopentyl)(2,6-diazaspiro[3.4]octan-6-yl)methanone | 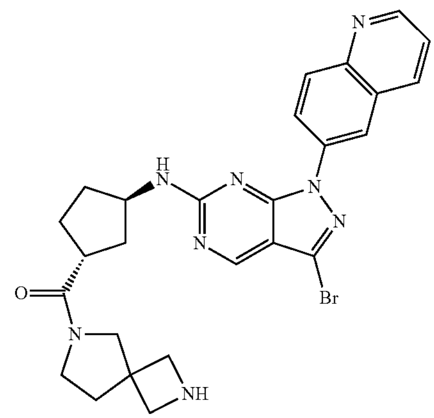 [SMILES: O=C([C@@H]1CC[C@@H](Nc2ncc3c(Br)nn(-c4ccc5ncccc5c4)c3n2)C1)N1CCC2(CNC2)C1] | AA |
| Methyl 4-((1R,3R)-3-((3-bromo-1-(quinolin-6-yl)-1H-pyrazolo[3,4-d]pyrimidin-6-yl)amino)cyclopentane-1-carbonyl)piperazine-2-carboxylate (as a mixture of diastereomers) | 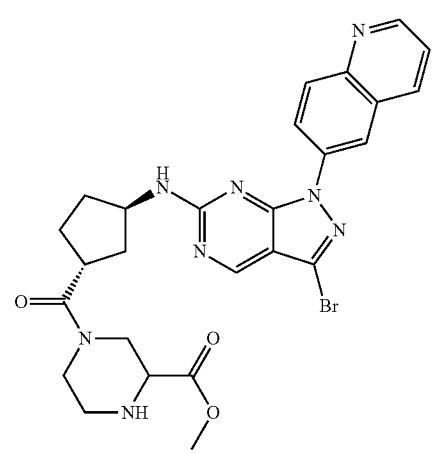 [SMILES: COC(=O)C1CN(C(=O)[C@@H]2CC[C@@H](Nc3ncc4c(Br)nn(-c5ccc6ncccc6c5)c4n3)C2)CCN1] | A |

TABLE 3-continued

| Chemical Name | Chemical Structure | IC$_{50}$ Activity |
|---|---|---|
| 4-((1R,3R)-3-((3-bromo-1-(quinolin-6-yl)-1H-pyrazolo[3,4-d]pyrimidin-6-yl)amino)cyclopentane-1-carbonyl)-1-methylpiperazin-2-one | 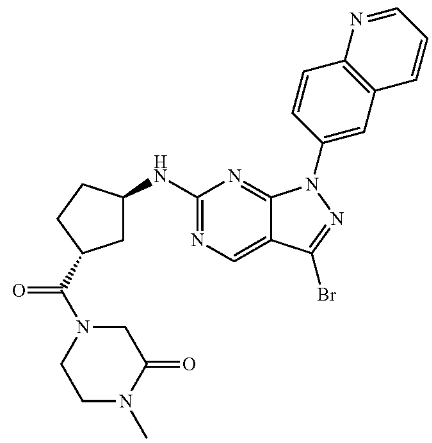 [SMILES: CN1CCN(C(=O)[C@@H]2CC[C@@H](Nc3ncc4c(Br)nn(-c5ccc6ncccc6c5)c4n3)C2)CC1=O] | A |
| (1R,3R)-3-((3-bromo-1-(quinolin-6-yl)-1H-pyrazolo[3,4-d]pyrimidin-6-yl)amino)-N-((1s,4S)-4-hydroxy-4-(trifluoromethyl)cyclohexyl)cyclopentane-1-carboxamide | 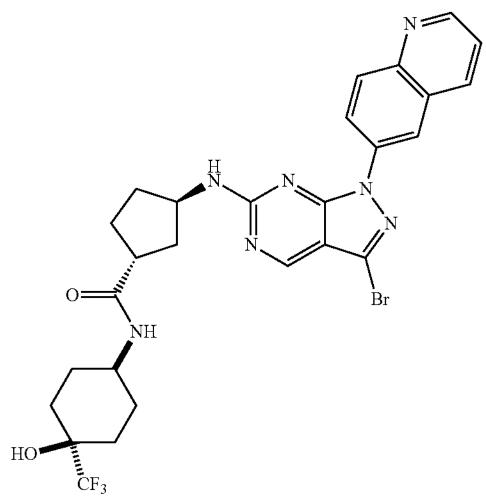 | C |
| 4-((1R,3R)-3-((3-bromo-1-(quinolin-6-yl)-1H-pyrazolo[3,4-d]pyrimidin-6-yl)amino)cyclopentane-1-carbonyl)piperazine-2-carboxylic acid (as a mixture of diastereomers) | 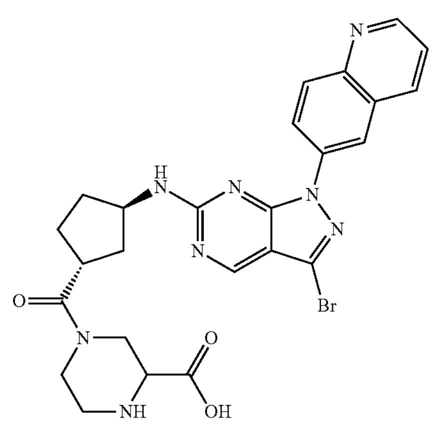 [SMILES: O=C(O)C1CN(C(=O)[C@@H]2CC[C@@H](Nc3ncc4c(Br)nn(-c5ccc6ncccc6c5)c4n3)C2)CCN1] | AA |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(1,1-dioxidothiomorpholino)methanone | 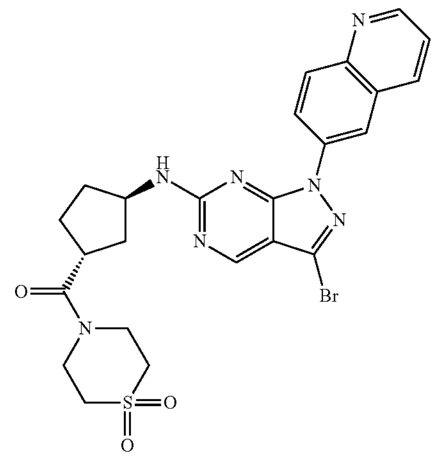 [SMILES: O=C([C@@H]1CC[C@@H](Nc2ncc3c(Br)nn(-c4ccc5ncccc5c4)c3n2)C1)N1CCS(=O)(=O)CC1] | A |
| ((1R,3R)-3-((3-bromo-1-(quinolin-6-yl)-1H-pyrazolo[3,4-d]pyrimidin-6-yl)amino)cyclopentyl)(1-oxidothiomorpholino)methanone | 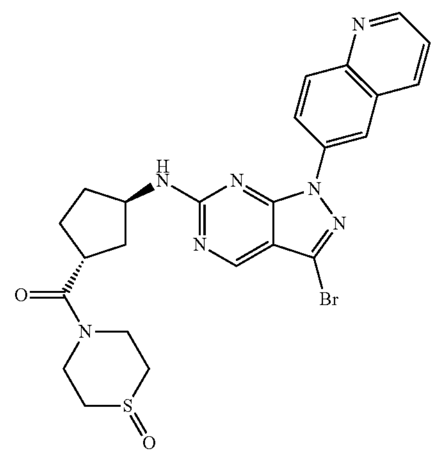 [SMILES: O=C([C@@H]1CC[C@@H](Nc2ncc3c(Br)nn(-c4ccc5ncccc5c4)c3n2)C1)N1CCS(=O)CC1] | A |
| (1R,3R)-3-((3-bromo-1-(quinolin-6-yl)-1H-pyrazolo[3,4-d]pyrimidin-6-yl)amino)-N-((1r,4R)-4-hydroxy-4-(trifluoromethyl)cyclohexyl)cyclopentane-1-carboxamide | 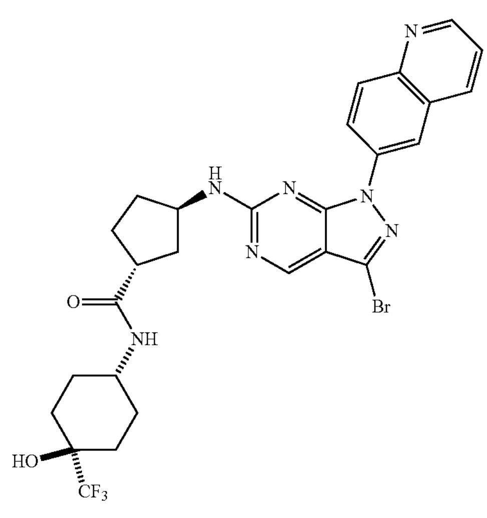 | A |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(4-hydroxy-4-(trifluoromethyl)piperidin-1-yl)methanone | 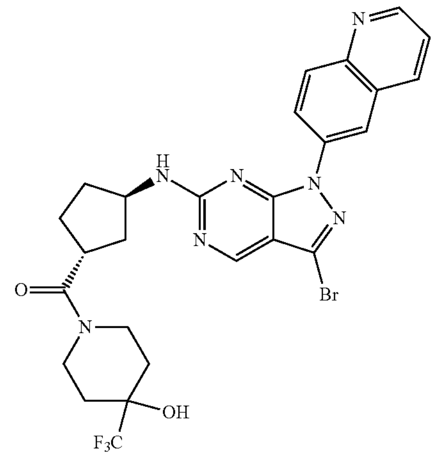 [SMILES: O=C([C@@H]1CC[C@@H](Nc2ncc3c(Br)nn(-c4ccc5ncccc5c4)c3n2)C1)N1CCC(O)(C(F)(F)F)CC1] | B |
| 4-((1R,3R)-3-((3-bromo-1-(8-fluoroquinolin-6-yl)-1H-pyrazolo[3,4-d]pyrimidin-6-yl)amino)cyclopentane-1-carbonyl)-1-methyl-piperazin-2-one | | A |
| ((1R,3R)-3-((3-bromo-1-(8-fluoroquinolin-6-yl)-1H-pyrazolo[3,4-d]pyrimidin-6-yl)amino)cyclopentyl)(1,1-dioxidothiomorpholino)methanone | 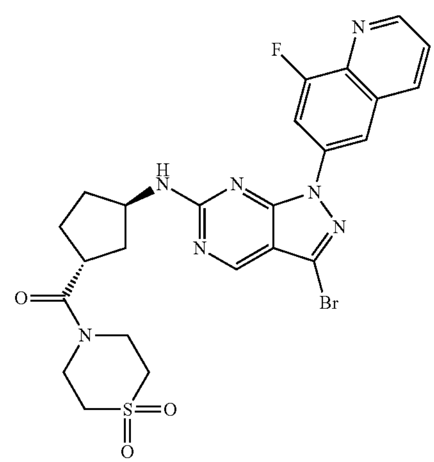 [SMILES: O=C([C@@H]1CC[C@@H](Nc2ncc3c(Br)nn(-c4cc(F)c5ncccc5c4)c3n2)C1)N1CCS(=O)(=O)CC1] | A |

TABLE 3-continued

| Chemical Name | Chemical Structure | IC$_{50}$ Activity |
|---|---|---|
| (1R,3R)-3-((3-bromo-1-(8-fluoroquinolin-6-yl)-1H-pyrazolo[3,4-d]pyrimidin-6-yl)amino)-N-(2-(methylsulfonyl)ethyl)cyclopentane-1-carboxamide | 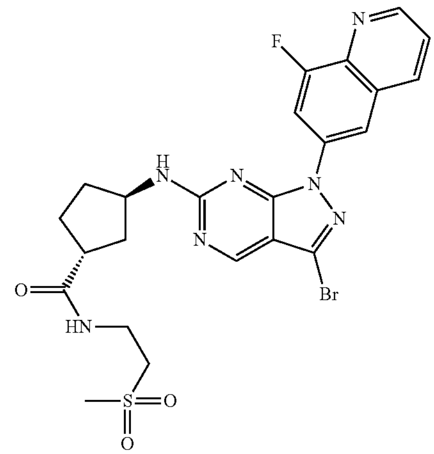 [SMILES: CS(=O)(=O)CCNC(=O)[C@@H]1CC[C@@H](Nc2ncc3c(Br)nn(-c4cc(F)c5ncccc5c4)c3n2)C1] | B |
| (1R,3R)-3-((3-bromo-1-(quinoxalin-6-yl)-1H-pyrazolo[3,4-d]pyrimidin-6-yl)amino)-N-(2-(methylsulfonyl)ethyl)cyclopentane-1-carboxamide | 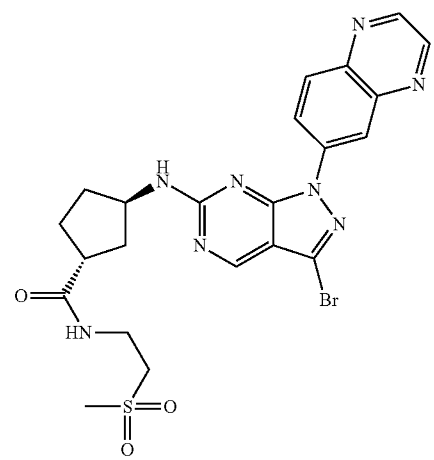 [SMILES: CS(=O)(=O)CCNC(=O)[C@@H]1CC[C@@H](Nc2ncc3c(Br)nn(-c4ccc5nccnc5c4)c3n2)C1] | B |
| (1R,3R)-3-((3-bromo-1-(8-(difluoromethyl)quinolin-6-yl)-1H-pyrazolo[3,4-d]pyrimidin-6-yl)amino)-N-(2-(methylsulfonyl)ethyl)cyclopentane-1-carboxamide | 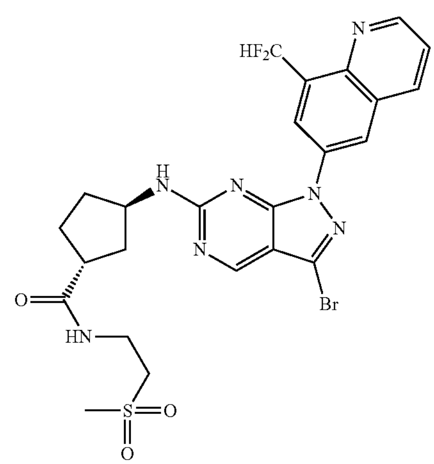 | B |

TABLE 3-continued

| Chemical Name | Chemical Structure | IC$_{50}$ Activity |
|---|---|---|
| (3R)-3-((3-bromo-1-(3-(hydroxymethyl)-5-methoxyphenyl)-1H-pyrazolo[3,4-d]pyrimidin-6-yl)amino)-N,1-dimethylcyclopentane-1-carboxamide (mixture of diastereomers) | 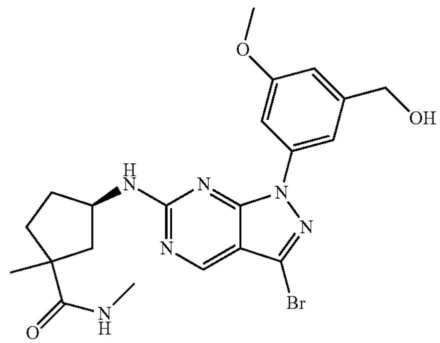 [SMILES: CNC(=O)C1(C)CC[C@@H](Nc2ncc3c(Br)nn(-c4cc(CO)cc(OC)c4)c3n2)C1] | A |
| (5R,7R)-7-((3-bromo-1-(8-fluoroquinolin-6-yl)-1H-pyrazolo[3,4-d]pyrimidin-6-yl)amino)-2-oxaspiro[4.4]nonan-1-one | 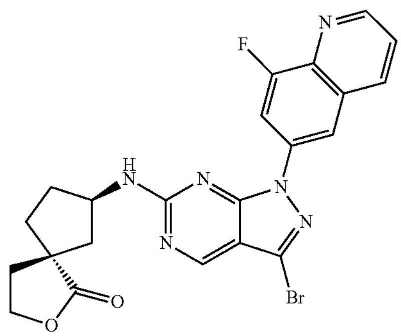 [SMILES: O=C1OCC[C@]12CC[C@@H](Nc1ncc3c(Br)nn(-c4cc(F)c5ncccc5c4)c3n1)C2] | AA |
| 6-(3-bromo-6-(((1R,3R)-3-(3-oxopiperazine-1-carbonyl)cyclopentyl)amino)-1H-pyrazolo[3,4-d]pyrimidin-1-yl)quinoline-8-carbonitrile | 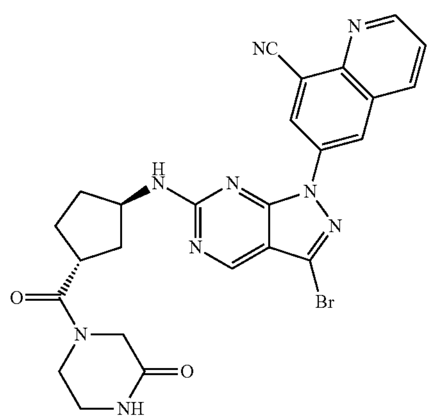 [SMILES: N#Cc1cc(-n2nc(Br)c3cnc(N[C@@H]4CC[C@@H](C(=O)N5CCNC(=O)C5)C4)nc32)cc2cccnc12] | AA |
| 4-((1R,3R)-3-((3-bromo-1-(8-(difluoromethyl)quinolin-6-yl)-1H-pyrazolo[3,4-d]pyrimidin-6-yl)amino)cyclopentane-1-carbonyl)-1-methyl-piperazin-2-one | 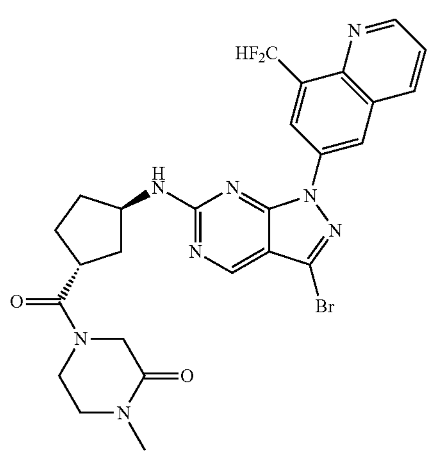 | A |

TABLE 3-continued

| Chemical Name | Chemical Structure | IC$_{50}$ Activity |
|---|---|---|
| (1R,3R)-3-((3-bromo-1-(8-(difluoromethyl) quinolin-6-yl)-1H-pyrazolo[3,4-d]pyrimidin-6-yl)amino)-N-methylcyclopentane-1-carboxamide | 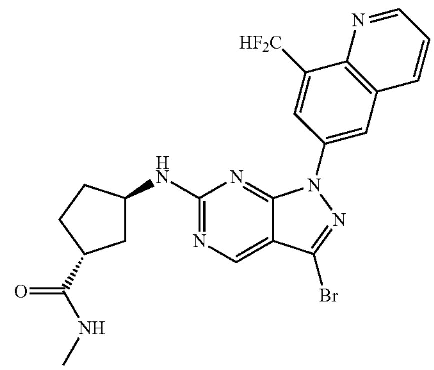 | A |
| 4-((1R,3R)-3-((3-bromo-1-(4-(oxazol-2-yl) phenyl)-1H-pyrazolo[3,4-d]pyrimidin-6-yl) amino)cyclopentane-1-carbonyl)piperazin-2-one | 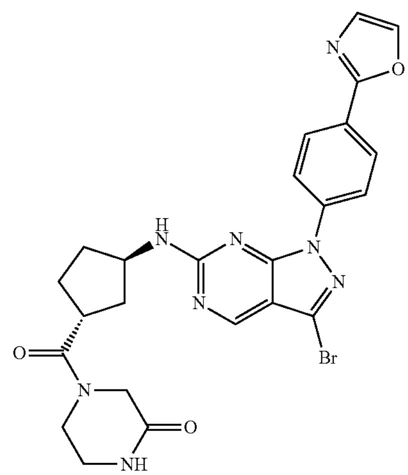 [SMILES: O=C1CN(C(=O)[C@@H]2CC[C@@H](Nc3ncc4c(Br)nn(-c5ccc(-c6ncco6)cc5)c4n3)C2)CCN1] | A |
| 4-((1R,3R)-3-((3-bromo-1-(8-fluoroquinolin-6-yl)-1H-pyrazolo[3,4-d]pyrimidin-6-yl)amino) cyclopentane-1-carbonyl)piperazin-2-one | 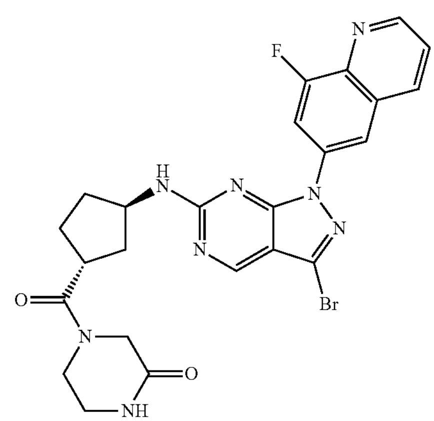 [SMILES: O=C1CN(C(=O)[C@@H]2CC[C@@H](Nc3ncc4c(Br)nn(-c5cc(F)c6ncccc6c5)c4n3)C2)CCN1] | A |

TABLE 3-continued

| Chemical Name | Chemical Structure | IC₅₀ Activity |
|---|---|---|
| 4-((1R,3R)-3-((3-bromo-1-(8-(difluoromethyl) quinolin-6-yl)-1H-pyrazolo[3,4-d]pyrimidin-6-yl)amino)cyclopentane-1-carbonyl)piperazin-2-one | 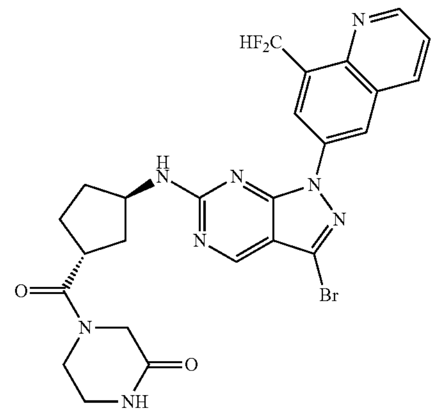 | A |
| (1S,3R)-3-((3-bromo-1-(8-cyanoquinolin-6-yl)-1H-pyrazolo[3,4-d]pyrimidin-6-yl)amino)-N,1-dimethylcyclopentane-1-carboxamide | 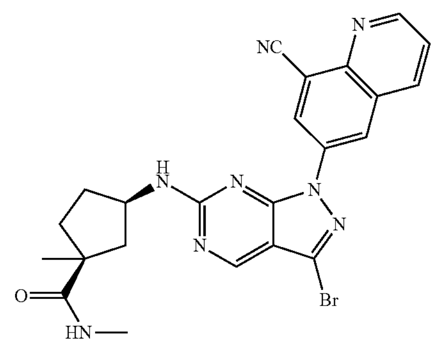 [SMILES: CNC(=O)[C@@]1(C)CC[C@@H](Nc2ncc3c(Br)nn(-c4cc(C#N)c5ncccc5c4)c3n2)C1] | A |
| (1R,3R)-3-((3-bromo-1-(8-fluoroquinolin-6-yl)-1H-pyrazolo[3,4-d]pyrimidin-6-yl)amino)-N,1-dimethylcyclopentane-1-carboxamide | 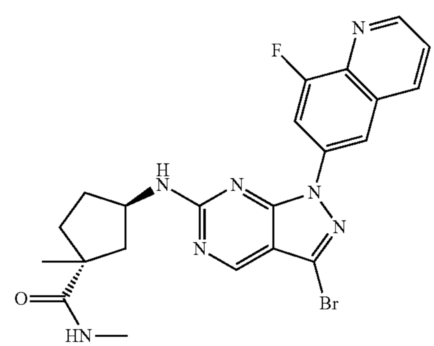 [SMILES: CNC(=O)[C@]1(C)CC[C@@H](Nc2ncc3c(Br)nn(-c4cc(F)c5ncccc5c4)c3n2)C1] | A |
| (1r,3r)-3-((3-bromo-1-(8-fluoroquinolin-6-yl)-1H-pyrazolo[3,4-d]pyrimidin-6-yl)amino)-N-methylcyclobutane-1-carboxamide | 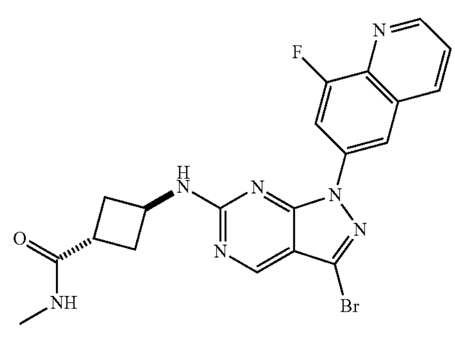 | B |

TABLE 3-continued

| Chemical Name | Chemical Structure | IC$_{50}$ Activity |
|---|---|---|
| (1R,3R)-3-((3-bromo-1-(2-methylquinolin-6-yl)-1H-pyrazolo[3,4-d]pyrimidin-6-yl)amino)-N-(2-methoxyethyl)cyclopentane-1-carboxamide | 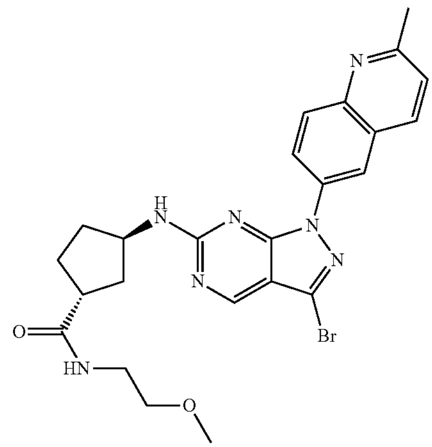 [SMILES: COCCNC(=O)[C@@H]1CC[C@@H](Nc2ncc3c(Br)nn(-c4ccc5nc(C)ccc5c4)c3n2)C1] | B |
| (1R,3R)-3-((3-bromo-1-(8-chloroquinolin-6-yl)-1H-pyrazolo[3,4-d]pyrimidin-6-yl)amino)-N-(2-methoxyethyl)cyclopentane-1-carboxamide | 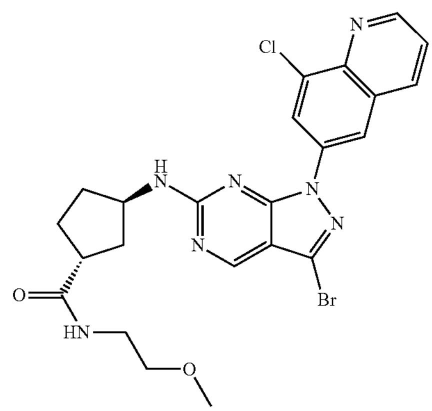 [SMILES: COCCNC(=O)[C@@H]1CC[C@@H](Nc2ncc3c(Br)nn(-c4cc(Cl)c5ncccc5c4)c3n2)C1] | A |
| (1R,3R)-3-((3-bromo-1-(quinolin-6-yl)-1H-pyrazolo[3,4-d]pyrimidin-6-yl)amino)-N-(1-methoxy-2-methylpropan-2-yl)cyclopentane-1-carboxamide | 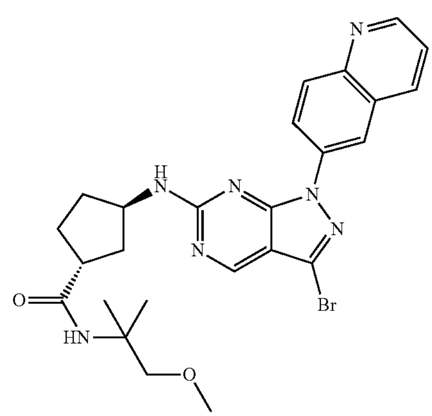 [SMILES: COCC(C)(C)NC(=O)[C@@H]1CC[C@@H](Nc2ncc3c(Br)nn(-c4ccc5ncccc5c4)c3n2)C1] | B |

TABLE 3-continued

| Chemical Name | Chemical Structure | IC$_{50}$ Activity |
|---|---|---|
| ((1R,3R)-3-((3-bromo-1-(quinolin-6-yl)-1H-pyrazolo[3,4-d]pyrimidin-6-yl)amino)cyclopentyl)(morpholino)methanone | | A |
| (1R,3R)-3-((3-bromo-1-(quinolin-6-yl)-1H-pyrazolo[3,4-d]pyrimidin-6-yl)amino)-N-((S)-1-methoxypropan-2-yl)cyclopentane-1-carboxamide | 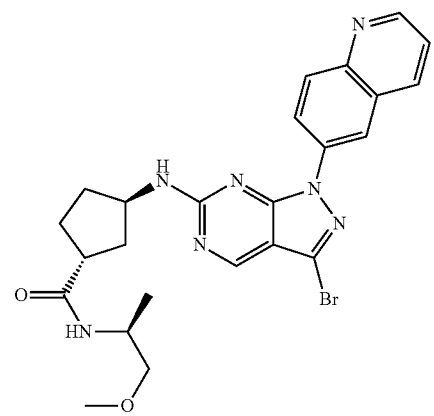 [SMILES: COC[C@H](C)NC(=O)[C@@H]1CC[C@@H](Nc2ncc3c(Br)nn(-c4ccc5ncccc5c4)c3n2)C1] | A |
| (1R,3R)-3-((3-bromo-1-(quinolin-6-yl)-1H-pyrazolo[3,4-d]pyrimidin-6-yl)amino)-N-(tetrahydro-2H-pyran-4-yl)cyclopentane-1-carboxamide | 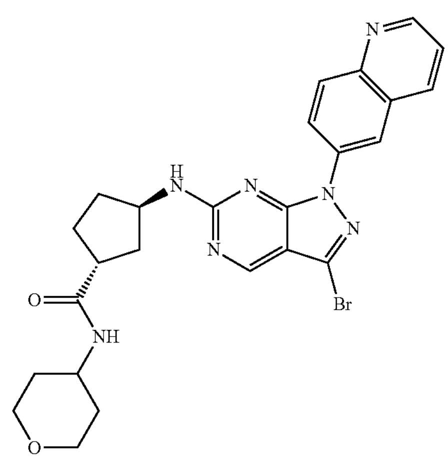 [SMILES: O=C(NC1CCOCC1)[C@@H]1CC[C@@H](Nc2ncc3c(Br)nn(-c4ccc5ncccc5c4)c3n2)C1] | A |

TABLE 3-continued

| Chemical Name | Chemical Structure | IC$_{50}$ Activity |
|---|---|---|
| (1R,3R)-3-((3-bromo-1-(quinolin-6-yl)-1H-pyrazolo[3,4-d]pyrimidin-6-yl)amino)-N-(oxetan-3-yl)cyclopentane-1-carboxamide | 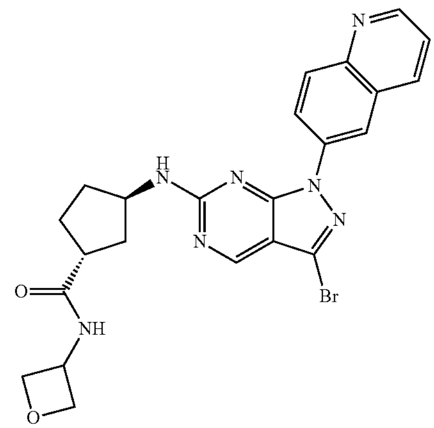 [SMILES: O=C(NC1COC1)[C@@H]1CC[C@@H](Nc2ncc3c(Br)nn(-c4ccc5ncccc5c4)c3n2)C1] | A |
| (1R,3R)-3-((3-bromo-1-(quinolin-6-yl)-1H-pyrazolo[3,4-d]pyrimidin-6-yl)amino)-N-((S)-tetrahydrofuran-3-yl)cyclopentane-1-carboxamide | 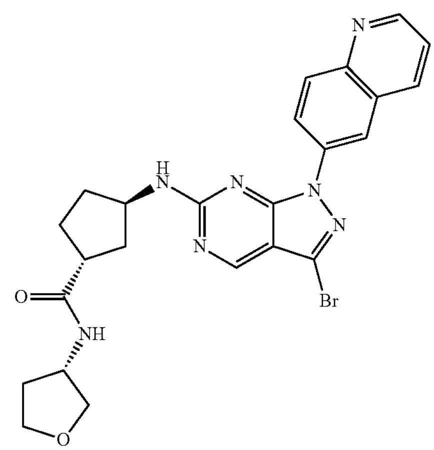 [SMILES: O=C(N[C@H]1CCOC1)[C@@H]1CC[C@@H](Nc2ncc3c(Br)nn(-c4ccc5ncccc5c4)c3n2)C1] | A |
| (1R,3R)-3-((3-bromo-1-(quinolin-6-yl)-1H-pyrazolo[3,4-d]pyrimidin-6-yl)amino)-N-((R)-tetrahydrofuran-3-yl)cyclopentane-1-carboxamide | 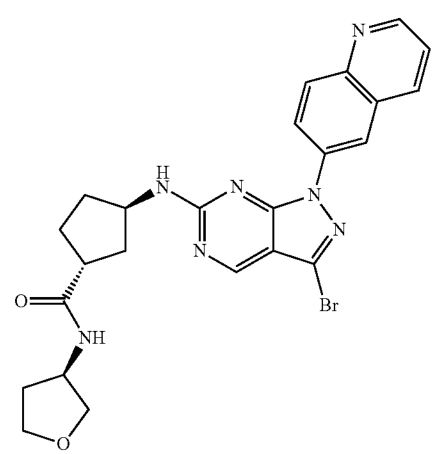 [SMILES: O=C(N[C@@H]1CCOC1)[C@@H]1CC[C@@H](Nc2ncc3c(Br)nn(-c4ccc5ncccc5c4)c3n2)C1] | A |

TABLE 3-continued

| Chemical Name | Chemical Structure | IC$_{50}$ Activity |
|---|---|---|
| (1R,3R)-3-((3-bromo-1-(3-fluoroquinolin-6-yl)-1H-pyrazolo[3,4-d]pyrimidin-6-yl)amino)-N-(2-methoxyethyl)cyclopentane-1-carboxamide | 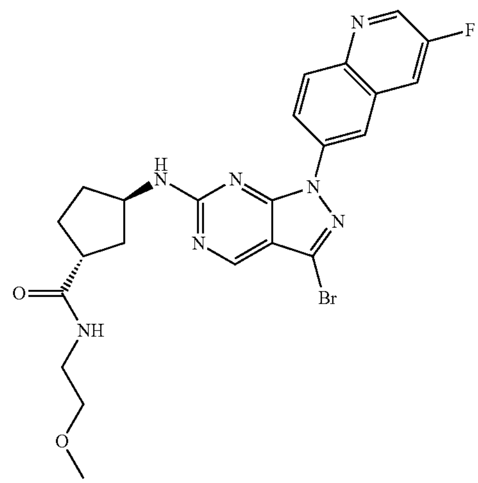 [SMILES: COCCNC(=O)[C@@H]1CC[C@@H](Nc2ncc3c(Br)nn(-c4ccc5ncc(F)cc5c4)c3n2)C1] | A |
| (1Rr,3R)-3-((3-bromo-1-(quinolin-6-yl)-1H-pyrazolo[3,4-d]pyrimidin-6-yl)amino)-1-methyl-N-(tetrahydro-2H-pyran-4-yl)cyclobutane-1-carboxamide | 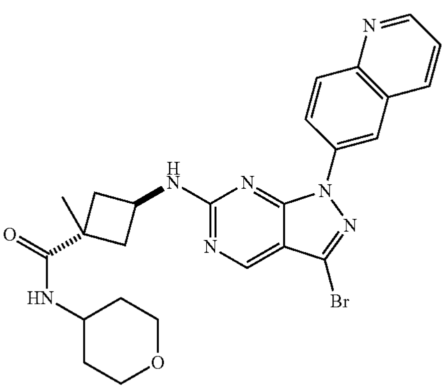 | A |
| (1r,3r)-3-((3-bromo-1-(quinolin-6-yl)-1H-pyrazolo[3,4-d]pyrimidin-6-yl)amino)-1-methyl-N-((R)-tetrahydrofuran-3-yl)cyclobutane-1-carboxamide | 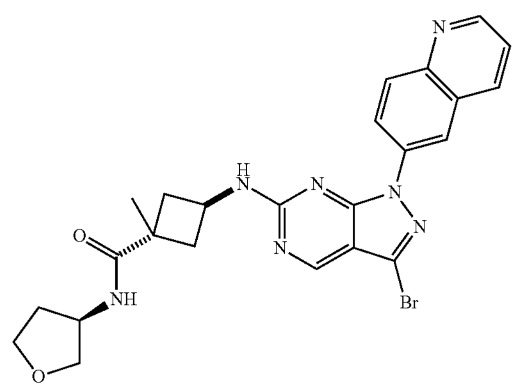 | A |
| (1r,3r)-3-((3-bromo-1-(quinolin-6-yl)-1H-pyrazolo[3,4-d]pyrimidin-6-yl)amino)-1-methylcyclobutane-1-carboxylic acid | 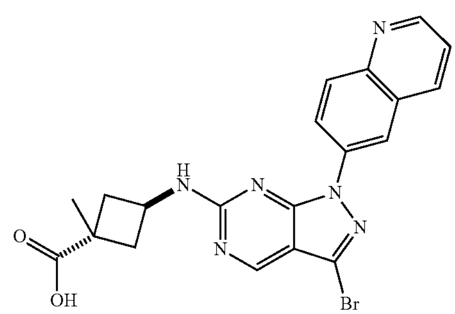 | B |

TABLE 3-continued

| Chemical Name | Chemical Structure | IC$_{50}$ Activity |
|---|---|---|
| (1R,3R)-3-((3-bromo-1-(4-(pyridin-4-yl)phenyl)-1H-pyrazolo[3,4-d]pyrimidin-6-yl)amino)-N-(2-methoxyethyl)cyclopentane-1-carboxamide | 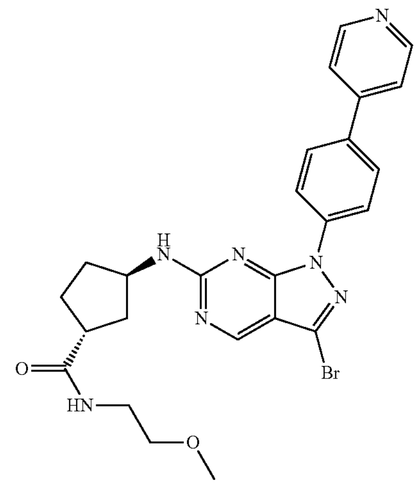 [SMILES: COCCNC(=O)[C@@H]1CC[C@@H](Nc2ncc3c(Br)nn(-c4ccc(-c5ccncc5)cc4)c3n2)C1] | C |
| (1R,3R)-3-((3-bromo-1-(8-chloroquinolin-6-yl)-1H-pyrazolo[3,4-d]pyrimidin-6-yl)amino)-N-((R)-tetrahydrofuran-3-yl)cyclopentane-1-carboxamide | 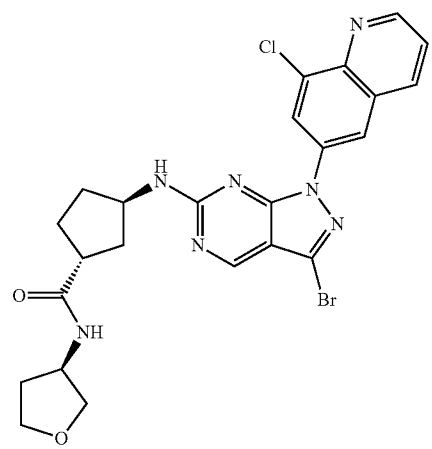 [SMILES: O=C(N[C@@H]1CCOC1)[C@@H]1CC[C@@H](Nc2ncc3c(Br)nn(-c4cc(Cl)c5ncccc5c4)c3n2)C1] | AA |
| (1R,3R)-3-((3-bromo-1-(8-fluoroquinolin-6-yl)-1H-pyrazolo[3,4-d]pyrimidin-6-yl)amino)-N-((R)-tetrahydrofuran-3-yl)cyclopentane-1-carboxamide | 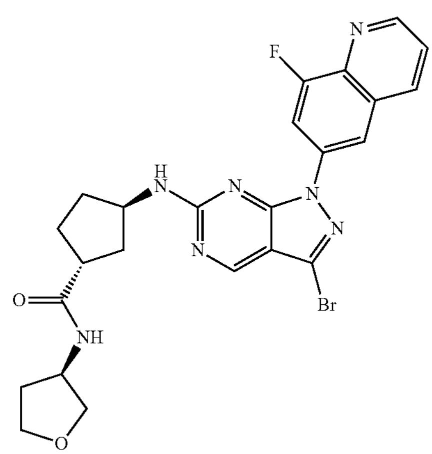 | AA |

TABLE 3-continued

| Chemical Name | Chemical Structure | IC$_{50}$ Activity |
|---|---|---|
| 3-bromo-N-(trans-3-(1-methyl-1H-imidazol-2-yl)cyclopentyl)-1-(quinolin-6-yl)-1H-pyrazolo[3,4-d]pyrimidin-6-amine | 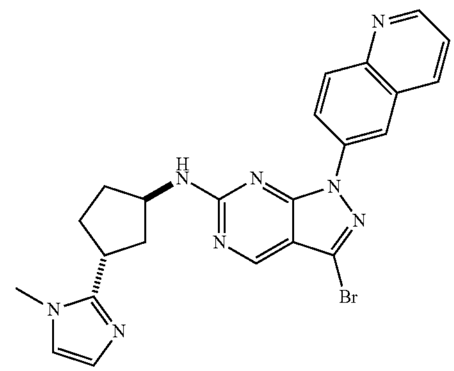 | A |
| (1R,3R)-3-((3-bromo-1-(4-chloro-2-methyl-quinolin-6-yl)-1H-pyrazolo[3,4-d]pyrimidin-6-yl)amino)-N-(2-methoxyethyl)cyclopentane-1-carboxamide | 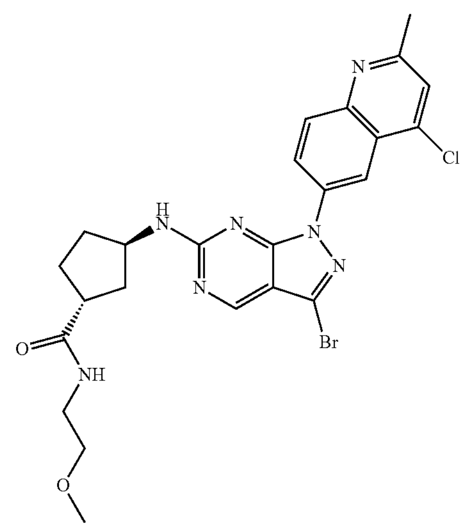 [SMILES: COCCNC(=O)[C@@H]1CC[C@@H](Nc2ncc3c(Br)nn(-c4ccc5nc(C)cc(Cl)c5c4)c3n2)C1] | B |
| (1R,3R)-3-((3-bromo-1-(imidazo[1,2-a]pyridin-6-yl)-1H-pyrazolo[3,4-d]pyrimidin-6-yl)amino)-N-(2-methoxyethyl)cyclopentane-1-carboxamide | 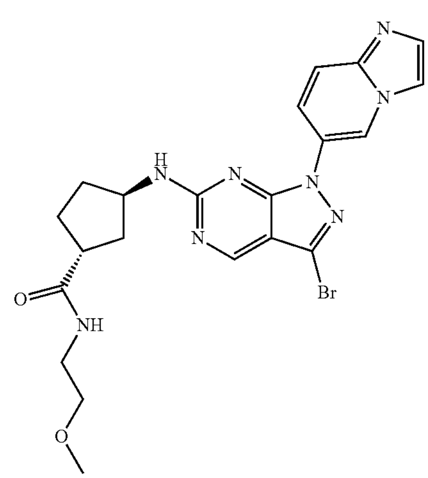 [SMILES: COCCNC(=O)[C@@H]1CC[C@@H](Nc2ncc3c(Br)nn(-c4ccc5nccn5c4)c3n2)C1] | C |

TABLE 3-continued

| Chemical Name | Chemical Structure | IC$_{50}$ Activity |
|---|---|---|
| (1R,3R)-3-((3-bromo-1-(1-methyl-1H-indazol-6-yl)-1H-pyrazolo[3,4-d]pyrimidin-6-yl)amino)-N-(2-methoxyethyl)cyclopentane-1-carboxamide | 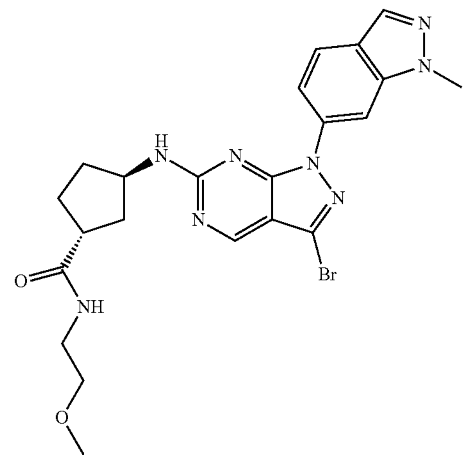 [SMILES: COCCNC(=O)[C@@H]1CC[C@@H](Nc2ncc3c(Br)nn(-c4ccc5cnn(C)c5c4)c3n2)C1] | B |
| (1S,3S)-3-((3-bromo-1-(quinolin-6-yl)-1H-pyrazolo[3,4-d]pyrimidin-6-yl)amino)-N-(2-methoxyethyl)cyclopentane-1-carboxamide | 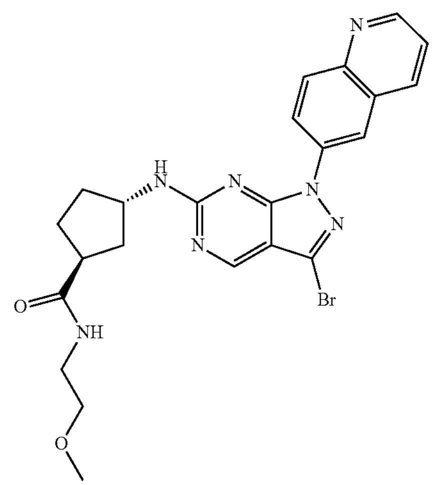 [SMILES: COCCNC(=O)[C@H]1CC[C@H](Nc2ncc3c(Br)nn(-c4ccc5ncccc5c4)c3n2)C1] | C |
| (1R,3R)-3-((1-(4-(1H-pyrazol-5-yl)phenyl)-3-bromo-1H-pyrazolo[3,4-d]pyrimidin-6-yl)amino)-N-(2-methoxyethyl)cyclopentane-1-carboxamide | 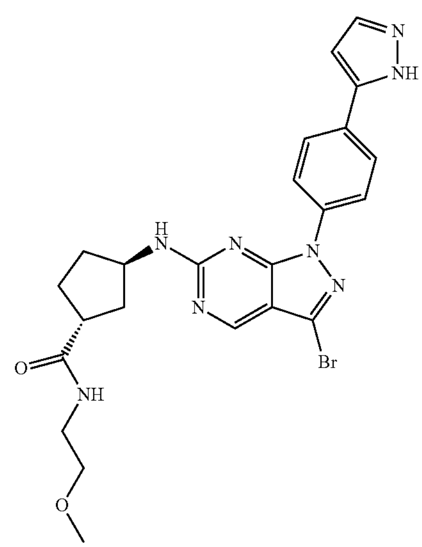 [SMILES: COCCNC(=O)[C@@H]1CC[C@@H](Nc2ncc3c(Br)nn(-c4ccc(-c5ccn[nH]5)cc4)c3n2)C1] | B |

TABLE 3-continued

| Chemical Name | Chemical Structure | IC$_{50}$ Activity |
|---|---|---|
| (1R,3R)-3-[[3-bromo-1-[6-(5-methyl-1,3,4-thiadiazol-2-yl)-3-pyridyl]pyrazol[3,4-d]pyrimidin-6-yl]amino]-N,1-dimethyl-cyclopentanecarboxmide | 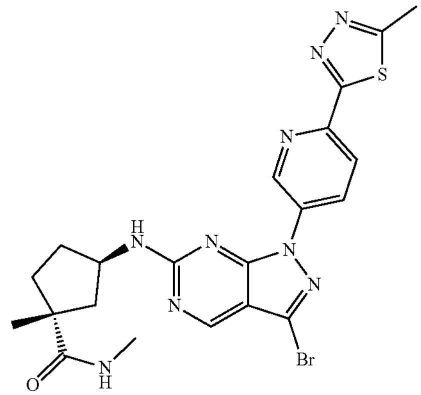 | A |
| (1R,3R)-3-((1-(4-(1H-pyrazol-1-yl)phenyl)-3-bromo-1H-pyrazolo[3,4-d]pyrimidin-6-yl)amino)-N-(2-methoxyethyl)cyclopentane-1-carboxamide | | B |
| (1R,3R)-3-((3-bromo-1-(8-(difluoromethyl)quinolin-6-yl)-1H-pyrazolo[3,4-d]pyrimidin-6-yl)amino)-N-(2-methoxyethyl)cyclopentane-1-carboxamide | | A |
| (1R,3R)-3-((3-bromo-1-(1-(pyridin-4-yl)-1H-pyrazol-4-yl)-1H-pyrazolo[3,4-d]pyrimidin-6-yl)amino)-N-(2-(methylsulfonyl)ethyl)cyclopentane-1-carboxamide | | B |
| (1R,3R)-3-((3-bromo-1-(4-(1-methyl-1H-imidazol-2-yl)phenyl)-1H-pyrazolo[3,4-d]pyrimidin-6-yl)amino)-N-(2-(methylsulfonyl)ethyl)cyclopentane-1-carboxamide | | C |
| 6-[3-bromo-6-[[(1R,3R)-3-[(2R)-2,4-dimethyl-3-oxo-piperazine-1-carbonyl]cyclopentyl]amino]pyrazolo[3,4-d]pyrimidin-1-yl]quinoline-8-carbonitrile | | AA |
| (1R,3R)-3-((3-bromo-1-(3-fluoroquinolin-6-yl)-1H-pyrazolo[3,4-d]pyrimidin-6-yl)amino)-N-(2-(methylsulfonyl)ethyl)cyclopentane-1-carboxamide | | B |
| 4-((1R,3R)-3-((3-bromo-1-(3-fluoro-4-(5-methyl-1,3,4-oxadiazol-2-yl)phenyl)-1H-pyrazolo[3,4-d]pyrimidin-6-yl)amino)cyclopentane-1-carbonyl)-1-methylpiperazin-2-one | | A |
| 4-((1R,3R)-3-((3-bromo-1-(4-(5-methyl-1,3,4-oxadiazol-2-yl)phenyl)-1H-pyrazolo[3,4-d]pyrimidin-6-yl)amino)cyclopentane-1-carbonyl)-1-methylpiperazin-2-one | | A |
| 4-((1R,3R)-3-((3-bromo-1-(3,8-difluoro-2-methylquinolin-6-yl)-1H-pyrazolo[3,4-d]pyrimidin-6-yl)amino)cyclopentane-1-carbonyl)-1-methylpiperazin-2-one | | A |
| 4-((1R,3R)-3-((3-bromo-1-(8-chloro-1,7-naphthyridin-3-yl)-1H-pyrazolo[3,4-d]pyrimidin-6-yl)amino)cyclopentane-1-carbonyl)-1-methylpiperazin-2-one | | A |
| 1-((1R,3R)-3-((5-bromo-7-(8-fluoroquinolin-6-yl)-7H-pyrrolo[2,3-d]pyrimidin-2-yl)amino)cyclopentane-1-carbonyl)azetidine-3-carbonitrile | | AA |
| 4-((3-bromo-1-(quinolin-6-yl)-1H-pyrazolo[3,4-d]pyrimidin-6-yl)amino)bicyclo[2.1.1]hexane-1-carboxylic acid | | C |
| 4-((3-bromo-1-(quinolin-6-yl)-1H-pyrazolo[3,4-d]pyrimidin-6-yl)amino)-N-(2-(methylsulfonyl)ethyl)bicyclo[2.1.1]hexane-1-carboxamide | | B |
| (1R,3R)-3-((3-bromo-1-(8-cyanoquinolin-6-yl)-1H-pyrazolo[3,4-d]pyrimidin-6-yl)amino)-N-(1,1-dioxidotetrahydro-2H-thiopyran-4-yl)cyclopentane-1-carboxamide | | A |

TABLE 3-continued

| Chemical Name | Chemical Structure | IC$_{50}$ Activity |
|---|---|---|
| 6-(3-bromo-6-(((1R,3R)-3-(4-methyl-3-oxo-piperazine-1-carbonyl)cyclopentyl)amino)-1H-pyrazolo[3,4-d]pyrimidin-1-yl)quinoline-8-carbonitrile | | A |
| (1R,3R)-3-((3-bromo-1-(8-cyanoquinolin-6-yl)-1H-pyrazolo[3,4-d]pyrimidin-6-yl)amino)-N-(((S)-morpholin-3-yl)methyl)cyclopentane-1-carboxamide | | AA |
| (1R,3R)-3-((3-bromo-1-(8-cyanoquinolin-6-yl)-1H-pyrazolo[3,4-d]pyrimidin-6-yl)amino)-N-((3R,4S)-4-fluoropyrrolidin-3-yl)cyclo-pentane-1-carboxamide | | AA |
| (1R,3R)-3-((3-bromo-1-(8-cyanoquinolin-6-yl)-1H-pyrazolo[3,4-d]pyrimidin-6-yl)amino)-N-((1-methyl-5-oxopyrrolidin-2-yl)methyl)cyclopentane-1-carboxamide | | AA |
| (1R,3R)-3-((3-bromo-1-(8-cyanoquinolin-6-yl)-1H-pyrazolo[3,4-d]pyrimidin-6-yl)amino)-N-(((R)-morpholin-3-yl)methyl)cyclopentane-1-carboxamide | | AA |
| 6-(3-bromo-6-(((1R,3R)-3-((S)-2,4-dimethyl-3-oxopiperazine-1-carbonyl)cyclopentyl)amino)-1H-pyrazolo[3,4-d]pyrimidin-1-yl)quinoline-8-carbonitrile | | AA |
| 6-(3-bromo-6-(((1R,3R)-3-((R)-2,4-dimethyl-3-oxopiperazine-1-carbonyl)cyclopentyl)amino)-1H-pyrazolo[3,4-d]pyrimidin-1-yl)quinoline-8-carbonitrile | | AA |
| 6-(3-bromo-6-(((1R,3R)-3-(4-(2-hydroxyacetyl)piperazine-1-carbonyl)cyclopentyl)amino)-1H-pyrazolo[3,4-d]pyrimidin-1-yl)quinoline-8-carbonitrile | | A |
| 2-(4-(((1R,3R)-3-((3-bromo-1-(8-cyanoquinolin-6-yl)-1H-pyrazolo[3,4-d]pyrimidin-6-yl)amino)cyclopentane-1-carbonyl)piperazin-1-yl)-2-oxoethyl acetate | | AA |
| (1R,3R)-3-((3-bromo-1-(8-cyanoquinolin-6-yl)-1H-pyrazolo[3,4-d]pyrimidin-6-yl)amino)-N-(1-(2,2,2-trifluoroethyl)pyrrolidin-3-yl)cyclopentane-1-carboxamide (as a mixture of diastereomers) | | A |
| (1R,3R)-3-((3-bromo-1-(8-cyanoquinolin-6-yl)-1H-pyrazolo[3,4-d]pyrimidin-6-yl)amino)-N-((3-fluoroazetidin-3-yl)methyl)cyclopentane-1-carboxamide | | AA |
| (1S,3R)-3-((3-bromo-1-(8-cyanoquinolin-6-yl)-1H-pyrazolo[3,4-d]pyrimidin-6-yl)amino)-N-((3-fluoroazetidin-3-yl)methyl)cyclo-pentane-1-carboxamide | | A |
| (1R,3R)-3-((3-bromo-1-(8-cyanoquinolin-6-yl)-1H-pyrazolo[3,4-d]pyrimidin-6-yl)amino)-N-((S)-pyrrolidin-3-yl)cyclopentane-1-carboxamide | | AA |
| (1R,3R)-3-((3-bromo-1-(8-cyanoquinolin-6-yl)-1H-pyrazolo[3,4-d]pyrimidin-6-yl)amino)-N-((R)-pyrrolidin-3-yl)cyclopentane-1-carboxamide | | AA |
| 6-(3-bromo-6-(((1R,3R)-3-(4-(cyclopropanecarbonyl)piperazine-1-carbonyl)cyclopentyl)amino)-1H-pyrazolo[3,4-d]pyrimidin-1-yl)quinoline-8-carbonitrile | | A |
| 6-(3-bromo-6-(((1R,3R)-3-(1-imino-1-oxido-1$\lambda^6$-thiomorpholine-4-carbonyl)cyclopentyl)amino)-1H-pyrazolo[3,4-d]pyrimidin-1-yl)quinoline-8-carbonitrile | | AA |
| (1R,3R)-3-((3-bromo-1-(8-cyanoquinolin-6-yl)-1H-pyrazolo[3,4-d]pyrimidin-6-yl)amino)-N-(1-oxido-1$\lambda^6$-thiomorpholin-1-ylidene)cyclopentane-1-carboxamide | | A |
| 6-(3-bromo-6-(((1R,3R)-3-(3-(3,3-difluoro-pyrrolidin-1-yl)azetidine-1-carbonyl)cyclo-pentyl)amino)-1H-pyrazolo[3,4-d]pyrimidin-1-yl)quinoline-8-carbonitrile | | A |
| 6-(3-bromo-6-(((1R,3R)-3-(3-methyl-4-oxo-imidazolidine-1-carbonyl)cyclopentyl)amino)-1H-pyrazolo[3,4-d]pyrimidin-1-yl)quinoline-8-carbonitrile | | A |

TABLE 3-continued

| Chemical Name | Chemical Structure | IC$_{50}$ Activity |
|---|---|---|
| (1R,3R)-3-((3-bromo-1-(8-fluoroquinolin-6-yl)-1H-pyrazolo[3,4-d]pyrimidin-6-yl)amino)-N-((3S,4R)-3-fluoropiperidin-4-yl)cyclopentane-1-carboxamide | | AA |
| (1R,3R)-3-((3-bromo-1-(8-fluoroquinolin-6-yl)-1H-pyrazolo[3,4-d]pyrimidin-6-yl)amino)-N-((3R,4R)-3-fluoropiperidin-4-yl)cyclopentane-1-carboxamide | | A |
| (1R,3R)-3-((3-bromo-1-(8-fluoroquinolin-6-yl)-1H-pyrazolo[3,4-d]pyrimidin-6-yl)amino)-N-(1-(2-fluoroethyl)piperidin-3-yl)cyclopentane-1-carboxamide (as a mixture of diastereomers) | | A |
| (1R,3R)-3-((3-bromo-1-(8-fluoroquinolin-6-yl)-1H-pyrazolo[3,4-d]pyrimidin-6-yl)amino)-N-(2-(2-oxoimidazolidin-1-yl)ethyl)cyclopentane-1-carboxamide | | A |
| (1R,3R)-3-((3-bromo-1-(8-fluoroquinolin-6-yl)-1H-pyrazolo[3,4-d]pyrimidin-6-yl)amino)-N-(2-hydroxyethyl)cyclopentane-1-carboxamide | | A |
| (1R,3R)-N-((1H-tetrazol-5-yl)methyl)-3-((3-bromo-1-(8-fluoroquinolin-6-yl)-1H-pyrazolo[3,4-d]pyrimidin-6-yl)amino)cyclopentane-1-carboxamide | | A |
| (1R,3R)-3-((3-bromo-1-(8-fluoroquinolin-6-yl)-1H-pyrazolo[3,4-d]pyrimidin-6-yl)amino)-N-((3R,4R)-4-fluoropyrrolidin-3-yl)cyclopentane-1-carboxamide | | A |
| (1R,3R)-3-((3-bromo-1-(8-fluoroquinolin-6-yl)-1H-pyrazolo[3,4-d]pyrimidin-6-yl)amino)-N-(2,2-difluoro-3-hydroxypropyl)cyclopentane-1-carboxamide carboxamide | | A |
| 7-((1R,3R)-3-((3-bromo-1-(8-fluoroquinolin-6-yl)-1H-pyrazolo[3,4-d]pyrimidin-6-yl)amino)cyclopentane-1-carbonyl)-2-methyl-2,7-diazaspiro[4.4]nonan-1-one | | A |
| (S)-4-((1R,3R)-3-((3-bromo-1-(8-fluoroquinolin-6-yl)-1H-pyrazolo[3,4-d]pyrimidin-6-yl)amino)cyclopentane-1-carbonyl)-1,5-dimethylpiperazin-2-one | | A |
| (1R,3R)-3-((3-bromo-1-(8-cyanoquinolin-6-yl)-1H-pyrazolo[3,4-d]pyrimidin-6-yl)amino)-N-isopropylcyclopentane-1-carboxamide | | A |
| 6-(3-bromo-6-(((1R,3R)-3-(3-fluoroazetidine-1-carbonyl)cyclopentyl)amino)-1H-pyrazolo[3,4-d]pyrimidin-1-yl)quinoline-8-carbonitrile | | AA |
| (1R,3R)-3-((3-bromo-1-(8-cyanoquinolin-6-yl)-1H-pyrazolo[3,4-d]pyrimidin-6-yl)amino)-N-methylcyclopentane-1-carboxamide | | AA |
| (1R,3R)-3-((3-bromo-1-(8-cyanoquinolin-6-yl)-1H-pyrazolo[3,4-d]pyrimidin-6-yl)amino)-N-(2,2-difluoropropyl)cyclopentane-1-carboxamide | | A |
| (1R,3R)-3-((3-bromo-1-(8-cyanoquinolin-6-yl)-1H-pyrazolo[3,4-d]pyrimidin-6-yl)amino)-N-butylcyclopentane-1-carboxamide | | B |
| 6-(3-bromo-6-(((1R,3R)-3-(pyrrolidine-1-carbonyl)cyclopentyl)amino)-1H-pyrazolo[3,4-d]pyrimidin-1-yl)quinoline-8-carbonitrile | | A |
| (1R,3R)-3-((3-bromo-1-(8-cyanoquinolin-6-yl)-1H-pyrazolo[3,4-d]pyrimidin-6-yl)amino)-N-(cyclopropylmethyl)cyclopentane-1-carboxamide | | A |
| (1R,3R)-N-(1-amino-2-methyl-1-oxopropan-2-yl)-3-((3-bromo-1-(8-cyanoquinolin-6-yl)-1H-pyrazolo[3,4-d]pyrimidin-6-yl)amino)cyclopentane-1-carboxamide | | AA |
| 6-(6-(((1R,3R)-3-(azetidine-1-carbonyl)cyclopentyl)amino)-3-bromo-1H-pyrazolo[3,4-d]pyrimidin-1-yl)quinoline-8-carbonitrile | | A |
| (1R,3R)-3-((3-bromo-1-(8-cyanoquinolin-6-yl)-1H-pyrazolo[3,4-d]pyrimidin-6-yl)amino)-N-(trans-3-cyanocyclopentyl)cyclopentane-1-carboxamide | | A |

TABLE 3-continued

| Chemical Name | Chemical Structure | IC$_{50}$ Activity |
|---|---|---|
| (1R,3R)-3-((3-bromo-1-(8-fluoroquinolin-6-yl)-1H-pyrazolo[3,4-d]pyrimidin-6-yl)amino)-N,N-dimethylcyclopentane-1-carboxamide | | A |
| 3-((1R,3R)-3-((3-bromo-1-(8-fluoroquinolin-6-yl)-1H-pyrazolo[3,4-d]pyrimidin-6-yl)amino)cyclopentane-1-carboxamido)propanoic acid | | A |
| 1-((1R,3R)-3-((3-bromo-1-(8-fluoroquinolin-6-yl)-1H-pyrazolo[3,4-d]pyrimidin-6-yl)amino)cyclopentane-1-carbonyl)-3-methylazetidine-3-carboxylic acid | | A |
| (1R,3R)-3-((1-(4-(1H-tetrazol-5-yl)phenyl)-3-bromo-1H-pyrazolo[3,4-d]pyrimidin-6-yl)amino)-N-methylcyclopentane-1-carboxamide | | A |
| (1R,3R)-3-((3-bromo-1-(8-fluoroquinolin-6-yl)-1H-pyrazolo[3,4-d]pyrimidin-6-yl)amino)-N-(2-(N,S-dimethylsulfonimidoyl)ethyl)cyclopentane-1-carboxamide | | AA |
| (1R,3R)-3-((3-bromo-1-(8-(trifluoromethoxy)quinolin-6-yl)-1H-pyrazolo[3,4-d]pyrimidin-6-yl)amino)-N-methylcyclopentane-1-carboxamide | | A |
| (1R,3R)-3-((3-bromo-1-(8-fluoroquinolin-6-yl)-1H-pyrazolo[3,4-d]pyrimidin-6-yl)amino)-N-((1r,3r)-3-hydroxycyclobutyl)cyclopentane-1-carboxamide | | A |
| 1-((1R,3R)-3-((3-bromo-1-(8-fluoroquinolin-6-yl)-1H-pyrazolo[3,4-d]pyrimidin-6-yl)amino)cyclopentane-1-carbonyl)-N-methylpyrrolidine-3-carboxamide (as a mixture of diastereomers) | | A |
| 1-((1R,3R)-3-((3-bromo-1-(8-fluoroquinolin-6-yl)-1H-pyrazolo[3,4-d]pyrimidin-6-yl)amino)cyclopentane-1-carbonyl)-3-ethyl-imidazolidin-4-one | | A |
| (1R,3R)-3-((3-bromo-1-(8-fluoroquinolin-6-yl)-1H-pyrazolo[3,4-d]pyrimidin-6-yl)amino)-N-(2-hydroxy-2-methylpropyl)cyclopentane-1-carboxamide | | A |
| 1-((1R,3R)-3-((3-bromo-1-(8-fluoroquinolin-6-yl)-1H-pyrazolo[3,4-d]pyrimidin-6-yl)amino)cyclopentane-1-carbonyl)-2,3-dimethylimidazolidin-4-one (as a mixture of diastereomers) | | AA |
| 1-((1R,3R)-3-((3-bromo-1-(8-fluoroquinolin-6-yl)-1H-pyrazolo[3,4-d]pyrimidin-6-yl)amino)cyclopentane-1-carbonyl)imidazolidin-4-one) | | A |
| 4-((1R,3R)-3-((3-bromo-1-(8-fluoroquinolin-6-yl)-1H-pyrazolo[3,4-d]pyrimidin-6-yl)amino)cyclopentane-1-carbonyl)piperazine-2,6-dione | | AA |
| ((1R,3R)-3-((3-bromo-1-(8-fluoroquinolin-6-yl)-1H-pyrazolo[3,4-d]pyrimidin-6-yl)amino)cyclopentyl)(3-(trifluoromethyl)-1H-pyrazol-1-yl)methanone | | A |
| (1R,3R)-3-((3-bromo-1-(8-fluoroquinolin-6-yl)-1H-pyrazolo[3,4-d]pyrimidin-6-yl)amino)-N-(1-cyclopropyl-1H-pyrazol-4-yl)cyclopentane-1-carboxamide | | B |
| (1R,3R)-3-[[3-bromo-1-(8-fluoro-6-quinolyl)pyrazolo[3,4-d]pyrimidin-6-yl]amino]-N-(1-methyl-2-oxo-3-pyridyl)cyclopentanecarboxamide | | A |
| (1R,3R)-3-[[3-bromo-1-(3-chloro-6-quinolyl)pyrazolo[3,4-d]pyrimidin-6-yl]amino]-N-methyl-cyclopentanecarboxamide | | A |
| 1-[(1R,3R)-3-[[3-bromo-1-(8-fluoro-6-quinolyl)pyrazolo[3,4-d]pyrimidin-6-yl]aminocyclopentanecarbonyl]azetidine-3-carbonitrile | | AA |
| 1-[(1R,3R)-3-[[3-bromo-1-(8-fluoro-6-quinolyl)pyrazolo[3,4-d]pyrimidin-6-yl]amino]cyclopentanecarbonyl]-3-(cyclopropylmethyl)imidazolidin-4-one | | A |

TABLE 3-continued

| Chemical Name | Chemical Structure | IC$_{50}$ Activity |
|---|---|---|
| 1-[3-[(1R,3R)-3-[[3-bromo-1-(8-fluoro-6-quinolyl)pyrazolo[3,4-d]pyrimidin-6-yl]amino]cyclopentanecarbonyl]imidazolidin-1-yl]propan-1-one | | AA |
| (1R,3R)-3-[(3-bromo-1-pyrazolo[1,5-a]pyridin-5-yl-pyrazolo[3,4-d]pyrimidin-6-yl)amino]-N-methyl-cyclopentanecarboxamide | | A |
| (1R,3R)-3-[[3-bromo-1-(8-fluoro-6-quinolyl)pyrazolo[3,4-d]pyrimidin-6-yl]amino]-1-ethyl-N-methyl-cyclopentanecarboxamide | | AA |
| (1R,3R)-3-[[3-bromo-1-(8-methoxy-6-quinolyl)pyrazolo[3,4-d]pyrimidin-6-yl]amino]-N-methyl-cyclopentanecarboxamide | | AA |
| (1R,3R)-3-[[3-bromo-1-(8-cyano-3-quinolyl)pyrazolo[3,4-d]pyrimidin-6-yl]amino]-N-methyl-cyclopentanecarboxamide | | A |
| (1S,3R)-3-[[3-bromo-1-(8-cyano-3-quinolyl)pyrazolo[3,4-d]pyrimidin-6-yl]amino]-N-methyl-cyclopentanecarboxamide | | A |
| (1R,3R)-3-[[3-bromo-1-(8-fluoro-6-quinolyl)pyrazolo[3,4-d]pyrimidin-6-yl]amino]-1-(methoxymethyl)-N-methyl-cyclopentanecarboxamide | | AA |
| (1R,3R)-3-[[3-bromo-1-(8-fluoro-6-quinolyl)pyrazolo[3,4-d]pyrimidin-6-yl]amino]-N-ethyl-cyclopentanecarboxamide | | A |
| [(1R,3R)-3-[[3-bromo-1-(8-fluoro-6-quinolyl)pyrazolo[3,4-d]pyrimidin-6-yl]amino]cyclopentyl]-[3-(trifluoromethyl)piperazin-1-yl]methanone | | A |
| (1R,3R)-3-[[3-bromo-1-(8-fluoro-6-quinolyl)pyrazolo[3,4-d]pyrimidin-6-yl]amino]-N-[1-(dimethylcarbamoyl)cyclopropyl]cyclopentanecarboxamide | | A |
| (1S,3R)-3-[[3-bromo-1-(8-fluoro-6-quinolyl)pyrazolo[3,4-d]pyrimidin-6-yl]amino]-N-methyl-1-(trifluoromethyl)cyclopentanecarboxamide | | A |
| N-[3-bromo-1-(8-fluoro-6-quinolyl)pyrazolo[3,4-d]pyrimidin-6-yl]-1-oxa-8-azaspiro[4.5]decan-3-amine | | A |
| (1R,3R)-3-[[3-bromo-1-(8-fluoro-6-quinolyl)pyrazolo[3,4-d]pyrimidin-6-yl]amino]-N-(2-hydroxyethyl)-1-methyl-cyclopentanecarboxamide | | AA |
| (1S,3R)-3-[[3-bromo-1-(8-fluoro-6-quinolyl)pyrazolo[3,4-d]pyrimidin-6-yl]amino]-N-(2-hydroxyethyl)-1-methyl-cyclopentanecarboxamide | | A |
| (1R,3R)-3-[[3-bromo-1-(8-fluoro-6-quinolyl)pyrazolo[3,4-d]pyrimidin-6-yl]amino]-N-(1-carbamoylcyclobutyl)cyclopentanecarboxamide | | A |
| 3-bromo-1-(8-fluoro-6-quinolyl)-N-[(1R,3R)-3-methoxycyclopentyl]pyrazolo[3,4-d]pyrimidin-6-amine | | A |
| (1S,3R)-3-[[3-bromo-1-(8-fluoro-6-quinolyl)pyrazolo[3,4-d]pyrimidin-6-yl]amino]-1-fluoro-N-methyl-cyclopentanecarboxamide | | A |
| (1R,3R)-3-[[3-bromo-1-(8-fluoro-6-quinolyl)pyrazolo[3,4-d]pyrimidin-6-yl]amino]-N-isopropyl-1-methyl-cyclopentanecarboxamide | | AA |
| 1-[(3R)-3-[[3-bromo-1-(8-fluoro-6-quinolyl)pyrazolo[3,4-d]pyrimidin-6-yl]amino]-1-methyl-cyclopentanecarbonyl]-3-methyl-imidazolidin-4-one | | AA |
| 1-[(3R)-3-[[3-bromo-1-(8-fluoro-6-quinolyl)pyrazolo[3,4-d]pyrimidin-6-yl]amino]-1-methyl-cyclopentanecarbonyl]imidazolidin-4-one | | AA |
| (1R,3R)-3-[[3-bromo-1-(8-fluoro-6-quinolyl)pyrazolo[3,4-d]pyrimidin-6-yl]amino]-N-[(1-hydroxycyclopropyl)methyl]-1-methyl-cyclopentanecarboxamide | | AA |
| 1-[(3R)-3-[[3-bromo-1-(8-fluoro-6-quinolyl)pyrazolo[3,4-d]pyrimidin-6-yl]amino]-1-methyl-cyclopentanecarbonyl]-3-fluoro-pyrrolidine-3-carbonitrile | | A |

TABLE 3-continued

| Chemical Name | Chemical Structure | IC$_{50}$ Activity |
|---|---|---|
| (1R,3R)-3-[[3-bromo-1-(8-fluoro-6-quinolyl)pyrazolo[3,4-d]pyrimidin-6-yl]amino]-N-(2-hydroxy-2-methyl-propyl)-N,1-dimethyl-cyclopentanecarboxamide | | AA |
| (1R,3R)-3-[[3-bromo-1-[8-(methoxymethyl)-6-quinolyl]pyrazolo[3,4-d]pyrimidin-6-yl]amino]-N,1-dimethyl-cyclopentane-carboxamide | | A |
| (1R,3R)-3-[[3-bromo-1-[4-(5-methyl-1,3,4-oxadiazol-2-yl)phenyl]pyrazolo[3,4-d]pyrimidin-6-yl]amino]-N-methyl-cyclopentanecarboxamide | | A |
| (1S,3R)-3-[[3-bromo-1-(8-fluoro-6-quinolyl)pyrazolo[3,4-d]pyrimidin-6-yl]amino]-1-hydroxy-N-methyl-cyclopentanecarboxamide | | A |
| (1R,3R)-3-[[3-bromo-1-(1,8-naphthyridin-3-yl)pyrazolo[3,4-d]pyrimidin-6-yl]amino]-N-methyl-cyclopentanecarboxamide | | A |
| 1-[(3R)-3-[[3-bromo-1-(8-fluoro-6-quinolyl)pyrazolo[3,4-d]pyrimidin-6-yl]amino]-1-methyl-cyclopentanecarbonyl]-3-(2-methoxyethyl)imidazolidin-4-one | | AA |
| (1S,3R)-3-[[3-bromo-1-(8-fluoro-6-quinolyl)pyrazolo[3,4-d]pyrimidin-6-yl]amino]-1-methoxy-N-methyl-cyclopentanecarboxamide | | A |
| (1R,3R)-3-[[3-bromo-1-(8-fluoro-6-quinolyl)pyrazolo[3,4-d]pyrimidin-6-yl]amino]-1-(2,2-difluoroethyl)-N-methyl-cyclopentane-carboxamide | | AA |
| [(1R,3R)-3-[[3-bromo-1-(8-fluoro-6-quinolyl)pyrazolo[3,4-d]pyrimidin-6-yl]amino]cyclopentyl]-(5,5-difluoro-2,7-diazaspiro[3.5]nonan-7-yl)methanone | | AA |
| 2-[4-[(1R,3R)-3-[[3-bromo-1-(8-fluoro-6-quinolyl)pyrazolo[3,4-d]pyrimidin-6-yl]amino]cyclopentanecarbonyl]piperazin-1-yl]acetonitrile | | A |
| (8aS)-2-[(1R,3R)-3-[[3-bromo-1-(8-fluoro-6-quinolyl)pyrazolo[3,4-d]pyrimidin-6-yl]amino]cyclopentane-carbonyl]-1,3,4,7,8,8a-hexahydro-pyrrolo[1,2-a]pyrazin-6-one | | AA |
| (8aR)-2-[(1R,3R)-3-[[3-bromo-1-(8-fluoro-6-quinolyl)pyrazolo[3,4-d]pyrimidin-6-yl]amino]cyclopentane-carbonyl]-1,3,4,7,8,8a-hexahydro-pyrrolo[1,2-a]pyrazin-6-one | | AA |
| (8aR)-2-[(1R,3R)-3-[[3-bromo-1-(8-fluoro-6-quinolyl)pyrazolo[3,4-d]pyrimidin-6-yl]amino]-1-methyl-cyclopentanecarbonyl]-1,3,4,7,8,8a-hexahydropyrrolo[1,2-a]pyrazin-6-one | | A |
| 8-[(1R,3R)-3-[[3-bromo-1-(8-fluoro-6-quinolyl)pyrazolo[3,4-d]pyrimidin-6-yl]amino]-1-methyl-cyclopentane-carbonyl]-6,7,9,9a-tetrahydro-1H-pyrazino[2,1-c][1,4]oxazin-4-one | | A |
| [(1R,3R)-3-[[3-bromo-1-(8-fluoro-6-quinolyl)pyrazolo[3,4-d]pyrimidin-6-yl]amino]-1-methyl-cyclopentyl]-(3-methoxypyrrolidin-1-yl)methanone | | A |
| (1R,3R)-3-[[3-bromo-1-[4-(5-methyl-1,3,4-oxadiazol-2-yl)phenyl]pyrazolo[3,4-d]pyrimidin-6-yl]amino]-N,1-dimethyl-cyclopentanecarboxamide | | AA |
| 4-[(1R,3R)-3-[[3-bromo-1-(8-fluoro-6-quinolyl)pyrazolo[3,4-d]pyrimidin-6-yl]amino]-1-methyl-cyclopentanecarbonyl]piperazin-2-one | | AA |
| (1R,3R)-3-[[3-bromo-1-(6-quinolyl)pyrazolo[3,4-d]pyrimidin-6-yl]amino]-N-methyl-cyclopentanecarboxamide | | A |
| (3R)-3-[[3-bromo-1-(3-methoxy-6-isoquinolyl)pyrazolo[3,4-d]pyrimidin-6-yl]amino]-N,1-dimethyl-cyclopentanecarboxamide | | A |
| 4-[(1R,3R)-3-[[3-bromo-1-[4-(5-methyl-1,3,4-oxadiazol-2-yl)phenyl]pyrazolo[3,4-d]pyrimidin-6-yl]amino]-1-methyl-cyclopentanecarbonyl]piperazin-2-one | | A |

TABLE 3-continued

| Chemical Name | Chemical Structure | IC$_{50}$ Activity |
|---|---|---|
| (1R,3R)-3-[[3-bromo-1-(8-fluoro-6-quinolyl)pyrazolo[3,4-d]pyrimidin-6-yl]amino]-N-(2-methoxy-2-methyl-propyl)-N,1-dimethyl-cyclopentanecarboxamide | | AA |
| (3R)-3-[[3-bromo-1-[2-(1-hydroxy-1-methyl-ethyl)-6-quinolyl]pyrazolo[3,4-d]pyrimidin-6-yl]amino]-N,1-dimethyl-cyclopentane-carboxamide | | A |
| (1R,3R)-3-[[3-bromo-1-(8-fluoro-6-quinolyl)pyrazolo[3,4-d]pyrimidin-6-yl]amino]-N-(1-carbamoylcyclopropyl)cyclopentane-carboxamide | | A |
| [(1R,3R)-3-[[3-bromo-1-(8-fluoro-6-quinolyl)pyrazolo[3,4-d]pyrimidin-6-yl]amino]cyclopentyl]-(2-methyl-6,8-dihydro-5H-imidazo[1,2-a]pyrazin-7-yl)methanone | | A |
| (8aS)-2-[(1R,3R)-3-[[3-bromo-1-(8-fluoro-6-quinolyl)pyrazolo[3,4-d]pyrimidin-6-yl]amino]-1-methyl-cyclopentanecarbonyl]-1,3,4,7,8,8a-hexahydropyrrolo[1,2-a]pyrazin-6-one | | A |
| (1R,3R)-3-[[3-bromo-1-(8-fluoro-6-quinolyl)pyrazolo[3,4-d]pyrimidin-6-yl]amino]-N-ethyl-1-methyl-cyclopentanecarboxamide | | AA |
| [(9aS)-3,4,6,7,9,9a-hexahydro-1H-pyrazino[2,1-c][1,4]oxazin-8-yl]-[(3R)-3-[[3-bromo-1-(8-fluoro-6-quinolyl)pyrazolo[3,4-d]pyrimidin-6-yl]amino]-1-methyl-cyclopentyl]methanone | | A |
| (1R,3R)-3-[[3-bromo-1-(8-fluoro-2-methyl-6-quinolyl)pyrazolo[3,4-d]pyrimidin-6-yl]amino]-N,1-dimethyl-cyclopentane-carboxamide | | AA |
| [(1R,3R)-3-[[3-bromo-1-(8-fluoro-6-quinolyl)pyrazolo[3,4-d]pyrimidin-6-yl]amino]-1-methyl-cyclopentyl]-(3-methoxy-3-methyl-azetidin-1-yl)methanone | | AA |
| (1R,3R)-3-[[3-bromo-1-(8-fluoro-6-quinolyl)pyrazolo[3,4-d]pyrimidin-6-yl]amino]-N-(2-methoxyethyl)-N,1-dimethyl-cyclopentane-carboxamide | | AA |
| (1R,3R)-3-[[3-bromo-1-(8-fluoro-6-quinolyl)pyrazolo[3,4-d]pyrimidin-6-yl]amino]-1-[2-(dimethylamino)-2-oxo-ethyl]-N-methyl-cyclopentanecarboxamide | | AA |
| (1R,3R)-3-[[3-bromo-1-(8-fluoro-6-quinolyl)pyrazolo[3,4-d]pyrimidin-6-yl]amino]-N-(2-hydroxy-1,1-dimethyl-ethyl)-N,1-dimethyl-cyclopentanecarboxamide | | AA |
| (1R,3R)-3-[[3-bromo-1-(2-methoxy-6-quinolyl)pyrazolo[3,4-d]pyrimidin-6-yl]amino]-N-methyl-cyclopentanecarboxamide | | A |
| (1S,3R)-3-[[3-bromo-1-(2-methoxy-6-quinolyl)pyrazolo[3,4-d]pyrimidin-6-yl]amino]-N-methyl-cyclopentanecarboxamide | | A |
| (1R,3R)-3-[[3-bromo-1-(7-cyano-2,3-dihydro-benzofuran-5-yl)pyrazolo[3,4-d]pyrimidin-6-yl]amino]-N-methyl-cyclopentanecarboxamide | | A |
| (1R,3R)-3-[[3-bromo-1-(4-methoxy-6-quinolyl)pyrazolo[3,4-d]pyrimidin-6-yl]amino]-N,1-dimethyl-cyclopentanecarboxamide | | AA |
| (1R,3R)-3-[[3-bromo-1-(8-fluoro-6-quinolyl)pyrazolo[3,4-d]pyrimidin-6-yl]amino]-N-ethyl-N,1-dimethyl-cyclopentanecarboxamide | | AA |
| (1R,3R)-3-[[3-bromo-1-[3-chloro-5-(hydroxymethyl)phenyl]pyrazolo[3,4-d]pyrimidin-6-yl]amino]-N-methyl-cyclopentanecarboxamide | | A |
| (1R,3R)-3-[[3-bromo-1-(1,3-dimethylindazol-6-yl)pyrazolo[3,4-d]pyrimidin-6-yl]amino]-N-methyl-cyclopentanecarboxamide | | A |
| (1R,3R)-3-[[3-bromo-1-[8-(1-hydroxy-1-methyl-ethyl)-6-quinolyl]pyrazolo[3,4-d]pyrimidin-6-yl]amino]-N,1-dimethyl-cyclopentanecarboxamide | | A |
| (1S,3R)-3-[[3-bromo-1-(8-fluoro-6-quinolyl)pyrazolo[3,4-d]pyrimidin-6-yl]amino]-N-methyl-1-(3,3,3-trifluoropropyl)cyclopentane-carboxamide | | A |
| (3R)-3-[[3-bromo-1-(2-methoxy-6-quinolyl)pyrazolo[3,4-d]pyrimidin-6-yl]amino]-N,1-dimethyl-cyclopentanecarboxamide | | A |

| Chemical Name | Chemical Structure | IC$_{50}$ Activity |
|---|---|---|
| (1R,3R)-3-[[3-bromo-1-[3-(1-hydroxy-1-methyl-ethyl)-6-quinolyl]pyrazolo[3,4-d]pyrimidin-6-yl]amino]-N,1-dimethyl-cyclopentanecarboxamide | | A |
| (1R,3R)-3-[[3-bromo-1-[4-[1-(2-methoxy-ethyl)pyrazol-4-yl]phenyl]pyrazolo[3,4-d]pyrimidin-6-yl]amino]-N-methyl-cyclopentanecarboxamide | | A |
| (3R)-3-[[3-bromo-1-[4-[1-(2-methoxyethyl)pyrazol-4-yl]phenyl]pyrazolo[3,4-d]pyrimidin-6-yl]amino]-N,1-dimethyl-cyclopentanecarboxamide | | A |
| (1S,3R)-3-[[3-bromo-1-(8-fluoro-6-quinolyl)pyrazolo[3,4-d]pyrimidin-6-yl]amino]-1-(3-methoxypropyl)-N-methyl-cyclopentane-carboxamide | | AA |
| (1R,3R)-3-[[1-(8-fluoro-6-quinolyl)-3-iodo-pyrazolo[3,4-d]pyrimidin-6-yl]amino]-N-methyl-cyclopentanecarboxamide | | AA |
| (1R,3R)-3-[[3-iodo-1-[4-(5-methyl-1,3,4-oxadiazol-2-yl)phenyl]pyrazolo[3,4-d]pyrimidin-6-yl]amino]-N-methyl-cyclopentanecarboxamide | | A |
| (3R)-3-[[3-bromo-1-(8-fluoro-6-quinolyl)pyrazolo[3,4-d]pyrimidin-6-yl]amino]-N-(1-cyanocyclopropyl)-1-methyl-cyclopentane-carboxamide | | AA |
| (3R)-3-[[3-bromo-1-(8-fluoro-6-quinolyl)pyrazolo[3,4-d]pyrimidin-6-yl]amino]-1-methyl-N-(2,2,2-trifluoroethyl)cyclo-pentanecarboxamide | | A |
| 1-[(1R,3R)-3-[[3-bromo-1-(8-fluoro-6-quinolyl)pyrazolo[3,4-d]pyrimidin-6-yl]amino]-1-methyl-cyclopentanecarbonyl]imidazolidin-4-one | | AA |
| 1-[(1S,3R)-3-[[3-bromo-1-(8-fluoro-6-quinolyl)pyrazolo[3,4-d]pyrimidin-6-yl]amino]-1-methyl-cyclopentanecarbonyl]imidazolidin-4-one | | A |
| (3R)-3-[[3-bromo-1-[3-chloro-5-(hydroxy-methyl)phenyl]pyrazolo[3,4-d]pyrimidin-6-yl]amino]-N,1-dimethyl-cyclopentane-carboxamide | | A |
| (1R,3R)-3-[[3-bromo-1-(8-fluoro-6-quinolyl)pyrazolo[3,4-d]pyrimidin-6-yl]amino]-N-methyl-1-(2,2,2-trifluoroethyl)cyclopentane-carboxamide | | AA |
| (5S,8R)-8-[[3-bromo-1-(8-fluoro-6-quinolyl)pyrazolo[3,4-d]pyrimidin-6-yl]amino]-2-oxaspiro[4.4]nonan-1-one | | A |
| (3R)-3-[[3-bromo-1-[3-(hydroxymethyl)-5-methoxy-phenyl]pyrazolo[3,4-d]pyrimidin-6-yl]amino]-N,1-dimethyl-cyclopentanecarboxamide | | A |
| 3-bromo-1-(8-fluoro-6-quinolyl)-N-[(1R,3R)-3-methoxycyclopentyl]pyrazolo[3,4-d]pyrimidin-6-amine | | A |
| 1-[(1R,3R)-3-[[3-bromo-1-(8-fluoro-6-quinolyl)pyrazolo[3,4-d]pyrimidin-6-yl]amino]-1-methyl-cyclopentanecarbonyl]-3-methyl-imidazolidin-4-one | | AA |
| 1-[(1S,3R)-3-[[3-bromo-1-(8-fluoro-6-quinolyl)pyrazolo[3,4-d]pyrimidin-6-yl]amino]-1-methyl-cyclopentanecarbonyl]-3-methyl-imidazolidin-4-one | | A |
| (3R)-3-[[3-bromo-1-(8-cyano-4-methyl-6-quinolyl)pyrazolo[3,4-d]pyrimidin-6-yl]amino]-N,1-dimethyl-cyclopentane-carboxamide | | AA |
| (1R,3R)-3-[[3-bromo-1-[4-(cyanomethoxy)phenyl]pyrazolo[3,4-d]pyrimidin-6-yl]amino]-N,1-dimethyl-cyclopentane-carboxamide | | A |
| (3R)-3-[[3-bromo-1-(3-fluoro-4-oxazol-2-yl-phenyl)pyrazolo[3,4-d]pyrimidin-6-yl]amino]-1-methyl-cyclopentanecarboxamide | | AA |
| (3R)-3-[[3-bromo-1-(4-pyrazin-2-ylphenyl)pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (3R)-3-[[3-bromo-1-[3-(1-hydroxyethyl)-5-(trifluoromethoxy)phenyl]pyrazolo[3,4-d]pyrimidin-6-yl]amino]-N,1-dimethyl-cyclopentanecarboxamide | | A |
| (1R,3R)-3-[[3-bromo-1-[8-(2,5-dihydro-1H-pyrrol-3-yl)-6-quinolyl]pyrazolo[3,4-d]pyrimidin-6-yl]amino]-N,1-dimethyl-cyclopentanecarboxamide | | A |
| (1R,3R)-3-[[3-bromo-1-(2-methoxy-6-quinolyl)pyrazolo[3,4-d]pyrimidin-6-yl]amino]-N,1-dimethyl-cyclopentane-carboxamide | | A |
| (1S,3R)-3-[[3-bromo-1-(2-methoxy-6-quinolyl)pyrazolo[3,4-d]pyrimidin-6-yl]amino]-N,1-dimethyl-cyclopentane-carboxamide | | AA |
| (1R,3R)-3-[[3-bromo-1-(8-tetrahydrofuran-2-yl-6-quinolyl)pyrazolo[3,4-d]pyrimidin-6-yl]amino]-N,1-dimethyl-cyclopentane-carboxamide | | A |
| (1R,3R)-3-[[3-iodo-1-[4-(5-methyl-1,3,4-oxadiazol-2-yl)phenyl]pyrazolo[3,4-d]pyrimidin-6-yl]amino]-N,1-dimethyl-cyclopentanecarboxamide | | AA |
| (3R)-3-[[3-bromo-1-(4-chloro-2-methyl-6-quinolyl)pyrazolo[3,4-d]pyrimidin-6-yl]amino]-N,1-dimethyl-cyclopentane-carboxamide | | A |
| (3R)-3-[[3-bromo-1-[4-(imidazol-1-ylmethyl)phenyl]pyrazolo[3,4-d]pyrimidin-6-yl]amino]-N,1-dimethyl-cyclopentanecarboxamide | | A |
| (3R)-3-[[3-bromo-1-(8-fluoro-6-quinolyl)pyrazolo[3,4-d]pyrimidin-6-yl]amino]-N-(2-fluoroethyl)-1-methyl-cyclopentane-carboxamide | | A |
| (3R)-3-[[3-bromo-1-(8-fluoro-6-quinolyl)pyrazolo[3,4-d]pyrimidin-6-yl]amino]-N-(2,2-difluoroethyl)-1-methyl-cyclopentane-carboxamide | | A |
| (1S,3R)-3-[[3-bromo-1-[4-(2-hydroxyethoxy)phenyl]pyrazolo[3,4-d]pyrimidin-6-yl]amino]-N,1-dimethyl-cyclopentane-carboxamide | | A |
| (3R)-3-[[3-bromo-1-[3-(hydroxymethyl)-5-methyl-phenyl]pyrazolo[3,4-d]pyrimidin-6-yl]amino]-N,1-dimethyl-cyclopentanecarboxamide | | A |
| 3-[3-bromo-6-[[(1R)-3-methyl-3-(methylcarbamoyl)cyclopentyl]amino]pyrazolo[3,4-d]pyrimidin-1-yl]-5-chloro-benzamide | | AA |
| (1R,3R)-3-[[3-bromo-1-(3-chloro-5-cyano-phenyl)pyrazolo[3,4-d]pyrimidin-6-yl]amino]-N,1-dimethyl-cyclopentanecarboxamide | | A |
| (1R,3R)-3-[[3-bromo-1-[3-fluoro-5-(2-hydroxyethyl)phenyl]pyrazolo[3,4-d]pyrimidin-6-yl]amino]-N,1-dimethyl-cyclopentanecarboxamide | | AA |
| (3R)-3-[[3-bromo-1-[3-fluoro-5-(hydroxymethyl)phenyl]pyrazolo[3,4-d]pyrimidin-6-yl]amino]-N,1-dimethyl-cyclopentanecarboxamide | | A |
| 3-[3-bromo-6-[[(1R,3R)-3-methyl-3-(methylcarbamoyl)cyclopentyl]amino]pyrazolo[3,4-d]pyrimidin-1-yl]-5-fluoro-benzamide | | A |
| (3R)-3-[[3-bromo-1-[3-(methylaminomethyl)-5-(trifluoromethoxy)phenyl]pyrazolo[3,4-d]pyrimidin-6-yl]amino]-N,1-dimethyl-cyclopentanecarboxamide | | A |
| (1R,3R)-3-[[1-(8-fluoro-6-quinolyl)-3-iodo-pyrazolo[3,4-d]pyrimidin-6-yl]amino]-1-(methoxymethyl)-N-methyl-cyclopentane-carboxamide | | AA |
| (1S,3R)-3-[[1-(8-fluoro-6-quinolyl)-3-iodo-pyrazolo[3,4-d]pyrimidin-6-yl]amino]-1-(methoxymethyl)-N-methyl-cyclopentane-carboxamide | | A |

TABLE 3-continued

| Chemical Name | Chemical Structure | IC$_{50}$ Activity |
|---|---|---|
| (1R,3R)-1-ethyl-3-[[1-(8-fluoro-6-quinolyl)-3-iodo-pyrazolo[3,4-d]pyrimidin-6-yl]amino]-N-methyl-cyclopentanecarboxamide | | AA |
| (1R,3R)-3-[[3-bromo-1-[3-cyano-5-fluoro-4-(3-pyridyl)phenyl]pyrazolo[3,4-d]pyrimidin-6-yl]amino]-N-methyl-cyclopentane-carboxamide | | A |
| (1S,3R)-3-[[3-bromo-1-(8-fluoro-6-quinolyl)pyrazolo[3,4-d]pyrimidin-6-yl]amino]-N-methyl-cyclopentanecarboxamide | | AA |
| (1R,3R)-3-[[3-bromo-1-[3-(cyanomethyl)-5-fluoro-phenyl]pyrazolo[3,4-d]pyrimidin-6-yl]amino]-N,1-dimethyl-cyclopentane-carboxamide | | A |
| (1R,3R)-3-[[3-bromo-1-[4-[5-(2-methoxy-ethyl)-1,3,4-oxadiazol-2-yl]phenyl]pyrazolo[3,4-d]pyrimidin-6-yl]amino]-N,1-dimethyl-cyclopentanecarboxamide | | AA |
| (3R)-3-[[3-bromo-1-[3-tert-butyl-5-(hydroxy-methyl)phenyl]pyrazolo[3,4-d]pyrirnidin-6-yl]amino]-N,1-dimethyl-cyclopentane-carboxamide | | A |
| (1R,3R)-3-[[3-bromo-1-[3-[(2-methoxy-ethylamino)methyl]-5-(trifluoromethoxy)phenyl]pyrazolo[3,4-d]pyrimidin-6-yl]amino]-N,1-dimethyl-cyclopentanecarboxamide | | A |
| (1R,3R)-3-[[3-bromo-1-[3-[(2-cyanoethyl-amino)methyl]-5-(trifluoromethoxy)phenyl]pyrazolo[3,4-d]pyrimidin-6-yl]amino]-N,1-dimethyl-cyclopentane-carboxamide | | A |
| (1R,3R)-3-[[3-bromo-1-[8-[(2-methoxy-ethylamino)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-[(2-cyanoethyl-amino)methyl]-6-quinolyl]pyrazolo[3,4-d]pyrimidin-6-yl]amino]-N,1-dimethyl-cyclopentanecarboxamide | | A |
| (3R)-3-[[3-bromo-1-(4-methyl-2-oxo-1H-quinolin-6-yl)pyrazolo[3,4-d]pyrimidin-6-yl]amino]-N,1-dimethyl-cyclopentanecarboxamide | | A |
| (1R,3R)-3-[[3-bromo-1-[3-chloro-4-(2-hydroxyethoxy)phenyl]pyrazolo[3,4-d]pyrimidin-6-yl]amino]-N,1-dimethyl-cyclopentanecarboxamide | | A |
| (1R,3R)-3-[[3-bromo-1-[8-[(2,2-difluoroethylamino)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[4-[5-(1-hydroxy-1-methyl-ethyl)-1,3,4-oxadiazol-2-yl]phenyl]pyrazolo[3,4-d]pyrimidin-6-yl]amino]-N,1-dimethyl-cyclopentanecarboxamide | | A |
| (1R,3R)-3-[[3-bromo-1-[8-(2-hydroxy-2-methyl-propyl)-6-quinolyl]pyrazolo[3,4-d]pyrimidin-6-yl]amino]-N,1-dimethyl-cyclopentanecarboxamide | | A |
| (3R)-3-[[3-bromo-1-[4-(3-methyl-1,2,4-oxadiazol-5-yl)phenyl]pyrazolo[3,4-d]pyrimidin-6-yl]amino]-N,1-dimethyl-cyclopentanecarboxamide | | A |
| (3R)-3-[[3-bromo-1-[4-(5-methyl-1,2,4-oxadiazol-3-yl)phenyl]pyrazolo[3,4-d]pyrimidin-6-yl]amino]-N,1-dimethyl-cyclopentanecarboxamide | | A |
| (3R)-3-[[3-bromo-1-[3-(1-hydroxy-1-methyl-ethyl)phenyl]pyrazolo[3,4-d]pyrimidin-6-yl]amino]-N,1-dimethyl-cyclopentane-carboxamide | | A |
| (3R)-3-[[3-bromo-1-[3-(3-hydroxypropyl)phenyl]pyrazolo[3,4-d]pyrimidin-6-yl]amino]-N,1-dimethyl-cyclopentane-carboxamide | | A |
| (1R,3R)-3-[[3-bromo-1-[4-[5-(1-hydroxy-ethyl)-1,3,4-oxadiazol-2-yl]phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-[4-[5-(methoxy-methyl)-1,3,4-oxadiazol-2-yl]phenyl]pyrazolo[3,4-d]pyrimidin-6-yl]amino]-N,1-dimethyl-cyclopentanecarboxamide | | A |
| (1R,3R)-3-[[3-bromo-1-[4-(5-isopropyl-1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(5-cyclopropyl-1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(5-tert-butyl-1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(3-methylimidazol-4-yl)phenyl]pyrazolo[3,4-d]pyrimidin-6-yl]amino]-N,1-dimethyl-cyclopentanecarboxamide | | A |
| (1R,3R)-3-[[3-bromo-1-(7-fluoro-2,3-dihydro-benzofuran-5-yl)pyrazolo[3,4-d]pyrimidin-6-yl]amino]-N,1-dimethyl-cyclopentanecarboxamide | | A |
| (1R,3R)-3-[[3-bromo-1-[4-(2-methyloxazol-5-yl)phenyl]pyrazolo[3,4-d]pyrimidin-6-yl]amino]-N,1-dimethyl-cyclopentanecarboxamide | | A |
| (1R,3R)-3-[[3-bromo-1-[4-[5-(2-hydroxy-propyl)-1,3,4-oxadiazol-2-yl]phenyl]pyrazolo[3,4-d]pyrimidin-6-yl]amino]-N,1-dimethyl-cyclopentanecarboxamide | | A |
| (1R,3R)-3-[[3-bromo-1-[4-[5-(difluoro-methyl)-1,3,4-oxadiazol-2-yl]phenyl]pyrazolo[3,4-d]pyrimidin-6-yl]amino]-N,1-dimethyl-cyclopentanecarboxamide | | A |
| (1R,3R)-3-[[3-bromo-1-[3-[(2-cyanoethyl-amino)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-(6-pyrazin-2-yl-3-pyridyl)pyrazolo[3,4-d]pyrimidin-6-yl]amino]-N,1-dimethyl-cyclopentanecarboxamide | | A |
| (1R,3R)-3-[[3-bromo-1-(4-thiazol-5-ylphenyl)pyrazolo[3,4-d]pyrimidin-6-yl]amino]-N,1-dimethyl-cyclopentanecarboxamide | | A |
| (1R,3R)-3-[[3-bromo-1-[8-(2-hydroxy-1-methyl-ethyl)-6-quinolyl]pyrazolo[3,4-d]pyrimidin-6-yl]amino]-N,1-dimethyl-cyclopentanecarboxamide | | AA |
| (1R,3R)-3-[[3-bromo-1-(4-thiazol-2-ylphenyl)pyrazolo[3,4-d]pyrimidin-6-yl]amino]-N,1-dimethyl-cyclopentanecarboxamide | | A |
| (1R,3R)-3-[[3-bromo-1-[6-(5-methyl-1,3,4-oxadiazol-2-yl)-3-pyridyl]pyrazolo[3,4-d]pyrimidin-6-yl]amino]-N,1-dimethyl-cyclopentanecarboxamide | | A |
| (1R,3R)-3-[[3-bromo-1-[4-(5-methyl-1H-imidazol-2-yl)phenyl]pyrazolo[3,4-d]pyrimidin-6-yl]amino]-N,1-dimethyl-cyclopentanecarboxamide | | A |
| [(3R)-3-[[3-bromo-1-(8-fluoro-6-quinolyl)pyrazolo[3,4-d]pyrimidin-6-yl]amino]-1-methyl-cyclopentyl]-morpholino-methanone | | AA |
| (1R,3R)-3-[[3-bromo-1-(8-fluoro-4-hydroxy-2-methyl-6-quinolyl)pyrazolo[3,4-d]pyrimidin-6-yl]amino]-N,1-dimethyl-cyclopentanecarboxamide | | A |
| (1R,3R)-3-[[3-bromo-1-(4-chloro-8-fluoro-2-methyl-6-quinolyl)pyrazolo[3,4-d]pyrimidin-6-yl]amino]-N,1-dimethyl-cyclopentanecarboxamide | | A |
| (1R,3R)-3-[[3-bromo-1-[4-(5-methyl-4H-1,2,4-triazol-3-yl)phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| [(3R)-3-[[3-bromo-1-(8-fluoro-6-quinolyl)pyrazolo[3,4-d]pyrimidin-6-yl]amino]-1-methyl-cyclopentyl]-(8-oxa-3-azabicyclo[3.2.1]octan-3-yl)methanone | | AA |
| [(3R)-3-[[3-bromo-1-(8-fluoro-6-quinolyl)pyrazolo[3,4-d]pyrimidin-6-yl]amino]-1-methyl-cyclopentyl]-[(2R,6R)-2,6-dimethylmorpholin-4-yl]methanone | | A |
| (1R,3R)-3-[[3-bromo-1-(4-imidazol-1-ylphenyl)pyrazolo[3,4-d]pyrimidin-6-yl]amino]-N,1-dimethyl-cyclopentanecarboxamide | | A |
| (1R,3R)-3-[[3-bromo-1-[4-[5-(2-hydroxy-1-methyl-ethyl)-1,3,4-oxadiazol-2-yl]phenyl]pyrazolo[3,4-d]pyrimidin-6-yl]amino]-N,1-dimethyl-cyclopentanecarboxamide | | AA |
| (1S,3R)-3-[[3-iodo-1-[4-(5-methyl-1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(5-methyl-1,3,4-oxadiazol-2-yl)phenyl]pyrazolo[3,4-d]pyrimidin-6-yl]amino]-1-(2,2-difluoroethyl)-N-methyl-cyclopentanecarboxamide | | A |
| (1S,3R)-3-[[3-bromo-1-[4-(5-methyl-1,3,4-oxadiazol-2-yl)phenyl]pyrazolo[3,4-d]pyrimidin-6-yl]amino]-1-(2,2-difluoroethyl)-N-methyl-cyclopentanecarboxamide | | A |
| (1R,3R)-3-[[3-bromo-1-[3-cyano-4-(3-pyridyl)phenyl]pyrazolo[3,4-d]pyrimidin-6-yl]amino]-1-(2,2-difluoroethyl)-N-methyl-cyclopentanecarboxamide | | A |
| (1R,3R)-3-[[3-bromo-1-(4-pyrazin-2-ylphenyl)pyrazolo[3,4-d]pyrimidin-6-yl]amino]-1-(2,2-difluoroethyl)-N-methyl-cyclopentanecarboxamide | | A |
| (1R,3R)-3-[[3-bromo-1-[8-(2-hydroxy-2-methyl-propyl)-6-quinolyl]pyrazolo[3,4-d]pyrimidin-6-yl]amino]-1-(2,2-difluoroethyl)-N-methyl-cyclopentanecarboxamide | | A |
| (1R,3R)-3-[[3-bromo-1-[3-(2-hydroxyethyl)-4-(5-methyl-1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(triazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[3-fluoro-4-(5-methyl-1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(1,3,4-oxadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-(8-cyano-2-methyl-6-quinolyl)pyrazolo[3,4-d]pyrimidin-6-yl]amino]-N,1-dimethyl-cyclopentanecarboxamide | | AA |
| (1R,3R)-3-[[3-bromo-1-[4-(1,2,5-oxadiazol-3-yl)phenyl]pyrazolo[3,4-d]pyrimidin-6-yl]amino]-N,1-dimethyl-cyclopentanecarboxamide | | A |
| [(3R)-3-[[3-bromo-1-[4-(5-methyl-1,3,4-oxadiazol-2-yl)phenyl]pyrazolo[3,4-d]pyrimidin-6-yl]amino]-1-methyl-cyclopentyl]-morpholino-methanone | | A |
| (1R,3R)-3-[[3-bromo-1-[8-(2-hydroxyethyl)-6-quinolyl]pyrazolo[3,4-d]pyrimidin-6-yl]amino]-1-(2,2-difluoroethyl)-N-methyl-cyclopentanecarboxamide | | A |
| (1S,3R)-3-[[3-bromo-1-[8-(2-hydroxyethyl)-6-quinolyl]pyrazolo[3,4-d]pyrimidin-6-yl]amino]-1-(2,2-difluoroethyl)-N-methyl-cyclopentanecarboxamide | | A |

TABLE 3-continued

| Chemical Name | Chemical Structure | IC$_{50}$ Activity |
|---|---|---|
| [(3R)-3-[[3-bromo-1-[4-(5-methyl-1,3,4-oxadiazol-2-yl)phenyl]pyrazolo[3,4-d]pyrimidin-6-yl]amino]-1-methyl-cyclopentyl]-[(2R,6R)-2,6-dimethylmorpholin-4-yl]methanone | | A |
| (1R,3R)-3-[[3-bromo-1-[2-[(2-cyanoethylamino)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-(4-isoxazol-3-ylphenyl)pyrazolo[3,4-d]pyrimidin-6-yl]amino]-N,1-dimethyl-cyclopentanecarboxamide | | A |
| [(3R)-3-[[3-bromo-1-(8-fluoro-6-quinolyl)pyrazolo[3,4-d]pyrimidin-6-yl]amino]-1-methyl-cyclopentyl]-piperazin-1-yl-methanone | | AA |
| (3R)-3-[[3-bromo-1-(8-fluoro-6-quinolyl)pyrazolo[3,4-d]pyrimidin-6-yl]amino]-N,N-diethyl-1-methyl-cyclopentanecarboxamide | | A |
| (1R,3R)-3-[[3-bromo-1-[4-[5-(2-cyano-1-methyl-ethyl)-1,3,4-oxadiazol-2-yl]phenyl]pyrazolo[3,4-d]pyrimidin-6-yl]amino]-N,1-dimethyl-cyclopentanecarboxamide | | AA |
| (1R,3R)-3-[[3-bromo-1-[3-(2-hydroxyethyl)-6-quinolyl]pyrazolo[3,4-d]pyrimidin-6-yl]amino]-N,1-dimethyl-cyclopentanecarboxamide | | AA |
| (3R)-3-[[3-bromo-1-(8-fluoro-6-quinolyl)pyrazolo[3,4-d]pyrimidin-6-yl]amino]-N,1-dimethyl-N-[(3-methyloxetan-3-yl)methyl]cyclopentanecarboxamide | | AA |
| [(3R)-3-[[3-bromo-1-[4-(5-methyl-1,3,4-oxadiazol-2-yl)phenyl]pyrazolo[3,4-d]pyrimidin-6-yl]amino]-1-methyl-cyclopentyl]-piperazin-1-yl-methanone | | A |
| (1S,3R)-3-[[3-bromo-1-[3-(2-hydroxy-ethyl)-6-quinolyl]pyrazolo[3,4-d]pyrimidin-6-yl]amino]-N,1-dimethyl-cyclopentanecarboxamide | | AA |
| (1R,3R)-3-[[3-bromo-1-[4-(4,5-dihydro-isoxazol-3-yl)phenyl]pyrazolo[3,4-d]pyrimidin-6-yl]amino]-N,1-dimethyl-cyclopentanecarboxamide | | A |
| (1R,3R)-3-[[3-bromo-1-[8-(2-hydroxy-propyl)-6-quinolyl]pyrazolo[3,4-d]pyrimidin-6-yl]amino]-N,1-dimethyl-cyclopentanecarboxamide | | AA |
| (1R,3R)-3-[[3-bromo-1-[8-(2-hydroxy-ethyl)-2-methyl-6-quinolyl]pyrazolo[3,4-d]pyrimidin-6-yl]amino]-N,1-dimethyl-cyclopentanecarboxamide | | A |
| (1R,3R)-3-[[3-bromo-1-[8-[2-(methane-sulfonamido)ethyl]-6-quinolyl]pyrazolo[3,4-d]pyrimidin-6-yl]amino]-N,1-dimethyl-cyclopentanecarboxamide | | A |
| methyl N-[2-[6-[3-bromo-6-[[(1R,3R)-3-methyl-3-(methylcarbamoyl)cyclopentyl]amino]pyrazolo[3,4-d]pyrimidin-1-yl]-8-quinolyl]ethyl]carbamate | | A |
| (1R,3R)-3-[[1-[8-(2-acetamidoethyl)-6-quinolyl]-3-bromo-pyrazolo[3,4-d]pyrimidin-6-yl]amino]-N,1-dimethyl-cyclopentanecarboxamide | | A |
| (1R,3R)-3-[[3-bromo-1-[8-[2-(2-methyl-propanoylamino)ethyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-[(1S)-2-hydroxy-1-methyl-ethyl]-6-quinolyl]pyrazolo[3,4-d]pyrimidin-6-yl]amino]-N,1-dimethyl-cyclopentanecarboxamide | | AA |
| (1R,3R)-3-[[3-bromo-1-[8-[(1R)-2-hydroxy-1-methyl-ethyl]-6-quinolyl]pyrazolo[3,4-d]pyrimidin-6-yl]amino]-N,1-dimethyl-cyclopentanecarboxamide | | AA |
| (1R,3R)-3-[[3-bromo-1-(4-pyrimidin-5-ylphenyl)pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-(1-oxo-3,4-dihydro-2H-isoquinolin-6-yl)pyrazolo[3,4-d]pyrimidin-6-yl]amino]-N,1-dimethyl-cyclopentanecarboxamide | | A |
| (1R,3R)-3-[[3-bromo-1-[4-(4,5-dihydro-oxazol-2-yl)phenyl]pyrazolo[3,4-d]pyrimidin-6-yl]amino]-N,1-dimethyl-cyclopentanecarboxamide | | A |
| (1R,3R)-3-[[1-[8-[(1-aminocyclopropyl)methyl]-6-quinolyl]-3-bromo-pyrazolo[3,4-d]pyrimidin-6-yl]amino]-N,1-dimethyl-cyclopentanecarboxamide | | A |
| (1R,3R)-3-[[3-bromo-1-(3,3-dimethyl-2H-benzofuran-5-yl)pyrazolo[3,4-d]pyrimidin-6-yl]amino]-N,1-dimethyl-cyclopentane-carboxamide | | A |
| (1R,3R)-3-[[1-[8-[1-(aminomethyl)cyclo-propyl]-6-quinolyl]-3-bromo-pyrazolo[3,4-d]pyrimidin-6-yl]amino]-N,1-dimethyl-cyclopentanecarboxamide | | A |
| (1R,3R)-3-[[3-bromo-1-([1,2,4]triazolo[1,5-a]pyridin-6-yl)pyrazolo[3,4-d]pyrimidin-6-yl]amino]-N,1-dimethyl-cyclopentane-carboxamide | | A |
| (1R,3R)-3-[[1-[3-(2-aminoethyl)-4-fluoro-phenyl]-3-bromo-pyrazolo[3,4-d]pyrimidin-6-yl]amino]-N,1-dimethyl-cyclopentane-carboxamide | | A |
| (1R,3R)-3-[[1-[3-(2-aminoethyl)-4-fluoro-phenyl]-3-bromo-pyrazolo[3,4-d]pyrimidin-6-yl]amino]-N,1-dimethyl-cyclopentane-carboxamide | | A |
| (1R,3R)-3-[[3-bromo-1-[4-(1,2,4-triazol-1-yl)phenyl]pyrazolo[3,4-d]pyrimidin-6-yl]amino]-N,1-dimethyl-cyclopentane-carboxamide | | A |
| N-[3-[3-bromo-6-[[(1R,3R)-3-methyl-3-(methylcarbamoyl)cyclopentyl]amino]pyrazolo[3,4-d]pyrimidin-1-yl]phenyl]pyrimidine-5-carboxamide | | A |
| (1S,3R)-3-[[1-[8-(2-aminoethyl)-6-quinolyl]-3-bromo-pyrazolo[3,4-d]pyrimidin-6-yl]amino]-1-methyl-cyclopentanecarboxylic acid | | A |
| (1R,3R)-3-[[1-[8-(2-aminoethyl)-6-quinolyl]-3-bromo-pyrazolo[3,4-d]pyrimidin-6-yl]amino]-1-methyl-cyclopentanecarboxylic acid | | AA |
| (1R,3R)-3-[[1-[3-(2-aminoethyl)-4-(5-methyl-1,3,4-thiadiazol-2-yl)phenyl]-3-bromo-pyrazolo[3,4-d]pyrimidin-6-yl]amino]-N,1-dimethyl-cyclopentane-carboxamide | | A |
| (1R,3R)-3-[[1-[3-(2-aminoethyl)-4-(5-methyl-1,3,4-oxadiazol-2-yl)phenyl]-3-bromopyrazolo[3,4-d]pyrimidin-6-yl]amino]-N,1-dimethyl-cyclopentane-carboxamide | | A |
| (1R,3R)-3-[[3-bromo-1-[8-(2-methoxy-ethoxy)-6-quinolyl]pyrazolo[3,4-d]pyrimidin-6-yl]amino]-N,1-dimethyl-cyclopentanecarboxamide | | AA |
| (1R,3R)-3-[[3-bromo-1-[4-(isoxazole-5-carbonyl)phenyl]pyrazolo[3,4-d]pyrimidin-6-yl]amino]-N,1-dimethyl-cyclopentanecarboxamide | | A |
| (1R,3R)-3-[[3-bromo-1-[8-[(E)-2-methyl-sulfonylvinyl]-6-quinolyl]pyrazolo[3,4-d]pyrimidin-6-yl]amino]-N,1-dimethyl-cyclopentanecarboxamide | | AA |
| (1R,3R)-3-[[3-bromo-1-[3-(2-methoxy-ethoxy)-6-quinolyl]pyrazolo[3,4-d]pyrimidin-6-yl]amino]-N,1-dimethyl-cyclopentanecarboxamide | | A |
| (1R,3R)-3-[[3-bromo-1-[6-(5-methyl-1,3,4-thiadiazol-2-yl)-3-pyridyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
| --- | --- | --- |
| (1R,3R)-3-[[3-bromo-1-[3-(3-methoxy-propanoylamino)-6-quinolyl]pyrazolo[3,4-d]pyrimidin-6-yl]amino]-N,1-dimethyl-cyclopentanecarboxamide | | A |
| (1R,3R)-3-[[3-bromo-1-[4-(5-ethyl-1,3,4-thiadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[4-[5-(methoxymethyl)-1,3,4-thiadiazol-2-yl]phenyl]pyrazolo[3,4-d]pyrimidin-6-yl]amino]-N,1-dimethyl-cyclopentanecarboxamide | | A |
| (1R,3R)-3-[[3-bromo-1-(8-morpholin-2-yl-6-quinolyl)pyrazolo[3,4-d]pyrimidin-6-yl]amino]-N,1-dimethyl-cyclopentane-carboxamide | | A |
| (1R,3R)-3-[[1-[8-(2-aminoethyl)-3-cyano-6-quinolyl]-3-bromo-pyrazolo[3,4-d]pyrimidin-6-yl]amino]-N,1-dimethyl-cyclopentane-carboxamide | | A |
| (1R,3R)-3-[[3-bromo-1-(8-piperazin-1-yl-6-quinolyl)pyrazolo[3,4-d]pyrimidin-6-yl]amino]-N,1-dimethyl-cyclopentanecarboxamide | | A |
| (1S,3R)-3-[[3-bromo-1-(8-piperazin-1-yl-6-quinolyl)pyrazolo[3,4-d]pyrimidin-6-yl]amino]-N,1-dimethyl-cyclopentane-carboxamide | | A |
| (1R,3R)-3-[[1-[8-(azetidin-3-yl)-6-quinolyl]-3-bromo-pyrazolo[3,4-d]pyrimidin-6-yl]amino]-N,1-dimethyl-cyclopentane-carboxamide | | A |
| (1R,3R)-3-[[1-[3-(aminomethyl)-4-(3-pyridyl)phenyl]-3-bromo-pyrazolo[3,4-d]pyrimidin-6-yl]amino]-N,1-dimethyl-cyclopentane-carboxamide | | A |
| (1R)-3-[[3-bromo-1-[3-fluoro-5-(oxetan-3-yl)phenyl]pyrazolo[3,4-d]pyrimidin-6-yl]amino]-N,1-dimethyl-cyclopentane-carboxamide | | A |
| 4-[3-bromo-6-[[(3R)-3-methyl-3-(methylcarbamoyl)cyclopentyl]amino]pyrazolo[3,4-d]pyrimidin-1-yl]-2-chloro-benzamide | | A |
| (1R)-3-[[3-bromo-1-(1-oxoisoindolin-5-yl)pyrazolo[3,4-d]pyrimidin-6-yl]amino]-N,1-dimethyl-cyclopentanecarboxamide | | A |
| (1R)-3-[[3-bromo-1-(2-oxo-3,4-dihydro-1H-quinolin-6-yl)pyrazolo[3,4-d]pyrimidin-6-yl]amino]-N,1-dimethyl-cyclopentane-carboxamide | | A |
| N-[6-[3-bromo-6-[[(1R,3R)-3-methyl-3-(methylcarbamoyl)cyclopentyl]amino]pyrazolo[3,4-d]pyrimidin-1-yl]-3-quinolyl]azetidine-3-carboxamide | | AA |
| (1R,3R)-3-[[1-[3-(3-aminopropanoylamino)-6-quinolyl]-3-bromo-pyrazolo[3,4-d]pyrimidin-6-yl]amino]-N,1-dimethyl-cyclopentanecarboxamide | | AA |
| (1R,3R)-3-[[1-[7-(2-aminoethyl)-2,3-dihydrobenzofuran-5-yl]-3-bromo-pyrazolo[3,4-d]pyrimidin-6-yl]amino]-N,1-dimethyl-cyclopentanecarboxamide | | A |
| (1R,3R)-3-[[1-[8-(3-aminopropanoylamino)-6-quinolyl]-3-bromo-pyrazolo[3,4-d]pyrimidin-6-yl]amino]-N,1-dimethyl-cyclopentanecarboxamide | | AA |
| N-[3-[3-bromo-6-[[(1R,3R)-3-methyl-3-(methylcarbamoyl)cyclopentyl]amino]pyrazolo[3,4-d]pyrimidin-1-yl]phenyl]thiazole-4-carboxamide | | A |
| (1R,3R)-3-[[1-[8-[(2-aminoacetyl)amino]-6-quinolyl]-3-bromo-pyrazolo[3,4-d]pyrimidin-6-yl]amino]-N,1-dimethyl-cyclopentanecarboxamide | | A |
| (1R)-3-[[3-bromo-1-(2-oxo-3,4-dihydro-1H-quinolin-7-yl)pyrazolo[3,4-d]pyrimidin-6-yl]amino]-N,1-dimethyl-cyclopentane-carboxamide | | A |

TABLE 3-continued

| Chemical Name | Chemical Structure | IC$_{50}$ Activity |
|---|---|---|
| (1R)-3-[[1-[2-(2-aminoethyl)indazol-5-yl]-3-bromo-pyrazolo[3,4-d]pyrimidin-6-yl]amino]-N,1-dimethyl-cyclopentane-carboxamide | | A |
| N-[3-[3-bromo-6-[[(1R,3R)-3-methyl-3-(methylcarbamoyl)cyclopentyl]amino]pyrazolo[3,4-d]pyrimidin-1-yl]phenyl]-1H-pyrazole-5-carboxamide | | A |
| (1R,3R)-3-[[1-[3-(2-aminoethyl)-4-cyano-phenyl]-3-bromo-pyrazolo[3,4-d]pyrimidin-6-yl]amino]-N,1-dimethyl-cyclopentanecarboxamide | | A |
| (1R,3R)-3-[[1-[3-(2-aminoethyl)-4-oxazol-2-yl-phenyl]-3-bromo-pyrazolo[3,4-d]pyrimidin-6-yl]amino]-N,1-dimethyl-cyclopentanecarboxamide | | A |
| (1R,3R)-3-[[1-[8-(2-aminoethyl)quinoxalin-6-yl]-3-bromo-pyrazolo[3,4-d]pyrimidin-6-yl]amino]-N,1-dimethyl-cyclopentane-carboxamide | | A |
| (1R,3R)-3-[[3-bromo-1-[4-oxazol-2-yl-3-[(3R)-pyrrolidin-3-yl]phenyl]pyrazolo[3,4-d]pyrimidin-6-yl]amino]-N,1-dimethyl-cyclopentane-carboxamide | | A |
| (1R,3R)-3-[[3-bromo-1-[4-oxazol-2-yl-3-[(3S)-pyrrolidin-3-yl]phenyl]pyrazolo[3,4-d]pyrimidin-6-yl]amino]-N,1-dimethyl-cyclopentanecarboxamide | | AA |
| (1R,3R)-3-[[1-[3-(azetidin-3-yl)-5-cyano-phenyl]-3-bromo-pyrazolo[3,4-d]pyrimidin-6-yl]amino]-N,1-dimethyl-cyclopentane-carboxamide | | A |
| (1R,3R)-3-[[1-[3-(2-aminoethyl)-4-(5-methyl-1,3,4-thiadiazol-2-yl)phenyl]-3-bromo-pyrazolo[3,4-d]pyrimidin-6-yl]amino]-1-methyl-cyclopentanecarboxylic acid | | A |
| (1R,3R)-3-[[1-[8-(4-aminobutanoylamino)-6-quinolyl]-3-bromo-pyrazolo[3,4-d]pyrimidin-6-yl]amino]-N,1-dimethyl-cyclopentanecarboxamide | | A |
| (1R,3R)-3-[[3-bromo-1-[3-(4-pyridyloxy)phenyl]pyrazolo[3,4-d]pyrimidin-6-yl]amino]-N,1-dimethyl-cyclopentane-carboxamide | | A |
| 3-[[3-bromo-1-(8-fluoro-6-quinolyl)pyrazolo[3,4-d]pyrimidin-6-yl]amino]cyclobutanol | | A |
| (1R,3R)-3-[[3-bromo-1-[4-oxazol-2-yl-3-(4-piperidyl)phenyl]pyrazolo[3,4-d]pyrimidin-6-yl]amino]-N,1-dimethyl-cyclopentanecarboxamide | | A |
| (1R,3R)-3-[[3-bromo-1-(3-oxo-4H-1,4-benzoxazin-7-yl)pyrazolo[3,4-d]pyrimidin-6-yl]amino]-N,1-dimethyl-cyclopentanecarboxamide | | A |
| (1R,3R)-3-[[1-[3-(3-aminopropyl)-4-(5-methyl-1,3,4-thiadiazol-2-yl)phenyl]-3-bromopyrazolo[3,4-d]pyrimidin-6-yl]amino]-N,1-dimethyl-cyclopentanecarboxamide | | A |
| (1R,3R)-3-[[1-[8-(3-aminopropyl)-6-quinolyl]-3-bromo-pyrazolo[3,4-d]pyrimidin-6-yl]amino]-N,1-dimethyl-cyclopentanecarboxamide | | A |
| 3-bromo-1-(8-fluoro-6-quinolyl)-N-tetrahydrofuran-3-yl-pyrazolo[3,4-d]pyrimidin-6-amine | | A |
| (1R)-3-[[3-bromo-1-(1-oxo-2H-isoquinolin-6-yl)pyrazolo[3,4-d]pyrimidin-6-yl]amino]-N,1-dimethyl-cyclopentanecarboxamide | | A |
| (1R,3R)-3-[[3-bromo-1-(8-fluoro-6-quinolyl)pyrazolo[3,4-d]pyrimidin-6-yl]amino]cyclopentanol | | A |
| (1R,2S)-2-[[3-bromo-1-(8-fluoro-6-quinolyl)pyrazolo[3,4-d]pyrimidin-6-yl]amino]cyclopentanol | | A |
| (1S,2S)-2-[[3-bromo-1-(8-fluoro-6-quinolyl)pyrazolo[3,4-d]pyrimidin-6-yl]amino]cyclopentanol | | A |

TABLE 3-continued

| Chemical Name | Chemical Structure | IC$_{50}$ Activity |
|---|---|---|
| 3-bromo-1-(8-fluoro-6-quinolyl)-N-(3-methoxycyclobutyl)pyrazolo[3,4-d]pyrimidin-6-amine | | A |
| (1R,3R)-3-[[3-bromo-1-[8-[2-[[(E)-4-(dimethylamino)but-2-enoyl]amino]ethyl]-6-quinolyl]pyrazolo[3,4-d]pyrimidin-6-yl]amino]-N,1-dimethyl-cyclopentane-carboxamide | | A |
| (1R,3R)-3-[[3-bromo-1-[8-[2-(prop-2-enoylamino)ethyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-[2-(but-2-ynoylamino)ethyl]-6-quinolyl]pyrazolo[3,4-d]pyrimidin-6-yl]amino]-N,1-dimethyl-cyclopentanecarboxamide | | A |
| (1R,3R)-3-[[1-[8-(2-aminoethyl)-3-quinolyl]-3-bromo-pyrazolo[3,4-d]pyrimidin-6-yl]amino]-N,1-dimethyl-cyclopentane-carboxamide | | A |
| (1R,3R)-3-[[3-bromo-1-[4-oxazol-2-yl-3-(3-piperidyl)phenyl]pyrazolo[3,4-d]pyrimidin-6-yl]amino]-N,1-dimethyl-cyclopentanecarboxamide | | A |
| 3-bromo-1-(8-fluoro-6-quinolyl)-N-(oxetan-3-yl)pyrazolo[3,4-d]pyrimidin-6-amine | | A |
| 3-[[1-[8-(2-aminoethyl)-6-quinolyl]-3-bromo-pyrazolo[3,4-d]pyrimidin-6-yl]amino]cyclobutanol | | A |
| 1-[4-[[3-bromo-1-(8-fluoro-6-quinolyl)pyrazolo[3,4-d]pyrimidin-6-yl]amino]-1-piperidyl]ethanone | | A |
| (1R,3R)-3-[[3-bromo-1-(1,2,3,4-tetrahydroquinolin-6-yl)pyrazolo[3,4-d]pyrimidin-6-yl]amino]-N,1-dimethyl-cyclopentanecarboxamide | | A |
| (1R,3R)-3-[[1-(8-amino-6-quinolyl)-3-bromo-pyrazolo[3,4-d]pyrimidin-6-yl]amino]-N,1-dimethyl-cyclopentane-carboxamide | | A |
| 3-bromo-1-(8-fluoro-6-quinolyl)-N-[(3S)-tetrahydrofuran-3-yl]pyrazolo[3,4-d]pyrimidin-6-amine | | A |
| (1R,3R)-3-[[3-bromo-1-[8-(2-morpholinoethyl)-6-quinolyl]pyrazolo[3,4-d]pyrimidin-6-yl]amino]-N,1-dimethyl-cyclopentanecarboxamide | | A |
| N-[5-[3-bromo-6-[[(1R,3R)-3-methyl-3-(methylcarbamoyl)cyclopentyl]amino]pyrazolo[3,4-d]pyrimidin-1-yl]-2-oxazol-2-yl-phenyl]azetidine-3-carboxamide | | AA |
| (3S)-N-[5-[3-bromo-6-[[(1R,3R)-3-methyl-3-(methylcarbamoyl)cyclopentyl]amino]pyrazolo[3,4-d]pyrimidin-1-yl]-2-oxazol-2-yl-phenyl]pyrrolidine-3-carboxamide | | AA |
| (3R)-N-[5-[3-bromo-6-[[(1R,3R)-3-methyl-3-(methylcarbamoyl)cyclopentyl]amino]pyrazolo[3,4-d]pyrimidin-1-yl]-2-oxazol-2-yl-phenyl]pyrrolidine-3-carboxamide | | AA |
| N-[5-[3-bromo-6-[[(1R,3R)-3-methyl-3-(methylcarbamoyl)cyclopentyl]amino]pyrazolo[3,4-d]pyrimidin-1-yl]-2-oxazol-2-yl-phenyl]piperidine-4-carboxamide | | AA |
| (1R,3R)-3-[[3-bromo-1-(4-dimethylphosphoryl-6-quinolyl)pyrazolo[3,4-d]pyrimidin-6-yl]amino]-N,1-dimethyl-cyclopentanecarboxamide | | A |
| (1R,3R)-3-[[3-bromo-1-[8-(hydroxymethyl)-6-quinolyl]pyrazolo[3,4-d]pyrimidin-6-yl]amino]-N,1-dimethyl-cyclopentanecarboxamide | | AA |
| (1R,3R)-3-[[3-bromo-1-[8-[(2,5-dioxopyrrolidin-1-yl)methyl]-6-quinolyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-[8-[(2,5-dioxo-imidazolidin-1-yl)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-[(2,6-dioxo-piperazin-1-yl)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-(methylsulfonylmethyl)-6-quinolyl]pyrazolo[3,4-d]pyrimidin-6-yl]amino]-N,1-dimethyl-cyclopentanecarboxamide | | A |
| (1R,3R)-3-[[1-[4-[5-(1-amino-1-methyl-ethyl)-1,3,4-thiadiazol-2-yl]-3-cyano-phenyl]-3-bromo-pyrazolo[3,4-d]pyrimidin-6-yl]amino]-N,1-dimethyl-cyclopentanecarboxamide | | A |
| (1R,3R)-3-[[1-(1,3-benzothiazol-6-yl)-3-bromo-pyrazolo[3,4-d]pyrimidin-6-yl]amino]-N,1-dimethyl-cyclopentane-carboxamide | | A |
| (1R,3R)-3-[[1-[4-[5-(1-amino-1-methyl-ethyl)-1,3,4-thiadiazol-2-yl]-3-fluoro-phenyl]-3-bromo-pyrazolo[3,4-d]pyrimidin-6-yl]amino]-N,1-dimethyl-cyclopentanecarboxamide | | AA |
| (1R,3R)-3-[[3-bromo-1-(5-cyano-3-pyridyl)pyrazolo[3,4-d]pyrimidin-6-yl]amino]-N,1-dimethyl-cyclopentane-carboxamide | | A |
| (1R,3R)-3-[[1-[8-(3-aminopropyl)-3-quinolyl]-3-bromo-pyrazolo[3,4-d]pyrimidin-6-yl]amino]-N,1-dimethyl-cyclopentanecarboxamide | | A |
| (1R,3R)-3-[[3-bromo-1-(3-oxo-2,4-dihydro-1H-isoquinolin-7-yl)pyrazolo[3,4-d]pyrimidin-6-yl]amino]-N,1-dimethyl-cyclopentanecarboxamide | | A |
| (1R,3R)-3-[[3-bromo-1-[4-(2-hydroxyethyl)-3-oxo-1,4-benzoxazin-7-yl]pyrazolo[3,4-d]pyrimidin-6-yl]amino]-N,1-dimethyl-cyclopentanecarboxamide | | A |
| (1R,3R)-3-[[3-bromo-1-[3-(2-methyl-sulfonylethyl)phenyl]pyrazolo[3,4-d]pyrimidin-6-yl]amino]-N,1-dimethyl-cyclopentanecarboxamide | | A |
| (1R,3R)-3-[[3-bromo-1-(4-cyano-3,5-dimethyl-phenyl)pyrazolo[3,4-d]pyrimidin-6-yl]amino]-N,1-dimethyl-cyclopentanecarboxamide | | A |
| 3-[[3-bromo-1-[4-(5-methyl-1,3,4-thiadiazol-2-yl)phenyl]pyrazolo[3,4-d]pyrimidin-6-yl]amino]cyclobutanol | | A |
| (1R,3R)-3-[[3-bromo-1-(2-oxo-1,5-dihydro-4,1-benzoxazepin-8-yl)pyrazolo[3,4-d]pyrimidin-6-yl]amino]-N,1-dimethyl-cyclopentanecarboxamide | | A |
| (1R,3R)-3-[[1-[3-(3-aminopropanoylamino)-4-oxazol-2-yl-phenyl]-3-bromo-pyrazolo[3,4-d]pyrimidin-6-yl]amino]-N,1-dimethyl-cyclopentane-carboxamide | | AA |
| 3-[[3-bromo-1-[4-(5-methyl-1,3,4-thiadiazol-2-yl)phenyl]pyrazolo[3,4-d]pyrimidin-6-yl]amino]cyclobutanol | | A |
| (1R,3R)-3-[[3-bromo-1-(2-oxo-1,5-dihydro-4,1-benzoxazepin-8-yl)pyrazolo[3,4-d]pyrimidin-6-yl]amino]-N,1-dimethyl-cyclopentanecarboxamide | | A |
| (1R,3R)-3-[[3-bromo-1-[8-(cyanomethyl)-6-quinolyl]pyrazolo[3,4-d]pyrimidin-6-yl]amino]-N,1-dimethyl-cyclopentane-carboxamide | | AA |
| (1R,3R)-3-[[3-bromo-1-[8-[(2-oxopiperazin-1-yl)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-[(7-oxo-1,4-diazepan-1-yl)methyl]-6-quinolyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[1-[4-[5-(1-amino-1-methyl-ethyl)-1,3,4-oxadiazol-2-yl]-3-fluoro-phenyl]-3-bromo-pyrazolo[3,4-d]pyrimidin-6-yl]amino]-N,1-dimethyl-cyclopentanecarboxamide | | A |
| (1R,3R)-3-[[1-[4-[5-(1-amino-1-methyl-ethyl)-1,3,4-oxadiazol-2-yl]-3-cyano-phenyl]-3-bromo-pyrazolo[3,4-d]pyrimidin-6-yl]amino]-N,1-dimethyl-cyclopentanecarboxamide | | AA |
| (1R,3R)-3-[[3-bromo-1-[8-[(E)-2-dimethylphosphorylvinyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[1-(2-hydroxy-ethyl)-2-oxo-3,4-dihydroquinolin-6-yl]pyrazolo[3,4-d]pyrimidin-6-yl]amino]-N,1-dimethyl-cyclopentanecarboxamide | | A |
| (1R,3R)-3-[[3-bromo-1-(2,3-dioxo-indolin-5-yl)pyrazolo[3,4-d]pyrimidin-6-yl]amino]-N,1-dimethyl-cyclo-pentanecarboxamide | | A |
| (1R,3R)-3-[[1-[2-(azetidine-3-carbonyl)isoindolin-5-yl]-3-bromo-pyrazolo[3,4-d]pyrimidin-6-yl]amino]-N,1-dimethyl-cyclopentanecarboxamide | | A |
| (1R,3R)-3-[[1-[2-(azetidine-3-carbonyl)-3,4-dihydro-1H-isoquinolin-6-yl]-3-bromo-pyrazolo[3,4-d]pyrimidin-6-yl]amino]-N,1-dimethyl-cyclopentanecarboxamide | | A |
| (1R,3R)-3-[[3-bromo-1-([1,2,4]triazolo[4,3-a]pyridin-6-yl)pyrazolo[3,4-d]pyrimidin-6-yl]amino]-N,1-dimethyl-cyclopentanecarboxamide | | A |
| (1R,3R)-3-[[3-bromo-1-(4-oxopyrido[1,2-a]pyrimidin-7-yl)pyrazolo[3,4-d]pyrimidin-6-yl]amino]-N,1-dimethyl-cyclopentanecarboxamide | | A |
| (1R,3R)-3-[[3-bromo-1-[8-[(1,1-dioxo-1,2-thiazolidin-2-yl)methyl]-6-quinolyl]pyrazolo[3,4-d]pyrimidin-6-yl]amino]-N,1-dimethyl-cyclopentanecarboxamide | | A |
| (1R,3R)-3-[[3-bromo-1-[8-(2-oxopiperazin-1-yl)-6-quinolyl]pyrazolo[3,4-d]pyrimidin-6-yl]amino]-N,1-dimethyl-cyclopentane-carboxamide | | A |
| (1R,3R)-3-[[3-bromo-1-(4-oxopyrido[1,2-a]pyrimidin-8-yl)pyrazolo[3,4-d]pyrimidin-6-yl]amino]-N,1-dimethyl-cyclopentane-carboxamide | | A |
| (1R,3R)-3-[[3-bromo-1-[3-(1-cyano-1-methyl-ethyl)-4-oxazol-2-yl-phenyl]pyrazolo[3,4-d]pyrimidin-6-yl]amino]-N,1-dimethyl-cyclopentanecarboxamide | | A |
| (1R,3R)-3-[[1-[4-[5-(1-aminoethyl)-1,3,4-thiadiazol-2-yl]phenyl]-3-bromo-pyrazolo[3,4-d]pyrimidin-6-yl]amino]-N,1-dimethyl-cyclopentanecarboxamide | | A |
| (1R,3R)-3-[[1-[3-(1-amino-1-methyl-ethyl)-8-fluoro-6-quinolyl]-3-bromo-pyrazolo[3,4-d]pyrimidin-6-yl]amino]-N,1-dimethyl-cyclopentanecarboxamide | | A |
| (1R,3R)-3-[[1-[4-[5-(aminomethyl)-1,3,4-thiadiazol-2-yl]phenyl]-3-bromo-pyrazolo[3,4-d]pyrimidin-6-yl]amino]-N,1-dimethyl-cyclopentanecarboxamide | | A |
| (1R,3R)-3-[[3-bromo-1-[8-(2-cyanoethyl)-6-quinolyl]pyrazolo[3,4-d]pyrimidin-6-yl]amino]-N,1-dimethyl-cyclopentane-carboxamide | | AA |
| (1R,3R)-3-[[3-bromo-1-(2-formyl-3,4-dihydro-1H-isoquinolin-7-yl)pyrazolo[3,4-d]pyrimidin-6-yl]amino]-N,1-dimethyl-cyclopentanecarboxamide | | A |
| (1R,3R)-3-[[3-bromo-1-(2-methylsulfonyl-3,4-dihydro-1H-isoquinolin-7-yl)pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-(2-methylsulfonyl-3,4-dihydro-1H-isoquinolin-6-yl)pyrazolo[3,4-d]pyrimidin-6-yl]amino]-N,1-dimethyl-cyclopentanecarboxamide | | A |
| (1R,3R)-3-[[3-bromo-1-[2-(2-hydroxyacetyl)-3,4-dihydro-1H-isoquinolin-7-yl]pyrazolo[3,4-d]pyrimidin-6-yl]amino]-N,1-dimethyl-cyclopentanecarboxamide | | A |
| (1R,3R)-3-[[3-bromo-1-[2-(1-methylazetidine-3-carbonyl)-3,4-dihydro-1H-isoquinolin-6-yl]pyrazolo[3,4-d]pyrimidin-6-yl]amino]-N,1-dimethyl-cyclopentanecarboxamide | | A |
| (1R,3R)-3-[[3-bromo-1-[(3R)-3-(methanesulfonamido)indan-5-yl]pyrazolo[3,4-d]pyrimidin-6-yl]amino]-N,1-dimethyl-cyclopentanecarboxamide | | A |
| N-[3-[3-bromo-6-[[(1R,3R)-3-methyl-3-(methylcarbamoyl)cyclopentyl]amino]pyrazolo[3,4-d]pyrimidin-1-yl]-5-chloro-phenyl]azetidine-3-carboxamide | | A |
| N-(azetidin-3-yl)-3-[3-bromo-6-[[(1R,3R)-3-methyl-3-(methylcarbamoyl)cyclopentyl]amino]pyrazolo[3,4-d]pyrimidin-1-yl]-5-chloro-benzamide | | A |
| N-(azetidin-3-yl)-3-[3-bromo-6-[[(1R,3R)-3-methyl-3-(methylcarbamoyl)cyclopentyl]amino]pyrazolo[3,4-d]pyrimidin-1-yl]-5-chloro-N-methyl-benzamide | | A |
| (1R,3R)-3-[[3-bromo-1-[3-chloro-5-(piperazine-1-carbonyl)phenyl]pyrazolo[3,4-d]pyrimidin-6-yl]amino]-N,1-dimethyl-cyclopentanecarboxamide | | A |
| 3-[3-bromo-6-[[(1R,3R)-3-methyl-3-(methylcarbamoyl)cyclopentyl]amino]pyrazolo[3,4-d]pyrimidin-1-yl]-5-chloro-N-methyl-benzamide | | A |
| 3-[3-bromo-6-[[(1R,3R)-3-methyl-3-(methylcarbamoyl)cyclopentyl]amino]pyrazolo[3,4-d]pyrimidin-1-yl]-5-chloro-N,N-dimethyl-benzamide | | A |
| (1R,3R)-3-[[3-bromo-1-(1,3-dioxo-isoindolin-5-yl)pyrazolo[3,4-d]pyrimidin-6-yl]amino]-N,1-dimethyl-cyclopentanecarboxamide | | A |
| 3-[6-[3-bromo-6-[[(1R,3R)-3-methyl-3-(methylcarbamoyl)cyclopentyl]amino]pyrazolo[3,4-d]pyrimidin-1-yl]-8-quinolyl]propanoic acid | | AA |
| 3-[5-[3-bromo-6-[[(1R,3R)-3-methyl-3-(methylcarbamoyl)cyclopentyl]amino]pyrazolo[3,4-d]pyrimidin-1-yl]-2-(5-methyl-1,3,4-thiadiazol-2-yl)phenyl]propanoic acid | | A |
| (1R,3R)-3-[[1-[8-(2-aminoethyl)-6-iso-quinolyl]-3-bromo-pyrazolo[3,4-d]pyrimidin-6-yl]amino]-N,1-dimethyl-cyclopentanecarboxamide | | AA |
| (1R,3R)-3-[[1-[1-(azetidine-3-carbonyl)indolin-6-yl]-3-bromo-pyrazolo[3,4-d]pyrimidin-6-yl]amino]-N,1-dimethyl-cyclopentanecarboxamide | | A |
| (1R,3R)-3-[[3-bromo-1-[4-cyano-3-(hydroxymethyl)phenyl]pyrazolo[3,4-d]pyrimidin-6-yl]amino]-N,1-dimethyl-cyclopentanecarboxamide | | A |
| (1R,3R)-3-[[3-bromo-1-[3-(hydroxymethyl)-4-oxazol-2-yl-phenyl]pyrazolo[3,4-d]pyrimidin-6-yl]amino]-N,1-dimethyl-cyclopentanecarboxamide | | A |
| (1R,3R)-3-[[3-bromo-1-[2-[1-(2,2,2-trifluoroacetyl)azetidine-3-carbonyl]-3,4-dihydro-1H-isoquinolin-7-yl]pyrazolo[3,4-d]pyrimidin-6-yl]amino]-N,1-dimethyl-cyclopentanecarboxamide | | A |
| (1R,3R)-3-[[3-bromo-1-[4-cyano-3-(methanesulfonamidomethyl)phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-(1-oxo-3H-iso-benzofuran-5-yl)pyrazolo[3,4-d]pyrimidin-6-yl]amino]-N,1-dimethyl-cyclopentane-carboxamide | | A |
| (1R,3R)-3-[[3-bromo-1-[4-(1-methyl-pyrazol-3-yl)phenyl]pyrazolo[3,4-d]pyrimidin-6-yl]amino]-N,1-dimethyl-cyclopentanecarboxamide | | A |
| (1R,3R)-3-[[3-bromo-1-[4-(1-methyl-pyrazol-4-yl)phenyl]pyrazolo[3,4-d]pyrimidin-6-yl]amino]-N,1-dimethyl-cyclopentanecarboxamide | | A |
| (1R,3R)-3-[[3-bromo-1-[3-[(2-cyanoacetyl)amino]-4-oxazol-2-yl-phenyl]pyrazolo[3,4-d]pyrimidin-6-yl]amino]-N,1-dimethyl-cyclopentanecarboxamide | | A |
| (1R,3R)-3-[[1-[3-(azetidin-3-ylmethoxy)-5-cyano-phenyl]-3-bromo-pyrazolo[3,4-d]pyrimidin-6-yl]amino]-N,1-dimethyl-cyclopentanecarboxamide | | AA |
| (1R,3R)-3-[[1-[3-(azetidin-3-yloxy)-5-cyano-phenyl]-3-bromo-pyrazolo[3,4-d]pyrimidin-6-yl]amino]-N,1-dimethyl-cyclopentanecarboxamide | | A |
| (1R,3R)-3-[[3-bromo-1-[3-(2-methyl-sulfonylethyl)-4-(5-methyl-1,3,4-thiadiazol-2-yl)phenyl]pyrazolo[3,4-d]pyrimidin-6-yl]amino]-N,1-dimethyl-cyclopentanecarboxamide | | A |
| (1R,3R)-3-[[1-[2-(1-amino-1-methyl-ethyl)-8-fluoro-6-quinolyl]-3-bromo-pyrazolo[3,4-d]pyrimidin-6-yl]amino]-N,1-dimethyl-cyclopentanecarboxamide | | A |
| (1R,3R)-3-[[1-[3-(2-amino-1,1-dimethyl-ethyl)-4-oxazol-2-yl-phenyl]-3-bromo-pyrazolo[3,4-d]pyrimidin-6-yl]amino]-N,1-dimethyl-cyclopentanecarboxamide | | A |
| (1R,3R)-3-[[3-bromo-1-[3-[2-(methylamino)ethyl]-4-oxazol-2-yl-phenyl]pyrazolo[3,4-d]pyrimidin-6-yl]amino]-N,1-dimethyl-cyclopentanecarboxamide | | A |
| (1R,3R)-3-[[3-bromo-1-[3-[2-(dimethylamino)-2-oxo-ethyl]-4-oxazol-2-yl-phenyl]pyrazolo[3,4-d]pyrimidin-6-yl]amino]-N,1-dimethyl-cyclopentanecarboxamide | | A |
| (1R,3R)-3-[[3-bromo-1-(4-methyl-3-oxo-pyrido[3,2-b][1,4]oxazin-7-yl)pyrazolo[3,4-d]pyrimidin-6-yl]amino]-N,1-dimethyl-cyclopentanecarboxamide | | A |
| (1R,3R)-3-[[1-[3-(azetidin-3-ylmethoxy)-5-cyano-phenyl]-3-bromo-pyrazolo[3,4-d]pyrimidin-6-yl]amino]-1-(2,2-difluoroethyl)-N-methyl-cyclopentanecarboxamide | | A |
| (1R,3R)-3-[[3-bromo-1-(4-ethyl-3-oxo-1,4-benzoxazin-7-yl)pyrazolo[3,4-d]pyrimidin-6-yl]amino]-N,1-dimethyl-cyclopentane-carboxamide | | A |
| (1R,3R)-3-[[3-bromo-1-[3-oxo-4-(2,2,2-trifluoroethyl)-1,4-benzoxazin-7-yl]pyrazolo[3,4-d]pyrimidin-6-yl]amino]-N,1-dimethyl-cyclopentanecarboxamide | | A |
| (1R,3R)-3-[[3-bromo-1-(4-isopropyl-3-oxo-1,4-benzoxazin-7-yl)pyrazolo[3,4-d]pyrimidin-6-yl]amino]-N,1-dimethyl-cyclopentanecarboxamide | | A |
| (1R,3R)-3-[[3-bromo-1-[4-(cyanomethyl)-3-oxo-1,4-benzoxazin-7-yl]pyrazolo[3,4-d]pyrimidin-6-yl]amino]-N,1-dimethyl-cyclopentanecarboxamide | | A |
| (1R,3R)-3-[[3-bromo-1-[3-(2-hydroxypropyl)-4-(5-methyl-1,3,4-thiadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[3-(2-hydroxyethyl)-4-(5-methyl-1,3,4-thiadiazol-2-yl)phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-(8-pyrrolidin-3-yl-6-quinolyl)pyrazolo[3,4-d]pyrimidin-6-yl]amino-N,1-dimethyl-cyclopentane-carboxamide | | AA |
| (1R,3R)-3-[[3-bromo-1-[3-cyano-5-(cyanomethoxy)phenyl]pyrazolo[3,4-d]pyrimidin-6-yl]amino]-N,1-dimethyl-cyclopentanecarboxamide | | A |
| (1R,3R)-3-[[3-bromo-1-[3-cyano-5-(2-methoxyethoxy)phenyl]pyrazolo[3,4-d]pyrimidin-6-yl]amino]-N,1-dimethyl-cyclopentanecarboxamide | | A |
| (1R,3R)-3-[[3-bromo-1-[3-cyano-5-(2-hydroxyethoxy)phenyl]pyrazolo[3,4-d]pyrimidin-6-yl]amino]-N,1-dimethyl-cyclopentanecarboxamide | | A |
| (1R,3R)-3-[[3-bromo-1-[3-(methane-sulfonamidomethyl)-4-oxazol-2-yl-phenyl]pyrazolo[3,4-d]pyrimidin-6-yl]amino]-N,1-dimethyl-cyclopentanecarboxamide | | A |
| (1R,3R)-3-[[3-bromo-1-(1,7-naphthyridin-6-yl)pyrazolo[3,4-d]pyrimidin-6-yl]amino-N,1-dimethyl-cyclopentane-carboxamide | | A |
| (1R,3R)-3-[[3-bromo-1-[3-(oxetan-3-ylamino)phenyl]pyrazolo[3,4-d]pyrimidin-6-yl]amino]-N,1-dimethyl-cyclopentanecarboxamide | | A |
| (1R,3R)-3-[[3-bromo-1-(2,4-dimethyl-3-oxo-1,4-benzoxazin-7-yl)pyrazolo[3,4-d]pyrimidin-6-yl]amino]-N,1-dimethyl-cyclopentanecarboxamide | | A |
| (1R,3R)-3-[[3-bromo-1-(2,2-dioxo-1,3-dihydro-2-benzothiophen-5-yl)pyrazolo[3,4-d]pyrimidin-6-yl]amino]-N,1-dimethyl-cyclopentanecarboxamide | | A |
| (1R,3R)-3-[[3-bromo-1-(2,2,4-trimethyl-3-oxo-1,4-benzoxazin-7-yl)pyrazolo[3,4-d]pyrimidin-6-yl]amino]-N,1-dimethyl-cyclopentanecarboxamide | | A |
| (1R,3R)-3-[[3-bromo-1-(1,3-dimethyl-2,4-dioxo-quinazolin-7-yl)pyrazolo[3,4-d]pyrimidin-6-yl]amino]-N,1-dimethyl-cyclopentanecarboxamide | | AA |
| (1R,3R)-3-[[1-[3-(azetidin-3-ylmethoxy)-4-oxazol-2-yl-phenyl]-3-bromo-pyrazolo[3,4-d]pyrimidin-6-yl]amino]-N,1-dimethyl-cyclopentanecarboxamide | | A |
| [(1R,3R)-3-[[3-bromo-1-[4-(5-methyl-1,3,4-thiadiazol-2-yl)phenyl]pyrazolo[3,4-d]pyrimidin-6-yl]amino]-1-methyl-cyclopentyl]-morpholino-methanone | | A |
| [(1R,3R)-3-[[3-bromo-1-[4-(5-methyl-1,3,4-thiadiazol-2-yl)phenyl]pyrazolo[3,4-d]pyrimidin-6-yl]amino]-1-methyl-cyclopentyl]-pyrrolidin-1-yl-methanone | | A |
| 3-bromo-N-(3-dimethylphosphorylcyclobutyl)-1-[4-(5-methyl-1,3,4-thiadiazol-2-yl)phenyl]pyrazolo[3,4-d]pyrimidin-6-amine | | A |
| (1R,3R)-3-[[3-bromo-1-[3-[(1R)-1-cyanoethyl]-4-oxazol-2-yl-phenyl]pyrazolo[3,4-d]pyrimidin-6-yl]amino]-N,1-dimethyl-cyclopentane-carboxamide | | A |
| (1R,3R)-3-[[3-bromo-1-[3-[(1S)-1-cyanoethyl]-4-oxazol-2-yl-phenyl]pyrazolo[3,4-d]pyrimidin-6-yl]amino]-N,1-dimethyl-cyclopentane-carboxamide | | A |
| (1R,3R)-3-[[3-bromo-1-[8-(hydroxymethyl)quinoxalin-6-yl]pyrazolo[3,4-d]pyrimidin-6-yl]amino]-N,1-dimethyl-cyclopentane-carboxamide | | A |
| (1R,3R)-3-[[3-bromo-1-[4-cyano-3-[(3-fluoroazetidin-3-yl)methoxy]phenyl]pyrazolo[3,4-d]pyrimidin-6-yl]amino]-N,1-dimethyl-cyclopentanecarboxamide | | A |
| (1R,3R)-3-[[3-bromo-1-[3-cyano-5-(2-hydroxypropoxy)phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-[4-cyano-3-(2-hydroxypropoxy)phenyl]pyrazolo[3,4-d]pyrimidin-6-yl]amino]-N,1-dimethyl-cyclopentanecarboxamide | | A |
| (1R,3R)-3-[[3-bromo-1-[4-cyano-3-(2-hydroxyethoxy)phenyl]pyrazolo[3,4-d]pyrimidin-6-yl]amino]-N,1-dimethyl-cyclopentanecarboxamide | | A |
| (1R,3R)-3-[[3-bromo-1-[4-cyano-3-(2-methoxyethoxy)phenyl]pyrazolo[3,4-d]pyrimidin-6-yl]amino]-N,1-dimethyl-cyclopentanecarboxamide | | A |
| (1R,3R)-3-[[3-bromo-1-[4-(5-methyl-1,3,4-thiadiazol-2-yl)-3-(2-morpholino-ethyl)phenyl]pyrazolo[3,4-d]pyrimidin-6-yl]amino]-N,1-dimethyl-cyclo-pentanecarboxamide | | A |
| (1R,3R)-3-[[3-bromo-1-(4-methyl-3-oxo-1,4-benzothiazin-7-yl)pyrazolo[3,4-d]pyrimidin-6-yl]amino]-N,1-dimethyl-cyclopentanecarboxamide | | A |
| (1R,3R)-3-[[1-[3-[(1S)-2-amino-1-methyl-ethyl]-4-oxazol-2-yl-phenyl]-3-bromo-pyrazolo[3,4-d]pyrimidin-6-yl]amino]-N,1-dimethyl-cyclopentanecarboxamide | | A |
| (1R,3R)-3-[[3-bromo-1-(5-hydroxy-4-methyl-3-oxo-1,4-benzoxazin-7-yl)pyrazolo[3,4-d]pyrimidin-6-yl]amino]-N,1-dimethyl-cyclo-pentanecarboxamide | | A |
| (1R,3R)-3-[[1-[8-(aminomethyl)quinoxalin-6-yl]-3-bromo-pyrazolo[3,4-d]pyrimidin-6-yl]amino]-N,1-dimethyl-cyclopentane-carboxamide | | A |
| (1R,3R)-3-[[3-bromo-1-[8-(methane-sulfonamidomethyl)quinoxalin-6-yl]pyrazolo[3,4-d]pyrimidin-6-yl]amino]-N,1-dimethyl-cyclopentanecarboxamide | | A |
| (1R,3R)-3-[[3-bromo-1-[8-(methyl-sulfonylmethyl)quinoxalin-6-yl]pyrazolo[3,4-d]pyrimidin-6-yl]amino]-N,1-dimethyl-cyclopentanecarboxamide | | A |
| (1R,3R)-3-[[3-bromo-1-[8-(cyanomethyl)quinoxalin-6-yl]pyrazolo[3,4-d]pyrimidin-6-yl]amino]-N,1-dimethyl-cyclopentane-carboxamide | | A |
| 3-bromo-N-[(1R,3R)-3-dimethylphosphoryl-cyclopentyl]-1-[3-(2-methylsulfonylethyl)-4-(5-methyl-1,3,4-thiadiazol-2-yl)phenyl]pyrazolo[3,4-d]pyrimidin-6-amine | | A |
| 3-[3-bromo-6-[[(1R,3R)-3-dimethylphosphorylcyclopentyl]amino]pyrazolo[3,4-d]pyrimidin-1-yl]-5-[(3-fluoroazetidin-3-yl)methoxy]benzonitrile | | A |
| 3-bromo-N-[(1R,3R)-3-dimethylphosphoryl-cyclopentyl]-1-(8-fluoro-2-methyl-6-quinolyl)pyrazolo[3,4-d]pyrimidin-6-amine | | A |
| 2-[6-[3-bromo-6-[[(1R,3R)-3-dimethyl-phosphorylcyclopentyl]amino]pyrazolo[3,4-d]pyrimidin-1-yl]-2-methyl-8-quinolyl]ethanol | | A |
| 3-bromo-N-[(1R,3R)-3-dimethylphosphoryl-cyclopentyl]-1-(8-pyrrolidin-3-yl-6-quinolyl)pyrazolo[3,4-d]pyrimidin-6-amine | | A |
| 1-[8-(2-aminoethyl)quinoxalin-6-yl]-3-bromo-N-[(1R,3R)-3-dimethylphosphorylcyclopentyl]pyrazolo[3,4-d]pyrimidin-6-amine | | A |
| 3-bromo-N-(3-dimethylphosphorylcyclo-butyl)-1-[3-(2-methylsulfonylethyl)-4-(5-methyl-1,3,4-thiadiazol-2-yl)phenyl]pyrazolo[3,4-d]pyrimidin-6-amine | | A |
| 3-[5-[3-bromo-6-[(3-dimethylphosphoryl-cyclobutyl)amino]pyrazolo[3,4-d]pyrimidin-1-yl]-2-(5-methyl-1,3,4-thiadiazol-2-yl)phenyl]propanenitrile | | A |
| (1R,3R)-3-[[3-bromo-1-(4-pyrazol-1-ylphenyl)pyrazolo[3,4-d]pyrimidin-6-yl]amino]-N,1-dimethyl-cyclopentane-carboxamide | | A |

TABLE 3-continued

| Chemical Name | Chemical Structure | IC$_{50}$ Activity |
|---|---|---|
| (1R,3R)-3-[[3-bromo-1-[5-(cyanomethoxy)-4-methyl-3-oxo-1,4-benzoxazin-7-yl]pyrazolo[3,4-d]pyrimidin-6-yl]amino]-N,1-dimethyl-cyclopentanecarboxamide | | AA |
| (1R,3R)-3-[[3-bromo-1-[5-(2-hydroxyethoxy)-4-methyl-3-oxo-1,4-benzoxazin-7-yl]pyrazolo[3,4-d]pyrimidin-6-yl]amino]-N,1-dimethyl-cyclopentanecarboxamide | | AA |
| (1R,3R)-3-[[3-bromo-1-[5-(2,2-difluoroethoxy)-4-methyl-3-oxo-1,4-benzoxazin-7-yl]pyrazolo[3,4-d]pyrimidin-6-yl]amino]-N,1-dimethyl-cyclopentanecarboxamide | | AA |
| (1R,3R)-3-[[3-bromo-1-[4-(5-methyl-pyrazol-1-yl)phenyl]pyrazolo[3,4-d]pyrimidin-6-yl]amino]-N,1-dimethyl-cyclopentanecarboxamide | | A |
| (1R)-3-[[3-bromo-1-[5-chloro-6-(5-methyl-1,3,4-thiadiazol-2-yl)-3-pyridyl]pyrazolo[3,4-d]pyrimidin-6-yl]amino]-N,1-dimethyl-cyclopentanecarboxamide | | A |
| (1R)-3-[[3-bromo-1-[5-fluoro-6-(5-methyl-1,3,4-thiadiazol-2-yl)-3-pyridyl]pyrazolo[3,4-d]pyrimidin-6-yl]amino]-N,1-dimethyl-cyclopentanecarboxamide | | A |
| (1R,3R)-3-[[3-bromo-1-[4-[5-(morpholine-4-carbonyl)-1,3,4-thiadiazol-2-yl]phenyl]pyrazolo[3,4-d]pyrimidin-6-yl]amino]-N,1-dimethyl-cyclopentanecarboxamide | | A |
| 3-bromo-1-[4-(5-methyl-1,3,4-thiadiazol-2-yl)phenyl]-N-[(3R)-tetrahydrofuran-3-yl]pyrazolo[3,4-d]pyrimidin-6-amine | | A |
| 3-bromo-1-[4-(5-methyl-1,3,4-thiadiazol-2-yl)phenyl]-N-tetrahydrofuran-3-yl-pyrazolo[3,4-d]pyrimidin-6-amine | | A |
| (1R,3R)-3-[[3-bromo-1-[4-(5-methyl-1,3,4-thiadiazol-2-yl)-3-(3,3,3-trifluoro-2-hydroxy-propyl)phenyl]pyrazolo[3,4-d]pyrimidin-6-yl]amino]-N,1-dimethyl-cyclopentanecarboxamide | | A |
| 3-bromo-N-[(1R,3R)-3-dimethylphosphoryl-cyclohexyl]-1-[4-(5-methyl-1,3,4-thiadiazol-2-yl)phenyl]pyrazolo[3,4-d]pyrimidin-6-amine | | A |
| (1R,3R)-3-[[3-bromo-1-(5-methoxy-4-methyl-3-oxo-1,4-benzoxazin-7-yl)pyrazolo[3,4-d]pyrimidin-6-yl]amino]-N,1-dimethyl-cyclopentanecarboxamide | | AA |
| 3-bromo-N-[(1R,3S)-3-dimethylphosphoryl-cyclopentyl]-1-[4-(5-methyl-1,3,4-thiadiazol-2-yl)phenyl]pyrazolo[3,4-d]pyrimidin-6-amine | | A |
| (1R,3R)-3-[[3-bromo-1-[3-[(2,2-difluoroethylamino)methyl]-4-oxazol-2-yl-phenyl]pyrazolo[3,4-d]pyrimidin-6-yl]amino]-N,1-dimethyl-cyclopentanecarboxamide | | A |
| (1R,3R)-3-[[3-bromo-1-[4-(5-methyl-1,2,4-oxadiazol-3-yl)phenyl]pyrazolo[3,4-d]pyrimidin-6-yl]amino]-N,1-dimethyl-cyclopentanecarboxamide | | A |
| (1R,3R)-3-[[1-[3-(2-amino-3,3,3-trifluoro-propyl)-4-(5-methyl-1,3,4-thiadiazol-2-yl)phenyl]-3-bromo-pyrazolo[3,4-d]pyrimidin-6-yl]amino]-N,1-dimethyl-cyclopentanecarboxamide | | A |
| (1R,3R)-3-[[3-bromo-1-[4-(5-methyl-1,3,4-thiadiazol-2-yl)-3-[2-(2,2,2-trifluoroethylamino)ethyl]phenyl]pyrazolo[3,4-d]pyrimidin-6-yl]amino]-N,1-dimethyl-cyclopentanecarboxamide | | A |
| (1R,3R)-3-[[3-bromo-1-[3-(2-hydroxy-ethoxy)-4-oxazol-2-yl-phenyl]pyrazolo[3,4-d]pyrimidin-6-yl]amino]-N,1-dimethyl-cyclopentanecarboxamide | | AA |
| (1R,3R)-3-[[3-bromo-1-[3-(2-morpholino-ethyl)-4-oxazol-2-yl-phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[3-bromo-1-[4-(5-cyano-1-methyl-pyrazol-4-yl)phenyl]pyrazolo[3,4-d]pyrimidin-6-yl]amino]-N,1-dimethyl-cyclopentane-carboxamide | | A |
| (1R,3R)-3-[[3-bromo-1-[3-[(3-fluoroazetidin-3-yl)methoxy]-5-(trifluoromethoxy)phenyl]pyrazolo[3,4-d]pyrimidin-6-yl]amino]-N,1-dimethyl-cyclopentanecarboxamide | | A |
| (1R,3R)-3-[[3-bromo-1-[3-chloro-5-[(3-fluoroazetidin-3-yl)methoxy]phenyl]pyrazolo[3,4-d]pyrimidin-6-yl]amino]-N,1-dimethyl-cyclopentanecarboxamide | | AA |
| (1R,3R)-3-[[3-bromo-1-[3-chloro-5-(2-hydroxypropoxy)phenyl]pyrazolo[3,4-d]pyrimidin-6-yl]amino]-N,1-dimethyl-cyclopentanecarboxamide | | A |
| (1R,3R)-3-[[3-bromo-1-[8-(1-hydroxy-ethyl)quinoxalin-6-yl]pyrazolo[3,4-d]pyrimidin-6-yl]amino]-N,1-dimethyl-cyclopentanecarboxamide | | A |
| (1R,3R)-3-[[3-bromo-1-[8-[(oxetan-3-ylsulfonylamino)methyl]quinoxalin-6-yl]pyrazolo[3,4-d]pyrimidin-6-yl]amino]-N,1-dimethyl-cyclopentane-carboxamide | | A |
| (1R,3R)-3-[[3-bromo-1-[8-(methane-sulfinamidomethyl)quinoxalin-6-yl]pyrazolo[3,4-d]pyrimidin-6-yl]amino]-N,1-dimethyl-cyclopentane-carboxamide | | A |
| (1R,3R)-3-[[1-[3-[2-(azetidin-3-yl)ethyl]-5-cyano-phenyl]-3-bromo-pyrazolo[3,4-d]pyrimidin-6-yl]amino]-N,1-dimethyl-cyclopentanecarboxamide | | A |
| (1R,3R)-3-[[3-bromo-1-[3-chloro-5-(methylsulfonylmethyl)phenyl]pyrazolo[3,4-d]pyrimidin-6-yl]amino]-N,1-dimethyl-cyclopentanecarboxamide | | A |
| (1R,3R)-3-[[3-bromo-1-[3-chloro-5-(cyanomethyl)phenyl]pyrazolo[3,4-d]pyrimidin-6-yl]amino]-N,1-dimethyl-cyclopentanecarboxamide | | A |
| (1R,3R)-3-[[3-bromo-1-[2-(oxetan-3-ylsulfonyl)isoindolin-5-yl]pyrazolo[3,4-d]pyrimidin-6-yl]amino]-N,1-dimethyl-cyclopentanecarboxamide | | A |
| (1R,3R)-3-[[3-bromo-1-[2-(2,2-difluoroethylsulfonyl)isoindolin-5-yl]pyrazolo[3,4-d]pyrimidin-6-yl]amino]-N,1-dimethyl-cyclopentanecarboxamide | | A |
| (1R,3R)-3-[[3-bromo-1-(4-methyl-1,1,3-trioxo-1λ^{6},4-benzothiazin-7-yl)pyrazolo[3,4-d]pyrimidin-6-yl]amino]-N,1-dimethyl-cyclopentanecarboxamide | | A |
| (1R,3R)-3-[[3-bromo-1-[3-chloro-5-(methanesulfonamidomethyl)phenyl]pyrazolo[3,4-d]pyrimidin-6-yl]amino]-N,1-dimethyl-cyclopentanecarboxamide | | A |
| (1R,3R)-3-[[3-bromo-1-(1,4-dimethyl-2,3-dioxo-quinoxalin-6-yl)pyrazolo[3,4-d]pyrimidin-6-yl]amino]-N,1-dimethyl-cyclopentanecarboxamide | | A |
| (1R,3R)-3-[[3-bromo-1-[1-(cyano-methyl)-2-oxo-3,4-dihydroquinolin-6-yl]pyrazolo[3,4-d]pyrimidin-6-yl]amino]-N,1-dimethyl-cyclopentane-carboxamide | | A |
| (1R,3R)-3-[[3-bromo-1-[1-(2,2-difluoro-ethyl)-2-oxo-3,4-dihydroquinolin-6-yl]pyrazolo[3,4-d]pyrimidin-6-yl]amino]-N,1-dimethyl-cyclopentanecarboxamide | | A |
| 3-bromo-N-[(1R)-3-methylsulfonylcyclopentyl]-1-[4-(5-methyl-1,3,4-thiadiazol-2-yl)phenyl]pyrazolo[3,4-d]pyrimidin-6-amine | | A |
| 5-[4-[3-bromo-6-[[(1R,3R)-3-methyl-3-(methylcarbamoyl)cyclopentyl]amino]pyrazolo[3,4-d]pyrimidin-1-yl]phenyl]-N-[2-(dimethylamino)ethyl]-N-methyl-1,3,4-thiadiazole-2-carboxamide | | A |

TABLE 3-continued

| Chemical Name | Chemical Structure | IC$_{50}$ Activity |
|---|---|---|
| (1R,3R)-3-[[3-bromo-1-[4-[5-(piperazine-1-carbonyl)-1,3,4-thiadiazol-2-yl]phenyl]pyrazolo[3,4-d]pyrimidin-6-yl]amino]-N,1-dimethyl-cyclopentanecarboxamide | | A |
| (1R,3R)-3-[[3-bromo-1-[3-(methylsulfonylmethoxy)-4-(5-methyl-1,3,4-thiadiazol-2-yl)phenyl]pyrazolo[3,4-d]pyrimidin-6-yl]amino]-N,1-dimethyl-cyclopentanecarboxamide | | A |
| (1R,3R)-3-[[3-bromo-1-[3-(cyanomethoxy)-4-(5-methyl-1,3,4-thiadiazol-2-yl)phenyl]pyrazolo[3,4-d]pyrimidin-6-yl]amino]-N,1-dimethyl-cyclopentanecarboxamide | | A |
| 1-[8-(2-aminoethyl)quinoxalin-6-yl]-3-bromo-N-[(1R)-3-methylsulfonylcyclopentyl]pyrazolo[3,4-d]pyrimidin-6-amine | | AA |
| (1R,3R)-3-[[3-bromo-1-(2-ethylsulfonyl-isoindolin-5-yl)pyrazolo[3,4-d]pyrimidin-6-yl]amino]-N,1-dimethyl-cyclopentanecarboxamide | | A |
| (1R,3R)-3-[[3-bromo-1-(6-ethylsulfonyl-5,7-dihydropyrrolo[3,4-b]pyridin-3-yl)pyrazolo[3,4-d]pyrimidin-6-yl]amino]-N,1-dimethyl-cyclopentanecarboxamide | | A |
| N-[[3-[3-bromo-6-[[(1R,3R)-3-methyl-3-(methylcarbamoyl)cyclopentyl]amino]pyrazolo[3,4-d]pyrimidin-1-yl]-5-chloro-phenyl]methyl]methanesulfonimidic acid | | A |
| (1R,3R)-3-[[1-[8-[(1S)-1-aminoethyl]quinoxalin-6-yl]-3-bromo-pyrazolo[3,4-d]pyrimidin-6-yl]amino]-N,1-dimethyl-cyclopentanecarboxamide | | A |
| (1R,3R)-3-[[3-bromo-1-[4-(5-methyl-1,3,4-thiadiazol-2-yl)phenyl]pyrazolo[3,4-d]pyrimidin-6-yl]amino]-N-(2-methoxyethyl)-1-methyl-cyclopentanecarboxamide | | A |
| (1R)-3-[[3-bromo-1-[4-(5-methyl-1,3,4-thiadiazol-2-yl)phenyl]pyrazolo[3,4-d]pyrimidin-6-yl]amino]-N-(2-methoxyethyl)cyclopentanecarboxamide | | A |
| (1R,3R)-3-[[3-bromo-1-[3-chloro-5-(2-hydroxyethyl)phenyl]pyrazolo[3,4-d]pyrimidin-6-yl]amino]-N,1-dimethyl-cyclopentanecarboxamide | | AA |
| 5-[4-[3-bromo-6-[[(1R,3R)-3-methyl-3-(methylcarbamoyl)cyclopentyl]amino]pyrazolo[3,4-d]pyrimidin-1-yl]phenyl]-N-[2-(dimethylamino)ethyl]-1,3,4-thiadiazole-2-carboxamide | | A |
| (1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-isopropyl-N-(2-methoxyethyl)cyclopentanecarboxamide | | A |
| (1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-isopropyl-N-methyl-cyclopentanecarboxamide | | A |
| 3-[5-[3-bromo-6-[[(1R,3R)-3-isopropyl-3-(piperazine-1-carbonyl)cyclopentyl]amino]pyrazolo[3,4-d]pyrimidin-1-yl]-2-(5-methyl-1,3,4-thiadiazol-2-yl)phenyl]propanenitrile | | AA |
| (1R,3R)-3-[[1-[3-(azetidin-3-ylmethoxy)-4-(5-methyl-1,3,4-thiadiazol-2-yl)phenyl]-3-bromo-pyrazolo[3,4-d]pyrimidin-6-yl]amino]-N,1-dimethyl-cyclopentanecarboxamide | | A |
| (1R,3R)-3-[[3-bromo-1-[8-(3-hydroxypropyl)-1-methyl-2-oxo-3,4-dihydroquinolin-6-yl]pyrazolo[3,4-d]pyrimidin-6-yl]amino]-N,1-dimethyl-cyclopentanecarboxamide; 2,2,2-trifluoroacetic acid | | AA |

TABLE 3-continued

| Chemical Name | Chemical Structure | IC$_{50}$ Activity |
|---|---|---|
| (1R,3R)-3-[[3-bromo-1-[3-cyano-5-(hydroxymethyl)phenyl]pyrazolo[3,4-d]pyrimidin-6-yl]amino]-N,1-dimethyl-cyclopentanecarboxamide | | A |
| (1R,3R)-3-[[3-bromo-1-[3-chloro-5-(2-methylsulfonylethyl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-5-(2-cyanoethyl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-5-[2-(methanesulfonamido)ethyl]phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[(3-bromo-1-quinazolin-6-yl-pyrazolo[3,4-d]pyrimidin-6-yl)amino]-N,1-dimethyl-cyclopentane-carboxamide | | A |
| (1R,3R)-3-[[1-[3-[(1R)-1-aminoethyl]-5-chloro-phenyl]-3-bromo-pyrazolo[3,4-d]pyrimidin-6-yl]amino]-N,1-dimethyl-cyclopentanecarboxamide; 2,2,2-trifluoroacetic acid | | AA |
| (1R,3R)-3-[[1-[3-(aminomethyl)-5-cyano-phenyl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-cyano-5-(methylsulfonylmethyl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-cyano-5-(cyanomethyl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-cyano-5-(methanesulfonamidomethyl)phenyl]pyrazolo[3,4-d]pyrimidin-6-yl]amino]-N,1-dimethyl-cyclopentane-carboxamide; 2,2,2-trifluoroacetic acid | | A |
| (1R,3R)-3-[[3-bromo-1-[8-(2-cyanoethyl)-1-methyl-2-oxo-3,4-dihydroquinolin-6-yl]pyrazolo[3,4-d]pyrimidin-6-yl]amino]-N,1-dimethyl-cyclopentanecarboxamide | | A |
| (1R,3R)-3-[[3-bromo-1-[8-(3-methoxy-propyl)-1-methyl-2-oxo-3,4-dihydro-quinolin-6-yl]pyrazolo[3,4-d]pyrimidin-6-yl]amino]-N,1-dimethyl-cyclopentane-carboxamide; 2,2,2-trifluoroacetic acid | | A |
| 3-bromo-N-(3-methylsulfonylcyclobutyl)-1-[4-(5-methyl-1,3,4-thiadiazol-2-yl)phenyl]pyrazolo[3,4-d]pyrimidin-6-amine | | A |
| (1S,3R)-3-[[3-bromo-1-[4-(5-methyl-1,3,4-thiadiazol-2-yl)phenyl]pyrazolo[3,4-d]pyrimidin-6-yl]amino]-N-(2-methoxyethyl)cyclopentanesulfonamide | | A |
| (3R)-3-[[3-bromo-1-[4-(5-methyl-1,3,4-thiadiazol-2-yl)phenyl]pyrazolo[3,4-d]pyrimidin-6-yl]amino]-N-(2-cyanoethyl)cyclopentanesulfonamide | | A |
| (1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-(hydroxymethyl)-N-methyl-cyclopentane-carboxamide | | A |
| (1R,3R)-3-[[3-bromo-1-[4-(5-methyl-1,3,4-thiadiazol-2-yl)phenyl]pyrazolo[3,4-d]pyrimidin-6-yl]amino]-1-(hydroxymethyl)-N-methyl-cyclo-pentanecarboxamide | | A |

TABLE 3-continued

| Chemical Name | Chemical Structure | IC$_{50}$ Activity |
|---|---|---|
| (1S,3R)-3-[[3-bromo-1-[4-(5-methyl-1,3,4-thiadiazol-2-yl)phenyl]pyrazolo[3,4-d]pyrimidin-6-yl]amino]-1-(hydroxymethyl)-N-methyl-cyclopentanecarboxamide | | A |
| (1R,3R)-3-[(3-bromo-1-quinazolin-7-yl-pyrazolo[3,4-d]pyrimidin-6-yl)amino]-N,1-dimethyl-cyclopentanecarboxamide; 2,2,2-trifluoroacetic acid | | A |
| (1R,3R)-3-[[1-[8-[(1R)-1-aminoethyl]quinoxalin-6-yl]-3-bromo-pyrazolo[3,4-d]pyrimidin-6-yl]amino]-1-isopropyl-N-methyl-cyclopentanecarboxamide; 2,2,2-trifluoroacetic acid | | AA |
| (1R,3R)-3-[[3-bromo-1-[3-chloro-4-fluoro-5-(hydroxymethyl)phenyl]pyrazolo[3,4-d]pyrimidin-6-yl]amino]-N,1-dimethyl-cyclopentanecarboxamide | | A |
| (1R,3R)-3-[[1-[3-(aminomethyl)-5-chloro-4-fluoro-phenyl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-4-fluoro-5-(methylsulfonylmethyl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-5-(cyanomethyl)-4-fluoro-phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-4-fluoro-5-(methanesulfonamidomethyl)phenyl]pyrazolo[3,4-d]pyrimidin-6-yl]amino]-N,1-dimethyl-cyclopentanecarboxamide; 2,2,2-trifluoroacetic acid | | A |
| (2R,4S)-4-[[3-bromo-1-[4-(5-methyl-1,3,4-thiadiazol-2-yl)phenyl]pyrazolo[3,4-d]pyrimidin-6-yl]amino]-N-methyl-tetrahydrofuran-2-carboxamide | | A |
| (2R,4S)-4-[[3-bromo-1-[3-chloro-5-(hydroxymethyl)phenyl]pyrazolo[3,4-d]pyrimidin-6-yl]amino]-N-methyl-tetrahydrofuran-2-carboxamide | | A |
| (3R)-3-[[3-bromo-1-[4-(5-methyl-1,3,4-thiadiazol-2-yl)phenyl]pyrazolo[3,4-d]pyrimidin-6-yl]amino]-1-(2-cyanoethyl)-N-methyl-cyclopentanecarboxamide | | A |
| (3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-(2-cyanoethyl)-N-methyl-cyclopentanecarboxamide | | A |
| (1R,3R)-3-[[3-bromo-1-[4-[5-(1-hydroxy-1-methyl-ethyl)-1,3,4-thiadiazol-2-yl]phenyl]pyrazolo[3,4-d]pyrimidin-6-yl]amino]-N,1-dimethyl-cyclopentanecarboxamide; 2,2,2-trifluoroacetic acid | | A |
| (3R)-3-[[3-bromo-1-[4-(5-methyl-1,3,4-thiadiazol-2-yl)phenyl]pyrazolo[3,4-d]pyrimidin-6-yl]amino]-N-methyl-1-(2-methylsulfonylethyl)cyclopentanecarboxamide | | A |
| (3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-N-methyl-1-(2-methylsulfonylethyl)cyclopentanecarboxamide | | A |
| (1R,3R)-3-[[1-(2-aminoquinazolin-6-yl)-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[(3-bromo-1-quinazolin-6-yl-pyrazolo[3,4-d]pyrimidin-6-yl)amino]-1-(2,2-difluoroethyl)-N-methyl-cyclopentanecarboxamide | | A |

TABLE 3-continued

| Chemical Name | Chemical Structure | IC$_{50}$ Activity |
|---|---|---|
| (1R,3R)-3-[[3-bromo-1-[3-ethyl-4-(5-methyl-1,3,4-thiadiazol-2-yl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-fluoro-4-(5-methyl-1,3,4-thiadiazol-2-yl)phenyl]pyrazolo[3,4-d]pyrimidin-6-yl]amino]-N,1-dimethyl-cyclopentane-carboxamide; 2,2,2-trifluoroacetic acid | | AA |
| (3R)-3-[[3-bromo-1-[4-(5-methyl-1,3,4-thiadiazol-2-yl)phenyl]pyrazolo[3,4-d]pyrimidin-6-yl]amino]-N-methyl-cyclopentanesulfonamide | | A |
| (3R)-3-[[3-bromo-1-[4-(5-methyl-1,3,4-thiadiazol-2-yl)phenyl]pyrazolo[3,4-d]pyrimidin-6-yl]amino]-1-(cyanomethyl)-N-methyl-cyclopentanecarboxamide; 2,2,2-trifluoroacetic acid | | A |
| (3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-(cyanomethyl)-N-methyl-cyclopentanecarboxamide; 2,2,2-trifluoroacetic acid | | A |
| (3R)-3-[[3-bromo-1-[4-(5-methyl-1,3,4-thiadiazol-2-yl)phenyl]pyrazolo[3,4-d]pyrimidin-6-yl]amino]-1-(1-cyanoethyl)-N-methyl-cyclopentanecarboxamide; 2,2,2-trifluoroacetic acid | | A |
| (3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-(1-cyanoethyl)-N-methyl-cyclopentanecarboxamide; 2,2,2-trifluoroacetic acid | | A |
| N-[(1R,3R)-3-[[3-bromo-1-[4-(5-methyl-1,3,4-thiadiazol-2-yl)phenyl]pyrazolo[3,4-d]pyrimidin-6-yl]amino]cyclopentyl]-3-hydroxy-3-methyl-cyclobutane-carboxamide | | A |
| (2R)-N-[(1R,3R)-3-[[3-bromo-1-[4-(5-methyl-1,3,4-thiadiazol-2-yl)phenyl]pyrazolo[3,4-d]pyrimidin-6-yl]amino]cyclopentyl]piperidine-2-carboxamide; 2,2,2-trifluoroacetic acid | | A |
| (2S)-N-[(1R,3R)-3-[[3-bromo-1-[4-(5-methyl-1,3,4-thiadiazol-2-yl)phenyl]pyrazolo[3,4-d]pyrimidin-6-yl]amino]cyclopentyl]piperidine-2-carboxamide; 2,2,2-trifluoroacetic acid | | A |
| N-[(1R,3R)-3-[[3-bromo-1-[4-(5-methyl-1,3,4-thiadiazol-2-yl)phenyl]pyrazolo[3,4-d]pyrimidin-6-yl]amino]cyclopentyl]azetidine-3-carboxamide; 2,2,2-trifluoroacetic acid | | A |
| N-[(1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]cyclopentyl]-2-methyl-propanamide | | C |
| N-[(1R,3R)-3-[[3-bromo-1-[4-(5-methyl-1,3,4-thiadiazol-2-yl)phenyl]pyrazolo[3,4-d]pyrimidin-6-yl]amino]cyclopentyl]-2-methyl-propanamide | | A |
| (1R,3R)-3-[[3-bromo-1-(2,4-diamino-quinazolin-6-yl)pyrazolo[3,4-d]pyrimidin-6-yl]amino]-N,1-dimethyl-cyclopentane-carboxamide; 2,2,2-trifluoroacetic acid | | A |
| (1R,3R)-3-[[3-bromo-1-[2-(dimethyl-amino)quinazolin-6-yl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[4-(5-methyl-1,3,4-thiadiazol-2-yl)phenyl]pyrazolo[3,4-d]pyrimidin-6-yl]amino]-1-(2-methoxyethyl)-N-methyl-cyclopentane-carboxamide; 2,2,2-trifluoroacetic acid | | A |

TABLE 3-continued

| Chemical Name | Chemical Structure | IC$_{50}$ Activity |
|---|---|---|
| (1R,3R)-3-[[3-bromo-1-[3-(2-cyano-ethyl)-4-(5-methyl-1,3,4-thiadiazol-2-yl)phenyl]pyrazolo[3,4-d]pyrimidin-6-yl]amino]-1-(2-methoxyethyl)-N-methyl-cyclopentanecarboxamide; 2,2,2-trifluoroacetic acid | | A |
| 3-bromo-N-[1-(2,2-difluoroethyl)pyrrolidin-3-yl]-1-[4-(5-methyl-1,3,4-thiadiazol-2-yl)phenyl]pyrazolo[3,4-d]pyrimidin-6-amine | | A |
| (1R,3R)-3-[[3-bromo-1-[3-(hydroxy-methyl)-5-(trifluoromethyl)phenyl]pyrazolo[3,4-d]pyrimidin-6-yl]amino]-N,1-dimethyl-cyclopentanecarboxamide | | A |
| (1R,3R)-3-[[3-bromo-1-[3-(hydroxy-methyl)-5-nitro-phenyl]pyrazolo[3,4-d]pyrimidin-6-yl]amino]-N,1-dimethyl-cyclopentanecarboxamide | | A |
| (5S,8R)-8-[[3-bromo-1-[4-(5-methyl-1,3,4-thiadiazol-2-yl)phenyl]pyrazolo[3,4-d]pyrimidin-6-yl]amino]-2-azaspiro[4.4]nonan-1-one; 2,2,2-trifluoroacetic acid | | A |
| (5R,8R)-8-[[3-bromo-1-[4-(5-methyl-1,3,4-thiadiazol-2-yl)phenyl]pyrazolo[3,4-d]pyrimidin-6-yl]amino]-2-azaspiro[4.4]nonan-1-one; 2,2,2-trifluoroacetic acid | | A |
| 3-[5-[3-bromo-6-[[(5S,8R)-1-oxo-2-azaspiro[4.4]nonan-8-yl]amino]pyrazolo[3,4-d]pyrimidin-1-yl]-2-(5-methyl-1,3,4-thiadiazol-2-yl)phenyl]propanenitrile; 2,2,2-trifluoroacetic acid | | A |
| 3-[5-[3-bromo-6-[[(5R,8R)-1-oxo-2-azaspiro[4.4]nonan-8-yl]amino]pyrazolo[3,4-d]pyrimidin-1-yl]-2-(5-methyl-1,3,4-thiadiazol-2-yl)phenyl]propanenitrile; 2,2,2-trifluoroacetic acid | | A |
| 3-[[3-bromo-1-[4-(5-methyl-1,3,4-thiadiazol-2-yl)phenyl]pyrazolo[3,4-d]pyrimidin-6-yl]amino]-1-[(dimethylamino)methyl]cyclo-pentanecarboxylic acid; 2,2,2-trifluoroacetic acid | | A |
| (3R)-3-[[3-bromo-1-[4-(5-methyl-1,3,4-thiadiazol-2-yl)phenyl]pyrazolo[3,4-d]pyrimidin-6-yl]amino]-1-(morpholino-methyl)cyclopentanecarboxylic acid; 2,2,2-trifluoroacetic acid | | A |
| 3-[5-[3-bromo-6-[[(1R,3S)-3-hydroxy-3-methyl-cyclopentyl]amino]pyrazolo[3,4-d]pyrimidin-1-yl]-2-(5-methyl-1,3,4-thiadiazol-2-yl)phenyl]propanenitrile | | A |
| (1R,3R)-3-[[3-bromo-1-[2-(methylamino)quinazolin-6-yl]pyrazolo[3,4-d]pyrimidin-6-yl]amino]-N,1-dimethyl-cyclopentane-carboxamide; 2,2,2-trifluoroacetic acid | | A |
| (1R,3R)-3-[[3-bromo-1-(2-oxo-1H-quinazolin-6-yl)pyrazolo[3,4-d]pyrimidin-6-yl]amino]-N,1-dimethyl-cyclopentane-carboxamide; 2,2,2-trifluoroacetic acid | | A |
| (1R,3R)-3-[[3-bromo-1-[3-(2-cyano-3-hydroxy-propyl)-4-(5-methyl-1,3,4-thiadiazol-2-yl)phenyl]pyrazolo[3,4-d]pyrimidin-6-yl]amino]-N,1-dimethyl-cyclopentanecarboxamide | | AA |
| (1R,3R)-3-[[3-bromo-1-[3-(hydroxymethyl)-5-methylsulfonyl-phenyl]pyrazolo[3,4-d]pyrimidin-6-yl]amino]-N,1-dimethyl-cyclo-pentanecarboxamide | | A |
| (1R,3R)-3-[[3-bromo-1-[3-fluoro-5-(hydroxymethyl)phenyl]pyrazolo[3,4-d]pyrimidin-6-yl]amino]-N,1-dimethyl-cyclopentanecarboxamide | | A |

TABLE 3-continued

| Chemical Name | Chemical Structure | IC$_{50}$ Activity |
|---|---|---|
| (1R,3R)-3-[[1-[3-[(1S)-1-aminoethyl]-5-fluoro-phenyl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[4-(5-methyl-1,3,4-thiadiazol-2-yl)phenyl]pyrazolo[3,4-d]pyrimidin-6-yl]amino]-N-methyl-1-(2,2,2-trifluoroethyl)cyclopentanecarboxamide; 2,2,2-trifluoroacetic acid | | A |
| (1S,3R)-3-[[3-bromo-1-[4-(5-methyl-1,3,4-thiadiazol-2-yl)phenyl]pyrazolo[3,4-d]pyrimidin-6-yl]amino]-N-methyl-1-(2,2,2-trifluoroethyl)cyclopentanecarboxamide; 2,2,2-trifluoroacetic acid | | A |
| (3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-N-methyl-1-(2,2,2-trifluoroethyl)cyclopentanecarboxamide; 2,2,2-trifluoroacetic acid | | A |
| (1R,3R)-3-[[1-(2-acetamidoquinazolin-6-yl)-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[4-[5-(2-methoxy-ethyl)-1,3,4-thiadiazol-2-yl]phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-(2-methoxy-quinazolin-6-yl)pyrazolo[3,4-d]pyrimidin-6-yl]amino]-N,1-dimethyl-cyclopentanecarboxamide; 2,2,2-trifluoroacetic acid | | AA |
| (1R,3R)-3-[[3-bromo-1-(2-pyrrolidin-1-ylquinazolin-6-yl)pyrazolo[3,4-d]pyrimidin-6-yl]amino]-N,1-dimethyl-cyclopentanecarboxamide; 2,2,2-trifluoroacetic acid | | A |
| (1R,3R)-3-[[1-[3-(aminomethyl)-5-(trifluoromethyl)phenyl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-5-[(4S)-2-oxooxazolidin-4-yl]phenyl]pyrazolo[3,4-d]pyrimidin-6-yl]amino]-N,1-dimethyl-cyclopentanecarboxamide | | A |
| (1R,3R)-3-[[3-bromo-1-[3-chloro-5-[(4R)-2-oxooxazolidin-4-yl]phenyl]pyrazolo[3,4-d]pyrimidin-6-yl]amino]-N,1-dimethyl-cyclopentanecarboxamide | | AA |
| (1R,3R)-3-[[3-bromo-1-(2-piperazin-1-ylquinazolin-6-yl)pyrazolo[3,4-d]pyrimidin-6-yl]amino]-N,1-dimethyl-cyclopentanecarboxamide; 2,2,2-trifluoroacetic acid | | AA |
| 2-[3-[[3-bromo-1-[4-(5-methyl-1,3,4-thiadiazol-2-yl)phenyl]pyrazolo[3,4-d]pyrimidin-6-yl]amino]cyclobutyl]-N-methyl-acetamide; 2,2,2-trifluoroacetic acid | | A |
| 2-[3-[[3-bromo-1-[3-(2-cyanoethyl)-4-(5-methyl-1,3,4-thiadiazol-2-yl)phenyl]pyrazolo[3,4-d]pyrimidin-6-yl]amino]cyclobutyl]-N-methyl-acetamide; 2,2,2-trifluoroacetic acid | | A |
| (1R,3R)-3-[[3-bromo-1-[4-(5-methyl-1,3,4-thiadiazol-2-yl)phenyl]pyrazolo[3,4-d]pyrimidin-6-yl]amino]-1-[(1R)-1-cyanoethyl]-N-methyl-cyclopentane-carboxamide | | A |
| (1R,3R)-3-[[3-bromo-1-[4-(5-methyl-1,3,4-thiadiazol-2-yl)phenyl]pyrazolo[3,4-d]pyrimidin-6-yl]amino]-1-[(1S)-1-cyanoethyl]-N-methyl-cyclopentane-carboxamide | | A |

TABLE 3-continued

| Chemical Name | Chemical Structure | IC$_{50}$ Activity |
|---|---|---|
| (1S,3R)-3-[[3-bromo-1-[4-(5-methyl-1,3,4-thiadiazol-2-yl)phenyl]pyrazolo[3,4-d]pyrimidin-6-yl]amino]-1-[(1S)-1-cyanoethyl]-N-methyl-cyclopentanecarboxamide | | A |
| (1R,3R)-3-[[3-bromo-1-[2-(4-methylpiperazin-1-yl)quinazolin-6-yl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-bromo-5-(hydroxymethyl)phenyl]pyrazolo[3,4-d]pyrimidin-6-yl]amino]-N,1-dimethyl-cyclopentanecarboxamide | | A |
| (1R,3R)-3-[[1-[3-(aminomethyl)-5-bromo-phenyl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-5-(3-methyl-2-oxo-oxazolidin-4-yl)phenyl]pyrazolo[3,4-d]pyrimidin-6-yl]amino]-N,1-dimethyl-cyclopentanecarboxamide | | A |
| (3R)-3-[[3-bromo-1-[4-(5-methyl-1,3,4-thiadiazol-2-yl)phenyl]pyrazolo[3,4-d]pyrimidin-6-yl]amino]-N-methyl-pyrrolidine-1-carboxamide | | A |
| (1R,3R)-3-[[1-[2-(4-acetylpiperazin-1-yl)quinazolin-6-yl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-(2-morpholino-quinazolin-6-yl)pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-(1,3-dimethyl-2,4-dioxo-quinazolin-6-yl)pyrazolo[3,4-d]pyrimidin-6-yl]amino]-N,1-dimethyl-cyclopentanecarboxamide; 2,2,2-trifluoroacetic acid | | AA |
| (1R,3R)-3-[[3-bromo-1-[3-chloro-5-[(1S)-1-(dimethylamino)ethyl]phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[1-(3-amino-2,3-dihydro-benzofuran-5-yl)-3-bromo-pyrazolo[3,4-d]pyrimidin-6-yl]amino]-N,1-dimethyl-cyclopentanecarboxamide; 2,2,2-trifluoroacetic acid | | A |
| (3R)-3-[[3-bromo-1-[2-(methylamino)quinazolin-6-yl]pyrazolo[3,4-d]pyrimidin-6-yl]amino]-1-methyl-cyclopentanol; 2,2,2-trifluoroacetic acid | | A |
| (3R)-3-[[1-[3-[(1S)-1-aminoethyl]-5-chloro-phenyl]-3-bromo-pyrazolo[3,4-d]pyrimidin-6-yl]amino]-N-methyl-cyclopentanesulfonamide; 2,2,2-trifluoroacetic acid | | A |
| (3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-N-methyl-cyclopentanesulfonamide | | A |
| methyl (3R)-3-[[3-bromo-1-[4-(5-methyl-1,3,4-thiadiazol-2-yl)phenyl]pyrazolo[3,4-d]pyrimidin-6-yl]amino]pyrrolidine-1-carboxylate | | A |
| (1R,3R)-3-[[3-bromo-1-[4-(5-methyl-1,3,4-thiadiazol-2-yl)phenyl]pyrazolo[3,4-d]pyrimidin-6-yl]amino]-1-methyl-cyclopentanecarbonitrile; 2,2,2-trifluoroacetic acid | | A |

TABLE 3-continued

| Chemical Name | Chemical Structure | IC$_{50}$ Activity |
|---|---|---|
| 3-[5-[6-[[(1R,3R)-3-amino-3-methyl-cyclopentyl]amino]-3-bromo-pyrazolo[3,4-d]pyrimidin-1-yl]-2-(5-methyl-1,3,4-thiadiazol-2-yl)phenyl]propanenitrile; 2,2,2-trifluoroacetic acid | | A |
| (1R,3R)-N3-[3-bromo-1-[4-(5-methyl-1,3,4-thiadiazol-2-yl)phenyl]pyrazolo[3,4-d]pyrimidin-6-yl]-1-methyl-cyclopentane-1,3-diamine; 2,2,2-trifluoroacetic acid | | A |
| (1R,3R)-N3-[3-bromo-1-[4-(5-methyl-1,3,4-thiadiazol-2-yl)phenyl]pyrazolo[3,4-d]pyrimidin-6-yl]-N1,N1,1-trimethyl-cyclopentane-1,3-diamine; 2,2,2-trifluoroacetic acid | | A |
| (1R,3R)-N3-[3-bromo-1-[4-(5-methyl-1,3,4-thiadiazol-2-yl)phenyl]pyrazolo[3,4-d]pyrimidin-6-yl]-N1,1-dimethyl-cyclopentane-1,3-diamine; 2,2,2-trifluoroacetic acid | | A |
| [(1R,3R)-3-[[1-[3-[(1S)-1-aminoethyl]-5-chloro-phenyl]-3-bromo-pyrazolo[3,4-d]pyrimidin-6-yl]amino]-1-methyl-cyclopentyl]methanol hydrochloride | | A |
| 3-[5-[3-bromo-6-[[(1R,3R)-3-(hydroxymethyl)-3-methyl-cyclopentyl]amino]pyrazolo[3,4-d]pyrimidin-1-yl]-2-(5-methyl-1,3,4-thiadiazol-2-yl)phenyl]propanenitrile | | A |
| [(1R,3R)-3-[[3-bromo-1-[4-(5-methyl-1,3,4-thiadiazol-2-yl)phenyl]pyrazolo[3,4-d]pyrimidin-6-yl]amino]-1-methyl-cyclopentyl]methanol | | A |
| (8R)-8-[[3-bromo-1-[4-(5-methyl-1,3,4-thiadiazol-2-yl)phenyl]pyrazolo[3,4-d]pyrimidin-6-yl]amino]-2-methyl-2-azaspiro[4.4]nonane-1,3-dione; 2,2,2-trifluoroacetic acid | | AA |
| (1R,3R)-3-[[3-bromo-1-[3-chloro-5-(1-hydroxyethyl)phenyl]pyrazolo[3,4-d]pyrimidin-6-yl]amino]-N,1-dimethyl-cyclopentanecarboxamide; 2,2,2-trifluoroacetic acid | | AA |
| (1R,3R)-3-[[3-bromo-1-(4-oxo-3H-quinazolin-6-yl)pyrazolo[3,4-d]pyrimidin-6-yl]amino]-N,1-dimethyl-cyclopentanecarboxamide; 2,2,2-trifluoroacetic acid | | A |
| (1R,3R)-3-[[1-[3-(2-amino-1-methoxy-ethyl)-5-chloro-phenyl]-3-bromo-pyrazolo[3,4-d]pyrimidin-6-yl]amino]-N,1-dimethyl-cyclopentanecarboxamide; 2,2,2-trifluoroacetic acid | | A |
| [(1R,3R)-3-[[3-bromo-1-[4-(5-methyl-1,3,4-thiadiazol-2-yl)phenyl]pyrazolo[3,4-d]pyrimidin-6-yl]amino]-1-methyl-cyclopentyl]-piperazin-1-yl-methanone | | A |
| 3-[5-[3-bromo-6-[[(1R,3R)-3-methyl-3-(piperazine-1-carbonyl)cyclopentyl]amino]pyrazolo[3,4-d]pyrimidin-1-yl]-2-(5-methyl-1,3,4-thiadiazol-2-yl)phenyl]propanenitrile | | A |
| [(1R,3R)-3-[[1-[3-[(1S)-1-aminoethyl]-5-chloro-phenyl]-3-bromo-pyrazolo[3,4-d]pyrimidin-6-yl]amino]-1-methyl-cyclopentyl]-piperazin-1-yl-methanone | | A |
| [(1R,3R)-3-[[3-bromo-1-[4-(5-methyl-1,3,4-thiadiazol-2-yl)phenyl]pyrazolo[3,4-d]pyrimidin-6-yl]amino]-1-methyl-cyclopentyl]-(4-methyl-4-oxo-1,4λ$^{5}$-azaphosphinan-1-yl)methanone; 2,2,2-trifluoroacetic acid | | A |
| (1R,3R)-3-[[1-[3-[(1S)-1-aminoethyl]-5-chloro-phenyl]-3-bromo-pyrazolo[3,4-d]pyrimidin-6-yl]amino]-1-methyl-cyclopentanecarbonitrile; 2,2,2-trifluoroacetic acid | | A |

TABLE 3-continued

| Chemical Name | Chemical Structure | IC$_{50}$ Activity |
|---|---|---|
| [(1R,3R)-3-[[1-[3-[(1S)-1-aminoethyl]-5-chloro-phenyl]-3-bromo-pyrazolo[3,4-d]pyrimidin-6-yl]amino]-1-methyl-cyclopentyl]-(4-methyl-4-oxo-1,4λ^{5}-azaphosphinan-1-yl)methanone; 2,2,2-trifluoroacetic acid | | A |
| (8R)-8-[[1-[3-[(1S)-1-aminoethyl]-5-chloro-phenyl]-3-bromo-pyrazolo[3,4-d]pyrimidin-6-yl]amino]-2-methyl-2-azaspiro[4.4]nonane-1,3-dione; 2,2,2-trifluoroacetic acid | | A |
| (1R,3R)-3-[[3-bromo-1-[4-(1,3,4-thiadiazol-2-yl)phenyl]pyrazolo[3,4-d]pyrimidin-6-yl]amino]-N,1-dimethyl-cyclopentanecarboxamide; 2,2,2-trifluoroacetic acid | | A |
| (3R)-3-[[1-[8-(2-aminoethyl)-6-quinolyl]-3-bromo-pyrazolo[3,4-d]pyrimidin-6-yl]amino]-1-methyl-cyclopentanol; 2,2,2-trifluoroacetic acid | | A |
| (1R,3R)-3-[[1-[8-(2-aminoethyl)-6-quinolyl]-3-bromo-pyrazolo[3,4-d]pyrimidin-6-yl]amino]-1-methyl-cyclopentanol; 2,2,2-trifluoroacetic acid | | AA |
| [(1R,3R)-3-[[1-[8-(2-aminoethyl)-6-quinolyl]-3-bromo-pyrazolo[3,4-d]pyrimidin-6-yl]amino]-1-methyl-cyclopentyl]methanol; 2,2,2-trifluoroacetic acid | | A |
| 3-[5-[3-bromo-6-[[(1R,3R)-3-(dimethylamino)-3-methyl-cyclopentyl]amino]pyrazolo[3,4-d]pyrimidin-1-yl]-2-(5-methyl-1,3,4-thiadiazol-2-yl)phenyl]propanenitrile | | A |
| 3-[5-[3-bromo-6-[[(8R)-2-methyl-1,3-dioxo-2-azaspiro[4.4]nonan-8-yl]amino]pyrazolo[3,4-d]pyrimidin-1-yl]-2-(5-methyl-1,3,4-thiadiazol-2-yl)phenyl]propanenitrile; 2,2,2-trifluoroacetic acid | | A |
| (1R,3R)-3-[[3-bromo-1-[3-[2-(1,3-dioxoisoindolin-2-yl)ethyl]-4-oxo-quinazolin-6-yl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-(3-methyl-4-oxo-quinazolin-7-yl)pyrazolo[3,4-d]pyrimidin-6-yl]amino]-N,1-dimethyl-cyclopentanecarboxamide; 2,2,2-trifluoroacetic acid | | A |
| (1R,3R)-3-[[1-[3-(2-aminoethyl)-4-oxo-quinazolin-6-yl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[4-(5-methyl-1,3,4-thiadiazol-2-yl)phenyl]pyrazolo[3,4-d]pyrimidin-6-yl]amino]-N-(2,2-difluoroethyl)-1-methyl-cyclopentanecarboxamide | | A |
| (1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-N-(2,2-difluoroethyl)-1-methyl-cyclopentanecarboxamide | | A |
| (1R,3R)-3-[[1-[3-[(1S)-1-aminoethyl]-5-chloro-phenyl]-3-bromo-pyrazolo[3,4-d]pyrimidin-6-yl]amino]-N-(2,2-difluoroethyl)-1-methyl-cyclopentanecarboxamide | | A |
| (1R,3R)-3-[[3-bromo-1-[4-(5-methyl-1,3,4-thiadiazol-2-yl)phenyl]pyrazolo[3,4-d]pyrimidin-6-yl]amino]-N-cyclopropyl-1-methyl-cyclopentanecarboxamide | | A |

TABLE 3-continued

| Chemical Name | Chemical Structure | IC$_{50}$ Activity |
|---|---|---|
| (1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-N-cyclopropyl-1-methyl-cyclopentane-carboxamide | | A |
| (1R,3R)-3-[[3-bromo-1-[3-bromo-5-(1-hydroxyethyl)phenyl]pyrazolo[3,4-d]pyrimidin-6-yl]amino]-N,1-dimethyl-cyclopentanecarboxamide; 2,2,2-trifluoroacetic acid | | A |
| (1R,3R)-3-[[3-bromo-1-[3-chloro-5-(5-oxomorpholin-2-yl)phenyl]pyrazolo[3,4-d]pyrimidin-6-yl]amino]-N,1-dimethyl-cyclopentanecarboxamide | | A |
| (1R,3R)-3-[[3-bromo-1-[3-chloro-5-(4-methyl-5-oxo-morpholin-2-yl)phenyl]pyrazolo[3,4-d]pyrimidin-6-yl]amino]-N,1-dimethyl-cyclopentane-carboxamide | | A |
| (3R)-3-[[3-bromo-1-[3-cyano-4-(5-methyl-1,3,4-thiadiazol-2-yl)phenyl]pyrazolo[3,4-d]pyrimidin-6-yl]amino]-N-methyl-cyclopentanesulfonamide | | A |
| (1R,3R)-3-[[1-[3-[(1S)-1-aminopropyl]-5-chloro-phenyl]-3-bromo-pyrazolo[3,4-d]pyrimidin-6-yl]amino]-N,1-dimethyl-cyclopentanecarboxamide; 2,2,2-trifluoroacetic acid | | A |
| (1R,3R)-3-[[1-[3-[(1R)-1-aminopropyl]-5-chloro-phenyl]-3-bromo-pyrazolo[3,4-d]pyrimidin-6-yl]amino]-N,1-dimethyl-cyclopentanecarboxamide; 2,2,2-trifluoroacetic acid | | AA |
| (1R,3R)-3-[[3-bromo-1-[3-(2-hydroxyethyl)-4-oxo-quinazolin-6-yl]pyrazolo[3,4-d]pyrimidin-6-yl]amino]-N,1-dimethyl-cyclopentanecarboxamide; 2,2,2-trifluoroacetic acid | | A |
| 2-[3-[[1-[4-(2-aminoethyl)-2-naphthyl]-3-bromo-pyrazolo[3,4-d]pyrimidin-6-yl]amino]cyclobutyl]-N-methyl-acetamide; 2,2,2-trifluoroacetic acid | | A |
| 3-[5-[3-bromo-6-[[(1R)-3-(dimethyl-phosphorylmethyl)-3-methyl-cyclopentyl]amino]pyrazolo[3,4-d]pyrimidin-1-yl]-2-(5-methyl-1,3,4-thiadiazol-2-yl)phenyl]propanenitrile; 2,2,2-trifluoroacetic acid | | A |
| (1R,3R)-3-[[3-bromo-1-[4-(5-methyl-1,3,4-thiadiazol-2-yl)phenyl]pyrazolo[3,4-d]pyrimidin-6-yl]amino]-1-cyano-N-methyl-cyclopentanecarboxamide; 2,2,2-trifluoroacetic acid | | A |
| (3R)-3-[[1-[3-[(1S)-1-aminoethyl]-5-chloro-phenyl]-3-bromo-pyrazolo[3,4-d]pyrimidin-6-yl]amino]-1-cyano-N-methyl-cyclopentanecarboxamide; 2,2,2-trifluoroacetic acid | | A |
| 3-[(3R)-3-[[3-bromo-1-[4-(5-methyl-1,3,4-thiadiazol-2-yl)phenyl]pyrazolo[3,4-d]pyrimidin-6-yl]amino]-1-cyano-cyclopentyl]-N-methyl-propanamide; 2,2,2-trifluoroacetic acid | | AA |
| (1R,3R)-3-[[3-bromo-1-[3-(2-cyanoethyl)-4-(5-methyl-1,3,4-thiadiazol-2-yl)phenyl]pyrazolo[3,4-d]pyrimidin-6-yl]amino]-1-cyano-N-methyl-cyclopentanecarboxamide; 2,2,2-trifluoroacetic acid | | A |
| 3-[5-[3-bromo-6-[[(1R,3R)-3-methyl-3-(morpholine-4-carbonyl)cyclopentyl]amino]pyrazolo[3,4-d]pyrimidin-1-yl]-2-(5-methyl-1,3,4-thiadiazol-2-yl)phenyl]propanenitrile; 2,2,2-trifluoroacetic acid | | A |
| (1R,3R)-3-[[1-[3-(3-aminopropyl)-4-oxo-quinazolin-6-yl]-3-bromo-pyrazolo[3,4-d]pyrimidin-6-yl]amino]-N,1-dimethyl-cyclopentanecarboxamide; 2,2,2-trifluoroacetic acid | | A |

The above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A compound of formula (I):

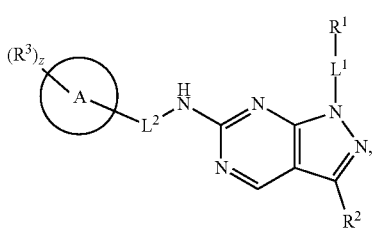

or a pharmaceutically acceptable salt thereof,
wherein:

z is an integer from 0 to 6;

ring A is a $R^6$-substituted or unsubstituted cycloalkyl or $R^6$-substituted or unsubstituted 3 to 5 membered heterocycloalkyl, $R^6$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^8$-substituted or unsubstituted alkyl, $R^8$-substituted or unsubstituted heteroalkyl, $R^8$-substituted or unsubstituted cycloalkyl, $R^8$-substituted or unsubstituted heterocycloalkyl, $R^8$-substituted or unsubstituted aryl, or $R^8$-substituted or unsubstituted heteroaryl;

$R^8$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl;

$R^9$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl, unsubstituted heteroalkyl, unsubstituted cycloalkyl, unsubstituted heterocycloalkyl, unsubstituted aryl, or unsubstituted heteroaryl;

$L^1$ is a bond;

$L^2$ is a bond, $R^{22}$-substituted or unsubstituted alkylene, or $R^{22}$-substituted or unsubstituted heteroalkylene;

$R^{22}$ is independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —C(O)NHCH_3, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, unsubstituted alkyl, unsubstituted heteroalkyl, unsubstituted cycloalkyl, unsubstituted heterocycloalkyl, unsubstituted aryl, or unsubstituted heteroaryl;

$R^1$ is $R^7$-substituted or unsubstituted aryl or $R^7$-substituted or unsubstituted heteroaryl;

$R^7$ is halogen, —$CF_3$, —$CCl_3$, —$CBr_3$, —$C_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl), or $R^{10}$-substituted or unsubstituted heteroaryl;

$R^{10}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl;

$R^{11}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl, unsubstituted heteroalkyl, unsubstituted cycloalkyl, unsubstituted heterocycloalkyl, unsubstituted aryl), or unsubstituted heteroaryl;

$R^2$ is independently hydrogen, halogen, —$CX^2_3$, —$CHX^2_2$, —$CH_2X^2$, —$OCX^2_3$, —$OCHX^2_2$, —OCH$_2$X$^2$, —CN, —S(O)$_2$R$^{2A}$, —SR$^{2A}$, —S(O)R$^{2A}$, —SO$_2$NR$^{2A}$R$^{2B}$, —NHC(O)NR$^{2A}$R$^{2B}$, —N(O)$_2$, —NR$^{2A}$R$^{2B}$, —NR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein each substituted alkyl, substituted heteroalkyl, substituted cycloalkyl, substituted heterocycloalkyl, substituted aryl or substituted heteroaryl is substituted with at least one substituent group;

R$^3$ is independently halogen, —CX$^3_3$, —CHX$^3_2$, —CH$_2$X$_3$, —OCX$^3_3$, —OCHX$^3_2$, —OCH$_2$X$_3$, —CN, —S(O)$_2$R$^{3A}$, —SR$^{3A}$, —S(O)R$^{3A}$, —SO$_2$NR$^{3A}$R$^{3B}$, —NHC(O)NR$^{3A}$R$^{3B}$, —N(O)$_2$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —P(O)R$^{3A}$R$^{3B}$, —C(O)NHNR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl, or R$^{12}$-substituted or unsubstituted heteroaryl; or two R$^3$ may optionally be joined to form a R$^{12}$-substituted or unsubstituted heterocycloalkyl or R$^{12}$-substituted or unsubstituted heteroaryl;

R$^{12}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{13}$-substituted or unsubstituted alkyl, R$^{13}$-substituted or unsubstituted heteroalkyl, R$^{13}$-substituted or unsubstituted cycloalkyl, R$^{13}$-substituted or unsubstituted heterocycloalkyl, R$^{13}$-substituted or unsubstituted aryl, or R$^{13}$-substituted or unsubstituted heteroaryl;

R$^{13}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{14}$-substituted or unsubstituted alkyl, R$^{14}$-substituted or unsubstituted heteroalkyl, R$^{14}$-substituted or unsubstituted cycloalkyl, R$^{14}$-substituted or unsubstituted heterocycloalkyl, R$^{14}$-substituted or unsubstituted aryl, or R$^{14}$-substituted or unsubstituted heteroaryl;

R$^{14}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, or unsubstituted heteroaryl;

R$^{2A}$ and R$^{2B}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; R$^{2A}$ and R$^{2B}$ may optionally be joined to form a substituted or unsubstituted heterocycloalkyl or substituted or unsubstituted heteroaryl; wherein each substituted alkyl, substituted heteroalkyl, substituted cycloalkyl, substituted heterocycloalkyl, substituted aryl or substituted heteroaryl is substituted with at least one substituent group;

R$^{3A}$ and R$^{3B}$ are independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl or R$^{12}$-substituted or unsubstituted heteroaryl; R$^{3A}$ and R$^{3B}$ may optionally be joined to form a R$^{12}$-substituted or unsubstituted heterocycloalkyl or R$^{12}$-substituted or unsubstituted heteroaryl; and X$^2$ and X$^3$ are independently halogen;

with the proviso that when ring A is cyclohexyl, then R$^3$ is not an ortho-substituted —NH$_2$ or —HNC═(O)t-BuO, or para-substituted —NHSO$_2$CH$_2$CH$_2$CF$_3$, —NHSO$_2$CH$_3$, or —OH.

2. The compound of claim 1, wherein R$^3$ is not a substituted or unsubstituted amine attached to ring A at the ortho position.

3. The compound of claim 1, wherein R$^3$ is not attached to ring A at the ortho position.

4. The compound of claim 1, wherein L$^2$ is a bond.

5. The compound of claim 1, wherein L$^2$ is substituted or unsubstituted C$_1$-C$_8$ alkylene or substituted or unsubstituted 2 to 8 membered heteroalkylene.

6. The compound of claim 5, wherein L$^2$ is unsubstituted C$_1$-C$_8$ alkylene or unsubstituted 2 to 8 membered heteroalkylene.

7. The compound of claim 1, having the formula:

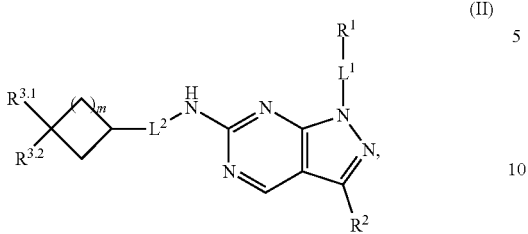

(II)

or a pharmaceutically acceptable salt thereof,
wherein:
m is an integer from 1 to 4;
$R^{3.1}$ is independently hydrogen, halogen, —$CX^{3.1}_3$, —$CHX^{3.1}_2$, —$CH_2X^{3.1}$, —$OCX^{3.1}_3$, —$OCHX^{3.1}_2$, —$OCH_2X^{3.1}$, —CN, —$S(O)_2R^{3.1A}$, —$SR^{3.1A}$, —$S(O)R^{3.1A}$, —$SO_2NR^{3.1A}R^{3.1B}$, —$NHC(O)NR^{3.1A}R^{3.1B}$, —$N(O)_2$, —$NR^{3.1A}R^{3.1B}$, —$NHNR^{3.1A}R^{3.1B}$, —$C(O)R^{3.1A}$, —$C(O)$—$OR^{3.1A}$, —$C(O)NR^{3.1A}R^{3.1B}$, —$P(O)R^{3.1A}R^{3.1B}$, —$C(O)NHNR^{3.1A}R^{3.1B}$, —$OR^{3.1A}$, —$NR^{3.1A}SO_2R^{3.1B}$, —$NR^{3.1A}C(O)R^{3.1B}$, —$NR^{3.1A}C(O)OR^{3.1B}$, —$NR^{3.1A}OR^{3.1B}$, —$N_3$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl; or $R^{3.1}$ and $R^{3.2}$ may optionally be joined to form a $R^{12}$-substituted or unsubstituted heterocycloalkyl or $R^{12}$-substituted or unsubstituted heteroaryl;

$R^{3.2}$ is independently hydrogen, halogen, —$CX^{3.2}_3$, —$CHX^{3.2}_2$, —$CH_2X^{3.2}$, —$OCX^{3.2}_3$, —$OCHX^{3.2}_2$, —$OCH_2X^{3.2}$, —CN, —$S(O)_2R^{3.2A}$, —$SR^{3.2A}$, —$S(O)R^{3.2A}$, —$SO_2NR^{3.2A}R^{3.2B}$, —$NHC(O)NR^{3.2A}R^{3.2B}$, —$N(O)_2$, —$NR^{3.2A}R^{3.2B}$, —$NHNR^{3.2A}R^{3.2B}$, —$C(O)R^{3.2A}$, —$C(O)$—$OR^{3.2A}$, —$C(O)NR^{3.2A}R^{3.2B}$, —$P(O)R^{3.2A}R^{3.2B}$, $C(O)NHNR^{3.2A}R^{3.2B}$, —$OR^{3.2A}$, —$NR^{3.2A}SO_2R^{3.2B}$, —$NR^{3.2A}C(O)R^{3.2B}$, —$NR^{3.2A}C(O)OR^{3.2B}$, —$NR^{3.2A}OR^{3.2B}$, —$N_3$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl; or $R^{3.1}$ and $R^{3.2}$ may optionally be joined to form a $R^{12}$-substituted or unsubstituted heterocycloalkyl or $R^{12}$-substituted or unsubstituted heteroaryl; and $R^{3.1A}$, $R^{3.1B}$, $R^{3.2A}$, and $R^{3.2B}$ are independently hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl or $R^{12}$-substituted or unsubstituted heteroaryl; or $R^{3.1A}$ and $R^{3.1B}$ may optionally be joined to form a $R^{12}$-substituted or unsubstituted heterocycloalkyl or $R^{12}$-substituted or unsubstituted heteroaryl; or $R^{3.2A}$ and $R^{3.2B}$ may optionally be joined to form a $R^{12}$-substituted or unsubstituted heterocycloalkyl or $R^{12}$-substituted or unsubstituted heteroaryl.

8. The compound of claim 7 having the formula:

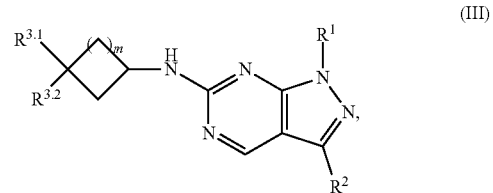

(III)

or a pharmaceutically acceptable salt thereof.

9. The compound of claim 1, wherein:
ring A is substituted or unsubstituted $C_4$-$C_7$ cycloalkyl, or substituted or unsubstituted 4 to 5-membered heterocycloalkyl.

10. The compound of claim 7, having the formula:

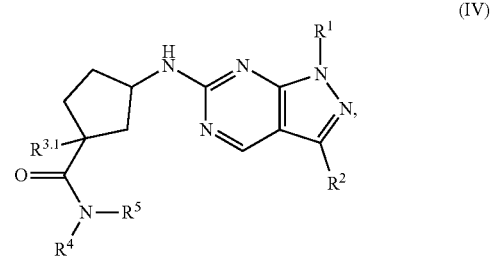

(IV)

wherein:
$R^4$ is hydrogen, $R^{15}$-substituted or unsubstituted $C_1$-$C_8$ alkyl, $R^{15}$-substituted or unsubstituted 2 to 8 membered heteroalkyl, $R^{15}$-substituted or unsubstituted $C_3$-$C_8$ cycloalkyl, or $R^{15}$-substituted or unsubstituted 3 to 8 membered heterocycloalkyl;

$R^{15}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —$NHC(O)H$, —$NHC(O)$—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl;

$R^{16}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —$NHC(O)H$, —$NHC(O)$—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{17}$-substituted or unsubstituted alkyl, R$^{17}$-substituted or unsubstituted heteroalkyl, R$^{17}$-substituted or unsubstituted cycloalkyl, R$^{17}$-substituted or unsubstituted heterocycloalkyl, R$^{17}$-substituted or unsubstituted aryl, or R$^{17}$-substituted or unsubstituted heteroaryl;

R$^{17}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, or unsubstituted heteroaryl;

R$^5$ is independently hydrogen, R$^{18}$-substituted or unsubstituted C$_1$-C$_8$ alkyl, R$^{18}$-substituted or unsubstituted 2 to 8 membered heteroalkyl, R$^{18}$-substituted or unsubstituted C$_3$-C$_8$ cycloalkyl, or R$^{18}$-substituted or unsubstituted 3 to 8 membered heterocycloalkyl;

R$^{18}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{19}$-substituted or unsubstituted alkyl, R$^{19}$-substituted or unsubstituted heteroalkyl, R$^{19}$-substituted or unsubstituted cycloalkyl, R$^{19}$-substituted or unsubstituted heterocycloalkyl, R$^{19}$-substituted or unsubstituted aryl, or R$^{19}$-substituted or unsubstituted heteroaryl;

R$^{19}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{20}$-substituted or unsubstituted alkyl, R$^{20}$-substituted or unsubstituted heteroalkyl, R$^{20}$-substituted or unsubstituted cycloalkyl, R$^{20}$-substituted or unsubstituted heterocycloalkyl, R$^{20}$-substituted or unsubstituted aryl, or R$^{20}$-substituted or unsubstituted heteroaryl;

R$^{20}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl, unsubstituted heteroalkyl, unsubstituted cycloalkyl, unsubstituted heterocycloalkyl, unsubstituted aryl, or unsubstituted heteroaryl;

wherein R$^4$ and R$^5$ may optionally be joined to form a R$^{15}$-substituted or unsubstituted C$_3$-C$_8$ cycloalkyl, R$^{15}$-substituted or unsubstituted 3 to 8 membered heterocycloalkyl or R$^{15}$-substituted or unsubstituted 5 or 6 membered heteroaryl.

11. The compound of claim 10, wherein R$^4$ and R$^5$ are independently hydrogen or substituted or unsubstituted C$_1$-C$_4$ alkyl.

12. The compound of claim 11, wherein R$^4$ and R$^5$ are independently hydrogen, methyl, ethyl, propyl, isopropyl, butyl, isobutyl, tert-butyl, propan-1-ol, 2,2-difluorobutane, or 2-fluorobutane.

13. The compound of claim 10, wherein R$^4$ and R$^5$ are independently hydrogen or substituted or unsubstituted 2 to 4 membered heteroalkyl.

14. The compound of claim 13, wherein R$^4$ and R$^5$ are independently hydrogen, 1-methoxypropane, 1-methoxy-2-methylpropane, N,N-dimethylpropan-1-amine, 1-(methylsulfonyl)propane, (2,2-difluorobutyl)-1-oxidane, 1-(1-azaneyl)-2,2-difluoropropan-1-one, methyl(methylimino)(propyl)-6-sulfanone, or 2-methoxy-2-methylbutane.

15. The compound of claim 10, wherein R$^4$ and R$^5$ are independently hydrogen or R$^4$ and R$^5$ are joined together to form a substituted or unsubstituted C$_3$-C$_5$ cycloalkyl.

16. The compound of claim 15, wherein R$^4$ and R$^5$ are independently hydrogen or R$^4$ and R$^5$ are joined together to form a substituted or unsubstituted cyclobutyl or cyclopentyl.

17. The compound of claim 10, wherein R$^4$ and R$^5$ are independently hydrogen, or R$^4$ and R$^5$ are joined together to form a substituted or unsubstituted C$_3$-C$_7$ heterocycloalkyl.

18. The compound of claim 17, wherein R$^4$ and R$^5$ are independently hydrogen, or R$^4$ and R$^5$ are joined together to form pyrrolidinyl, morpholinyl, piperazinyl, azetidinyl, 1,4-piperazin-2-one, piperidinyl, 1,3-imidazolidin-4-one, 1,3-imidazolidine, 6-oxa-2-azaspiro[4.5]decane, tetrahydropyranyl, 2-oxa-5,2-azabicyclo[2.2.1]heptane, (1R,5S)-3-oxa-8-azabicyclo[3.2.1]octane, 2,6-diazaspiro[3,4]octane, 4-thiomorpholine-1,1-dioxide, 4-thiomorpholine-1-oxide, tetrahydro-2H-thiopyran-1,1-oxide, 1-oxa-8-azaspiro[4,5]decane, 1-pyrrolidin-2-one, 1-imidazolidin-4-one, 2,7-diazaspiro[4.4]nolan-1-one, tetrahydro-1H-8-pyrazino[3,4-c][1,4]oxazin-4(3H)-one, or hexahydro-1H-8-pyrazino[3,4-c][1,4]oxazine.

19. The compound of claim 1, wherein:

R$^1$ is R$^7$-substituted or unsubstituted C$_6$-C$_{10}$ aryl or R$^7$-substituted or unsubstituted 5 to 10 membered heteroaryl;

R$^7$ is independently hydrogen, —F, —Cl, Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl.

20. The compound of claim 19, wherein:
R[1] is R[7A]-substituted or unsubstituted phenyl, R[7A]-substituted or unsubstituted quinolonyl, or R[7A]-substituted or unsubstituted pyridinyl.

21. The compound of claim 1, or a pharmaceutically acceptable salt thereof, wherein:
R[2] is halogen or substituted or unsubstituted $C_1$-$C_2$-alkyl.

22. The compound of claim 21, wherein R[2] is halogen.

23. The compound of claim 22, wherein halogen is Cl or Br.

24. The compound of claim 21, wherein R[2] is substituted or unsubstituted $C_1$-$C_2$-alkyl.

25. The compound of claim 24, wherein R[2] is methyl.

26. A pharmaceutical composition comprising a compound of claim 1, and a pharmaceutically acceptable excipient.

27. A method of treating a disease or disorder mediated by GCN2, comprising administering to a subject in need thereof a therapeutically effective amount of the compound of formula (I) of claim 1, wherein the disease or disorder is cancer and the cancer is melanoma, non-small cell lung cancer, bladder cancer, pancreatic cancer, head and neck cancer, or brain tumor.

28. A method of treating a disease or disorder mediated by GCN2, comprising administering to a subject in need thereof a therapeutically effective amount of a pharmaceutical composition of claim 26, wherein the disease or disorder is cancer and the cancer is melanoma, non-small cell lung cancer, bladder cancer, pancreatic cancer, head and neck cancer, or brain tumor.

29. The method of claim 27, comprising administering a compound of Formula (II), a compound of formula (III), a compound of formula (IV), or a pharmaceutically acceptable salt thereof.

30. The compound of claim 7, wherein R[3.1] is independently hydrogen, —C(O)NR[3.1A]R[3.1B], —OR[3.1A] or unsubstituted alkyl; and R[3.2] is —C(O)NR[3.2A]R[3.2B], —OR[3.2], or unsubstituted alkyl.

31. The compound of claim 1, wherein R[2] is halogen.

32. The compound of claim 7, wherein R[2] is halogen.

33. The compound of claim 8, wherein R[2] is halogen.

34. The compound of claim 8 having the formula:

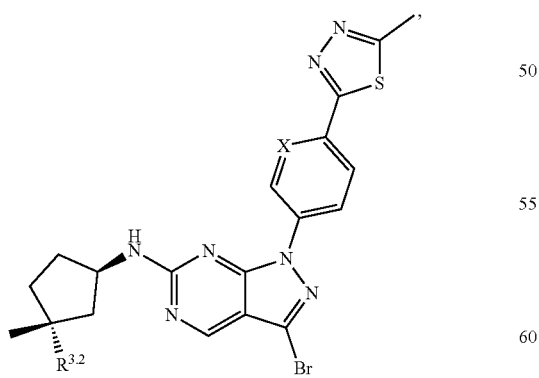

or a pharmaceutically acceptable salt thereof, wherein X is N or CH.

35. The compound of claim 34, wherein R[3.2] is —OH or —C(O)NH—CH₃.

36. A compound having the formula:

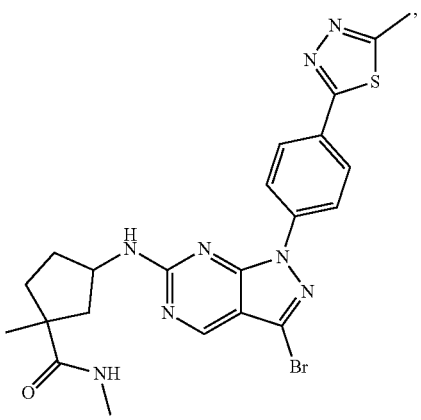

or a pharmaceutically acceptable salt thereof.

37. The compound of claim 36 having the formula:

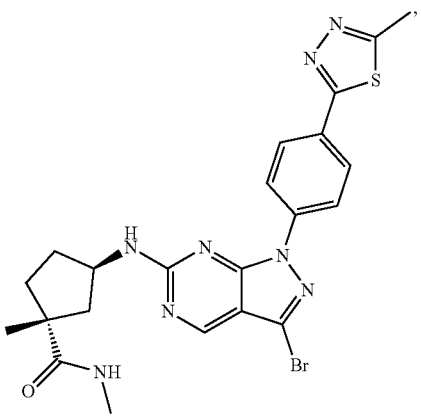

or a pharmaceutically acceptable salt thereof.

38. A compound having the formula:

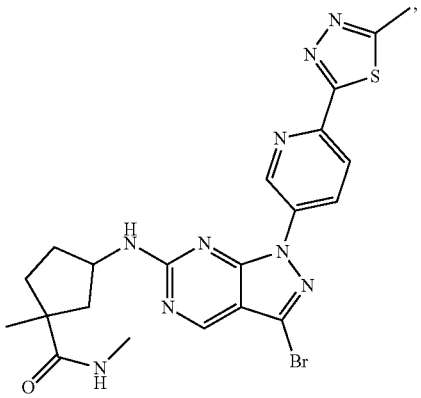

or a pharmaceutically acceptable salt thereof.

39. The compound of claim 38 having the formula:

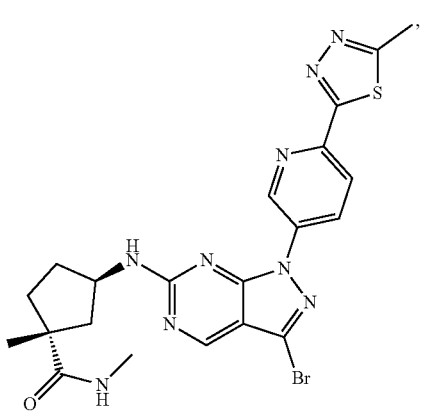

or a pharmaceutically acceptable salt thereof.

40. The compound of claim 8 having the formula:

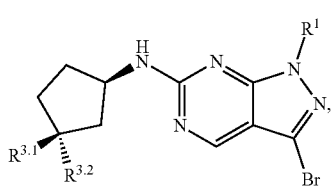

or a pharmaceutically acceptable salt thereof.

41. The compound of claim 40, wherein $R^1$ is $R^7$-substituted aryl, $R^{3.1}$ is unsubstituted alkyl and $R^{3.2}$ is —$OR^{3.24}$.

42. The compound of claim 41, wherein $R^1$ is $R^7$-substituted quinazolinyl, $R^{3.1}$ is methyl, and $R^{3.2}$ is —OH.

43. The compound of claim 8 having the formula:

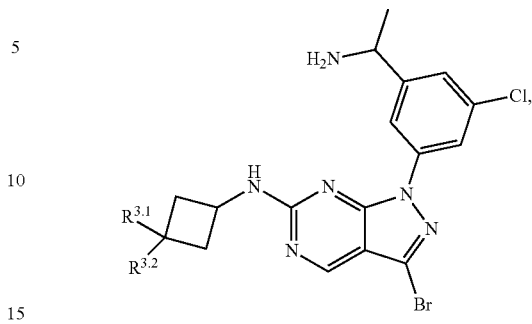

or a pharmaceutically acceptable salt thereof.

44. The compound of claim 43, wherein $R^{3.1}$ is hydrogen and $R^{3.2}$ is $R^{12}$-substituted heteroalkyl.

45. The compound of claim 44, wherein $R^{3.2}$ is substituted N-methylacetamide.

46. The compound of claim 43 having the formula:

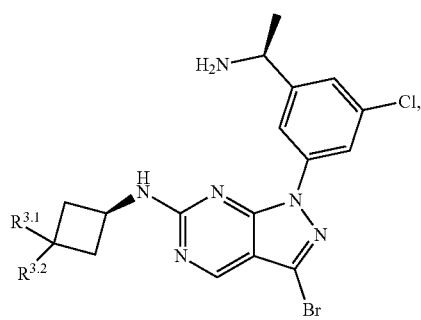

or a pharmaceutically acceptable salt thereof.

* * * * *